United States Patent [19]
Murayama et al.

[11] Patent Number: 5,478,833
[45] Date of Patent: Dec. 26, 1995

[54] ACONITINE COMPOUNDS AND ANALGESIC/ANTI-INFLAMMATORY AGENT CONTAINING THE SAME

[75] Inventors: Mitsuo Murayama; Takao Mori, both of Utsunomiya, Japan

[73] Assignee: Sanwa Shoyaku Kabushiki Kaisha, Japan

[21] Appl. No.: 266,638

[22] Filed: Jun. 28, 1994

Related U.S. Application Data

[62] Division of Ser. No. 50,281, filed as PCT/JP91/01297, Sep. 27, 1991, abandoned.

[51] Int. Cl.$^6$ .................. C07D 221/22; A61K 31/435
[52] U.S. Cl. .................................. 514/279; 546/39
[58] Field of Search ..................... 546/39; 514/279

[56] References Cited

FOREIGN PATENT DOCUMENTS

| | | |
|---|---|---|
| A1357611 | 11/1959 | France . |
| 56-120620 | 9/1981 | Japan . |
| 63-211269 | 9/1988 | Japan . |
| 63-211268 | 9/1988 | Japan . |
| 63-275583 | 11/1988 | Japan . |
| 64-34965 | 2/1989 | Japan . |
| 1-143859 | 6/1989 | Japan . |
| 1-254625 | 10/1989 | Japan . |
| 2-76856 | 3/1990 | Japan . |

OTHER PUBLICATIONS

*Chemical and Pharmaceutical Bulletin*, vol. 39, No. 2, Feb. 1991, Tokyo JP, pp. 379–383; Mori et al: "Studies on the Constitutents of Aconitum Species. XII. Syntheses of Jesaconitine Derivatives and Their Analgesic and Toxic Activities".

*Chemical Abstracts*, vol. 116, No. 11, 16 Mar. 1992, Columbus, Ohio; Abstract No. 106574, p. 808; & JP–A–03 223 255 (Sanwa Seeiyaku Co., Ltd.) 2 Oct. 1991, Murayama et al.

Grant & Hackh's Chemical Dictionary, 5th ed (1987), Ruger Grant et al., p. 22.

*Primary Examiner*—Philip I. Datlow
*Attorney, Agent, or Firm*—Nixon & Vanderhye

[57] ABSTRACT

Novel aconitine compounds of the formula

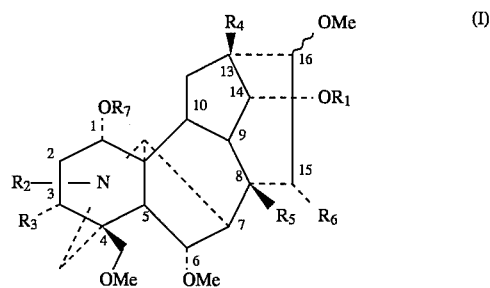

wherein the symbols are as defined in the description, as well as analgesic/anti-inflammatory agent containing them or salts thereof as active ingredient.

2 Claims, No Drawings

ACONITINE COMPOUNDS AND ANALGESIC/ANTI-INFLAMMATORY AGENT CONTAINING THE SAME

This application is a divisional of U.S. application Ser. No. 08/050,281, filed as PCT/JP91/01297, Sep. 27, 1991, now abandoned.

TECHNICAL FIELD

This invention relates to novel aconitine compounds as well as to an analgesic/anti-inflammatory agent containing the same.

Background Art

Aconitine alkaloids contained in the tuberous root of plants of the genus Aconitium have already been reported to have a potent analgesic and anti-inflammatory action. They, however, are supposed to show a narrow safety margin because of their high toxicity.

Disclosure of Invention

As a result of extensive studies in an attempt to develop novel aconitine alkaloid derivatives which are low in toxicity but maintain the analgesic/anti-inflammatory activity that aconitine alkaloids have, we have now succeeded in providing novel compounds of the formula (I) according to the present invention:

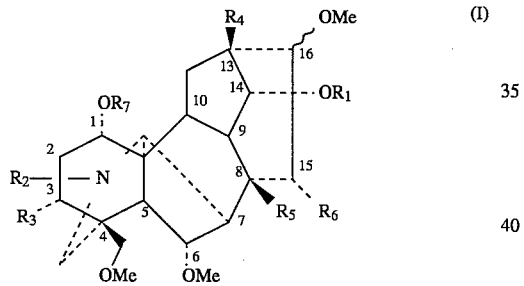

wherein $R_1$ and $R_2$ are independently
  (i) hydrogen,
  (ii) acyclic or cyclic, saturated or unsaturated alkyl having 1–8 carbon atoms,
  (iii) oxygen- or nitrogen-containing 5- or 6-membered heterocyclic group,
  (iv) acyl derived from acyclo- or cyclo-aliphatic, aromatic or aromatic-aliphatic carboxylic acid, or
  (v) aralkyl;

$R_3$ and $R_4$ are hydrogen or hydroxyl;

$R_5$ is hydrogen, hydroxyl or acetyloxy;

$R_6$ is hydrogen or hydroxyl, or a group forming carbonyl together with the carbon atom at the position 15; and $R_7$ is hydrogen, methyl or aliphatic or aromatic acyl; provided that:

a) if $R_1$ is benzoyl, $R_2$ and $R_7$ are methyl, $R_3$ is hydrogen or hydroxyl and $R_4$ and $R_6$ are hydroxyl, then $R_5$ is hydrogen;

b) if $R_1$ is benzoyl, $R_2$ and $R_7$ are methyl, $R_3$ and $R_4$ are hydrogen and $R_6$ is hydroxyl, then $R_5$ is hydrogen;

c) if $R_1$ is benzoyl, $R_2$ is ethyl, $R_3$ is hydrogen, $R_4$ is hydrogen or hydroxyl, $R_6$ is hydroxyl and $R_7$ is methyl, then $R_5$ is hydrogen or hydroxyl;

d) if $R_1$ is anisoyl, $R_2$ is ethyl, $R_3$ is hydrogen, $R_4$ and $R_6$ are hydroxyl and $R_7$ is methyl, then $R_5$ is hydrogen or hydroxyl;

e) if $R_1$ is benzoyl or anisoyl, $R_2$ is ethyl, $R_3$, $R_4$ and $R_6$ are hydroxyl and $R_7$ is methyl, then $R_5$ is hydrogen;

f) if $R_1$ is benzoyl or anisoyl, $R_2$ is methyl or ethyl, $R_3$ is hydrogen or hydroxyl, $R_4$ is hydroxyl, $R_5$ is hydrogen and $R_7$ is methyl, then $R_6$ is hydrogen or hydroxyl;

g) if $R_1$ is veratroyl, anisoyl or benzoyl, $R_2$ is ethyl, $R_3$ and $R_4$ are hydroxyl, $R_6$ is hydrogen and $R_7$ is methyl, then $R_5$ is hydrogen;

h) if $R_1$ is anisoyl, $R_2$ is ethyl, $R_3$ is hydrogen, $R_4$ is hydroxyl, $R_6$ is hydrogen and $R_7$ is methyl, then $R_5$ is hydrogen;

i) if $R_1$ is anisoyl, $R_2$ is ethyl, $R_3$ is hydroxyl, $R_4$ and $R_6$ are hydrogen and $R_7$ is methyl, then $R_5$ is hydrogen;

j) if $R_1$ is anisoyl, $R_2$ is ethyl, $R_3$, $R_4$ and $R_6$ are hydrogen and $R_7$ is methyl, then $R_5$ is hydrogen or hydroxyl;

k) if $R_1$ is benzoyl, $R_2$ is methyl or ethyl, $R_3$ and $R_6$ are hydrogen, $R_4$ is hydroxyl and $R_7$ is methyl, then $R_5$ is hydrogen or hydroxyl;

l) if $R_1$ is veratroyl, $R_2$ is ethyl, $R_3$ and $R_6$ are hydrogen, $R_4$ is hydroxyl and $R_7$ is methyl, then $R_5$ is hydrogen or hydroxyl;

m) if $R_1$ is 3-phenylpropenoyl, $R_2$ is ethyl, $R_4$ is hydroxyl, $R_3$ and $R_6$ are hydrogen and $R_7$ is methyl, then $R_5$ is hydrogen or hydroxyl;

n) if $R_1$ is acetyl, $R_2$ is formyl, methyl or ethyl, $R_3$ and $R_4$ are hydrogen, $R_6$ is a group forming carbonyl together with the carbon atom at the position 15 and $R_7$ is methyl, then $R_5$ is hydrogen or acetyloxy;

o) if $R_1$ is acetyl, $R_2$ is hydrogen, formyl, methyl or ethyl, $R_3$, $R_4$ and $R_6$ are hydrogen and $R_7$ is methyl, then $R_5$ is hydrogen or hydroxyl;

p) if $R_1$ is benzoyl, $R_2$ is hydrogen or methyl, $R_3$, $R_4$ and $R_6$ are hydrogen and $R_7$ is methyl, then $R_5$ is hydrogen or hydroxyl;

q) if $R_1$ is benzoyl, $R_2$ is ethyl, $R_3$ and $R_4$ are hydrogen, $R_6$ is hydrogen or hydroxyl and $R_7$ is methyl, then $R_5$ is hydrogen;

r) if $R_1$, $R_3$, $R_4$ and $R_6$ are hydrogen, $R_2$ is ethyl and $R_7$ is hydrogen, anisoyl or trimethylgalloyl, then $R_5$ is hydrogen;

s) if $R_1$ is acetyl, $R_2$ is ethyl and $R_3$, $R_4$, $R_6$ and $R_7$ are hydrogen, then $R_5$ is hydrogen;

t) if $R_1$ is hydrogen or benzoyl, $R_2$ is ethyl, $R_3$, $R_4$ and $R_6$ are hydrogen and $R_7$ is benzoyl, then $R_5$ is hydrogen;

u) if $R_1$ is benzoyl, $R_2$ is ethyl and $R_3$, $R_4$, $R_6$ and $R_7$ are hydrogen, then $R_5$ is hydrogen;

v) if $R_1$ is acetyl, $R_2$ is ethyl, $R_3$, $R_4$ and $R_6$ are hydrogen and $R_7$ is acetyl, anisoyl or trimethylgalloyl, then $R_5$ is hydrogen;

w) if $R_1$, $R_3$, $R_4$ and $R_7$ are hydrogen, $R_2$ is ethyl and $R_6$ is hydroxyl, then $R_5$ is hydrogen or acetyloxy;

x) if $R_1$ is benzoyl, $R_2$, $R_3$, $R_4$ and $R_7$ are hydrogen and $R_6$ is hydroxyl, then $R_5$ is hydrogen or hydroxyl;

y) if both $R_1$ and $R_7$ are the same and represent anisoyl, o-methoxybenzoyl, trimethylgalloyl or p-nitrobenzoyl, $R_2$ is ethyl and $R_3$, $R_4$ and $R_6$ are hydrogen, then $R_5$ is hydrogen or acetyloxy; and z) if $R_1$ is benzoyl, $R_2$ is hydrogen, $R_4$ and $R_6$ are hydroxyl, $R_5$ is acetyloxy and $R_7$ is methyl, then $R_3$ is hydrogen.

We have also found that the compounds of the formula (I) have a potent analgesic/anti-inflammatory action as well as a lower toxicity than mesaconitine, aconitine, hypaconitine and jesaconitine.

The present invention has been accomplished based on these findings. Thus, the present invention provides novel compounds of the formula (I) mentioned above as well as an analgesic/anti-inflammatory agent containing as active ingredient one or more of the compounds of the formula (I) or salts thereof.

A preferred aspect of the invention includes compounds of formula (I) in which $R_1$ and $R_2$ are independently (i) hydrogen, (ii) an acyclic or cyclic, saturated or unsaturated alkyl having 1–8 carbon atoms, (iii) an oxygen- or nitrogen-containing 5- or 6-membered heterocyclic group, (iv) acyl derived from an acyclo- or cyclo-aliphatic, aromatic or aromatic-aliphatic carboxylic acid, or (v) aralkyl; $R_3$ and $R_4$ are hydrogen or hydroxyl; $R_5$ is hydrogen; $R_6$ is a group forming carbonyl together with the carbon atom at the position 15; and $R_7$ is methyl; provided that if $R_1$ is benzoyl or anisoyl then $R_2$ is acyl derived from an aliphatic or aromatic carboxylic acid.

The compounds according to the invention of the formula (I) shown above may be prepared from aconitine alkaloids described in the literature such as aconitine of the formula (II), mesaconitine of the formula (III), hypaconitine of the formula (IV), jesaconitine of the formula (V), 14-O-benzoylmesaconine of the formula (VI), 14-O-benzoylaconine of the formula (VII), 14-O-benzoylhypaconine of the formula (VIII), 14-O-anisoylaconine of the formula (IX), neolin of the formula (X) or pyroaconitines or 16-epipyroaconitines of the formula (XI) shown below as starting material by way of deoxygenation reaction at the position 3, 8, 13 or 15, replacement of substituents attached to the nitrogen atom or the position 1, 8 or 14 by other substituents, or combination thereof.

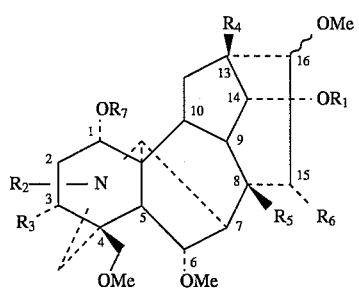

(II) ~ (X)

In the formulas (II)–(X), $R_1, R_2, R_3, R_4, R_5, R_6$ and $R_7$ are defined in each case to mean the following:

| | $R_1$ | $R_2$ | $R_3$ | $R_4$ | $R_5$ | $R_6$ | $R_7$ |
|---|---|---|---|---|---|---|---|
| II | Bz | $CH_2CH_3$ | OH | OH | OAc | OH | $CH_3$ |
| III | Bz | $CH_3$ | OH | OH | OAc | OH | $CH_3$ |
| IV | Bz | $CH_3$ | H | OH | OAc | OH | $CH_3$ |
| V | An | $CH_2CH_3$ | OH | OH | OAc | OH | $CH_3$ |
| VI | Bz | $CH_3$ | OH | OH | OH | OH | $CH_3$ |
| VII | Bz | $CH_2CH_3$ | OH | OH | OH | OH | $CH_3$ |
| VIII | Bz | $CH_3$ | H | OH | OH | OH | $CH_3$ |
| IX | An | $CH_2CH_3$ | OH | OH | OH | OH | $CH_3$ |
| X | H | $CH_2CH_3$ | H | H | OH | H | H |

Bz: $COC_6H_5$, An: $COC_6H_4OCH_3$, Ac: $COCH_3$

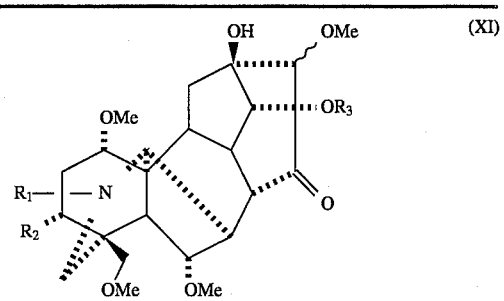

(wherein $R_1$ is $CH_3$ or $C_2H_5$, $R_2$ is OH or H and $R_3$ is Bz or An.)

The deoxygenation reaction mentioned above may be carried out by using ionic reaction, radical reaction, reduction reaction or the like or combination thereof, which is normally used in chemical reaction.

The ionic reaction mentioned above may be carried out by dissolving the corresponding compound in a dehydrating agent as solvent such as sulfuric acid or thionyl chloride, followed by heating under reflux. It may also be carried out by reacting the corresponding compound, while stirring or heating under reflux, with carbon disulfide and methyl iodide in an appropriate solvent such as tetrahydrofuran in the presence, for example, of imidazole and sodium hydride under an appropriate temperature condition to give thioacylated product, and adding tributyl-tin hydride or the like to the resultant product in a solvent such as benzene followed by stirring either at room temperature or while heating under reflux.

The radical reaction mentioned above may be carried out by dissolving the corresponding compound in a solvent such as water and phosphoric acid hexamethyltriamide, and irradiating the solution with the use of a low pressure mercury lamp either at room temperature or while cooling. It may also be carried out by converting the hydroxyl group of the corresponding compound into an active substituent with the use of oxalyl chloride or the like; adding a radical producing reagent such as α,α'-azoisobutyronitrile and a reducing agent such as tributyl-tin hydride using a solvent such as benzene, and heating under reflux, or stirring at room temperature, the mixture.

The reduction reaction mentioned above may be carried out by subjecting the corresponding compound dissolved in a solvent such as ethanol or acetic acid to contact hydrogenation, either at room temperature or under heating, using as catalyst platinum oxide, palladium/carbon, Raney nickel or the like.

The deoxygenation reaction may also be carried out by subjecting the corresponding compound to conversion of the hydroxyl group into ketone with an oxidizing agent such as sodium perchromate, followed by derivatization of the ketone into thioketal or hydrazone with ethane dithiol, p-toluenesulfonylhydrazine or the like, and then reducing the derivative either at room temperature or under heating or cooling, with an organometallic reducing agent such as lithium aluminum hydride in a solvent such as ether or tetrahydrofuran.

Replacement of a substituent attached to the nitrogen atom with another substituent may be carried out by reacting the corresponding compound with an appropriate oxidizing agent such as potassium permanganate in an appropriate solvent such as acetone to afford N-dealkylated product, and reacting the resultant N-dealkylated product, for example, with an alkylating or acylating agent such as an acid chloride, alkyl halide or aralkyl halide.

Acylation or alkylation of hydroxyl group may be carried out by reacting the corresponding compound with an acid chloride, a halogen compound or the like, which is conventionally used for esterification or etherification of hydroxyl group, in an appropriate solvent such as pyridine.

Replacement of an acyl group present in the form of ester bond with another acyl group or with an alkyl group may be carried out by deestrification into hydroxyl group through hydrolysis such as alkaline hydrolysis, followed by acylation or alkylation of the hydroxyl group.

The various reactions mentioned above may be appropriately combined to afford the compounds of the formula (I).

In the following will now be given examples of preparation of compounds of the formula (I). Physicochemical parameters and analytical data of the compounds prepared in these examples are given just after the description of the examples. Pharmacological activity, toxicity etc. of the compounds are shown in Tables 1–3 mentioned below.

Example 1

1) Under the condition of −70° C., the tetrahydrofuran (THF) solution containing pyrojesaconitine 60 mg was added in the tetrahydrofuran (THF) solution of $LiAl(OCH_3)_3H$ prepared from 72 mg of $LiAlH_4$ and 0.23 ml of methanol. After this solution was stirred for 1 hour at −70° C., stirring further continued about additional 1 hour at room temperature. After reaction, wet-THF was added to the reaction mixture at 0° C. and the solid product was filtered off. The filtrate was concentrated to dryness under reduced pressure to give 8-deoxyaconine (45.6 mg).

2) 8-Deoxyaconine 45 mg were dissolved in a mixture of 5 ml of pyridine and 1 ml of methylene chloride, followed by adding 15 μl of p-anisoyl chloride at −70° C. The reaction mixture was stirred at the rising temperature from −70° to −5° C., which took 2 hours. Then, ice water was added to the reaction mixture and it was made alkaline with 5% sodium bicarbonate solution. This alkaline solution was extracted three times with 30 ml of chloroform. The chloroform layer put together was washed with water, dried over anhydrous sodium sulfate and concentrated to dryness under reduced pressure. The residue was subjected to column chromatography on silica gel for separation and purification (eluting solvent: 5% methanol/ammonia-saturated chloroform) to yield 8-deoxy-14-O-anisoylaconine (37 mg).

Example 2

Jesaconitine 100 mg was dissolved in 1.5 ml of thionyl chloride and refluxed for 3 hours. After cooling, thionyl chloride was distilled off under reduced pressure. To the residue, ice water was added. After this solution was made alkaline with 5 % sodium bicarbonate, it was extracted three times with 30 ml of chloroform. The chloroform layer put together was washed with water, dried over anhydrous sodium sulfate and concentrated to dryness under reduced pressure. The residue was subjected to column chromatography on silica gel for separation and purification (eluting solvent: ammonia-saturated ether/n-hexane= 4:1) to obtain anhydrojesaconitine (72.3 mg).

Subsequently, anhydrojesaconitine 70 mg was dissolved in 10 ml of ethanol. To this solution, platinic oxide 33 mg was added and it was stirred vigorously in a hydrogen stream for 1.5 hours. After reaction, the catalyst was filtered off and the filtrate was concentrated to dryness under reduced pressure. The residue was subjected to column chromatography on silica gel for separation and purification (eluting solvent: ammonia-saturated ether/n-hexane= 4:1) to give 3-deoxyjesaconitine (37 mg).

Example 3

3-Deoxyjesaconitine 50 mg was dissolved in a mixture of dioxane (2 ml) and water (2 ml) and refluxed for 4 hours. After cooling, the solvent was distilled off under reduced pressure. The residue was subjected to thin-layer chromatography for separation and purification (eluting solvent: 5% methanol/ammonia-saturated chloroform) to give 3-deoxy-14-O-anisoylaconine (38 mg).

Example 4

1) 3-Deoxyjesaconitine 100 mg was heated at 180° C. for 30 minutes under reduced pressure (1–2 mmHg). The reaction products were subjected to column chromatography on silica gel for separation and purification (eluting solvent: 5% methanol/chloroform) to give 3-deoxypyrojesaconitine (60 mg).

2) 3,8-Dideoxy-14-O-anisoylaconine 32 mg was obtained in the same manner as in Example 1, except for the use of 60 mg of 3-deoxypyrojesaconitine as a substitute for pyrojesaconitine in Example 1-1).

Example 5

Jesaconitine 150 mg was dissolved in 10 ml of pyridine. To this solution, 0.5 ml of trifluoromethanesulfonic anhydride was added at 0° C. and the mixture was stirred at room temperature for 3 hours. After reaction, the reaction mixture was poured into an ice water. After this solution was made alkaline with ammonia and it was extracted three times with 50 ml of chloroform. The chloroform layer put together was washed with water, dried over anhydrous sodium sulfate and concentrated to dryness under reduced pressure. The residue was subjected to column chromatography on silica gel for separation and purification (eluting solvent: ammonia-saturated ether/n-hexane= 4:1) to give 13 -O-trifluoromethanesulfonyl-anhydrojesaconitine (98 mg).

Secondly, 13-O-trifluoromethanesulfonyl-anhydrojesaconitine 90 mg was dissolved in 100 ml of a mixture of hexamethylphosphoric triamide/water (95:5), and irradiated by low-pressure mercury lump (2537 Å) in a nitrogen stream at 0° C. for 1 hour. After reaction, the reaction mixture was quenched with five times volume of water and made alkaline with ammonia. The alkaline solution was extracted three times with 500 ml of ether. The ether layer put together was washed with water, dried over anhydrous sodium sulfate and concentrated to dryness under reduced pressure. The residue was subjected to column chromatography on silica gel for separation and purification (eluting solvent: ammonia-saturated ether/n-hexane= 4:1) to give 13-deoxyanhydrojesaconitine (41 mg).

Next, 13-deoxyanhydrojesaconitine 40 mg was dissolved in 7 ml of ethanol. To this solution, platinic oxide 15 mg was added and the mixture was stirred vigorously in a hydrogen stream for 1.5 hours. After reaction, the catalyst was filtered off and the filtrate was concentrated to dryness under reduced pressure. The residue was subjected to column chromatography on silica gel for separation and purification (eluting solvent: ammonia-saturated ether/n-hexane= 4:1) to give 3,13-dideoxyjesaconitine (23 mg).

Example 6

3,13-Dideoxy-14-O-anisoylaconine 22 mg was obtained in the same manner as in Example 3, except for the use of 30 mg of 3,13-dideoxyjesaconitine as a substitute for 3-deoxyjesaconitine in Example 3.

Example 7

3,13-Dideoxypyrojesaconitine 62 mg was obtained in the same manner as in Example 4-1), except for the use of 100 mg of 3,13-dideoxyjesaconitine as a substitute for 3-deoxyjesaconitine in Example 4-1).

Secondly, 3,8,13-trideoxyaconine 48 mg was obtained in the same manner as in Example 1-1), except for the use of 60 mg of 3,13-dideoxypyrojesaconitine as a substitute for pyrojesaconitine in Example 1-1).

Next, 3,8,13-trideoxy-14-O-anisoylaconine 31 mg was obtained in the same manner as in Example 1-2), except for the use of 45 mg of 3,8,13-trideoxyaconine as a substitute for 8-deoxyaconine in Example 1-2).

Example 8

8-Deoxy-14-O-benzoylaconine 32 mg was obtained in the same manner as in Example 1, except for the use of 20 µl of benzoyl chloride as a substitute for p-anisoyl chloride in Example 1-2).

Example 9

3-Deoxyaconitine 35 mg was obtained in the same manner as in Example 2, except for the use of 100 mg of aconitine as a substitute for jesaconitine in Example 2.

Example 10

3-Deoxy-14-O-benzoylaconine 40.2 mg was obtained in the same manner as in Example 3, except for the use of 50 mg of 3-deoxyaconitine as a substitute for 3-deoxyjesaconitine in Example 3.

Example 11

3-Deoxypyroaconitine 68 mg was obtained in the same manner as in Example 4-1), except for the use of 100 mg of 3-deoxyaconitine as a substitute for 3-deoxyjesaconitine in Example 4-1).

Secondly, 3,8-dideoxyaconine 49.5 mg was obtained in the same manner as in Example 1-1), except for the use of 60 mg of 3-deoxypyroaconitine as a substitute for pyrojesaconitine in Example 1-1).

Next, 3,8-dideoxy-14-O-benzoylaconine 35 mg was obtained in the same manner as in Example 1-2), except for the use of 45 mg of 3,8-dideoxyaconine and 20 µl of benzoyl chloride as each substitute for 8-deoxyaconine and p-anisoyl chloride in Example 1-2).

Example 12

3,13-Dideoxyaconitine 25 mg was obtained in the same manner as in Example 5, except for the use of 150 mg of aconitine as a substitute for jesaconitine in Example 5.

Example 13

3,13-Dideoxy-14-O-benzoylaconine 18 mg was obtained in the same manner as in Example 3, except for the use of 30 mg of 3,13-dideoxyaconitine as a substitute for 3-deoxyjesaconitine in Example 3.

Example 14

3,13-Dideoxypyroaconitine 60.5 mg was obtained in the same manner as in Example 4-1), except for the use of 100 mg of 3,13-dideoxyaconitine as a substitute for 3-deoxyjesaconitine in Example 4-1).

Next, 3,8,13-trideoxyaconine 50.6 mg was obtained in the same manner as in Example 1-1), except for the use of 60 mg of 3,13-dideoxypyroaconitine as a substitute for pyrojesaconitine in Example 1-1).

Subsequently, 3,8,13-trideoxy-14-O-benzoylaconine 33.2 mg was obtained in the same manner as in Example 1-2), except for the use of 45 mg of 3,8,13-trideoxyaconine and 20 µl of benzoyl chloride as each substitute for 8-deoxyaconine and p-anisoyl chloride in Example 1-2).

Example 15

8-Deoxymesaconine 47.2 mg was obtained in the same manner as in Example 1-1), except for the use of 60 mg of pyromesaconitine as a substitute for pyrojesaconitine in Example 1-1).

Next, 8-deoxy-14-O-benzoylmesaconine 34.8 mg was obtained in the same manner as in Example 1-2), except for the use of 45 mg of 8-deoxymesaconine and 20 µl of benzoyl chloride as each substitute for 8-deoxyaconine and p-anisoyl chloride in Example 1-2).

Example 16

3,8-Dideoxymesaconine 46.6 mg was obtained in the same manner as in Example 1-1), except for the use of 60 mg of pyrohypaconitine as a substitute for pyrojesaconitine in Example 1-1).

Next, 3,8-dideoxy-14-O-benzoylmesaconine 36.3 mg was obtained in the same manner as in Example 1-2), except for the use of 45 mg of 3,8-dideoxymesaconine and 20 µl of benzoyl chloride as each substitute for 8-deoxyaconine and p-anisoyl chloride in Example 1-2).

Example 17

3,13-Dideoxymesaconitine 23 mg was obtained in the same manner as in Example 5, except for the use of 150 mg of mesaconitine as a substitute for jesaconitine in Example 5.

Example 18

3,13-Dideoxy-14-O-benzoylmesaconine 16.8 mg was obtained in the same manner as in Example 3, except for the use of 30 mg of 3,13-dideoxymesaconitine as a substitute for 3-deoxyjesaconitine in Example 3.

Example 19

3,13-Dideoxypyromesaconitine 61.2 mg was obtained in the same manner as in Example 4-1), except for the use of 100 mg of 3,13-dideoxymesaconitine as a substitute for 3-deoxyjesaconitine in Example 4-1).

Next, 3,8,13-trideoxymesaconine 48.7 mg was obtained in the same manner as in Example 1-1), except for the use of 60 mg of 3,13-dideoxypyromesaconitine as a substitute for pyrojesaconitine in Example 1-1).

Subsequently, 3,8,13-trideoxy-14-O-benzoylmesaconine 31.5 mg was obtained in the same manner as in Example 1-2), except for the use of 45 mg of 3,8,13-trideoxymesaconine and 20μl of benzoyl chloride as each substitute for 8-deoxyaconine and p-anisoyl chloride in Example 1-2).

Example 20

8-Deoxymesaconine 47.2 mg was obtained in the same manner as in Example 1-1), except for the use of 60 mg of pyromesaconitine as a substitute for pyrojesaconitine in Example 1-1).

Next, 8-deoxy-14-O-anisoylmesaconine 32.5 mg was obtained in the same manner as in Example 1-2), except for the use of 45 mg of 8-deoxymesaconine as a substitute for 8-deoxyaconine in Example 1-2).

Example 21

1) Hypaconitine 50 mg was dissolved in a mixture of 2 ml of 5% sodium hydroxide and 5 ml of methanol, and heated under reflux for 3 hours. After cooling, the reaction mixture was extracted three times with 10 ml of methylene chloride. The layer of methylene chloride put together was washed with water, dried over anhydrous sodium sulfate and concentrated to dryness under reduced pressure. The residue was subjected to column chromatography on silica gel for separation and purification (eluting solvent: 15% methanol/ammonia-saturated chloroform) to obtain 3-deoxymesaconine (28.6 mg).

2) 3-Deoxymesaconine 25 mg was dissolved in a mixture of 3 ml of pyridine and 1 ml of methylene chloride. To this solution, 10 μl of p-anisoyl chloride was added at −70° C. The reaction mixture was stirred at the rising temperature from −70° to −5° C., which took 2 hours. Subsequently, to reaction mixture, ice water was added. Then, this solution was made alkaline with 5% of aqueous sodium bicarbonate solution and extracted three times with 10 ml of chloroform. The chloroform layer put together was washed with water, dried over anhydrous sodium sulfate and concentrated to dryness under reduced pressure. The residue was subjected to column chromatography on silica gel for separation and purification (eluting solvent: 5% methanol in ammonia-saturated chloroform) to give 3-deoxy-14-O-anisoylmesaconine (18.7 mg).

Example 22

3,8-Dideoxymesaconine 46 mg was obtained in the same manner as in Example 1-1), except for the use of 60 mg of pyrohypaconitine as a substitute for pyrojesaconitine in Example 1-1).

Subsequently, 3,8-dideoxy-14-O-anisoylmesaconine 17.5 mg was obtained in the same manner as in Example 21-2), except for the use of 25 mg of 3,8-dideoxymesaconine as a substitute for 3-deoxymesaconine in Example 21-2).

Example 23

3,13-Dideoxymesaconine 26.3 mg was obtained in the same manner as in Example 21-1), except for the use of 50 mg of 3,13-dideoxymesaconitine as a substitute for hypaconitine in Example 21-1).

Subsequently, 3,13-dideoxy-14-O-anisoylmesaconine 17.3 mg was obtained in the same manner as in Example 21-2), except for 25 mg of 3,13-dideoxymesaconine as a substitute for 3-deoxymesaconine in Example 21-2).

Example 24

3,13-Dideoxypyromesaconitine 63.7 mg was obtained in the same manner as in Example 4-1), except for the use of 100 mg of 3,13-dideoxymesaconitine as a substitute for 3-deoxyjesaconitine in Example 4-1).

Next, 3,8,13-trideoxymesaconine 31.5 mg was obtained in the same manner as in Example 1-1), except for the use of 60 mg of 3,13-dideoxypyromesaconitine as a substitute for pyrojesaconitine in Example 1-1).

Subsequently, 3,8,13-trideoxy-14-O-anisoylmesaconine 16.7 mg was obtained in the same manner as in Example 21-2), except for the use of 25 mg of 3,8,13-trideoxymesaconine as a substitute for 3-deoxymesaconine in Example 21-2).

Example 25

14-O-Benzoylmesaconine 30 mg was obtained in the same manner as in Example 21-1), except for the use of 50 mg of mesaconitine as a substitute for hypaconitine in Example 21-1).

Next, 14-O-anisoylmesaconine 15.5 mg was obtained in the same manner as in Example 21-2), except for the use of 25 mg of 14-O-benzoylmesaconine as a substitute for 3-deoxymesaconine in Example 21-2).

Example 26

1) Under the condition of −70° C., the THF solution containing 16-epi-pyrojesaconitine 60 mg was added in the THF solution of LiAl(OCH$_3$)$_3$H prepared from 72 mg of LiAlH$_4$ and 0.23 ml of methanol. After this solution was stirred at −70° C. for 1 hour, stirring further continued for additional 1 hour at room temperature. After reaction, wet-THF was added to the reaction mixture at 0° C. and solid product was filtrated off. The filtrate was concentrated to dryness under reduced pressure to give 16-epi- 8-deoxyaconine (45.2 mg).

2) 16-Epi-8-deoxyaconine 45 mg was dissolved in a mixture of pyridine 5 ml and methylene chloride 1 ml. To this solution, 15 μl of p-anisoyl chloride was added at −70° C. The reaction mixture was stirred at the rising temperature from −70° to −5° C., which took 2 hours.

Next, ice water was added to the reaction mixture and made alkaline with 5% of aqueous sodium bicarbonate solution. This alkaline solution was extracted three times with 30 ml of chloroform. The chloroform layer put together was washed with water, dried over anhydrous sodium sulfate and concentrated to dryness under reduced pressure. The residue was subjected to column chromatography on silica gel for separation and purification (eluting solvent: 5% methanol/ammonia-saturated chloroform) to give 16-epi-8-deoxy-14-O-anisoylaconine (35 mg).

Example 27

1) 3-Deoxyjesaconitine 150 mg was heated at 180° C. for 30 min under reduced pressure (1–2 mmHg). The reaction products were subjected to column chromatography on silica gel for separation and purification (eluting solvent: 5% methanol in chloroform) to give 16-epi-3-deoxypyrojesaconitine (63 mg).

2) 16-Epi-3,8-dideoxy-14-O-anisoylaconine 35 mg was obtained in the same manner as in Example 26, except for the use of 60 mg of 16-epi-3-deoxypyrojesaconitine as a substitute for 16-epi-pyrojesaconitine in Example 26-1).

Example 28

16-Epi-3,13-dideoxypyrojesaconitine 61.7 mg was obtained in the same manner as in Example 27-1), except for the use of 150 mg of 3,13-dideoxyjesaconitine as a substitute for 3-deoxyjesaconitine in Example 27-1).

Next, 16-epi-3,8,13-trideoxyaconine 50.1 mg was obtained in the same manner as in Example 26-1), except for the use of 60 mg of 16-epi-3,13-dideoxypyrojesaconitine as a substitute for 16-epi-pyrojesaconitine in Example 26-1).

Subsequently, 16-epi-3,8,13-trideoxy-14-O-anisoylaconine 29.7 mg was obtained in the same manner as in Example 26-2), except for the use of 45 mg of 16-epi-3,8,13-trideoxyaconine as a substitute for 16-epi-8-deoxyaconine in Example 26-2).

Example 29

16-Epi-8-deoxy-14-O-benzoylaconine 33.2 mg was obtained in the same manner as in Example 26, except for the use of 20 μl of benzoyl chloride as a substitute for p-anisoyl chloride in Example 26-2).

Example 30

16-Epi-3-deoxypyroaconitine 66.5 mg was obtained in the same manner as in Example 27-1), except for the use of 150 mg of 3-deoxyaconitine as a substitute for 3-deoxyjesaconitine in Example 27-1).

Next, 16-epi-3,8-dideoxyaconine 47.2 mg was obtained in the same manner as in Example 26-1), except for the use of 60 mg of 16-epi-3-deoxypyroaconitine as a substitute for 16-epi-pyrojesaconitine in Example 26-1).

Subsequently, 16-epi-3,8-dideoxy-14-O-benzoylaconine 36.2 mg was obtained in the same manner as in Example 26-2), except for the use of 45 mg of 16-epi-3,8-dideoxyaconine and 20 μl of benzoyl chloride as each substitute for 16-epi-8-deoxyaconine and p-anisoyl chloride in Example 26-2).

Example 31

16-Epi-3,13-dideoxypyroaconitine 61.2 mg was obtained in the same manner as in Example 27-1), except for the use of 150 mg of 3,13-dideoxyaconitine as a substitute for 3-deoxyjesaconitine in Example 27-1).

Next, 16-epi-3,8,13-trideoxyaconine 51.7 mg was obtained in the same manner as in Example 26-1), except for the use of 60 mg of 16-epi-3,13-dideoxypyroaconitine as a substitute for 16-epi-pyrojesaconitine in Example 26-1).

Subsequently, 16-epi-3,8,13-trideoxy-14-O-benzoylaconine 30.5 mg was obtained in the same manner as in Example 26-2), except for the use of 45 mg of 16-epi-3,8,13-trideoxyaconine and 20 μl of benzoyl chloride as each substitute for 16-epi-8-deoxyaconine and p-anisoyl chloride in Example 26-2).

Example 32

16-Epi-8-deoxymesaconine 46.1 mg was obtained in the same manner as in Example 26-1), except for the use of 60 mg of 16-epi-pyromesaconitine as a substitute for 16-epi-pyrojesaconitine in Example 26-1).

Next, 16-epi-8-deoxy-14-O-benzoylmesaconine 34.8 mg was obtained in the same manner as in Example 26-2), except for the use of 45 mg of 16-epi-8-deoxymesaconine and 20 μl of benzoyl chloride as each substitute for 16-epi-8-deoxyaconine and p-anisoyl chloride in Example 26-2).

Example 33

16-Epi-3,8-dideoxymesaconine 45.8 mg was obtained in the same manner as in Example 26-1), except for the use of 60 mg of 16-epi-pyrohypaconitine as a substitute for 16-epi-pyrojesaconitine in Example 26-1).

Next, 16-epi-3,8-dideoxy-14-O-benzoylmesaconine 35.7 mg was obtained in the same manner as in Example 26-2), except for the use of 45 mg of 16-epi-3,8-dideoxymesaconine and 20 μl of benzoyl chloride as each substitute for 16-epi-8-deoxyaconine and p-anisoyl chloride in Example 26-2).

Example 34

16-Epi-3,13-dideoxypyromesaconitine 63.5 mg was obtained in the same manner as in Example 27-1), except for the use of 150 mg of 3,13-dideoxymesaconitine as a substitute for 3-deoxyjesaconitine in Example 27-1).

Next, 16-epi-3,8,13-trideoxymesaconine 49.3 mg was obtained in the same manner as in Example 26-1), except for the use of 60 mg of 16-epi-3,13-dideoxypyromesaconitine as a substitute for 16-epi-pyrojesaconitine in Example 26-1).

Subsequently, 16-epi-3,8,13-trideoxy-14-O-benzoylmesaconine 30.5 mg was obtained in the same manner as in Example 26-2), except for the use of 45 mg of 16-epi-3,8,13-trideoxymesaconine and 20 μl of benzoyl chloride as each substitute for 16-epi-8 -deoxyaconine and p-anisoyl chloride in Example 26-2).

Example 35

16-Epi-8-deoxymesaconine 45.3 mg was obtained in the same manner as in Example 26-1), except for the use of 60 mg of 16 -epi-pyromesaconitine as a substitute for 16-epi-pyrojesaconitine in Example 26-1).

Next, 16-epi-8-deoxy-14-O-anisoylmesaconine 30.4 mg was obtained in the same manner as in Example 26-2), except for the use of 45 mg of 16-epi-8-deoxymesaconine as a substitute for 16-epi-8-deoxyaconine in Example 26-2).

Example 36

16-Epi-3,8-dideoxymesaconine 45 mg was obtained in the same manner as in Example 26-1), except for the use of 60 mg of 16 -epi-pyrohypaconitine as a substitute for 16-epi-pyrojesaconitine in Example 26-1).

Next, 16-epi-3,8-dideoxy-14-O-anisoylmesaconine 19.3 mg was obtained in the same manner as in Example 21-2), except for the use of 25 mg of 16-epi-3,8-dideoxymesaconine as a substitute for 3-deoxymesaconine in Example 21-2).

Example 37

16-Epi-3,13-dideoxypyromesaconitine 62.1 mg was obtained in the same manner as in Example 27-1), except for the use of 150 mg of 3,13-dideoxymesaconitine as a substitute for 3-deoxyjesaconitine in Example 27-1).

Next, 16-epi-3,8,13-trideoxymesaconine 31.2 mg was obtained in the same manner as in Example 26-1), except for the use of 60 mg of 16-epi-3,13-dideoxypyromesaconitine as a substitute for 16-epi-pyrojesaconitine in Example 26-1).

Subsequently, 16-epi-3,8,13-trideoxy-14-O-anisoylmesaconine 15.3 mg was obtained in the same manner as in Example 21-2), except for the use of 25 mg of 16-epi-3,8,13-trideoxymesaconine as a substitute for 3-deoxymesaconine in Example 21-2).

Example 38

8-Deoxyaconine 53 mg was obtained in the same manner as in Example 1-1), except for the use of 70 mg of pyrojesaconitine as a substitute for 60 mg of pyrojesaconitine in Example 1-1).

8-Deoxyaconine 50 mg was dissolved in 1 ml of pyridine. To this solution, 3,4,5-trimethoxybenzoyl chloride 30 mg was added and the mixture was stirred at 80° C. for 4 hours. After reaction, pyridine was distilled off under reduced pressure. To the residue, water was added and made alkaline with 5% of aqueous sodium bicarbonate solution. The alkaline solution was extracted with chloroform. The chloroform layer was washed with water, dried over anhydrous sodium sulfate and concentrated to dryness under reduced pressure. The residue was subjected to column chromatography on silica gel for separation and purification (ammonia-saturated ether) to yield 8-deoxy-14-O-trimethylgalloylaconine (28 mg).

Example 39

8-Deoxy-14-O-veratroylaconine 24 mg was obtained in the same manner as in Example 38, except for the use of 25 mg of 3,4-dimethoxybenzoyl chloride as a substitute for 3,4,5-trimethoxybenzoyl chloride in Example 38.

Example 40

8-Deoxy-14-O-p-chlorobenzoylaconine 23 mg was obtained in the same manner as in Example 38, except for the use of 20 mg of p-chlorobenzoyl chloride as a substitute for 3,4,5-trimethoxybenzoyl chloride in Example 38.

Example 41

8-Deoxy-14-O-m-chlorobenzoylaconine 20 mg was obtained in the same manner as in Example 38, except for the use of 20 mg of m-chlorobenzoyl chloride as a substitute for 3,4,5-trimethoxybenzoyl chloride in Example 38.

Example 42

8-Deoxy-14-O-α-methyl-(4-(α-methylacetic acid)-phenyl)-acetylaconine 22 mg was obtained in the same manner as in Example 38, except for the use of 50 μl of α-methyl-(4-(α-methylacetic acid)-phenyl)-acetyl chloride as a substitute for 3,4,5-trimethoxybenzoyl chloride in Example 38.

Example 43

8-Deoxyaconine was obtained in the same manner as in Example 1-1). 8-Deoxyaconine 15 mg was dissolved in 1 ml of dioxane. After 15 mg of sodium hydride was added to this solution, it was stirred at room temperature for 10 min. To this reaction mixture, 0.1 ml of methyl iodide was added and stirred for 2 hours. After reaction, the reaction mixture was poured into ice water and extracted with chloroform. The chloroform layer was washed with water, dried over anhydrous sodium sulfate and concentrated to dryness under reduced pressure. The residue was subjected to column chromatography on silica gel for separation and purification (5% methanol/ammonia-saturated chloroform) to give 8-deoxy-14-O-methylaconine (12 mg).

Example 44

8-Deoxyaconine was obtained in the same manner as in Example 1-1). 8-Deoxyaconine 30 mg was dissolved in 2 ml of 1,2-dimethoxyethane. To this solution, 60 mg of sodium hydride was added and the mixture was stirred at room temperature for 30 min. To this reaction mixture, 50 μl of benzyl chloride was added and the mixture was refluxed for 3 hours. After reaction, the reaction mixture was poured into ice water and extracted by chloroform. The chloroform layer was washed with water, dried over anhydrous sodium sulfate and concentrated to dryness under reduced pressure. The residue was subjected to column chromatography on silica gel for separation and purification (ammonia-saturated chloroform) to give 8-deoxy-14-O-benzylaconine (19 mg).

Example 45

8-Deoxyaconine was obtained in the same manner as in Example 1-1). 8-Deoxyaconine 17 mg was dissolved in 2 ml of 1,2-dimethoxyethane. To this solution, 50 mg of sodium hydride was added and the mixture was stirred at room temperature for 30 min. After 0.5 ml of crotyl chloride was added to this reaction mixture, it was heated under reflux for 30 min. After reaction, the reaction mixture was poured into ice water and extracted by chloroform. The chloroform layer was washed with water, dried over anhydrous sodium sulfate and concentrated to dryness under reduced pressure. The residue was subjected to column chromatography on silica gel for separation and purification (5% methanol/ammonia-saturated chloroform) to give 8-deoxy-14-O-crotylaconine (12 mg).

Example 46

8-Deoxy-14-O-o-chlorobenzoylaconine 23 mg was obtained in the same manner as in Example 38, except for the use of 20 mg of o-chlorobenzoyl chloride as a substitute for 3,4,5-trimethoxybenzoyl chloride in Example 38.

Example 47

8-Deoxy-14-O-m-anisoylaconine 21 mg was obtained in the same manner as in Example 38, except for the use of 20 mg of m-anisoyl chloride as a substitute for 3,4,5-trimethoxybenzoyl chloride in Example 38.

Example 48

8-Deoxyaconine was obtained in the same manner as in Example 1-1). 50 mg of 8-Deoxyaconine and 20 mg of p-toluene sulfonic acid were dissolved in 1.5 ml of acetic anhydride and the mixture was stirred at room temperature for 1 hour. After reaction, acetic anhydride was distilled off under reduced pressure. To the residue, ice water was added and made alkaline with 5% sodium bicarbonate. The alkaline solution was extracted with chloroform. The chloroform layer was washed with water, dried over anhydrous sodium sulfate and concentrated to dryness under reduced pressure. The residue was subjected to column chromatography on silica gel for separation and purification (ammonia-saturated ether) to give 8-deoxy-14-O-acetylaconine (35 mg).

Example 49

8-Deoxyaconine was obtained in the same manner as in Example 1-1). 8-Deoxyaconine 30 mg was dissolved in 3.6 ml of 1,2-dimethoxyethane. To this solution, 90 mg of sodium hydride was added and the mixture was stirred at room temperature for 30 min. To this reaction mixture, 0.9 ml of 1-bromo-4-methylpentane was added and the mixture was heated under reflux for 30 min. After reaction, the reaction mixture was poured into ice water and extracted with chloroform. The chloroform layer was washed with water, dried over anhydrous sodium sulfate and concentrated to dryness under reduced pressure. The residue was subjected to column chromatography on silica gel for separation and purification (ammonia-saturated chloroform) to give 8-deoxy-14 -O-(4-methylpentyl)aconine (15 mg).

Example 50

8-Deoxy-14-O-anisoylaconine was obtained in the same manner as in Example 1. 8-Deoxy-14-O-anisoylaconine 660 mg was dissolved in 66 ml of acetone. To this solution, 25 ml of aqueous potassium permanganate solution (887 mg in 25 ml of water) and 4.5 ml of aqueous potassium carbonate solution (556 mg in 4.5 ml of water) were added and the mixture was stirred at room temperature for 30 min. After reaction, the reaction mixture was concentrated under reduced pressure until the oder of acetone was no longer apparent and, to this residual solution, 33 ml of 2N sulfuric acid and 22 ml of aqueous sodium thiosulfate solution (887 mg in 22 ml of water) cooled in advance were added. Then, this solution was washed with methylene chloride. The aqueous layer was adjusted to pH 8–9 with sodium carbonate and extracted with methylene chloride. After the layer of methylene chloride was dried over anhydrous sodium sulfate, it was concentrated to dryness under reduced pressure. The residue was subjected to column chromatography on silica gel for separation and purification (5% methanol/ammonia-saturated chloroform) to give de-N-ethyl-8 -deoxy-14-O-anisoylaconine (649 mg).

Example 51

De-N-ethyl-8-deoxy-14-O-anisoylaconine was obtained in the same manner as in Example 50. De-N-ethyl-8-deoxy-14 -O-anisoylaconine 50 mg was dissolved in 2 ml of the mixture of methanol/ether (1:1). To this solution, 65 mg of calcium carbonate and 0.2 ml of n-amyl iodide were added and the mixture was heated under reflux for 2 hours. After reaction, the reaction mixture was filtrated off to remove insolubles and concentrated to dryness under reduced pressure. The residue was subjected to column chromatography on silica gel for separation and purification (5% methanol/ammonia-saturated chloroform) to yield de-N-ethyl-N-amyl-8-deoxy-14-O-anisoylaconine (28 mg).

Example 52

De-N-ethyl-N-propyl-8-deoxy-14-O-anisoylaconine 26 mg was obtained in the same manner as in Example 51, except for the use of 0.5 ml of n-propyl iodide as a substitute for n-amyl iodide in Example 51.

Example 53

De-N-ethyl-N-(4-methylpentyl)-8-deoxy-14-O-anisoylaconine 32 mg was obtained in the same manner as in Example 51, except for the use of 0.5 ml of 1-bromo-4-methylpentane as a substitute for n-amyl iodide in Example 51.

Example 54

De-N-ethyl-8-deoxy-14-O-anisoylaconine was obtained in the same manner as in Example 50. De-N-ethyl-8-deoxy-14 -O-anisoylaconine 50 mg was dissolved in 1 ml of methanol. To this solution, 50 mg of potassium carbonate, 0.1 ml of water and 20 μl of acetyl chloride were added and the mixture was stirred at room temperature for 1 hour. After reaction, the reaction mixture was concentrated to dryness under reduced pressure and the residue was dissolved in 20 ml of chloroform. The chloroform layer was washed with water, dried over anhydrous sodium sulfate and concentrated to dryness under reduced pressure. The residue was subjected to column chromatography on silica gel for separation and purification (5% methanol/ammonia-saturated chloroform) to give de-N-ethyl-N-acetyl-8-deoxy-14-O-anisoylaconine (32 mg).

Example 55

De-N-ethyl-N-benzoyl-8-deoxy-14-O-anisoylaconine 28 mg was obtained in the same manner as in Example 54, except for the use of 20 μl of benzoyl chloride as a substitute for acetyl chloride in Example 54.

Example 56

16-Epi-8-deoxyaconine 60 mg was obtained in the same manner as in Example 26-1), except for the use of 80 mg of 16 -epi-pyrojesaconitine as a substitute for 60 mg of 16 -epi-pyrojesaconitine in Example 26-1). 16-Epi-deoxyaconine 60 mg was dissolved in 1 ml of pyridine. To this solution, 3,4,5 -trimethoxybenzoyl chloride 30 mg was added and the mixture was stirred at 80° C. for four hours. After reaction, pyridine was distilled off under reduced pressure and water was added to the residue. This solution was made alkaline with 5% of aqueous sodium bicarbonate solution and extracted with chloroform. The chloroform layer was washed with water, dried over anhydrous sodium sulfate and concentrated to dryness under reduced pressure. The obtained residue was subjected to column chromatography on silica gel for separation and purification (ammonia-saturated ether) to afford 16-epi-8-deoxy-14-O-trimethylgalloylaconine (26 mg).

Example 57

16-Epi-8-deoxy-14-O-veratroylaconine 23 mg was obtained in the same manner as in Example 56, except for the use of 25 mg of 3,4-dimethoxybenzoyl chloride as a substitute for 3,4,5 -trimethoxybenzoyl chloride in Example 56.

Example 58

16-Epi-8-deoxy-14-O-p-chlorobenzoylaconine 22 mg was obtained in the same manner as in Example 56, except for the use of 20 mg of p-chlorobenzoyl chloride as a substitute for 3,4,5 -trimethoxybenzoyl chloride in Example 56.

Example 59

16-Epi-8-deoxy-14-O-m-chlorobenzoylaconine 21 mg was obtained in the same manner as in Example 56, except for the use of 20 mg of m-chlorobenzoyl chloride as a substitute for 3,4,5 -trimethoxybenzoyl chloride in Example 56.

Example 60

16-Epi-8-deoxy-14-O-α-methyl-(4-(α-methylacetic acid)-phenyl)-acetylaconine 22 mg was obtained in the same manner as in Example 56, except for the use of 50 μl of α-methyl-(4-(α -methylacetic acid)-phenyl)-acetyl chloride as a substitute for 3,4,5-trimethoxybenzoyl chloride in Example 56.

Example 61

16-Epi-8-deoxyaconine 60 mg was obtained in the same manner as in Example 26-1), except for the use of 80 mg of 16-epi-pyrojesaconitine as a substitute for 60 mg of 16-epi-pyrojesaconitine in Example 26-1). 16-Epi-8-deoxyaconine 15 mg was dissolved in 1 ml of dioxane. To this solution, 15 mg of sodium hydride was added and the mixture was stirred at room temperature for 10 min. To this reaction mixture, 0.1 ml of methyl iodide was added and the mixture was stirred for 2 hours. After reaction, the reaction mixture was poured into ice water and then, it was extracted with chloroform.. The chloroform layer was washed with water, dried over anhydrous sodium sulfate and concentrated to dryness under reduced pressure. The residue was subjected to column chromatography on silica gel for separation and purification (5% methanol/ammonia-saturated chloroform) to give 16-epi-8-deoxy-14-O-methylaconine (11 mg).

Example 62

16-Epi-8-deoxyaconine 60 mg was obtained in the same manner as in Example 26-1), except for the use of 80 mg of 16-epi-pyrojesaconitine as a substitute for 60 mg of 16-epi-pyrojesaconitine in Example 26-1). 16-Epi-8-deoxyaconine 30 mg was dissolved in 2 ml of 1,2-dimethoxyethane. To this solution, 60 mg of sodium hydride was added and the mixture was stirred at room temperature for 30 min. To this reaction mixture, 50 μl of benzyl chloride was added and the mixture was heated under reflux for 3 hours. After reaction, the reaction mixture was poured into ice water and extracted with chloroform. The chloroform layer was washed with water, dried over sodium sulfate and concentrated to dryness under reduced pressure. The residue was subjected to column chromatography on silica gel for separation and purification (ammonia-saturated chloroform) to give 16-epi-8-deoxy-14-O-benzylaconine (18 mg).

Example 63

16-Epi-8-deoxyaconine was obtained in the same manner as in Example 26-1), except for the use of 80 mg of 16-epi-pyrojesaconitine as a substitute for 60 mg of 16-epi-pyrojesaconitine in Example 26-1). 16-Epi-8-deoxyaconine 17 mg was dissolved in 2 ml of 1,2-dimethoxyethane. To this solution, 50 mg of sodium hydride was added and the mixture was stirred at room temperature for 30 min. To this reaction mixture, 0.5 ml of crotyl chloride was added and the mixture was heated under reflux for 30 min. After reaction, the reaction mixture was poured into ice water and extracted with chloroform. The chloroform layer was washed with water, dried over anhydrous sodium sulfate and concentrated to dryness under reduced pressure. The residue was subjected to column chromatography on silica gel for separation and purification (5% methanol/ammonia-saturated chloroform) to give 16-epi-8-deoxy-14-O-crotylaconine (12 mg).

Example 64

16-Epi-8-deoxy-14-O-o-chlorobenzoylaconine 22 mg was obtained in the same manner as in Example 56, except for the use of 20 mg of o-chlorobenzoyl chloride as a substitute for 3,4,5-trimethoxybenzoyl chloride in Example 56.

Example 65

16-Epi-8-deoxy-14-O-m-anisoylaconine 20 mg was obtained in the same manner as in Example 56, except for the use of 20 mg of m-anisoyl chloride as a substitute for 3,4,5-trimethoxybenzoyl chloride in Example 56.

Example 66

16-Epi-8-deoxy-14-O-anisoylaconine was obtained in the same manner as in Example 26. 16-Epi-8-deoxy-14-O-anisoylaconine 660 mg was dissolved in 66 ml of acetone. To this solution, 25 ml of aqueous potassium permanganate solution (887 mg in 25 ml of water) and 4.5 ml of aqueous potassium carbonate solution (556 mg in 4.5 ml of water) were added and the mixture was stirred at room temperature for 30 min. After reaction, the reaction mixture was concentrated under reduced pressure until the odor of acetone was no longer apparent and, to this residual solution, 33 ml of 2N sulfuric acid and 22 ml of aqueous sodium thiosulfate solution (887 mg in 22 ml of water) cooled in advance were added. Then, this solution was washed with methylene chloride. The aqueous layer was adjusted to pH 8–9 with sodium carbonate and extracted with methylene chloride. After the layer of methylene chloride was dried over anhydrous sodium sulfate, it was concentrated to dryness under reduced pressure. The residue was subjected to column chromatography on silica gel for separation and purification (5% methanol/ammonia-saturated chloroform) to give 16-epi-de-N-ethyl-8-deoxy-14-O-anisoylaconine (640 mg).

Example 67

16-Epi-de-N-ethyl-8-deoxy-14-O-anisoylaconine was obtained in the same manner as in Example 66. 16-Epi-de-N-ethyl-8-deoxy-14-O-anisoylaconine 50 mg was dissolved in 2 ml of a mixture of methanol/ether (1:1). To this solution, 65 mg of calcium carbonate and 0.2 ml of n-amyl iodide were added and the mixture was heated under reflux for 2 hours. After reaction, the reaction mixture was filtrated off to remove insolubles and concentrated to dryness under reduced pressure. The residue was subjected to column chromatography on silica gel for separation and purification (5% methanol/ammonia-saturated chloroform) to give 16-epi-de-N-ethyl-N-amyl-8-deoxy-14-O-anisoylaconine (25 mg).

Example 68

16-Epi-de-N-ethyl-8-deoxy-14-O-anisoylaconine was obtained in the same manner as in Example 66. 16-Epi-de-N-ethyl-N-propyl-8-deoxy-14-O-anisoylaconine 28 mg was obtained in the same manner as in Example 52, except for the use of 50 mg of 16-epi-de-N-ethyl-8-deoxy-14-O-anisoylaconine as a substitute for de-N-ethyl-8-deoxy-14-O-anisoylaconine in Example 52.

Example 69

16-Epi-de-N-ethyl-N-(4-methyl)pentyl-8-deoxy-14-O-anisoylaconine 30 mg was obtained in the same manner as in Example 68, except for the use of 0.5 ml of 1-bromo-4-methylpentane as a substitute for n-amyl iodide in Example 68.

Example 70

16-Epi-de-N-ethyl-8-deoxy-14-anisoylaconine was obtained in the same manner as in Example 66. 16-Epi-de-N-ethyl-N-acetyl-8-deoxy-14-O-anisoylaconine 29 mg was obtained in the same manner as in Example 54, except for the use of 50 mg of 16-epi-de-N-ethyl-8-deoxy-14-anisoylaconine as a substitute for de-N-ethyl-8-deoxy-14-O-anisoylaconine in Example 54.

Example 71

16-Epi-de-N-ethyl-N-benzoyl-8-deoxy-14-O-anisoylaconine 27 mg was obtained in the same manner as in Example 70, except for the use of 20 µl of benzoyl chloride as a substitute for acetyl chloride in Example 70.

Example 72

8-Deoxy-14-O-p-methoxybenzylaconine 17 mg was obtained in the same manner as in Example 44, except for the use of 50 µl of p-methoxybenzyl chloride as a substitute for benzyl chloride in Example 44.

Example 73

8-Deoxy-14-O-amylaconine 16 mg was obtained in the same manner as in Example 49, except for the use of 0.5 ml of n-amyl iodide as a substitute for 1-bromo-4-methylpentane in Example 49.

Example 74

8-Deoxy-14-O-m-bromobenzoylaconine 19 mg was obtained in the same manner as in Example 41, except for the use of 20 mg of m-bromobenzoyl chloride as a substitute for m-chlorobenzoyl chloride in Example 41.

Example 75

8-Deoxy-14-O-m-fluorobenzoylaconine 21 mg was obtained in the same manner as in Example 41, except for the use of 20 mg of m-fluorobenzoyl chloride as a substitute for m-chlorobenzoyl chloride in Example 41.

Example 76

1) 3,13-Dideoxypyrojesaconitine 62 mg was obtained in the same manner as in Example 4-1), except for the use of 100 mg of 3,13-dideoxyjesaconitine as a substitute for 3-deoxyjesaconitine in Example 4-1). Next, 3,8,13-trideoxyaconine 48 mg was obtained in the same manner as in Example 1-1), except for the use of 60 mg of 3,13-dideoxypyrojesaconitine as a substitute for pyrojesaconitine in Example 1-1).

2) 3,8,13-Trideoxyaconine 30 mg was dissolved in 1 ml of pyridine. To this solution, 30 mg of 3,4-dimethoxybenzoyl chloride was added and the mixture was stirred at 80° C. for 4 hours. After reaction, pyridine was distilled off under reduced pressure. To the residue, water was added and the mixture was made alkaline with 5% sodium bicarbonate. This alkaline solution was extracted with chloroform. The chloroform layer was washed with water, dried over anhydrous sodium sulfate and concentrated to dryness under reduced pressure. The residue was subjected to column chromatography on silica gel for separation and purification (ammonia-saturated ether) to give 3,8,13-trideoxy-14-O-veratroylaconine (19 mg).

Example 77

3,8,13-Trideoxyaconine was obtained in the same manner as in Example 76-1). 3,8,13-Trideoxyaconine 30 mg and p-toluenesulfonic acid 20 mg were dissolved in 1.5 ml of acetic anhydride and the mixture was stirred at room temperature for 1 hour. After reaction, acetic anhydride was distilled off under reduced pressure and ice water was added to the residue. This solution was made alkaline with 5% sodium bicarbonate and extracted with chloroform. The chloroform layer was washed with water, dried over sodium sulfate and concentrated to dryness under reduced pressure. The residue was subjected to column chromatography on silica gel for separation and purification (ammonia-saturated ether) to give 3,8,13-trideoxy-14-O-acetylaconine (31 mg).

Example 78

3,8,13-Trideoxy-14-O-m-chlorobenzoylaconine 20 mg was obtained in the same manner as in Example 76, except for the use of 30 mg of m-chlorobenzoyl chloride as a substitute for 3,4-dimethoxybenzoyl chloride in Example 76.

Example 79

3,8,13-Trideoxyaconine was obtained in the same manner as in Example 76-1). 3,8,13-Trideoxyaconine 30 mg was dissolved in 2 ml of 1,2-dimethoxyethane. To this solution, 60 mg of sodium hydride was added and the mixture was stirred at room temperature for 30 min. To this reaction mixture, 50 µl of benzyl chloride was added and the mixture was heated under reflux for 3 hours. After reaction, the reaction mixture was poured into ice water and extracted with chloroform. The chloroform layer was washed with water, dried over anhydrous sodium sulfate and concentrated to dryness under reduced pressure. The residue was subjected to column chromatography on silica gel for separation and purification (ammonia-saturated chloroform) to give 3,8,13-trideoxy-14-O-benzylaconine (15 mg).

Example 80

3,8,13-Trideoxyaconine was obtained in the same manner as in Example 76-1). 3,8,13-Trideoxyaconine 30 mg was dissolved in 3.6 ml of 1,2-dimethoxyethane. To this solution, 90 mg of sodium hydride was added and the mixture was stirred at room temperature for 30 min. To this reaction mixture, 0.9 ml of 1-bromo-4-methylpentane was added and the mixture was heated under reflux for 30 min. After reaction, the reaction mixture was poured into ice water and extracted with chloroform. The chloroform layer was washed with water, dried over anhydrous sodium sulfate and concentrated to dryness under reduced pressure. The residue was subjected to column chromatography on silica gel for separation and purification (ammonia-saturated chloroform) to give 3,8,13-trideoxy-14-O-(4-methylpentyl)aconine (14 mg).

Example 81

3,8,13-Trideoxyaconine was obtained in the same manner as in Example 76-1). 3,8,13-Trideoxyaconine 30 mg was dissolved in 4 ml of 1,2-dimethoxyethane. To this solution, 50 mg of sodium hydride was added and the mixture was stirred at room temperature for 30 min. To this reaction mixture, 0.8 ml of crotyl chloride was added and the mixture was heated under reflux for 30 min. After reaction, the reaction mixture was poured into ice water and extracted with chloroform. The chloroform layer was washed with water, dried over anhydrous sodium sulfate and concentrated to dryness under reduced pressure. The residue was subjected to column chromatography on silica gel for separation and purification (5% methanol/ammonia-saturated chloroform) to give 3,8,13-trideoxy-14-O-crotylaconine (15 mg).

Example 82

1) 3,8-Dideoxy-14-O-anisoylaconine was obtained in the same manner as in Example 4. 3,8-Dideoxyaconine 62 mg was obtained in the same manner as in Example 94-2), except for the use of 140 mg of 3,8-dideoxy-14-O-anisoylaconine as a substitute for 3,13-dideoxy-14-O-anisoylaconine in Example 94-2).

2) 3,8-Dideoxyaconine 50 mg was dissolved in 1 ml of pyridine. To this solution, 30 mg of 3,4-dimethoxybenzoyl chloride was added and the mixture was stirred at 80° C. for 4 hours. After reaction, pyridine was distilled off under reduced pressure. To the residue, water was added and it was made alkaline with 5% of aqueous sodium bicarbonate solution. This alkaline solution was extracted with chloroform. The chloroform layer was washed with water, dried over anhydrous sodium sulfate and concentrated to dryness under reduced pressure. The residue was subjected to column chromatography on silica gel for separation and purification (ammonia-saturated ether) to give 3,8-dideoxy-14-O-veratroylaconine (22 mg).

Example 83

3,8-Dideoxyaconine was obtained in the same manner as in Example 82-1). 3,8-Dideoxy-14-O-acetylaconine 37 mg was obtained in the same manner as in Example 48, except for the use of 50 mg of 3,8-dideoxyaconine as a substitute for 8-deoxyaconine in Example 48.

Example 84

3,8-Dideoxy-14-O-m-chlorobenzoylaconine 23 mg was obtained in the same manner as in Example 82, except for the use of 28 mg of m-chlorobenzoyl chloride as a substitute for 3,4-dimethoxybenzoyl chloride in Example 82.

Example 85

3,8-Dideoxyaconine was obtained in the same manner as in Example 82-1). 3,8-Dideoxy-14-O-benzylaconine 18 mg was obtained in the same manner as in Example 79, except for the use of 30 mg of 3,8-dideoxyaconine as a substitute for 3,8,13-trideoxyaconine in Example 79.

Example 86

3,8-Dideoxyaconine was obtained in the same manner as in Example 82-1). 3,8-Dideoxy-14-O-(4-methyl)pentylaconine 17 mg was obtained in the same manner as in Example 80, except for the use of 30 mg of 3,8-dideoxyaconine as a substitute for 3,8,13-trideoxyaconine in Example 80.

Example 87

3,8-Dideoxyaconine was obtained in the same manner as in Example 82-1). 3,8-Dideoxy-14-O-crotylaconine 17 mg was obtained in the same manner as in Example 81, except for the use of 30 mg of 3,8-dideoxyaconine as a substitute for 3,8,13-trideoxyaconine in Example 81.

Example 88

1) Aconine 32 mg was obtained in the same manner as in Example 94-2), except for the use of 70 mg of aconitine as a substitute for 3,13-dideoxy-14-O-anisoylaconine in Example 94-2).

2) 14-O-Veratroylaconine 18 mg was obtained in the same manner as in Example 76-2), except for the use of 30 mg of aconine as a substitute for 3,8,13-trideoxyaconine in Example 76-2).

Example 89

Aconine was obtained in the same manner as in Example 88-1). 14-O-Acetylaconine 28 mg was obtained in the same manner as in Example 77, except for the use of 30 mg of aconine as a substitute for 3,8,13-trideoxyaconine in Example 77.

Example.90

Aconine was obtained in the same manner as in Example 88-1). 14-O-m-Chlorobenzoylaconine 21 mg was obtained in the same manner as in Example 78, except for the use of 30 mg of aconine as a substitute for 3,8,13-trideoxyaconine in Example 78.

Example 91

Aconine was obtained in the same manner as in Example 88-1). 14-O-Benzylaconine 20 mg was obtained in the same manner as in Example 79, except for the use of 30 mg of aconine as a substitute for 3,8,13-trideoxyaconine in Example 79.

Example 92

Aconine was obtained in the same manner as in Example 88-1). 14-O-(4-Methyl)pentylaconine 20 mg was obtained in the same manner as in Example 80, except for the use of 30 mg of aconine as a substitute for 3,8,13-trideoxyaconine in Example 80.

Example 93

Aconine was obtained in the same manner as in Example 88-1). 14-O-Crotylaconine 13 mg was obtained in the same manner as in Example 81, except for the use of 30 mg of aconine as a substitute for 3,8,13-trideoxyaconine in Example 81.

Example 94

1) 3,13-Dideoxy-14-anisoylaconine was obtained in the same manner as in Example 6.

2) 3,13-Dideoxy-14-anisoylaconine 70 mg was dissolved in 5 ml of methanol. To this solution, 1 ml of 5% potassium hydroxid was added and the mixture was heated under reflux for 3 hours. After methanol in the reaction mixture was distilled off under reduced pressure, 5 ml of water was added to the residue and the aqueous solution was extracted 3 times with 10 ml of methylene chloride. The extract was dried over anhydrous sodium sulfate and concentrated to dryness under reduced pressure. The residue was subjected to thin-layer chromatography for separation and purification (eluting solvent: 10% methanol/ammonia-saturated chloroform) to give 3,13-dideoxyaconine (30 mg).

3) 3,13-Dideoxyaconine 30 mg was dissolved in 1 ml of pyridine. To this solution, 30 mg of 3,4-dimethoxybenzoyl chloride was added and the mixture was stirred at 80° C. for 4 hours. After reaction, pyridine was distilled off under reduced pressure. To the residue, water was added and the reaction mixture was made alkaline with 5% of aqueous sodium bicarbonate solution and extracted with chloroform. The chloroform layer was washed with water, dried over anhydrous sodium sulfate and concentrated to dryness under reduced pressure. The residue was subjected to column chromatography on silica gel for separation and purification (ammonia-saturated ether) to give 3,13-dideoxy- 14-O-veratroylaconine (18 mg).

Example 95

3,13-Dideoxyaconine was obtained in the same manner as in Example 94-1) and -2). 3,13-Dideoxyaconine 30 mg and p-toluenesulfonic acid 20 mg were dissolved in 1.5 ml of acetic anhydride and the mixture was stirred at room temperature for 1 hour. After reaction, acetic anhydride was distilled off under reduced pressure. To the residue, ice water was added and the mixture was made alkaline with 5% sodium bicarbonate. The alkaline solution was extracted with chloroform. The chloroform layer was washed with water, dried over anhydrous sodium sulfate and concentrated to dryness under reduced pressure. The residue was subjected to column chromatography on silica gel for separation and purification (ammonia-saturated ether) to give 3,13-dideoxy-14-O-acetylaconine (31 mg).

Example 96

3,13-Dideoxy-14-O-m-chlorobenzoylaconine 15 mg was obtained in the same manner as in Example 94, except for the use of 30 mg of m-chlorobenzoyl chloride as a substitute for 3,4 -dimethoxybenzoyl chloride in Example 94.

Example 97

3,13-Dideoxyaconine was obtained in the same manner as in Example 94-1) and -2). 3,13-Dideoxyaconine 30 mg was dissolved in 2 ml of 1,2-dimethoxyethane. To this solution, 60 mg of sodium hydride was added and the mixture was stirred at room temperature for 30 min. To this reaction mixture, 50 µl of benzyl chloride was added and the mixture was heated under reflux for 3 hours. After reaction, the reaction mixture was poured into ice water and extracted with chloroform. The chloroform layer was washed with water, dried over anhydrous sodium sulfate and concentrated to dryness under reduced pressure. The residue was subjected to column chromatography on silica gel for separation and purification (ammonia-saturated chloroform) to give 3,13-dideoxy- 14-O-benzylaconine (16 mg).

Example 98

3,13-Dideoxyaconine was obtained in the same manner as in Example 94-1) and -2). 3,13-Dideoxyaconine 30 mg was dissolved in 3.6 ml of 1,2-dimethoxyethane. To this solution, 90 mg of sodium hydride was added and the mixture was stirred at room temperature for 30 min. To this reaction mixture, 0.9 ml of 1-bromo-4-methylpentane was added and the mixture was heated under reflux for 30 min. After reaction, the reaction mixture was poured into ice water and extracted with chloroform. The chloroform layer was washed with water, dried over anhydrous sodium sulfate and concentrated to dryness under reduced pressure. The residue was subjected to column chromatography on silica gel for separation and purification (ammonia-saturated chloroform) to give 3,13-dideoxy-14-O-(4-methylpentyl)aconine (15 mg).

Example 99

3,13-Dideoxyaconine was obtained in the same manner as in Example 94-1) and -2). 3,13-Dideoxyaconine 30 mg was dissolved in 4 ml of 1,2-dimethoxyethane. To this solution, 50 mg of sodium hydride was added and the mixture was stirred at room temperature for 30 min. To this reaction mixture, 0.8 ml of crotyl chloride was added and it was heated under reflux for 30 min. After reaction, the reaction mixture was poured into ice water and extracted with chloroform. The chloroform layer was washed with water, dried over anhydrous sodium sulfate and concentrated to dryness under reduced pressure. The residue was subjected to column chromatography on silica gel for separation and purification (5% methanol/ammonia-saturated chloroform) to give 3,13-dideoxy-14-O-crotylaconine (17 mg).

Example 100

1) 3-Deoxy-14-anisoylaconine was obtained in the same manner as in Example 3. 3-Deoxyaconine 35 mg was obtained in the same manner as in Example 94-2), except for the use of 70 mg of 3-deoxy-14-anisoylaconine as a substitute for 3,13-dideoxy-14 -O-anisoylaconine in Example 94-2).

2) 3-Deoxy-14-O-veratroylaconine 20 mg was obtained in the same manner as in Example 94-3), except for the use of 30 mg of 3-deoxyaconine as a substitute for 3,13-dideoxyaconine in Example 94-3).

Example 101

3-Deoxyaconine was obtained in the same manner as in Example 100-1). 3-Deoxyaconine 30 mg and p-toluenesulfonic acid 20 mg were dissolved in 1.5 ml of acetic anhydride and the mixture was stirred at room temperature for 1 hour. After reaction, acetic anhydride was distilled off under reduced pressure. To the residue, ice water was added and the aqueous solution was made alkaline with 5% sodium bicarbonate. The alkaline solution was extracted with chloroform. The chloroform layer was washed with water, dried over anhydrous sodium sulfate and concentrated to dryness under reduced pressure. The residue was subjected to column chromatography on silica gel for separation and purification (ammonia-saturated ether) to give 3-deoxy-14 -O-acetylaconine (22 mg).

Example 102

3-Deoxy-14-O-m-chlorobenzoylaconine 17 mg was obtained in the same manner as in Example 100, except for the use of 30 mg of m-chlorobenzoyl chloride as a substitute for 3,4-dimethoxybenzoyl chloride in Example 100.

Example 103

3-Deoxyaconine was obtained in the same manner as in Example 100-1). 3-Deoxyaconine 30 mg was dissolved in 2 ml of 1,2-dimethoxyethane. To this solution, 60 mg of sodium hydride was added and the mixture was stirred at room temperature for 30 min, To this reaction mixture, 50 µl of benzyl chloride was added and the mixture was heated under reflux for 3 hours. After reaction, the reaction mixture was poured into ice water and extracted with chloroform. The chloroform layer was washed with water, dried over anhydrous sodium sulfate and concentrated to dryness under reduced pressure. The residue was subjected to column chromatography on silica gel for separation and purification (ammonia-saturated chloroform) to give 3-deoxy-14 -O- benzylaconine (14 mg).

Example 104

3-Deoxyaconine was obtained in the same manner as in Example 100-1). 3-Deoxyaconine 30 mg was dissolved in 3.6 ml of 1,2-dimethoxyethane. To this solution, 90 mg of sodium hydride was added and the mixture was stirred at room temperature for 30 min. To this reaction mixture, 0.9 ml of 1-bromo-4-methylpentane was added and the mixture was heated under reflux for 30 min. After reaction, the reaction mixture was poured into ice water and extracted with chloroform. The chloroform layer was washed with water, dried over anhydrous sodium sulfate and concentrated to dryness under reduced pressure. The residue was subjected to column chromatography on silica gel for separation and purification (ammonia-saturated chloroform) to give 3-deoxy-14 -O-(4-methylpentyl)aconine (16 mg).

Example 105

3-Deoxyaconine was obtained in the same manner as in Example 100-1). 3-Deoxyaconine 30 mg was dissolved in 4 ml of 1,2-dimethoxyethane. To this solution, 50 mg of sodium hydride was added and the mixture was stirred at room temperature for 30 min. To this reaction mixture, 0.8 ml of crotyl chloride was added and the mixture was heated under reflux for 30 min. After reaction, the reaction mixture was poured into ice water and extracted with chloroform. The chloroform layer was washed with water, dried over anhydrous sodium sulfate and concentrated to dryness under reduced pressure. The residue was subjected to column chromatography on silica gel for separation and purification (5% methanol/ammonia-saturated chloroform) to give 3-deoxy-14-O-crotylaconine (15 mg).

Example 106

16-Epi-8-deoxyaconine was obtained in the same manner as in Example 26-1). 16-Epi-8-deoxy-14-O-p-methoxybenzylaconine 15 mg was obtained in the same manner as in Example 72, except for the use of 30 mg of 16-epi-8-deoxyaconine as a substitute for 8-deoxyaconine in Example 72.

Example 107

16-Epi-8-deoxyaconine was obtained in the same manner as in Example 26-1). 16-Epi-8-deoxy-14-O-amylaconine 15 mg was obtained in the same manner as in Example 73, except for the use of 30 mg of 16-epi-8-deoxyaconine as a substitute for 8-deoxyaconine in Example 73.

Example 108

1) 16-Epi-3,13-dideoxypyrojesaconitine 61.7 mg was obtained in the same manner as in Example 27-1), except for the use of 150 mg of 3,13-dideoxyjesaconitine as a substitute for 3-deoxyjesaconitine in Example 27-1). Next, 16-epi-3, 8,13 -trideoxyaconine 50.1 mg was obtained in the same manner as in Example 26-1), except for the use of 60 mg of 16-epi-3,13 -dideoxypyrojesaconitine as a substitute for 16 -epi-pyrojesaconitine in Example 26-1).

2) 16-Epi-3,8,13-trideoxyaconine 30 mg was dissolved in 1 ml of pyridine. To this solution, 30 mg of 3,4-dimethoxybenzoyl chloride was added and the mixture was stirred at 80° C. for 4 hours. After reaction, pyridine was distilled off under reduced pressure. To the residue, water was added and it was made alkaline with 5% of aqueous sodium bicarbonate solution. This alkaline solution was extracted with chloroform. The chloroform layer was washed with water, dried over anhydrous sodium sulfate and concentrated to dryness under reduced pressure. The residue was subjected to column chromatography on silica gel for separation and purification (ammonia-saturated ether) to give 16-epi-3,8,13-trideoxy-14-O-veratroylaconine (19 mg).

Example 109

16-Epi-3,8,13-trideoxy-14-O-m-chlorobenzoylaconine 21 mg was obtained in the same manner as in Example 108, except for the use of 30 mg of m-chlorobenzoyl chloride as a substitute for 3,4 -dimethoxybenzoyl chloride in Example 108.

Example 110

16-Epi-3,8,13-trideoxyaconine was obtained in the same manner as in Example 108-1). 3,8,13-Trideoxyaconine 30 mg was dissolved in 2 ml of 1,2-dimethoxyethane. To this solution, 60 mg of sodium hydride was added and the mixture was stirred at room temperature for 30 min. To this reaction mixture, 50 μl of benzyl chloride was added and the mixture was heated under reflux for 3 hours. After reaction, the reaction mixture was poured into ice water and extracted with chloroform. The chloroform layer was washed with water, dried over anhydrous sodium sulfate and concentrated to dryness under reduced pressure. The residue was subjected to column chromatography on silica gel for separation and purification (ammonia-saturated chloroform) to give 16-epi-3,8,13 -trideoxy-14-O-benzylaconine (16 mg).

Example 111

16-Epi-3,8,13-trideoxyaconine was obtained in the same manner as in Example 108-1). 16-Epi-3,8,13-trideoxyaconine 30 mg was dissolved in 4 ml of 1,2-dimethoxyethane. To this solution, 50 mg of sodium hydride was added and the mixture was stirred at room temperature for 30 min. To this reaction mixture, 0.8 ml of crotyl chloride was added and the mixture was heated under reflux for 30 min. After reaction, the reaction mixture was poured into ice water and extracted with chloroform. The chloroform layer was washed with water, dried over anhydrous sodium sulfate and concentrated to dryness under reduced pressure. The residue was subjected to column chromatography on silica gel for separation and purification (5% methanol/ammonia-saturated chloroform) to give 16-epi-3,8,13-trideoxy-14-O-crotylaconine (16 mg).

Example 112

1) 16-Epi-3-deoxypyroaconitine 66.5 mg was obtained in the same manner as in Example 27-1), except for the use of 150 mg of 3-deoxyaconitine as a substitute for 3-deoxyjesaconitine in Example 27-1). Next, 16-epi-3,8-dideoxyaconine 47.2 mg was obtained in the same manner as in Example 26-1), except for the use of 60 mg of 16-Epi-3-deoxypyroaconitine as a substitute for 16-epi-pyrojesaconitine in Example 26-1).

2) 16-Epi-3,8-dideoxyaconine 40 mg was dissolved in 1 ml of pyridine. To this solution, 30 mg of 3,4-dimethoxybenzoyl chloride was added and the mixture was stirred at 80° C. for 4 hours. After reaction, pyridine was distilled off under reduced pressure. To the residue, water was added and then it was made alkaline with 5% of aqueous sodium bicarbonate solution. This alkaline solution was extracted with chloroform. The chloroform layer was washed with water, dried over anhydrous sodium sulfate and concentrated to dryness under reduced pressure. The residue was subjected to column chromatography on silica gel for separation and purification (ammonia-saturated ether) to give 16-epi-3,8-dideoxy-14-O-veratroylaconine (20 mg).

Example 113

16-Epi-3,8-dideoxy-14-O-m-chlorobenzoylaconine 22 mg was obtained in the same manner as in Example 112, except for the use of 28 mg of m-chlorobenzoyl chloride as a substitute for 3,4-dimethoxybenzoyl chloride in Example 112.

Example 114

16-Epi-3,8-dideoxyaconine was obtained in the same manner as in Example 112-1). 16-Epi-3,8-dideoxy-14-O-benzylaconine 19 mg was obtained in the same manner as in Example 79, except for the use of 30 mg of 16-epi-3,8-dideoxyaconine as a substitute for 3,8,13-trideoxyaconine in Example 79.

Example 115

16-Epi-3,8-dideoxyaconine was obtained in the same manner as in Example 112-1). 16-Epi-3,8-dideoxy-14-O-crotylaconine 15 mg was obtained in the same manner as in Example 81, except for the use of 30 mg of 16-epi-3,8-dideoxyaconine as a substitute for 3,8,13-trideoxyaconine in Example 81.

Example 116

3,8-Dideoxy-14-O-anisoylaconine was obtained in the same manner as in Example 4. 3,8-Dideoxy-14-O-anisoylaconine 660 mg was dissolved in 66 ml of acetone. To this solution, 25 ml of aqueous potassium permanganate solution (887 mg in 25 ml of water) and 4.5 ml of aqueous potassium carbonate solution (556 mg in 4.5 ml of water) were added and the mixture was stirred at room temperature for 30 min. After reaction, the reaction mixture was concentrated under reduced pressure until the odor of acetone was no longer apparent. To this residual solution, 33 ml of 2N sulfuric acid and 22 ml of aqueous sodium thiosulfate solution (887 mg in 22 ml of water) cooled in advance were added and the mixture was washed with methylene chloride. The aqueous layer was adjusted to pH 8–9 with sodium carbonate and extracted with methylene chloride. The layer of methylene chloride was dried over anhydrous sodium sulfate and concentrated to dryness under reduced pressure. The residue was subjected to column chromatography on silica gel for separation and purification (5% methanol/ammonia-saturated chloroform) to give de-N-ethyl-3,8-dideoxy-14-O-anisoylaconine (630 mg).

Example 117

De-N-ethyl-3,8-dideoxy-14-O-anisoylaconine was obtained in the same manner as in Example 116. De-N-ethyl-3,8-dideoxy-14-O-anisoylaconine 50 mg was dissolved in 2 ml of a mixture of methanol/ether (1:1). To this solution, 65 mg of calcium carbonate and 0.2 ml of n-amyl iodide were added and the mixture was heated under reflux for 2 hours. After reaction, the reaction mixture was filtrated off to remove insolubles and concentrated to dryness under reduced pressure. The residue was subjected to column chromatography on silica gel for separation and purification (5% methanol/ammonia-saturated chloroform) to give de-N-ethyl-N-amyl-3,8-dideoxy-14-O-anisoylaconine (25 mg).

Example 118

De-N-ethyl-N-propyl-3,8-dideoxy-14-O-anisoylaconine 22 mg was obtained in the same manner as in Example 117, except for the use of 0.5 ml of n-propyl iodide as a substitute for n-amyl iodide in Example 117.

Example 119

De-N-ethyl-N-4-methylpentyl-3,8-dideoxy-14-O-anisoylaconine 31 mg was obtained in the same manner as in Example 117, except for the use of 0.5 ml of 1-bromo-4-methylpentane as a substitute for n-amyl iodide in Example 117.

Example 120

De-N-ethyl-3,8-dideoxy-14-O-anisoylaconine was obtained in the same manner as in Example 116. De-N-ethyl-3,8-dideoxy-14-O-anisoylaconine 50 mg was dissolved in 1 ml of methanol. To this solution, 50 mg of potassium carbonate, 0.1 ml of water and 20 µl of acetyl chloride were added, and the mixture was stirred at room temperature for 1 hour. After reaction, the reaction mixture was concentrated to dryness under reduced pressure and the residue was dissolved in 20 ml of chloroform. The chloroform layer was washed with water, dried over anhydrous sodium sulfate and concentrated to dryness under reduced pressure. The residue was subjected to column chromatography on silica gel for separation and purification (5% methanol/ammonia-saturated chloroform) to give de-N-ethyl-N-acetyl-3,8-dideoxy-14-O-anisoylaconine (30 mg).

Example 121

De-N-ethyl-N-benzoyl-3,8-dideoxy-14-O-anisoylaconine 25 mg was obtained in the same manner as in Example 120, except for the use of 20 µl of benzoyl chloride as a substitute for acetyl chloride in Example 120.

Example 122

3,8,13-Trideoxy-14-O-anisoylaconine was obtained in the same manner as in Example 7. 3,8,13-Trideoxy-14-O-anisoylaconine 660 mg was dissolved in 66 ml of acetone. To this solution, 25 ml of aqueous potassium permanganate solution (887 mg in 25 ml of water) and 4.5 ml of aqueous potassium carbonate solution (556 mg in 4.5 ml of water) were added and the mixture was stirred at room temperature for 30 min. After reaction, the reaction mixture was concentrated under reduced pressure until the odor of acetone was no longer apparent and, to this residual solution, 33 ml of 2N sulfuric acid and 22 ml of aqueous sodium thiosulfate solution (887 mg in 22 ml of water) cooled in advance were added. Then, this solution was washed with methylene chloride. The aqueous layer was adjusted to pH 8–9 with sodium carbonate and extracted with methylene chloride. The layer of methylene chloride was dried over anhydrous sodium sulfate and concentrated to dryness under reduced pressure. The residue was subjected to column chromatography on silica gel for separation and purification (5% methanol/ammonia-saturated chloroform) to give de-N-ethyl-3,8,13-trideoxy-14-O-anisoylaconine (620 mg).

Example 123

De-N-ethyl-3,8,13-trideoxy-14-O-anisoylaconine was obtained in the same manner as in Example 122. De-N-ethyl-3,8,13-trideoxy- 14-O-anisoylaconine 50 mg was dissolved in 2 ml of a mixture of methanol/ether (1:1). To this solution, 65 mg of calcium carbonate and 0.2 ml of n-amyl iodide were added and the mixture was heated under reflux for 2 hours. After reaction, the reaction mixture was filtrated off to remove insolubles and concentrated to dryness under reduced pressure. The residue was subjected to column chromatography on silica gel for separation and purification (5% methanol/ammonia-saturated chloroform) to give de-N-ethyl-N-amyl-3,8,13-trideoxy-14-O-anisoylaconine (21 mg).

Example 124

De-N-ethyl-N-propyl-3,8,13-trideoxy-14-O-anisoylaconine 20 mg was obtained in the same manner as in Example 123, except for the use of 0.5 ml of n-propyl iodide as a substitute for n-amyl iodide in Example 123.

Example 125

De-N-ethyl-N-4-methylpentyl-3,8,13-trideoxy-14-O-anisoylaconine 31 mg was obtained in the same manner as in Example 123, except for the use of 0.5 ml of 1-bromo-4-methylpentane as a substitute for n-amyl iodide in Example 123.

Example 126

De-N-ethyl-3,8,13-trideoxy-14-O-anisoylaconine was obtained in the same manner as in Example 122. De-N-ethyl-3,8,13-trideoxy- 14-O-anisoylaconine 50 mg was dissolved in 1 ml of methanol. To this solution, 50 mg of potassium carbonate, 0.1 ml of water and 20 µl of acetyl chloride were added, and the mixture was stirred at room temperature for 1 hour. After reaction, the reaction mixture was concentrated to dryness under reduced pressure and the residue was dissolved in 20 ml of chloroform. The chloroform layer was washed with water, dried over anhydrous sodium sulfate and concentrated to dryness under reduced pressure. The residue was subjected to column chromatography on silica gel for separation and purification (5% methanol/ammonia-saturated chloroform) to give de-N-ethyl-N-acetyl-3,8,13-trideoxy-14 -O-anisoylaconine (28 mg).

Example 127

De-N-ethyl-N-benzoyl-3,8,13-trideoxy-14-O-anisoylaconine 25 mg was obtained in the same manner as in Example 126, except for the use of 20 µl of benzoyl chloride as a substitute for acetyl chloride in Example 126.

Example 128

① 32 mg of Aconine was obtained in the same manner as in Example 94-2), except for the use of 70 mg of aconitine as a substitute for 3,13-dideoxy-14-O-anisoylaconine in Example 94-2). Aconine 45 mg was dissolved in a mixture of 5 ml of pyridine and 1 ml of methylene chloride. To this solution, 18 µl of p-anisoyl chloride was added under the condition of −70° C. The reaction mixture was stirred under the rising temperature from −70° C. to −5° C., which was took 2 hours. Then, to the reaction mixture, ice water was added and the mixture was made alkaline with 5% of aqueous sodium bicarbonate solution. The alkaline solution was extracted three times with 30 ml of chloroform. The chloroform layer put together was washed with water, dried over anhydrous sodium sulfate and concentrated to dryness under reduced pressure. The residue was subjected to column chromatography on silica gel for separation and purification (eluting solvent: 5% methanol/ammonia-saturated chloroform) to give 14-anisoylaconine (38 mg). 14-O-Anisoylaconine 660 mg was dissolved in 66 ml of acetone. To this solution, 25 ml of aqueous potassium permanganate solution (887 mg in 25 ml of water) and 4.5 ml of aqueous potassium carbonate solution (556 mg in 4.5 ml of water) were added and the mixture was stirred at room temperature for 30 min. After reaction, the reaction mixture was concentrated under reduced pressure until the odor of acetone was no longer apparent and, to this residual solution, 33 ml of 2N sulfuric acid and 22 ml of aqueous sodium thiosulfate solution (887 mg in 22 ml of water) cooled in advance were added. Then, this solution was washed with methylene chloride. The aqueous layer was adjusted to pH 8–9 with sodium carbonate and extracted with methylene chloride. The layer of methylene chloride was dried over anhydrous sodium sulfate and concentrated to dryness under reduced pressure. The residue was subjected to column chromatography on silica gel for separation and purification (5% methanol/ammonia-saturated chloroform) to give de-N-ethyl-14-O-anisoylaconine (640 mg).

Example 129

De-N-ethyl-14-O-anisoylaconine was obtained in the same manner as in Example 128. De-N-ethyl-14-O-anisoylaconine 50 mg was dissolved in 2 ml of a mixture of methanol/ether (1:1). To this solution, 65 mg of calcium carbonate and 0.2 ml of n-amyl iodide were added and the mixture was heated under reflux for 2 hours. After reaction, reaction mixture were filtrated off to remove insolubles and concentrated to dryness under reduced pressure. The residue was subjected to column chromatography on silica gel for separation and purification (5% methanol/ammonia-saturated chloroform) to give de-N-ethyl-N-amyl-14 -O-anisoylaconine (29 mg).

Example 130

De-N-ethyl-N-propyl-14-O-anisoylaconine 23 mg was obtained in the same manner as in Example 129, except for the use of 0.5 ml of n-propyl iodide as a substitute for n-amyl iodide in Example 129.

Example 131

De-N-ethyl-N-4-methylpentyl-14-O-anisoylaconine 30 mg was obtained in the same manner as in Example 51, except for the use of 0.5 ml of 1-bromo-4-methylpentane as a substitute for n-amyl iodide in Example 129.

Example 132

De-N-ethyl-14-O-anisoylaconine was obtained in the same manner as in Example 128. De-N-ethyl-14-O-anisoylaconine 50 mg was dissolved in 1 ml of methanol. To this solution, 50 mg of potassium carbonate, 0.1 ml of water and 20 µl of acetyl chloride were added, and the mixture was stirred at room temperature for 1 hour. After reaction, the reaction mixture was concentrated to dryness under reduced pressure and the residue was dissolved in 20 ml of chloroform. The chloroform layer was washed with water, dried over anhydrous sodium sulfate and concentrated to dryness under reduced pressure. The residue was subjected to column chromatography on silica gel for separation and purification (5% methanol/ammonia-saturated chloroform) to give de-N-ethyl-N-acetyl- 14-O-anisoylaconine (31 mg).

Example 133

De-N-ethyl-N-benzoyl-14-O-anisoylaconine 25 mg was obtained in the same manner as in Example 132, except for the use of 20 µl of benzoyl chloride as a substitute for acetyl chloride in Example 132.

Example 134

3-Deoxy-14-O-anisoylaconine was obtained in the same manner as in Example 3. 3-Deoxy-14-O-anisoylaconine 660 mg was dissolved in 66 ml of acetone. To this solution, 25 ml of aqueous potassium permanganate solution (887 mg in 25 ml of water) and 4.5 ml of aqueous potassium carbonate solution (556 mg in 4.5 ml of water) were added and the mixture was stirred at room temperature for 30 min. After reaction, the reaction mixture was concentrated under reduced pressure until the odor of acetone was no longer apparent and, to this residual solution, 33 ml of 2N sulfuric acid and 22 ml of aqueous sodium thiosulfate solution (887 mg in 22 ml of water) cooled in advance were added. Then, this solution was washed with methylene chloride. The aqueous layer was adjusted to pH 8–9 with sodium carbonate and extracted with methylene chloride. The layer of methylene chloride was dried over anhydrous sodium sulfate and concentrated to dryness under reduced pressure. The residue was subjected to column chromatography on silica gel for separation and purification (5% methanol/ammonia-saturated chloroform) to give de-N-ethyl-3-deoxy-14 -O- anisoylaconine (600 mg).

Example 135

De-N-ethyl-3-deoxy-14-O-anisoylaconine was obtained in the same manner as in Example 134. De-N-ethyl-3-deoxy-14 -O-anisoylaconine 50 mg was dissolved in 2 ml of a mixture of methanol/ether (1:1), To this solution, 65 mg of calcium carbonate and 0.2 ml of n-amyl iodide were added and the mixture was heated under reflux for 2 hours. After reaction, the reaction mixture was filtrated to remove insolubles off and concentrated to dryness under reduced pressure. The residue was subjected to column chromatography on silica gel for separation and purification (5% methanol/ammonia-saturated chloroform) to give de-N-ethyl-N-amyl-3-deoxy-14-O-anisoylaconine (25 mg).

Example 136

De-N-ethyl-N-propyl-3-deoxy-14-O-anisoylaconine 22 mg was obtained in the same manner as in Example 135, except for the use of 0.5 ml of n-propyl iodide as a substitute for n-amyl iodide in Example 135.

Example 137

De-N-ethyl-N-4-methylpentyl-3-deoxy-14-O-anisoylaconine 30 mg was obtained in the same manner as in Example 135, except for the use of 0.5 ml of 1-bromo-4-methylpentane as a substitute for n-amyl iodide in Example 135.

Example 138

De-N-ethyl-3-deoxy-14-O-anisoylaconine was obtained in the same manner as in Example 134. De-N-ethyl-3-deoxy-14 -O-anisoylaconine 50 mg was dissolved in 1 ml of methanol. To this solution, 50 mg of potassium carbonate, 0.1 ml of water and 20 µl of acetyl chloride were added, and the mixture was stirred at room temperature for 1 hour. After reaction, the reaction mixture was concentrated to dryness under reduced pressure and the residue was dissolved in 20 ml of chloroform. The chloroform layer was washed with water, dried over anhydrous sodium sulfate and concentrated to dryness under reduced pressure. The residue was subjected to column chromatography on silica gel for separation and purification (5% methanol/ammonia-saturated chloroform) to give de-N-ethyl-N-acetyl-3-deoxy-14-O-anisoylaconine (30 mg).

Example 139

De-N-ethyl-N-benzoyl-3-deoxy-14-O-anisoylaconine 24 mg was obtained in the same manner as in Example 138, except for the use of 20 µl of benzoyl chloride as a substitute for acetyl chloride in Example 138.

Example 140

3,13-Dideoxy-14-O-anisoylaconine was obtained in the same manner as in Example 6. 3,13-Dideoxy-14-O-anisoylaconine 660 mg was dissolved in 66 ml of acetone. To this solution, 25 ml of aqueous potassium permanganate solution (887 mg in 25 ml of water) and 4.5 ml of aqueous potassium carbonate solution (556 mg in 4.5 ml of water) were added and the mixture was stirred at room temperature for 30 min. After reaction, the reaction mixture was concentrated under reduced pressure until the odor of acetone was no longer apparent and, to this residual solution, 33 ml of 2N sulfuric acid and 22 ml of aqueous sodium thiosulfate solution (887 mg in 22 ml of water) cooled in advance were added. Then, this solution was washed with methylene chloride. The aqueous layer was adjusted to pH 8–9 with sodium carbonate and extracted with methylene chloride. The layer of methylene chloride was dried over anhydrous sodium sulfate and concentrated to dryness under reduced pressure. The residue was subjected to column chromatography on silica gel for separation and purification (5% methanol/ammonia-saturated chloroform) to give de-N-ethyl-3,13 -dideoxy-14-O-anisoylaconine (611 mg).

Example 141

De-N-ethyl-3,13-dideoxy-14-O-anisoylaconine was obtained in the same manner as in Example 140. De-N-ethyl-3,13-dideoxy-14 -O-anisoylaconine 50 mg was dissolved in 2 ml of a mixture of methanol/ether (1:1). To this solution, 65 mg of calcium carbonate and 0.2 ml of n-amyl iodide were added and the mixture was heated under reflux for 2 hours. After reaction, the reaction mixture was filtrated off to remove insolubles and concentrated to dryness under reduced pressure. The residue was subjected to column chromatography on silica gel for separation and purification (5% methanol/ammonia-saturated chloroform) to give de-N-ethyl-N-amyl-3,13-dideoxy-14-O-anisoylaconine (22 mg).

Example 142

De-N-ethyl-N-propyl-3,13-dideoxy-14-O-anisoylaconine 26 mg was obtained in the same manner as in Example 141, except for the use of 0.5 ml of n-propyl iodide as a substitute for n-amyl iodide in Example 141.

Example 143

De-N-ethyl-N-4-methylpentyl-3,13-dideoxy-14-O-anisoylaconine 30 mg was obtained in the same manner as in Example 141, except for the use of 0.5 ml of 1-bromo-4-methylpentane as a substitute for n-amyl iodide in Example 141.

Example 144

De-N-ethyl-3,13-dideoxy-14-O-anisoylaconine was obtained in the same manner as in Example 140. De-N-ethyl-3,13-dideoxy-14-O-anisoylaconine 50 mg was dissolved in 1 ml of methanol. To this solution, 50 mg of potassium carbonate, 0.1 ml of water and 20 µl of acetyl chloride were added, and the mixture was stirred at room temperature for 1 hour. After reaction, the reaction mixture was concentrated to dryness under reduced pressure and the residue was dissolved in 20 ml of chloroform. The chloroform layer was washed with water, dried over anhydrous sodium sulfate and concentrated to dryness under reduced pressure. The residue was subjected to column chromatography on silica gel for separation and purification (5% methanol/ammonia-saturated chloroform) to give de-N-ethyl-N-acetyl-3,13-dideoxy-14-O-anisoylaconine (31 mg).

Example 145

De-N-ethyl-N-benzoyl-3,13-dideoxy-14-O-anisoylaconine 28 mg was obtained in the same manner as in Example 144, except for the use of 20 µl of benzoyl chloride as a substitute for acetyl chloride in Example 144.

Example 146

16-Epi-3,8-dideoxy-14-O-anisoylaconine was obtained in the same manner as in Example 27. 16-Epi-3,8-dideoxy-14-O-anisoylaconine 660 mg was dissolved in 66 ml of acetone. To this solution, 25 ml of aqueous potassium permanganate solution (887 mg in 25 ml of water) and 4.5 ml of aqueous potassium carbonate solution (556 mg in 4.5 ml of water) were added and the mixture was stirred at room temperature for 30 min. After reaction, the reaction mixture was concentrated under reduced pressure until the odor of acetone was no longer apparent and, to this residual solution, 33 ml of 2N sulfuric acid and 22 ml of aqueous sodium thiosulfate solution (887 mg in 22 ml of water) cooled in advance were added. Then, this solution was washed with methylene chloride. The aqueous layer was adjusted to pH 8–9 with sodium carbonate and extracted with methylene chloride. The layer of methylene chloride was dried over anhydrous sodium sulfate and concentrated to dryness under reduced pressure. The residue was subjected to column chromatography on silica gel for separation and purification (5% methanol/ammonia-saturated chloroform) to give de-N-ethyl-16-epi-3,8-dideoxy-14-O-anisoylaconine (615 mg).

Example 147

De-N-ethyl-16-epi-3,8-dideoxy-14-O-anisoylaconine was obtained in the same manner as in Example 146. De-N-ethyl-16 -epi-3,8-dideoxy-14-O-anisoylaconine 50 mg was dissolved in 2 ml of a mixture of methanol/ether (1:1). To this solution, 65 mg of calcium carbonate and 0.2 ml of n-amyl iodide were added and the mixture was heated under reflux for 2 hours. After reaction, the reaction mixture was filtrated off to remove insolubles and concentrated to dryness under reduced pressure. The residue was subjected to column chromatography on silica gel for separation and purification (5% methanol/ammonia-saturated chloroform) to give de-N-ethyl-N-amyl-16-epi-3,8-dideoxy-14-O-anisoylaconine (21 mg).

Example 148

De-N-ethyl-N-propyl-16-epi-3,8-dideoxy-14-O-anisoylaconine 23 mg was obtained in the same manner as in Example 147, except for the use of 0.5 ml of n-propyl iodide as a substitute for n-amyl iodide in Example 147.

Example 149

De-N-ethyl-N-4-methylpentyl-16-epi-3,8-dideoxy-14 -O-anisoylaconine 29 mg was obtained in the same manner as in Example 147, except for the use of 0.5 ml of 1-bromo-4-methylpentane as a substitute for n-amyl iodide in Example 147.

Example 150

De-N-ethyl-16-epi-3,8-dideoxy-14-O-anisoylaconine was obtained in the same manner as in Example 146. De-N-ethyl-16 -epi-3,8-dideoxy-14-O-anisoylaconine 50 mg was dissolved in 1 ml of methanol. To this solution, 50 mg of potassium carbonate, 0.1 ml of water and 20 µl of acetyl chloride were added, and the mixture was stirred at room temperature for 1 hour. After reaction, the reaction mixture was concentrated to dryness under reduced pressure and the residue was dissolved in 20 ml of chloroform. The chloroform layer was washed with water, dried over anhydrous sodium sulfate and concentrated to dryness under reduced pressure. The residue was subjected to column chromatography on silica gel for separation and purification (5% methanol/ammonia-saturated chloroform) to give de-N-ethyl-N-acetyl-16-epi-3,8-dideoxy-14 -O-anisoylaconine (31 mg).

Example 151

De-N-ethyl-N-benzoyl-16-epi-3,8-dideoxy-14-O-anisoylaconine 22 mg was obtained in the same manner as in Example 120, except for the use of 20 µl of benzoyl chloride as a substitute for acetyl chloride in Example 150.

Example 152

16-Epi-3,8,13-trideoxy-14-O-anisoylaconine was obtained in the same manner as in Example 28. 16-Epi-3,8,13-trideoxy-14 -O-anisoylaconine 660 mg was dissolved in 66 ml of acetone. To this solution, 25 ml of aqueous potassium permanganate solution (887 mg in 25 ml of water) and 4.5 ml of aqueous potassium carbonate solution (556 mg in 4.5 ml of water) were added and the mixture was stirred at room temperature for 30 min. After reaction, the reaction mixture was concentrated under reduced pressure until the odor of acetone was no longer apparent and, to this residual solution, 33 ml of 2N sulfuric acid and 22 ml of aqueous sodium thiosulfate solution (887 mg in 22 ml of water) cooled in advance were added. Then, this solution was washed with methylene chloride. The aqueous layer was adjusted to pH 8–9 with sodium carbonate and extracted with methylene chloride. The layer of methylene chloride was dried over anhydrous sodium sulfate and concentrated to dryness under reduced pressure. The residue was subjected to column chromatography on silica gel for separation and purification (5% methanol/ammonia-saturated chloroform) to give de-N-ethyl-16-epi-3,8,13-trideoxy-14-O-anisoylaconine (615 mg).

Example 153

De-N-ethyl-16-epi-3,8,13-trideoxy-14-O-anisoylaconine was obtained in the same manner as in Example 152. De-N-ethyl-16 -epi-3,8,13-trideoxy-14-O-anisoylaconine 50 mg was dissolved in 2 ml of a mixture of methanol/ether (1:1). To this solution, 65 mg of calcium carbonate and 0.2 ml of n-amyl iodide were added and the mixture was heated under reflux for 2 hours. After reaction, the reaction mixture was filtrated off to remove insolubles and concentrated to dryness under reduced pressure. The residue was subjected to column chromatography on silica gel for separation and purification (5% methanol/ammonia-saturated chloroform) to give de-N-ethyl-N-amyl-16-epi-3,8,13-trideoxy-14-O-anisoylaconine (21 mg).

Example 154

De-N-ethyl-N-propyl-16-epi-3,8,13-trideoxy-14 -O-anisoylaconine 20 mg was obtained in the same manner as in Example 153, except for the use of 0.5 ml of n-propyl iodide as a substitute for n-amyl iodide in Example 153.

Example 155

De-N-ethyl-N-4-methylpentyl-16-epi-3,8,13-trideoxy-14 -O-anisoylaconine 29 mg was obtained in the same manner as in Example 153, except for the use of 0.5 ml of 1-bromo-4-methylpentane as a substitute for n-amyl iodide in Example 153.

Example 156

De-N-ethyl-16-epi-3,8,13-trideoxy-14-O-anisoylaconine was obtained in the same manner as in Example 152. De-N-ethyl-16 -epi-3,8,13-trideoxy-14-O-anisoylaconine 50 mg was dissolved in 1 ml of methanol. To this solution, 50 mg of potassium carbonate, 0.1 ml of water and 20 µl of acetyl chloride were added, and the mixture was stirred at room temperature for 1 hour. After reaction, the reaction mixture was concentrated to dryness under reduced pressure the residue was dissolved in 20 ml of chloroform. The chloroform layer was washed with water, dried over anhydrous sodium sulfate and concentrated to dryness under reduced pressure. The residue was subjected to column chromatography on silica gel for separation and purification (5% methanol/ammonia-saturated chloroform) to give de-N-ethyl-N-acetyl-16-epi-3,8,13-trideoxy-14 -O-anisoylaconine (25 mg).

Example 157

De-N-ethyl-N-benzoyl-16-epi-3,8,13-trideoxy-14 -O-anisoylaconine 22 mg was obtained in the same manner as in Example 126, except for the use of 20 µl of benzoyl chloride as a substitute for acetyl chloride in Example 156.

Example 158

1) Pyrojesaconitine 70 mg was dissolved in 5 ml of 90% methanol. To this solution, 15 mg of potassium carbonate was added, and the mixture was stirred at room temperature for 40 hours. After methanol in the reaction mixture was distilled off, 5 ml of water was added and it was extracted three times with 10 ml of methylene chloride. The extract was dried over anhydrous sodium sulfate and concentrated to dryness under reduced pressure. The residue was subjected to thin-layer chromatography for separation and purification (eluting solvent: 10% methanol/ammonia-saturated chloroform) to give 16-epi-pyroaconine (30 mg).

2) 16-Epi-pyroaconine 30 mg was dissolved in 1 ml of pyridine. To this solution, 20 mg of m-chlorobenzoyl chloride was added and the mixture was stirred at 80° C. for 4 hours. After reaction, pyridine was distilled off under reduced pressure and water was added to the residue. After this aqueous solution was made alkaline with 5% of aqueous sodium bicarbonate. This alkaline solution was extracted with chloroform. The chloroform layer was washed with water, dried over anhydrous sodium sulfate and concentrated to dryness under reduced pressure. The residue was subjected to column chromatography on silica gel for separation and purification (ammonia-saturated ether) to give 14-O-m-chlorobenzoyl-16-epi-pyroaconine (12 mg).

Example 159

16-Epi-pyroaconine was obtained in the same manner as in Example 158-1). 16-Epi-pyroaconine 30 mg and p-toluenesulfonic acid 20 mg were dissolved in 1.5 ml of acetic anhydride and the mixture was stirred at room temperature for 1 hour. After reaction, acetic anhydride was distilled off under reduced pressure. To the residue, ice water was added, and it was made alkaline with 5% sodium bicarbonate. The alkaline solution was extracted with chloroform. The chloroform layer was washed with water, dried over anhydrous sodium sulfate and concentrated to dryness under reduced pressure. The residue was subjected to column chromatography on silica gel for separation and purification (ammonia-saturated ether) to give 14-O-acetyl-16 -epi-pyroaconine (11 mg).

Example 160

16-Epi-pyroaconine was obtained in the same manner as in Example 158-1). 16-Epi-pyroaconine 30 mg was dissolved in 1 ml of dioxane. To this solution, 15 mg of sodium hydride was added and the mixture was stirred at room temperature for 10 min. To this reaction mixture, 0.1 ml of methyl iodide was added and the mixture was stirred for 2 hours. After reaction, the reaction mixture was poured into ice water and extracted with chloroform. The chloroform layer was washed with water, dried over anhydrous sodium sulfate and concentrated to dryness under reduced pressure. The residue was subjected to column chromatography on silica gel for separation and purification (5% methanol/ammonia-saturated chloroform) to give 14-O-methyl-16-epi-pyroaconine (10 mg).

Example 161

1) Pyrojesaconitine 660 mg was dissolved in 66 ml of acetone. To this solution, 25 ml of aqueous potassium permanganate solution (887 mg in 25 ml of water) and 4.5 ml of aqueous potassium carbonate solution (556 mg in 4.5 ml of water) were added and the mixture was stirred at room temperature for 30 min. After reaction, the reaction mixture was concentrated under reduced pressure until the odor of acetone was no longer apparent and, to the residual solution, 33 ml of 2N sulfuric acid and 22 ml of aqueous sodium thiosulfate solution (887 mg in 22 ml of water) cooled in advance were added. Then, this solution was washed with methylene chloride. The aqueous layer was adjusted to pH 8–9 with sodium carbonate and extracted with methylene chloride. The layer of methylene chloride was dried over anhydrous sodium sulfate and concentrated to dryness under reduced pressure. The residue was subjected to column chromatography on silica gel for separation and purification (5% methanol/ammonia-saturated chloroform) to give de-N-ethyl-16-epi-pyrojesaconitine (480 mg).

2) De-N-ethyl-16-epi-pyrojesaconitine 50 mg was dissolved in 1 ml of methanol. To this solution, 50 mg of potassium carbonate, 0.1 ml of water and 20 µl of benzoyl chloride were added, and the mixture was stirred at room temperature for 1 hour. After reaction, the reaction mixture was concentrated to dryness under reduced pressure and the residue was dissolved in 20 ml of chloroform. The chloroform layer was washed with water, dried over anhydrous sodium sulfate and concentrated to dryness under reduced pressure. The residue was subjected to column chromatography on silica gel for separation and purification (5% methanol/ammonia-saturated chloroform) to give de-N-ethyl-N-benzoyl- 16-epi-pyrojesaconitine (20 mg).

Example 162

De-N-ethyl-16-epi-pyrojesaconitine was obtained in the same manner as in Example 161-1). De-N-ethylpyrojesaconitine 50 mg was dissolved in 2 ml of a mixture of methanol/ether (1:1). To this solution, 65 mg of calcium carbonate and 0.5 ml of n-propyl iodide were added and the mixture was heated under reflux for 2 hours. After reaction, the reaction mixture was filtrated off to remove insolubles and concentrated to dryness under reduced pressure. The residue was subjected to column chromatography on silica gel for separation and purification (5% methanol/ammonia-saturated chloroform) to give de-N-ethyl-N-propyl-16 -epi-pyrojesaconitine (28 mg).

Example 163

De-N-ethyl-N-acetyl-16-epi-pyrojesaconitine 22 mg was obtained in the same manner as in Example 161, except for the use of 20 µl of anisoyl chloride as a substitute for benzoyl chloride in Example 161.

Example 164

1) 3-Deoxypyrojesaconitine 35 mg was obtained in the same manner as in Example 2, except for the use of 100 mg of pyrojesaconitine as a substitute for jesaconitine in Example 2. 3-Deoxypyrojesaconitine 35 mg was dissolved in 3 ml of 90% methanol. To this solution, 10 mg of potassium carbonate was added, and the mixture was stirred at room temperature for 40 hours. After methanol in the reaction mixture was distilled off, 5 ml of water was added to the residue and the mixture was extracted three times with 10 ml of methylene chloride. The extract was dried over anhydrous sodium sulfate and concentrated to dryness under reduced pressure. The residue was subjected to thin-layer chromatography for separation and purification (eluting solvent: 10% methanol/ammonia-saturated chloroform) to give 3-deoxy-16-epi-pyroaconine (20 mg).

2) 3-Deoxy-16-epi-pyroaconine 20 mg was dissolved in 1 ml of pyridine. To this solution, 20 mg of m-chlorobenzoyl chloride was added and the mixture was stirred at 80° C. for 4 hours. After reaction, pyridine was distilled off under reduced pressure. To the residue, water was added and the mixture was made alkaline with 5% of aqueous sodium bicarbonate solution. This alkaline solution was extracted with chloroform. The chloroform layer was washed with water, dried over anhydrous sodium sulfate and concentrated to dryness under reduced pressure. The residue was subjected to column chromatography on silica gel for separation and purification (ammonia-saturated ether) to give 3-deoxy-14-O-m-chlorobenzoyl- 16-epi-pyroaconine (10 mg).

Example 165

3-Deoxy-16-epi-pyroaconine was obtained in the same manner as in Example 164-1). 3-Deoxy-16-epi-pyroaconine 20 mg and p-toluenesulfonic acid 20 mg were dissolved in 1.5 ml of acetic anhydride and the mixture was stirred at room temperature for 1 hour. After reaction, acetic anhydride was distilled off under reduced pressure. To the residue, ice water was added, and the mixture was made alkaline with 5% sodium bicarbonate. The alkaline solution was extracted with chloroform. The chloroform layer was washed with water, dried over anhydrous sodium sulfate and concentrated to dryness under reduced pressure. The residue was subjected to column chromatography on silica gel for separation and purification (ammonia-saturated ether) to give 3-deoxy-14-O-acetyl-16-epi-pyroaconine (10 mg).

Example 166

3-Deoxy-16-epi-pyroaconine was obtained in the same manner as in Example 164-1). 3-Deoxy-16-epi-pyroaconine 20 mg was dissolved in 1 ml of dioxane. To this solution, 15 mg of sodium hydride was added and the mixture was stirred at room temperature for 10 min. To this reaction mixture, 0.1 ml of methyl iodide was added and the mixture was stirred for 2 hours. After reaction, the reaction mixture was poured into ice water and extracted with chloroform. The chloroform layer was washed with water, dried over anhydrous sodium sulfate and concentrated to dryness under reduced pressure. The residue was subjected to column chromatography on silica gel for separation and purification (5% methanol/ammonia-saturated chloroform) to give 3-deoxy-14-O-methyl-16-epi-pyroaconine (10 mg).

Example 167

1) 3-Deoxypyrojesaconitine 100 mg was obtained in the same manner as in Example 2, except for the use of 300 mg of pyrojesaconitine as a substitute for jesaconitine in Example 2. 3-Deoxypyrojesaconitine 300 mg was dissolved in 66 ml of acetone. To this solution, 25 ml of aqueous potassium permanganate solution (887 mg in 25 ml of water) and 4.5 ml of aqueous potassium carbonate solution (556 mg in 4.5 ml of water) were added and the mixture was stirred at room temperature for 30 min. After reaction, the reaction mixture was concentrated under reduced pressure until the odor of acetone was no longer apparent and, to this residual solution, 33 ml of 2N sulfuric acid and 22 ml of aqueous sodium thiosulfate solution (887 mg in 22 ml of water) cooled in advance were added. Then, this solution was washed with methylene chloride. The aqueous layer was adjusted to pH 8–9 with sodium carbonate and extracted with methylene chloride. The layer of methylene chloride was dried over anhydrous sodium sulfate and concentrated to dryness under reduced pressure. The residue was subjected to column chromatography on silica gel for separation and purification (5% methanol/ammonia-saturated chloroform) to give de-N-ethyl-3-deoxy-16-epi-pyrojesaconitine (250 mg).

2) De-N-ethyl-3-deoxy-16-epi-pyrojesaconitine 50 mg was dissolved in 1 ml of methanol. To this solution, 50 mg of potassium carbonate, 0.1 ml of water and 20 µl of benzoyl chloride were added, and the mixture was stirred at room temperature for 1 hour. After reaction, the reaction mixture was concentrated to dryness under reduced pressure and the residue was dissolved in 20 ml of chloroform. The chloroform layer was washed with water, dried over anhydrous sodium sulfate and concentrated to dryness under reduced pressure. The residue was subjected to column chromatography on silica gel for separation and purification (5% methanol/ammonia-saturated chloroform) to give de-N-ethyl-N-benzoyl-3-deoxy-16-epi-pyrojesaconitine (20 mg).

Example 168

De-N-ethyl-3-deoxy-16-epi-pyrojesaconitine was obtained in the same manner as in Example 167. De-N-ethyl-3-deoxy-16-epi-pyrojesaconitine 50 mg was dissolved in 2 ml of a mixture of methanol/ether (1:1). To this solution, 65 mg of calcium carbonate and 0.5 ml of n-propyl iodide were added and the mixture was heated under reflux for 2 hours. After reaction, the reaction mixture was filtrated off to remove insolubles and concentrated to dryness under reduced pressure. The residue was subjected to column chromatography on silica gel for separation and purification (5% methanol/ammonia-saturated chloroform) to give de-N-ethyl-N-propyl-3-deoxy-16-epi-pyrojesaconitine (28 mg).

Example 169

De-N-ethyl-N-acetyl-3-deoxy-16-epi-pyrojesaconitine 20 mg was obtained in the same manner as in Example 167, except for the use of 20 μl of anisoyl chloride as a substitute for benzoyl chloride in Example 167.

Example 170

1) 3,13-Dideoxypyrojesaconitine 35 mg was obtained in the same manner as in Example 5, except for the use of 100 mg of pyrojesaconitine as a substitute for jesaconitine in Example 5. 3,13-Dideoxypyrojesaconitine 35 mg was dissolved in 3 ml of 90% methanol. To this solution, 10 mg of potassium carbonate was added, and the mixture was stirred at room temperature for 40 hours. After methanol in the reaction mixture was distilled off, 5 ml of water was added to the residue and the mixture was extracted three times with 10 ml of methylene chloride. The extract was dried over anhydrous sodium sulfate and concentrated to dryness under reduced pressure. The residue was subjected to thin-layer chromatography for separation and purification (eluting solvent: 10% methanol/ammonia-saturated chloroform) to give 3,13-dideoxy-16-epi-pyroaconine (20 mg).

2) 3,13-Dideoxy-16-epi-pyroaconine 20 mg was dissolved in 1 ml of pyridine. To this solution, 20 mg of m-chlorobenzoyl chloride was added and the mixture was stirred at 80° C. for 4 hours. After reaction, pyridine was distilled off under reduced pressure. To the residue, water was added and the mixture was made alkaline with 5% of aqueous sodium bicarbonate solution. This alkaline solution was extracted with chloroform. The chloroform layer was washed with water, dried over anhydrous sodium sulfate and concentrated to dryness under reduced pressure. The residue was subjected to column chromatography on silica gel for separation and purification (ammonia-saturated ether) to give 3,13-dideoxy-14-O-m-chlorobenzoyl-16-epi-pyroaconine (10 mg).

Example 171

3,13-Dideoxy-16-epi-pyroaconine was obtained in the same manner as in Example 170-1). 3,13-Dideoxy-16-epi-pyroaconine 20 mg and p-toluenesulfonic acid 20 mg were dissolved in 1.5 ml of acetic anhydride and the mixture was stirred at room temperature for 1 hour. After reaction, acetic anhydride was distilled off under reduced pressure. To the residue, ice water was added, and the mixture was made alkaline with 5% sodium bicarbonate. The alkaline solution was extracted with chloroform. The chloroform layer was washed with water, dried over anhydrous sodium sulfate and concentrated to dryness under reduced pressure. The residue was subjected to column chromatography on silica gel for separation and purification (ammonia-saturated ether) to give 3,13-dideoxy-14-O-acetyl-16-epi-pyroaconine (10 mg).

Example 172

3,13-Dideoxy-16-epi-pyroaconine was obtained in the same manner as in Example 170-1). 3,13-Dideoxy-16-epi-pyroaconine 20 mg was dissolved in 1 ml of dioxane. To this solution, 15 mg of sodium hydride was added and the mixture was stirred at room temperature for 10 min. To this reaction mixture, 0.1 ml of methyl iodide was added and the mixture was stirred for 2 hours. After reaction, the reaction mixture was poured into ice water and extracted with chloroform. The chloroform layer was washed with water, dried over anhydrous sodium sulfate and concentrated to dryness under reduced pressure. The residue was subjected to column chromatography on silica gel for separation and purification (5% methanol/ammonia-saturated chloroform) to give 3,13-dideoxy-14-O-methyl-16-epi-pyroaconine (10 mg).

Example 173

1) 3,13-Dideoxypyrojesaconitine 100 mg was obtained in the same manner as in Example 5, except for the use of 300 mg of pyrojesaconitine as a substitute for jesaconitine in Example 5. 3,13-Dideoxypyrojesaconitine 100 mg was dissolved in 66 ml of acetone. To this solution, 25 ml of aqueous potassium permanganate solution (887 mg in 25 ml of water) and 4.5 ml of aqueous potassium carbonate solution (556 mg in 4.5 ml of water) were added and the mixture was stirred at room temperature for 30 min. After reaction, the reaction mixture was concentrated under reduced pressure until the odor of acetone was no longer apparent and, to this residual solution, 33 ml of 2N sulfuric acid and 22 ml of aqueous sodium thiosulfate solution (887 mg in 22 ml of water) cooled in advance were added. Then, this solution was washed with methylene chloride. The aqueous layer was adjusted to pH 8–9 with sodium carbonate and extracted with methylene chloride. The layer of methylene chloride was dried over anhydrous sodium sulfate and concentrated to dryness under reduced pressure. The residue was subjected to column chromatography on silica gel for separation and purification (5% methanol/ammonia-saturated chloroform) to give de-N-ethyl-3,13-dideoxy-16-epi-pyrojesaconitine (60 mg).

2) De-N-ethyl-3,13-dideoxy-16-epi-pyrojesaconitine 50 mg was dissolved in 1 ml of methanol. To this solution, 50 mg of potassium carbonate, 0.1 ml of water and 20 μl of benzoyl chloride were added, and the mixture was stirred at room temperature for 1 hour. After reaction, the reaction mixture was concentrated to dryness under reduced pressure and the residue was dissolved in 20 ml of chloroform. The chloroform layer was washed with water, dried over anhydrous sodium sulfate and concentrated to dryness under reduced pressure. The residue was subjected to column chromatography on silica gel for separation and purification (5% methanol/ammonia-saturated chloroform) to give de-N-ethyl-N-benzoyl-3,13-dideoxy-16-epi-pyrojesaconitine (20 mg).

Example 174

De-N-ethyl-3,13-dideoxy-16-epi-pyrojesaconitine was obtained in the same manner as in Example 173-1). De-N-ethyl-3,13-dideoxy-16-epi-pyrojesaconitine 50 mg was dissolved in 2 ml of a mixture of methanol/ether (1:1). To this solution, 65 mg of calcium carbonate and 0.5 ml of n-propyl iodide were added and the mixture was refluxed for 2 hours. After reaction, the reaction mixture was filtrated off to remove insolubles and the reaction mixture was concentrated to dryness under reduced pressure. The residue was subjected to column chromatography on silica gel for separation and purification (5% methanol/ammonia-saturated chloroform) to give de-N-ethyl-N-propyl-3,13-dideoxy-16-epi-pyrojesaconitine (28 mg).

Example 175

De-N-ethyl-N-acetyl-3,13-dideoxy-16-epi-pyrojesaconitine 20 mg was obtained in the same manner as in Example 173, except for the use of 20 μl of acetyl chloride as a substitute for benzoyl chloride in Example 173.

Example 176

De-N-ethyl-8-deoxy-14-O-anisoylaconine was obtained in the same manner as in Example 50. De-N-ethyl-8-deoxy-14-O-anisoylaconine 50 mg was dissolved in 1 ml of methanol. To this solution, 50 mg of potassium carbonate, 0.1 ml of water and 20 μl of 2-methyl-tetrahydro-2-furoyl-chloride were added, and the mixture was stirred at room temperature for 1 hour. After reaction, the reaction mixture was distilled off and the residue was dissolved in 20 ml of chloroform. After the chloroform layer was washed with 5% hydrochloric acid and water, it was dried over anhydrous sodium sulfate and concentrated to dryness under reduced pressure. Next, the residue was dissolved in 1.5 ml of tetrahydrofuran and, under cooling, its solution was added in the suspended solution of lithium alminium hydride 20 mg in THF 0.7 ml. Then, this solution was heated under reflux for 2 hours. After reaction, 0.1 ml of water was added to the reaction mixture and the mixture was filtrated off. The filtrate was concentrated to dryness under reduced pressure. The residue was dissolved in 1 ml of pyridine. To this solution, 20 μl of p-anisoyl chloride was added and the mixture was stirred at room temperature for 4 hours. After reaction, pyridine in the reaction mixture was distilled off. To the residue, water was added and then the mixture was made alkaline with 5% sodium bicarbonate. This alkaline solution was extracted with chloroform. The chloroform layer was washed with water saturated with sodium chloride, dried over anhydrous sodium sulfate and distilled off under reduced pressure. The residue was subjected to column chromatography on silica gel for separation and purification (5% methanol/ammonia-saturated chloroform) to give de-N-ethyl-N-(2-methyltetrahydrofurfuryl)-8-deoxy-14-O-anisoylaconine (21 mg).

Example 177

De-N-ethyl-3,8-dideoxy-14-O-anisoylaconine was obtained in the same manner as in Example 116. De-N-ethyl-N-(2-methyltetrahydrofurfuryl)-3,8-dideoxy-14-O-anisoylaconine 20 mg was obtained in the same manner as in Example 176, except for the use of 50 mg of de-N-ethyl-3,8-dideoxy-14-O-anisoylaconine as a substitute for de-N-ethyl-8-deoxy-14-O-anisoylaconine in Example 176.

Example 178

De-N-ethyl-3,8,13-trideoxy-14-O-anisoylaconine was obtained in the same manner as in Example 122. De-N-ethyl-N-(2-methyltetrahydrofurfuryl)-3,8,13-trideoxy-14-O-anisoylaconine 18 mg was obtained in the same manner as in Example 176, except for the use of 50 mg of de-N-ethyl-3,8,13-trideoxy-14-O-anisoylaconine as a substitute for de-N-ethyl-8-deoxy-14-O-anisoylaconine in Example 176.

Example 179

De-N-ethyl-14-O-anisoylaconine was obtained in the same manner as in Example 128. De-N-ethyl-N-(2-methyltetrahydrofurfuryl)-14-O-anisoylaconine 21 mg was obtained in the same manner as in Example 176, except for the use of 50 mg of de-N-ethyl-14-O-anisoylaconine as a substitute for de-N-ethyl-8-deoxy-14-O-anisoylaconine in Example 176.

Example 180

De-N-ethyl-3-deoxy-14-O-anisoylaconine was obtained in the same manner as in Example 134. De-N-ethyl-N-(2-methyltetrahydrofurfuryl)-3-deoxy-14-O-anisoylaconine 20 mg was obtained in the same manner as in Example 176, except for the use of 50 mg of de-N-ethyl-3-deoxy-14-O-anisoylaconine as a substitute for de-N-ethyl-8-deoxy-14-O-anisoylaconine in Example 176.

Example 181

De-N-ethyl-3,13-dideoxy-14-O-anisoylaconine was obtained in the same manner as in Example 140. De-N-ethyl-N-(2-methyltetrahydrofurfuryl)-3,13-dideoxy-14-O-anisoylaconine 22 mg was obtained in the same manner as in Example 176, except for the use of 50 mg of de-N-ethyl-3,13-dideoxy-14-O-anisoylaconine as a substitute for de-N-ethyl-8-deoxy-14-O-anisoylaconine in Example 176.

Example 182

De-N-ethyl-16-epi-8-deoxy-14-O-anisoylaconine was obtained in the same manner as in Example 66. De-N-ethyl-N-(2-methyltetrahydrofurfuryl)-16-epi-8-deoxy-14-O-anisoylaconine 23 mg was obtained in the same manner as in Example 176, except for the use of 50 mg of de-N-ethyl-16-epi-8-deoxy-14-O-anisoylaconine as a substitute for de-N-ethyl-8-deoxy-14-O-anisoylaconine in Example 176.

Example 183

De-N-ethyl-16-epi-3,8-dideoxy-14-O-anisoylaconine was obtained in the same manner as in Example 146. De-N-ethyl-N-(2-methyltetrahydrofurfuryl)-16-epi-3,8-dideoxy-14-O-anisoylaconine 19 mg was obtained in the same manner as in Example 176, except for the use of 50 mg of de-N-ethyl-16-epi-3,8-dideoxy-14-O-anisoylaconine as a substitute for de-N-ethyl-8-deoxy-14-O-anisoylaconine in Example 176.

Example 184

De-N-ethyl-16-epi-3,8,13-trideoxy-14-O-anisoylaconine was obtained in the same manner as in Example 152. De-N-ethyl-N-(2-methyltetrahydrofurfuryl)-16-epi-3,8,13-trideoxy-14-O-anisoylaconine 17 mg was obtained in the same manner as in Example 176, except for the use of 50 mg of de-N-ethyl-16-epi-3,8,13-trideoxy-14-O-anisoylaconine as a substitute for de-N-ethyl-8-deoxy-14-O-anisoylaconine in Example 176.

Example 185

Jesaconitine 100 mg and imidazole 6 mg were dissolved in 12 ml of a dried tetrahydrofuran. To this solution, 210 mg of sodium hydride was added under the condition of 0° C., and the mixture was stirred at room temperature. After 30 minutes, to this solution, 2.4 ml of carbon disulfide and 1.8 ml of methyl iodide were added and the mixture was heated under reflux for 1.5 hours. After cooling, the reaction mixture was poured into ice water and extracted three times with 30 ml of chloroform. The chloroform layer was washed with water, dried over anhydrous sodium sulfate and concentrated to dryness under reduced pressure. The residue was subjected to column chromatography on silica gel for separation and purification (5 g, ammonia-saturated ether: hexane=3:2) to give jesaconitine 3,13,15-trithiocarbonate (98 mg). Next, jesaconitine 3,13,15-trithiocarbonate 30 mg was dissolved in 1 ml of dried benzene. To this solution, 0.5 ml of dried benzene solution dissolving 0.2 ml of tributyl tin hydride was added, and the mixture was refluxed for 4 hours. After cooling, benzene in the reaction mixture was distilled off under reduced pressure and the residue was subjected to column chromatography on silica gel for separation and purification (5 g, ammonia-saturated ether: hexane= 3:2) to give 3,13,15-trideoxyjesaconitine (25 mg).

Example 186

Mesaconitine 70 mg was dissolved in 5 ml of methanol. To this solution, 1 ml of 5% potassium hydride was added, and the mixture was heated under reflux for 3 hours. After methanol in the reaction mixture was distilled off, 5 ml of water was added to the residue and the mixture was extracted three times with 10 ml of methylene chloride. The extract was dried over anhydrous sodium sulfate and concentrated to dryness under reduced pressure. The residue was subjected to thin-layer chromatography for separation and purification (eluting solvent: 10% methanol/ammonia-saturated chloroform) to give mesaconine (30 mg). 14-O-p-Chlorobenzoylmesaconine 20 mg was obtained in the same manner as in Example 90, except for the use of 30 mg of mesaconine and 30 mg of p-chlorobenzoyl chloride as each substitute for 30 mg of aconine and 30 mg of m-chlorobenzoyl chloride in Example 90.

Example 187

14-O-p-Fluorobenzoylaconine 19 mg was obtained in the same manner as in Example 90, except for the use of 30 mg of p-fluorobenzoyl chloride as a substitute for 30 mg of m-chlorobenzoyl chloride in Example 90.

Example 188

14-O-p-Bromobenzoylaconine 20 mg was obtained in the same manner as in Example 90, except for the use of 30 mg of p-bromobenzoyl chloride as a substitute for 30 mg of m-chlorobenzoyl chloride in Example 90.

Example 189

14-p-Chlorobenzoylaconine 21 mg was obtained in the same manner as in Example 90, except for the use of 30 mg of p-chlorobenzoyl chloride as a substitute for 30 mg of m-chlorobenzoyl chloride in Example 90. 14-p-Chlorobenzoylaconine 21 mg was dissolved in 3 ml of acetone. To this solution, 1 ml of aqueous potassium permanganate solution (887 mg in 25 ml of water) and 0.2 ml of aqueous potassium carbonate solution (556 mg in 4.5 ml of water) were added and the mixture was stirred at room temperature for 30 min. After reaction, the reaction mixture was concentrated under reduced pressure until the odor of acetone was no longer apparent and, to this residual solution, 1.3 ml of 2N sulfuric acid and 1 ml of aqueous sodium thiosulfate solution (887 mg in 22 ml of water) cooled in advance were added. Then, this solution was washed with methylene chloride. The aqueous layer was adjusted to pH 8–9 with sodium carbonate and extracted with methylene chloride. The layer of methylene chloride was dried over anhydrous sodium sulfate and concentrated to dryness under reduced pressure. The residue was subjected to column chromatography on silica gel for separation and purification (5% methanol/ammonia-saturated chloroform) to give de-N-ethyl-8-deoxy-14-O-anisoylaconine (15 mg).

Example 190

Neoline 8 mg was dissolved in 1 ml of pyridine. To this solution, 0.2 ml of acetic anhydride was added and it was permitted to stand at room temperature for 30 min. To the reaction mixture, 20 ml of water and 10 ml of 1N sodium carbonate were added and the mixture was extracted three times with 30 ml of ether. After the extract was concentrated to dryness, the residue was subjected to column chromatography on silica gel (7 g) with 30 ml of a mixture of chloroform/methanol (99.5:0.5) as a washing solvent and 30 ml of a mixture of chloroform/methanol (98:2) as an eluting solvent. The eluate was concentrated to dryness and 1,14-di-O-acetylneoline (8 mg) was obtained.

Example 191

Aconine 70 mg was obtained in the same manner as in Example 88-1). Aconine 30 mg was dissolved in 1 ml of pyridine. To this solution, 18 mg of 3-chloropropionyl chloride was added and the mixture was stirred at 80° C. for 4 hours. After reaction, pyridine was distilled off under reduced pressure. To the residue, water was added and then the mixture was made alkaline with 5% of aqueous sodium bicarbonate solution. This alkaline solution was extracted with chloroform. The chloroform layer was washed with water, dried over anhydrous sodium sulfate and concentrated to dryness under reduced pressure. The residue was subjected to column chromatography on silica gel for separation and purification (ammonia-saturated ether) to give 14-O-(3-chloropropionyl)aconine (18 mg).

Example 192

Aconine 70 mg was obtained in the same manner as in Example 88-1). Aconine 30 mg was dissolved in 3.6 ml of 1,2-dimethoxyethane. To this solution, 90 mg of sodium hydride was added and the mixture was stirred at room temperature for 30 min. To this reaction mixture, 0.7 ml of 4-chloro-1-butanol was added and the mixture was heated under reflux for 30 min. After reaction, the reaction mixture was poured into ice water and extracted with chloroform. The chloroform layer was washed with water, dried over anhydrous sodium sulfate and concentrated to dryness under reduced pressure. The residue was subjected to column chromatography on silica gel for separation and purification (ammonia-saturated chloroform) to give 14-O-(4-hydroxybutyl)aconine (17 mg).

Example 193

14-O-(4-Methyl-cyclohexyl)aconine 19 mg was obtained in the same manner as in Example 192, except for the use of 1 ml of 4-bromo-1-methylcyclohexane (the mixture of cis- and trans-forms) as a substitute for 4-chloro-1-butanol in Example 192.

Example 194

14-O-Benzoylaconine 660 mg was dissolved in 66 ml of acetone. To this solution, 25 ml of aqueous potassium permanganate solution (887 mg in 25 ml of water) and 4.5 ml of aqueous potassium carbonate solution (556 mg in 4.5 ml of water) were added and the mixture was stirred at room temperature for 30 min. After reaction, the reaction mixture was concentrated under reduced pressure until the odor of acetone was no longer apparent and, to this residual solution, 33 ml of 2N sulfuric acid and 22 ml of aqueous sodium thiosulfate solution (887 mg in 22 ml of water) cooled in advance were added. Then, this solution was washed with methylene chloride. The aqueous layer was adjusted to pH 8–9 with sodium carbonate and extracted with methylene chloride. The layer of methylene chloride was dried over anhydrous sodium sulfate and concentrated to dryness under reduced pressure. The residue was subjected to column chromatography on silica gel for separation and purification (5% methanol/ammonia-saturated chloroform) to give de-N-ethyl-14-O-benzoylaconine (610 mg). De-N-ethyl-14-O-benzoylaconine 50 mg was dissolved in 1 ml of methanol. To this solution, 50 mg of potassium carbonate, 0.1 ml of water and 50 mg of p-anisoyl chloride were added, and the mixture was stirred at room temperature for 1 hour. After reaction, the reaction mixture was concentrated to dryness under reduced pressure and the residue was dissolved in 20 ml of chloroform. The chloroform layer was washed with water, dried over anhydrous sodium sulfate and concentrated to dryness under reduced pressure. The residue was subjected to column chromatography on silica gel for separation and purification (5% methanol/ammonia-saturated chloroform) to give de-N-ethyl-N-(p-anisoyl)-14-O-benzoylaconine (30 mg).

Example 195

De-N-ethyl-N-(3-chloropropionyl)-14-O-benzoylaconine 27 mg was obtained in the same manner as in Example 194, except for the use of 0.03 ml of 3-chloropropionyl chloride as a substitute for p-anisoyl chloride in Example 194.

Example 196

De-N-ethyl-N-crotyl-14-O-benzoylaconine 29 mg was obtained in the same manner as in Example 51, except for the use of 50 mg of de-N-ethyl-14-O-benzoylaconine and 0.6 ml of crotyl chloride as each substitute for de-N-ethyl-8-deoxy-14-O-anisoylaconine and n-amyl iodide in Example 51.

Example 197

De-N-ethyl-N-(4-methyl-cyclohexyl)-14-O-benzoylaconine 26 mg was obtained in the same manner as in Example 51, except for the use of 50 mg of de-N-ethyl-14-O-benzoylaconine and 0.9 ml of 4-bromo-1-methylcyclohexane (the mixture of cis- and trans-forms) as each substitute for de-N-ethyl-8-deoxy-14-O-anisoylaconine and n-amyl iodide in Example 51.

Example 198

De-N-ethyl-N-(4-hydroxybutyl)-14-O-benzoylaconine 25 mg was obtained in the same manner as in Example 51, except for the use of 50 mg of de-N-ethyl-14-O-benzoylaconine and 0.6 ml of 4-chloro-1-butanol as each substitute for de-N-ethyl-8-deoxy-14-O-anisoylaconine and n-amyl iodide in Example 51.

Example 199

14-O-(2-Pyridylmethyl)aconine 21 mg was obtained in the same manner as in Example 191, except for the use of 20 mg of 2-chloromethylpyridine hydrochloride as a substitute for 4-chloro-1-butanol in Example 191.

Example 200

14-O-(2-Methyltetrahydrofurfuryl)aconine 19 mg was obtained in the same manner as in Example 191, except for the use of 20 µl of 2-methyl-tetrahydro-2-furoyl chloride as a substitute for 4-chloro-1-butanol in Example 191.

Example 201

Aconine 70 mg was obtained in the same manner as in Example 88-1). Aconine 30 mg was dissolved in 1 ml of pyridine. To this solution, 25 µl of cyclohexane carbonyl chloride was added and the mixture was stirred at 80° C. for 4 hours. After reaction, pyridine was distilled off under reduced pressure. To the residue, water was added and then the mixture was made alkaline with 5% of aqueous sodium bicarbonate solution. This alkaline solution was extracted with chloroform. The chloroform layer was washed with water, dried over anhydrous sodium sulfate and concentrated to dryness under reduced pressure. The residus was subjected to column chromatography on silica gel for separation and purification (ammonia-saturated ether) to give 14-O-cyclohexanecarbonylaconine (18 mg).

Example 202

De-N-ethyl-N-cyclohexanecarbonyl-14-O-benzoylaconine 27 mg was obtained in the same manner as in Example 193, except for the use of 0.03 ml of cyclohexane carbonyl chloride as a substitute for p-anisoyl chloride in Example 193.

Example 203

De-N-ethyl-N-α-methyl-(4-(α-methylacetic acid)-phenyl)-acetyl-14-O-benzoylaconine 27 mg was obtained in the same manner as in Example 193, except for the use of 50 µl of α-methyl-(4-(α-methylacetic acid)-phenyl)-acetyl chloride of as a substitute for p-anisoyl chloride in Example 193.

Example 204

De-N-ethyl-N-(2-pyridylmethyl)-14-O-benzoylaconine 30 mg was obtained in the same manner as in Example 51, except for the use of 50 mg of de-N-ethyl-14-O-benzoylaconine and 20 mg of 2-chloromethylpyridine hydrochloride as each substitute for de-N-ethyl-8-deoxy-14-O-anisoylaconine and n-amyl iodide in Example 51.

Example 205

Neoline 17 mg was dissolved in 0.8 ml of pyridine. To this solution, 2,2,2-trichloroethyl chloroformate 22 μl was added at 0° C. and the mixture was stirred for 30 min at 0° C. After 2 ml of ice water was added to the reaction mixture and it was made alkaline with 5% sodium bicarbonate, the alkaline solution was extracted three times with 10 ml of chloroform. The chloroform layer was washed with water, dried over anhydrous sodium sulfate and concentrated to dryness under reduced pressure. The residue was subjected to column chromatography on alumina (30 g) for separation and purification with chloroform to give 1-O-(β,β,β -trichloroethoxycarbonyl)neoline (21 mg). 1-O-(β,β,β -Trichloroethoxycarbonyl)neoline 18 mg was dissolved in 1.2 ml of dry-pyridine. To this solution, 40 μl of p-anisoyl chloride was added and the mixture was stirred at room temperature for 1 hour. Then, to the reaction mixture, 2 ml of ice water was added and the mixture was made alkaline with 5% sodium bicarbonate. This alkaline solution was extracted three times with 10 ml of chloroform. The extract was washed with water, dried over anhydrous sodium sulfate and concentrated to dryness under reduced pressure. The residue was subjected to column chromatography on silica gel for separation and purification (15 g, ammonia-saturated ether: hexane= 3:2) to afford 1-O-(β,β,β -trichloroethoxycarbonyl)-14-O-anisoylneoline (20 mg). 1 -O-(β,β,β-Trichloroethoxycarbonyl)-14-O-anisoylneoline 18 mg was dissolved in 5 ml of acetic acid. To this solution, 40 mg of zinc dust was added and the mixture was stirred for 1 hour. Then, the zinc dust was removed by filtration and the zinc dust on filter paper was washed with 50 ml of 5% methanol/chloroform. Then, the obtained filtrate and washing solution were put together and the mixture was washed with 50 ml of 1N sodium carbonate. The chloroform layer was dried over anhydrous sodium sulfate and concentrated to dryness under reduced pressure. The residue was subjected to preparative thin-layer chromatography (ammonia-saturated ether) to give 14-O-anisoylneoline (13 mg).

Example 206

Neoline 8 mg was dissolved in 1 ml of pyridine. To this solution, 0.08 ml of butyryl chloride was added and the mixture was permitted to stand at room temperature for 30 min. To the reaction mixture, 20 ml of water and 10 ml of 1N sodium carbonate were added and the mixture was extracted three times with 30 ml of ether. After the extract was concentrated to dryness, the residue was subjected to column chromatography on silica gel (7 g) with 30 ml of a mixture of chloroform/methanol (99.5:0.5) as a washing solvent and with 30 ml of a mixture of chloroform/methanol (98:2) as an eluting solvent. The eluate was concentrated to dryness to give 1,14-di-O-butanoylneoline (8 mg).

Example 207

Neoline 8 mg was dissolved in 1 ml of pyridine. To this solution, 0.04 ml of p-chlorobenzoyl chloride was added and the mixture was permitted to stand at room temperature for 30 min. To the reaction mixture, 20 ml of water and 10 ml of 1N sodium carbonate were added and the mixture was extracted three times with 30 ml of ether. The extract was concentrated to dryness and the residue was subjected to column chromatography on silica gel (7 g) with 30 ml of a mixture of chloroform/methanol (99.5:0.5) as a washing solvent and with 30 ml of a mixture of chloroform/methanol (98:2) as an eluting solvent. The eluate was concentrated to dryness to give 1,14-di-O-p-chlorobenzoylneoline (8 mg).

Example 208

Neoline 8 mg was dissolved in 1 ml of pyridine. To this solution, 0.02 ml of p-anisoyl chloride was added and the mixture was permitted to stand at room temperature for 30 min. To the reaction mixture, 20 ml of water and 10 ml of 1N sodium carbonate were added and the mixture was extracted three times with 30 ml of ether. After the extract was concentrated to dryness, the residue was subjected to column chromatography on silica gel (7 g) with 30 ml of a mixture of chloroform/methanol (99.5:0.5) as a washing solvent and with 30 ml of a mixture of chloroform/methanol (98:2) as an eluting solvent. The eluate was concentrated to dryness to give 1,14-di-p-anisoylneoline (8 mg).

(1) Physicochemical parameters and analytical data of 8-deoxy- 14-O-anisoylaconine
1) Property and solubility
Colorless and amorphous powder. Soluble in ether, chloroform, benzene, ethanol, methanol, ethylacetate, pyridine and dimethyl sulfoxide. Insoluble in hexane and water.
2) Analysis of IR spectra (KBr)
IR $v_{max}^{KBr}$: 3500, 1711 $cm^{-1}$.
3) Analysis of UV spectra (ethanol)
UV $\lambda_{max}^{EtOH}$ (log ε) nm: 257 (4.02).
4) Analysis of $^1$H-NMR spectra ($CDCl_3$)
The following signals are shown (δ, ppm). 7.99 and 6.93 (each 2H, d, J=8.9, anisoyl group), 4.43 (1H, d, J=5.0, C14-β-H), 3.87 (3H, s, $OCH_3$ of anisoyl group), 3.69, 3.30, 3.28 and 3.25 (each 3H, s, $OCH_3$ at C1, C6, C16 and C18), 1.11 (3H, t, J=6.9, $CH_3$ of $C_2H_5$ at the nitrogen atom).
5) Analysis of $^{13}$C-NMR spectra ($CDCl_3$)
The following signals are shown (δ, ppm). 165.9 (carbonyl of anisoyl group), 163.6, 131.8, 122.2 and 113.7 (anisoyl group), 94.3, 85.2, 83.7, 80.2, 77.4, 75.1, 72.4 and 72.0 (C16, C6, C1, C14, C18, C13, C15 and C3), 61.8, 59.1, 57.9 and 56.1 ($OCH_3$ at C16, C18, C6, and C1), 55.4 ($OCH_3$ of anisoyl group), 49.1 ($CH_2$ of $C_2H_5$ at the nitrogen atom), 13.4 ($C_3$ of $C_2H_5$ at the nitrogen atom).
6) Analysis of Mass spectra
m/z: 617 ($M^+$).

(2) Physicochemical parameters and analytical data of 3,13-dideoxy-14-O-anisoylaconine
1) Property and solubility
Colorless and amorphous powder. Soluble in ether, chloroform, benzene, ethanol, methanol, ethylacetate, pyridine and dimethyl sulfoxide. Insoluble in hexane and water.
2) Analysis of IR spectra (KBr)
IR $v_{max}^{KBr}$: 3450, 1715 $cm^{-1}$.
3) Analysis of UV spectra (ethanol)
UV $\lambda_{max}^{EtOH}$ (log ε) nm: 258 (4.01).
4) Analysis of $^1$H-NMR spectra ($CDCl_3$)
The following signals are shown (δ, ppm). 7.96 and 6.92 (each 2H, d, J=8.0, anisoyl group), 5.03 (1H, t, J=4.6, C14-β-H), 3.86 (3H, s, $OCH_3$ of anisoyl group), 3.60, 3.31, 3.29 and 3.17 (each 3H, s, $OCH_3$ at C1, C6, C16 and C18), 1.09 (3H, t, J=7.0, $CH_3$ of $C_2H_5$ at the nitrogen atom).
5) Analysis of $^{13}$C-NMR spectra ($CDCl_3$)
The following signals are shown (δ, ppm). 166.0 (carbonyl of anisoyl group), 163.4, 131.9, 122.1 and 113.6 (anisoyl group), 89.5, 85.1, 83.6, 82.0, 80.0, 79.7 and 78.6 (C16, C1, C6, C15, C18, C14 and C8), 59.1, 58.1, 57.9 and 56.1 ($OCH_3$ at C18, C16, C6 and C1), 55.4 ($OCH_3$ of anisoyl group), 48.5 ($CH_2$ of $C_2H_5$ at the nitrogen atom), 13.4 ($CH_3$ of $C_2H_5$ at the nitrogen atom).
6) Analysis of Mass spectra m/z: 597 (M$^+$).

(3) Physicochemical parameters of and analytical data 3,8,13-trideoxy-14-O-anisoylaconine 1) Property and solubility Colorless and amorphous powder. Soluble in ether, chloroform, benzene, ethanol, methanol, ethylacetate, pyridine and dimethyl sulfoxide. Insoluble in hexane and water.

2) Analysis of IR spectra (KBr)

IR $v_{max}^{KBr}$: 3500, 1711 cm$^{-1}$.

3) Analysis of UV spectra (ethanol)

UV $\lambda_{max}^{EtOH}$ (log $\epsilon$) nm: 258 (4.00).

4) Analysis of $^1$H-NMR spectra (CDCl$_3$)

The following signals are shown ($\delta$, ppm). 7.98 and 6.93 (each 2H, d, J=8.9, anisoyl group), 5.01 (1H, t, J=4.5, C14-β-H), 3.87 (3H, s, OCH$_3$ of anisoyl group), 3.60, 3.30, 3.28 and 3.16 (each 3H, s, OCH$_3$ at C1, C6, C16 and C18), 1.10 (3H, t, J=7.0, CH$_3$ of C$_2$H$_5$ at the nitrogen atom).

5) Analysis of $^{13}$C-NMR spectra (CDCl$_3$)

The following signals are shown ($\delta$, ppm). 166.0 (carbonyl of anisoyl group), 163.5, 131.6, 122.1 and 113.8 (anisoyl group), 93.2, 85.1, 84.6, 80.1, 79.9 and 72.0 (C16, C1, C6, C18, C14 and C15), 59.1, 58.3, 58.0 and 56.1 (OCH$_3$ at C16, C18, C6 and C1), 55.3 (OCH$_3$ of anisoyl group), 49.1 (CH$_2$ of C$_2$H$_5$ at the nitrogen atom), 13.4 (CH$_3$ of C$_2$H$_5$ at the nitrogen atom).

6) Analysis of Mass spectra m/z: 585 (M$^+$).

(4) Physicochemical parameters and analytical data of 3,8-dideoxy-14-O-anisoylaconine 1) Property and solubility Colorless and amorphous powder. Soluble in ether, chloroform, benzene, ethanol, methanol, ethylacetate, pyridine and dimethyl sulfoxide. Insoluble in hexane and water.

2) Analysis of IR spectra (KBr)

IR $v_{max}^{KBR}$: 3500, 1710 cm$^{-1}$.

3) Analysis of UV spectra (ethanol)

UV $\lambda_{max}^{EtOH}$ (log $\epsilon$) nm: 258 (4.01).

4) Analysis of $^1$H-NMR spectra (CDCl$_3$)

The following signals are shown ($\delta$, ppm). 7.98 and 6.92 (each 2H, d, J=8.9, anisoyl group), 4.45 (1H, d, J=5.0, C14-β-H), 3.87 (3H, s, OCH$_3$ of anisoyl group), 3.69, 3.30, 3.28 and 3.18 (each 3H, s, OCH$_3$ at C1, C6, C16 and C18), 1.10 (3H, t, J=7.0, CH$_3$ of C$_2$H$_5$ at the nitrogen atom).

5) Analysis of $^{13}$C-NMR spectra (CDCl$_3$)

The following signals are shown ($\delta$, ppm). 165.9 (carbonyl of anisoyl group), 163.5, 131.7, 122.2 and 113.8 (anisoyl group), 94.4, 85.3, 84.3, 80.2, 80.0, 75.0 and 72.5 (C16, C1, C6, C18, C14, C13 and C15), 61.8, 59.1, 57.9 and 56.1 (OCH$_3$ at C16, C18, C6 and C1), 55.4 (OCH$_3$ of anisoyl group), 49.1 (CH$_2$ of C$_2$H$_5$ at the nitrogen atom), 13.4 (CH$_3$ of C$_2$H$_5$ at the nitrogen atom).

6) Analysis of Mass spectra m/z: 601 (M$^+$).

(5) Physicochemical parameters and analytical data of 3-deoxyjesaconitine

1) Property and solubility

Colorless crystal. m.p. 175°–176° C. Soluble in ether, chloroform, benzene, ethanol, methanol, ethylacetate, pyridine and dimethyl sulfoxide. Insoluble in hexane and water.

2) Analysis of IR spectra (KBr)

IR $v_{max}^{KBR}$: 3500, 1715 cm$^{-1}$.

3) Analysis of UV spectra (ethanol)

UV $\lambda_{max}^{EtOH}$ (log $\epsilon$) nm: 257 (4.23).

4) Analysis of $^1$H-NMR spectra (CDCl$_3$)

The following signals are shown ($\delta$, ppm). 7.97 and 6.92 (each 2H, d, J=8.0, anisoyl group), 4.83 (1H, d, J=5.0, C14-β-H), 3.88 (3H, s, OCH$_3$ of anisoyl group), 3.74, 3.30, 3.28 and 3.17 (each 3H, s, OCH$_3$ at C1, C6, C16 and C18), 1.43 (3H, s, CH$_3$ of acetyl group at C8), 1.08 (3H, t, J=7.0, CH$_3$ of C$_2$H$_5$ at the nitrogen atom).

5) Analysis of $^{13}$C-NMR spectra (CDCl$_3$)

The following signals are shown ($\delta$, ppm). 172.4 (carbonyl of acetyl group), 165.8 (carbonyl of anisoyl group), 163.4, 131.6, 122.3 and 113.8 (anisoyl group), 92.1, 90.2, 85.2, 83.3, 80.3, 78.8, 78.7 and 74.2 (C8, C16, C1, C6, C18, C15, C14 and C13), 61.1, 59.1, 58.0 and 56.2 (OCH$_3$ at C16, C18, C6 and C1), 55.5 (OCH$_3$ of anisoyl group), 49.1 (CH$_2$ of C$_2$H$_5$ at the nitrogen atom), 13.4 (CH$_3$ of C$_2$H$_5$ at the nitrogen atom), 21.5 (CH$_3$ of acetyl group).

6) Analysis of Mass spectra m/z: 657 (M$^+$).

(6) Physicochemical parameters and analytical data of 3,13-dideoxyjesaconitine

1) Property and solubility

Colorless and amorphous powder. Soluble in ether, chloroform, benzene, ethanol, methanol, ethylacetate, pyridine and dimethyl sulfoxide. Insoluble in hexane and water.

2) Analysis of IR spectra (KBr)

IR $v_{max}^{KBR}$: 3450, 1715 cm$^{-1}$.

3) Analysis of UV spectra (ethanol)

UV $\lambda_{max}^{EtOH}$ (log $\epsilon$) nm: 257 (4.02).

4) Analysis of $^1$H-NMR spectra (CDCl$_3$)

The following signals are shown ($\delta$, ppm). 7.97 and 6.92 (each 2H, d, J=8.0, anisoyl group), 5.04 (1H, t, J=4.5, C14-β-H), 3.87 (3H, s, OCH$_3$ of anisoyl group), 3.60, 3.30, 3.28 and 3.17 (each 3H, s, OCH$_3$ at C1, C6, C16 and C18), 1.43 (3H, s, CH$_3$ of acetyl group at C8), 1.07 (3H, t, J=7.0, CH$_3$ of C$_2$H$_5$ at the nitrogen atom).

5) Analysis of $^{13}$C-NMR spectra (CDCl$_3$)

The following signals are shown ($\delta$, ppm). 172.4 (carbonyl of acetyl group at C8), 166.0 (carbonyl of anisoyl group), 163.5, 131.5, 122.2 and 113.8 (anisoyl group), 92.0, 89.3, 85.1, 83.6, 80.1, 76.3 and 75.4 (C8, C16, C1, C6, C18, C14 and C15), 59.1, 58.2, 58.0 and 56.0 (OCH$_3$ at C18, C16, C6 and C1), 55.4 (OCH$_3$ of anisoyl group), 49.0 (CH$_2$ of C$_2$H$_5$ at the nitrogen atom), 13.4 (CH$_3$ of C$_2$H$_5$ at the nitrogen atom), 21.5 (CH$_3$ of acetyl group).

6) Analysis of Mass spectra m/z: 641 (M$^+$).

(7) Physicochemical parameters and analytical data of 3-deoxy-14-O-anisoylaconine 1) Property and solubility Colorless and amorphous powder. Soluble in ether, chloroform, benzene, ethanol, methanol, ethylacetate, pyridine and dimethyl sulfoxide. Insoluble in hexane and water.

2) Analysis of IR spectra (KBr)

IR $v_{max}^{KBR}$: 3450, 1710 cm$^{-1}$.

3) Analysis of UV spectra (ethanol)

UV $\lambda_{max}^{EtOH}$ (log $\epsilon$) nm: 258 (3.95).

4) Analysis of $^1$H-NMR spectra (CDCl$_3$)

The following signals are shown ($\delta$, ppm). 7.96 and 6.89 (each 2H, d, J=8.9, anisoyl group), 4.97 (1H, d, J=5.3, C14-β-H), 3.85 (3H, s, OCH$_3$ of anisoyl group), 3.70, 3.31, 3.29 and 3.17 (each 3H, s, OCH$_3$ at C1, C6, C16 and C18), 1.08 (3H, t, J=7.0, CH$_3$ of C$_2$H$_5$ at the nitrogen atom).

5) Analysis of $^{13}$C-NMR spectra (CDCl$_3$)

The following signals are shown ($\delta$, ppm). 165.9 (carbonyl of anisoyl group), 163.5, 131.8, 122.1 and 113.6 (anisoyl group), 90.7, 85.3, 83.3, 81.9, 80.2, 79.5, 78.7 and 74.8 (C16, C1, C6, C15, C18, C14, C8 and C13), 60.9, 59.1, 58.0 and 56.2 (OCH$_3$ at C16, C18, C6 and C1), 55.4 (OCH$_3$ of anisoyl group), 48.4 (CH$_2$ of C$_2$H$_5$ at the nitrogen atom), 13.4 (CH$_3$ of C$_2$H$_5$ at the nitrogen atom).

6) Analysis of Mass spectra m/z: 613 (M$^+$).

(8) Physicochemical parameters and analytical data of 3-deoxy-14-O-benzoylaconine 1) Property and solubility Colorless and amorphous powder. Soluble in ether, chloroform, benzene, ethanol, methanol, ethylacetate, pyridine and dimethyl sulfoxide. Insoluble in hexane and water.

2) Analysis of IR spectra (KBr)

IR $v_{max}^{KBR}$: 3500, 1710 cm$^{-1}$.

3) Analysis of UV spectra (ethanol)

UV $\lambda_{max}^{EtOH}$ (log $\epsilon$) nm: 229.5 (3.95).

4) Analysis of $^1$H-NMR spectra (CDCl$_3$)

The following signals are shown ($\delta$, ppm). 7.40–8.18 (5H, m, benzoyl group), 4.85 (1H, d, J=4.5, C14-$\beta$-H), 3.71, 3.24, 3.24 and 3.14 (each 3H, s, OCH$_3$ at C1, C6, C16 and C18), 1.08 (3H, t, J=7.0, CH$_3$ of C$_2$H$_5$ at the nitrogen atom).

5) Analysis of $^{13}$C-NMR spectra (CDCl$_3$)

The following signals are shown ($\delta$, ppm). 165.9 (carbonyl of benzoyl group), 133.1, 129.9, 129.5 and 128.5 (benzoyl group), 90.6, 85.4, 83.2, 81.6, 80.2, 79.4, 78.7 and 74.0 (C16, C1, C6, C15, C18, C14, C8 and C13), 60.9, 59.1, 57.8 and 56.0 (OCH$_3$ at C16, C18, C6 and C1), 49.0 (CH$_2$ of C$_2$H$_5$ at the nitrogen atom), 13.4 (CH$_3$ of C$_2$H$_5$ at the nitrogen atom).

6) Analysis of Mass spectra m/z: 587 (M$^+$).

(9) Physicochemical parameters and analytical data of 3,13-dideoxy-14-O-benzoylaconine 1) Property and solubility Colorless and amorphous powder. Soluble in ether, chloroform, benzene, ethanol, methanol, ethylacetate, pyridine and dimethyl sulfoxide. Insoluble in hexane and water.

2) Analysis of IR spectra (KBr)

IR $v_{max}^{KBR}$: 3500, 1715 cm$^{-1}$.

3) Analysis of UV spectra (ethanol)

UV $\lambda_{max}^{EtOH}$ (log $\epsilon$) nm: 231 (3.95).

4) Analysis of $^1$H-NMR spectra (CDCl$_3$)

The following signals are shown ($\delta$, ppm). 7.38–8.14 (5H, m, benzoyl group), 5.04 (1H, t, J=4.5, C14-$\beta$-H), 3.52, 3.28, 3.26 and 3.17 (each 3H, s, OCH$_3$ at C1, C6, C16 and C18), 1.07 (3H, t, J=7.0, CH$_3$ of C$_2$H$_5$ at the nitrogen atom).

5) Analysis of $^{13}$C-NMR spectra (CDCl$_3$)

The following signals are shown ($\delta$, ppm). 166.0 (carbonyl of benzoyl group), 133.1, 130.0, 129.5 and 128.5 (benzoyl group), 89.3, 85.3, 83.2, 81.8, 80.3, 79.3 and 78.5 (C16, C1, C6, C15, C18, C14 and C8), 59.0, 57.9, 57.6 and 56.0 (OCH$_3$ at C18, C16, C6 and C1), 49.1 (CH$_2$ of C$_2$H$_5$ at the nitrogen atom), 13.4 (CH$_3$ of C$_2$H$_5$ at the nitrogen atom).

6) Analysis of Mass spectra m/z: 571 (M$^+$).

(10) Physicochemical parameters and analytical data of 8-deoxy-14-O-benzoylaconine 1) Property and solubility Colorless and amorphous powder. Soluble in ether, chloroform, benzene, ethanol, methanol, ethylacetate, pyridine and dimethyl sulfoxide. Insoluble in hexane and water.

2) Analysis of IR spectra (KBr)

IR $v_{max}^{KBR}$: 3500, 1710 cm$^{-1}$.

3) Analysis of UV spectra (ethanol)

UV $\lambda_{max}^{EtOH}$ (log $\epsilon$) nm: 229.5 (4.01).

4) Analysis of $^1$H-NMR spectra (CDCl$_3$)

The following signals are shown ($\delta$, ppm). 7.40–8.12 (5H, m, benzoyl group), 4.47 (1H, d, J=5.0, C14-$\beta$-H), 3.68, 3.28, 3.28 and 3.18 (each 3H, s, OCH$_3$ at C1, C6, C16 and C18), 1.07 (3H, t, J=7.0, CH$_3$ of C$_2$H$_5$ at the nitrogen atom).

5) Analysis of $^{13}$C-NMR spectra (CDCl$_3$)

The following signals are shown ($\delta$, ppm). 165.8 (carbonyl of benzoyl group), 133.2, 130.0, 129.6 and 128.6 (benzoyl group), 94.2, 85.2, 83.7, 80.1, 77.5, 75.2, 72.4 and 71.9 (C16, C6, C1, C14, C18, C13, C15 and C3), 60.9, 59.0, 57.9 and 56.1 (OCH$_3$ at C16, C18, C6 and C1), 49.0 (CH$_2$ of C$_2$H$_5$ at the nitrogen atom), 13.5 (CH$_3$ of C$_2$H$_5$ at the nitrogen atom).

6) Analysis of Mass spectra m/z: 587 (M$^+$).

(11) Physicochemical parameters and analytical data of 3,8-dideoxy-14-O-benzoylaconine 1) Property and solubility Colorless and amorphous powder. Soluble in ether, chloroform, benzene, ethanol, methanol, ethylacetate, pyridine and dimethyl sulfoxide. Insoluble in hexane and water.

2) Analysis of IR spectra (KBr)

IR $v_{max}^{KBR}$: 3500, 1715 cm$^{-1}$.

3) Analysis of UV spectra (ethanol)

UV $\lambda_{max}^{EtOH}$ (log $\epsilon$) nm: 231 (3.98).

4) Analysis of $^1$H-NMR spectra (CDCl$_3$)

The following signals are shown ($\delta$, ppm). 7.40–8.15 (5H, m, benzoyl group), 4.48 (1H, d, J=5.0, C14-$\beta$-H), 3.72, 3.29, 3.29 and 3.18 (each 3H, s, OCH$_3$ at C1, C6, C16 and C18), 1.08 (3H, t, J=7.0, CH$_3$ of C$_2$H$_5$ at the nitrogen atom).

5) Analysis of $^{13}$C-NMR spectra (CDCl$_3$)

The following signals are shown ($\delta$, ppm). 165.9 (carbonyl of benzoyl group), 133.1, 130.0, 129.6 and 128.6 (benzoyl group), 94.2, 85.2, 84.3, 80.2, 80.0 and 72.5 (C16, C1, C6, C18, C14 and C15), 60.9, 59.0, 57.9 and 56.1 (OCH$_3$ at C16, C18, C6 and C1), 49.0 (CH$_2$ of C$_2$H$_5$ at the nitrogen atom), 13.5 (CH$_3$ of C$_2$H$_5$ at the nitrogen atom).

6) Analysis of Mass spectra m/z: 571 (M$^+$).

(12) Physicochemical parameters and analytical data of 3,8,13-trideoxy-14-O-benzoylaconine 1) Property and solubility Colorless and amorphous powder. Soluble in ether, chloroform, benzene, ethanol, methanol, ethylacetate, pyridine and dimethyl sulfoxide. Insoluble in hexane and water.

2) Analysis of IR spectra (KBr)

IR $v_{max}^{KBR}$: 3450, 1710 cm$^{-1}$.

3) Analysis of UV spectra (ethanol)

UV $\lambda_{max}^{EtOH}$ (log $\epsilon$) nm: 230 (3.98).

4) Analysis of $^1$H-NMR spectra (CDCl$_3$)

The following signals are shown ($\delta$, ppm). 7.38–8.15 (5H, m, benzoyl group), 5.02 (1H, t, J=4.5, C14-$\beta$-H), 3.52, 3.28, 3.28 and 3.18 (each 3H, s, OCH$_3$ at C 1, C6, C 16 and C 18), 1.07 (3H, t, J=7.0, CH$_3$ of C$_2$H$_5$ at the nitrogen atom).

5) Analysis of $^{13}$C-NMR spectra (CDCl$_3$)

The following signals are shown ($\delta$, ppm). 166.0 (carbonyl of benzoyl group), 133.1, 130.0, 129.7 and 128.6 (benzoyl group), 93.2, 85.2, 84.5, 80.2, 79.9 and 72.0 (C16, C1, C6, C18, C14, and C15), 59.2, 57.9, 57.6 and 56.0 (OCH$_3$ at C18, C16, C6 and C1), 49.1 (CH$_2$ of C$_2$H$_5$ at the nitrogen atom), 13.4 (CH$_3$ of C$_2$H$_5$ at the nitrogen atom).

6) Analysis of Mass spectra m/z: 555 (M$^+$).

(13) Physicochemical parameters and analytical data of 3-deoxyaconitine

1) Property and solubility

Colorless crystal. m.p. 178°–180° C. Soluble in ether, chloroform, benzene, ethanol, methanol, ethylacetate, pyridine and dimethyl sulfoxide. Insoluble in hexane and water.

2) Analysis of IR spectra (KBr)

IR $v_{max}^{KBR}$: 3450, 1715 cm$^{-1}$.

3) Analysis of UV spectra (ethanol)

UV $\lambda_{max}^{EtOH}$ (log $\epsilon$) nm: 230 (4.01).

4) Analysis of $^1$H-NMR spectra (CDCl$_3$)

The following signals are shown ($\delta$, ppm). 7.40–8.18 (5H, m, benzoyl group), 4.86 (1H, d, J=4.5, C14-$\beta$-H), 3.72, 3.24, 3.24 and 3.14 (each 3H, s, OCH$_3$ at C1, C6, C16 and C18), 1.36 (3H, s, CH$_3$ of acetyl group at C8), 1.06 (3H, t, J=7.0, CH$_3$ of C$_2$H$_5$ at the nitrogen atom).

5) Analysis of $^{13}$C-NMR spectra (CDCl$_3$)

The following signals are shown (δ, ppm). 172.2 (carbonyl of acetyl group at C8), 165.9 (carbonyl of benzoyl group), 133.1, 129.9, 129.5 and 128.5 (benzoyl group), 92.0, 90.2, 85.2, 83.3, 80.2, 79.0, 78.8 and 74.0 (C8, C16, C1, C6, C18, C15, C14 and C13), 60.9, 59.0, 57.9 and 56.0 (OCH$_3$ at C16, C18, C6 and C1), 49.1 (CH$_2$ of C$_2$H$_5$ at the nitrogen atom), 13.4 (CH$_3$ of C$_2$H$_5$ at the nitrogen atom), 21.3 (CH$_3$ of acetyl group).
6) Analysis of Mass spectra
m/z: 629 (M$^+$).
(14) Physicochemical parameters and analytical data of 3,13-dideoxyaconitine
Colorless crystal. m.p. 165°–166° C. Soluble in ether, chloroform, benzene, ethanol, methanol, ethylacetate, pyridine and dimethyl sulfoxide. Insoluble in hexane and water.
2) Analysis of IR spectra (KBr)
IR $v_{max}^{KBR}$: 3450, 1715 cm$^{-1}$.
3) Analysis of UV spectra (ethanol)
UV $\lambda_{max}^{EtOH}$ (log ε) nm: 231 (3.95).
4) Analysis of $^1$H-NMR spectra (CDCl$_3$)
The following signals are shown (δ, ppm). 7.38–8.14 (5H, m, benzoyl group), 5.05 (1H, t, J=4.5, C14-β-H), 3.52, 3.28, 3.29 and 3.18 (each 3H, s, OCH$_3$ at C1, C6, C16 and C18), 1.43 (3H, s, CH$_3$ of acetyl group at C8), 1.06 (3H, t, J=7.0, CH$_3$ of C$_2$H$_5$ at the nitrogen atom).
5) Analysis of $^{13}$C-NMR spectra (CDCl$_3$)
The following signals are shown (δ, ppm). 172.2 (carbonyl of acetyl group at C8), 166.0 (carbonyl of benzoyl group), 133.1, 130.0, 129.5 and 128.5 (benzoyl group), 92.1, 89.2, 85.2, 83.6, 80.2, 76.2 and 75.4 (C8, C16, C1, C6, C18, C14 and C15), 59.0, 57.9, 57.6 and 56.0 (OCH$_3$ at C18, C16, C6 and C1), 49.2 (CH$_2$ of C$_2$H$_5$ at the nitrogen atom), 13.4 (CH$_3$ of C$_2$H$_5$ at the nitrogen atom), 21.4 (CH$_3$ of acetyl group at C8).
6) Analysis of Mass spectra
m/z: 613 (M$^+$).
(15) Physicochemical parameters and analytical data of 8-deoxy-14-O-benzoylmesaconine
1) Property and solubility
Colorless and amorphous powder. Soluble in ether, chloroform, benzene, ethanol, methanol, ethylacetate, pyridine and dimethyl sulfoxide. Insoluble in hexane and water.
2) Analysis of IR spectra (KBr)
IR $v_{max}^{KBR}$: 3500, 1720 cm$^{-1}$.
3) Analysis of UV spectra (ethanol)
UV $\lambda_{max}^{EtOH}$ (log ε) nm: 229 (4.01).
4) Analysis of $^1$H-NMR spectra (CDCl$_3$)
The following signals are shown (δ, ppm). 7.40–8.08 (5H, m, benzoyl group), 4.50 (1H, d, J=5.0, C14-β-H), 3.60, 3.29, 3.29 and 3.17 (each 3H, s, OCH$_3$ at C1, C6, C16 and C18), 2.36 (3H, s, CH$_3$ at the nitrogen atom).
5) Analysis of $^{13}$C-NMR spectra (CDCl$_3$)
The following signals are shown (δ, ppm). 165.7 (carbonyl of benzoyl group), 132.9, 129.3 and 128.3 (benzoyl group), 94.1, 85.2, 83.7, 80.1, 77.5, 74.0 and 72.8 (C16, C6, C1, C14, C18, C13 and C15), 60.7, 58.8, 57.8 and 55.8 (OCH$_3$ at C16, C18, C6 and C1), 42.3 (CH$_3$ at the nitrogen atom).
6) Analysis of Mass spectra
m/z: 589 (M$^+$).
(16) Physicochemical parameters and analytical data of 3,13-dideoxy-14-O-benzoylmesaconine
1) Property and solubility
Colorless and amorphous powder. Soluble in ether, chloroform, benzene, ethanol, methanol, ethylacetate, pyridine and dimethyl sulfoxide. Insoluble in hexane and water.
2) Analysis of IR spectra (KBr)
IR $v_{max}^{KBR}$: 3500, 1715 cm$^{-1}$.
3) Analysis of UV spectra (ethanol)
UV $\lambda_{max}^{EtOH}$ (log ε) nm: 231 (3.95).
4) Analysis of $^1$H-NMR spectra (CDCl$_3$)
The following signals are shown (δ, ppm). 7.41–8.22 (5H, m, benzoyl group), 5.03 (1H, t, J=4.3, C14-β-H), 3.53, 3.28, 3.28 and 3.17 (each 3H, s, OCH$_3$ at C1, C6, C16 and C18), 2.35 (3H, s, CH$_3$ at the nitrogen atom).
5) Analysis of $^{13}$C-NMR spectra (CDCl$_3$)
The following signals are shown (δ, ppm). 165.8 (carbonyl of benzoyl group), 133.1, 129.7 and 128.5 (benzoyl group), 89.4, 85.3, 83.2, 81.7, 80.2, 79.2 and 78.5 (C16, C1, C6, C15, C18, C14 and C8), 59.1, 58.0, 57.6 and 56.3 (OCH$_3$ at C18, C16, C6 and C1), 42.3 (CH$_3$ at the nitrogen atom).
6) Analysis of Mass spectra
m/z: 557 (M$^+$).
(17) Physicochemical parameters and analytical data of 3,13-dideoxymesaconitine
1) Property and solubility
Colorless crystal. m.p. 159°–161° C. Soluble in ether, chloroform, benzene, ethanol, methanol, ethylacetate, pyridine and dimethyl sulfoxide. Insoluble in hexane and water.
2) Analysis of IR spectra (KBr)
IR $v_{max}^{KBR}$: 3500, 1720 cm$^{-1}$.
3) Analysis of UV spectra (ethanol)
UV $\lambda_{max}^{EtOH}$ (log ε) nm: 229.5 (4.03).
4) Analysis of $^1$H-NMR spectra (CDCl$_3$)
The following signals are shown (δ, ppm). 7.40–8.20 (5H, m, benzoyl group), 5.05 (1H, t, J=4.3, C14-β-H), 3.52, 3.28, 3.28 and 3.18 (each 3H, s, OCH$_3$ at C1, C6, C16 and C18), 2.35 (3H, s, CH$_3$ at the nitrogen atom), 1.43 (3H, s, CH$_3$ of acetyl group at C8).
5) Analysis of $^{13}$C-NMR spectra (CDCl$_3$)
The following signals are shown (δ, ppm). 172.2 (carbonyl of acetyl group at C8), 166.0 (carbonyl of benzoyl group), 133.0, 129.6 and 128.5 (benzoyl group), 92.0, 89.2, 85.1, 83.6, 80.1, 76.3 and 75.5 (C8, C16, C1, C6, C18, C14 and C15), 59.0, 57.9, 57.6 and 56.4 (OCH$_3$ at C18, C16, C6 and C1), 42.6 (CH$_3$ at the nitrogen atom), 21.4 (CH$_3$ of acetyl group).
6) Analysis of Mass spectra
m/z: 599 (M$^+$).
(18) Physicochemical parameters and analytical data of 3,8,13-trideoxy-14-O-benzoylmesaconine
1) Property and solubility
Colorless and amorphous powder. Soluble in ether, chloroform, benzene, ethanol, methanol, ethylacetate, pyridine and dimethyl sulfoxide. Insoluble in hexane and water.
2) Analysis of IR spectra (KBr)
IR $v_{max}^{KBR}$: 3500, 1720 cm$^{-1}$.
3) Analysis of UV spectra (ethanol)
UV $\lambda_{max}^{EtOH}$ (log ε) nm: 230 (4.00).
4) Analysis of $^1$H-NMR spectra (CDCl$_3$)
The following signals are shown (δ, ppm). 7.41–8.22 (5H, m, benzoyl group), 5.02 (1H, t, J=4.3, C14-β-H), 3.53, 3.29, 3.29 and 3.18 (each 3H, s, OCH$_3$ at C1, C6, C16 and C18), 2.34 (3H, s, CH$_3$ at the nitrogen atom).
5) Analysis of $^{13}$C-NMR spectra (CDCl$_3$)
The following signals are shown (δ, ppm). 165.9 (carbonyl of benzoyl group), 133.0, 129.6 and 128.3 (benzoyl group), 93.1, 85.3, 84.4, 80.3, 80.0 and 72.1 (C16, C1, C6, C18, C14 and C15), 59.0, 58.0, 57.7 and 56.5 (OCH$_3$ at C18, C16, C6 and C1), 42.3 (CH$_3$ at the nitrogen atom).
6) Analysis of Mass spectra
m/z: 557 (M$^+$).
(19) Physicochemical parameters and analytical data of 3,8-dideoxy-14-O-benzoylmesaconine 1) Property and solubility Colorless and amorphous powder. Soluble in ether, chloroform, benzene, ethanol, methanol, ethylacetate, pyridine and dimethyl sulfoxide. Insoluble in hexane and water.

2) Analysis of IR spectra (KBr)
   IR $\nu_{max}^{KBR}$: 3450, 1715 cm$^{-1}$.

3) Analysis of UV spectra (ethanol)
   UV $\lambda_{max}^{EtOH}$ (log ε) nm: 230 (4.02).

4) Analysis of $^1$H-NMR spectra (CDCl$_3$)
   The following signals are shown (δ, ppm). 7.41–8.05 (5H, m, benzoyl group), 4.48 (1H, d, J=5.0, C14-β-H), 3.69, 3.30, 3.30 and 3.16 (each 3H, s, OCH$_3$ at C1, C6, C16 and C18), 2.35 (3H, s, CH$_3$ at the nitrogen atom).

5) Analysis of $^{13}$C-NMR spectra (CDCl$_3$)
   The following signals are shown (δ, ppm). 165.8 (carbonyl of benzoyl group), 133.0, 129.5 and 128.3 (benzoyl group), 94.2, 85.2, 84.2, 80.2, 80.0, 74.0 and 72.6 (C16, C1, C6, C18, C14, C13 and C15), 60.8, 58.9, 57.7 and 55.6 (OCH$_3$ at C16, C18, C6 and C1), 42.5 (CH$_3$ at the nitrogen atom).

6) Analysis of Mass spectra
   m/z: 573 (M$^+$).

(20) Physicochemical parameters and analytical data of 14-O-anisoylmesaconine

1) Property and solubility
   Colorless and amorphous powder. Soluble in ether, chloroform, benzene, ethanol, methanol, ethylacetate, pyridine and dimethyl sulfoxide. Insoluble in hexane and water.

2) Analysis of IR spectra (KBr)
   IR $\nu_{max}^{KBR}$: 3450, 1711 cm$^{-1}$.

3) Analysis of UV spectra (ethanol)
   UV $\lambda_{max}^{EtOH}$ (log ε) nm: 258 (4.01).

4) Analysis of $^1$H-NMR spectra (CDCl$_3$)
   The following signals are shown (δ, ppm). 7.96 and 6.89 (each 2H, d, J=8.9, anisoyl group), 4.96 (1H, d, J=5.3, C14-β-H), 3.85 (3H, s, OCH$_3$ of anisoyl group), 3.70, 3.31, 3.29 and 3.24 (each 3H, s, OCH$_3$ at C1, C6, C16 and C18), 2.35 (3H, s, CH$_3$ at the nitrogen atom).

5) Analysis of $^{13}$C-NMR spectra (CDCl$_3$)
   The following signals are shown (δ, ppm). 165.9 (carbonyl of anisoyl group), 163.5, 131.8, 122.1 and 113.5 (anisoyl group), 90.6, 83.6, 82.5, 81.8, 79.3, 78.8, 77.4, 74.8 and 71.9 (C16, C6, C1, C15, C14, C8, C18, C13 and C3), 60.9, 59.1, 58.0 and 55.7 (OCH$_3$ at C16, C18, C6 and C1), 55.4 (OCH$_3$ of anisoyl group), 42.3 (CH$_3$ at the nitrogen atom).

6) Analysis of Mass spectra
   m/z: 615 (M$^+$).

(21) Physicochemical parameters and analytical data of 8-deoxy-14-O-anisoylmesaconine 1) Property and solubility
   Colorless and amorphous powder. Soluble in ether, chloroform, benzene, ethanol, methanol, ethylacetate, pyridine and dimethyl sulfoxide. Insoluble in hexane and water.

2) Analysis of IR spectra (KBr)
   IR $\nu_{max}^{KBR}$: 3450, 1715 cm$^{-1}$.

3) Analysis of UV spectra (ethanol)
   UV $\lambda_{max}^{EtOH}$ (log ε) nm: 258 (4.00).

4) Analysis of $^1$H-NMR spectra (CDCl$_3$)
   The following signals are shown (δ, ppm). 7.99 and 6.93 (each 2H, d, J=8.9, anisoyl group), 4.46 (1H, d, J=5.0, C14-β-H), 3.87 (3H, s, OCH$_3$ of anisoyl group), 3.69, 3.31, 3.27 and 3.24 (each 3H, s, OCH$_3$ at C1, C6, C16 and C18), 2.34 (3H, s, CH$_3$ at the nitrogen atom).

5) Analysis of $^{13}$C-NMR spectra (CDCl$_3$)
   The following signals are shown (δ, ppm). 165.9 (carbonyl of anisoyl group), 163.5, 131.8, 122.1 and 113.8 (anisoyl group), 94.2, 85.3, 83.7, 80.2, 77.8, 75.0, 72.6 and 72.0 (C16, C6, C1, C14, C18, C13, C15 and C3), 61.8, 59.1, 58.0 and 56.0 (OCH$_3$ at C16, C18, C6 and C1), 55.4 (OCH$_3$ of anisoyl group), 42.4 (CH$_3$ at the nitrogen atom).

6) Analysis of Mass spectra
   m/z: 603 (M$^+$).

(22) Physicochemical parameters and analytical data of 3-deoxy-14-O-anisoylmesaconine 1) Property and solubility
   Colorless and amorphous powder. Soluble in ether, chloroform, benzene, ethanol, methanol, ethylacetate, pyridine and dimethyl sulfoxide. Insoluble in hexane and water.

2) Analysis of IR spectra (KBr)
   IR $\nu_{max}^{KBR}$: 3500, 1715 cm$^{-1}$.

3) Analysis of UV spectra (ethanol)
   UV $\lambda_{max}^{EtOH}$ (log ε) nm: 257 (4.01).

4) Analysis of $^1$H-NMR spectra (CDCl$_3$)
   The following signals are shown (δ, ppm). 7.96 and 6.89 (each 2H, d, J=8.9, anisoyl group), 4.96 (1H, d, J=5.3, C14-β-H), 3.85 (3H, s, OCH$_3$ of anisoyl group), 3.72, 3.30, 3.28 and 3.16 (each 3H, s, OCH$_3$ at C1, C6, C16 and C18), 2.34 (3H, s, CH$_3$ at the nitrogen atom).

5) Analysis of $^{13}$C-NMR spectra (CDCl$_3$)
   The following signals are shown (δ, ppm). 166.0 (carbonyl of anisoyl group), 163.5, 131.8, 122.1 and 113.6 (anisoyl group), 90.7, 85.2, 83.1, 81.4, 80.2, 79.4, 78.7 and 75.3 (C16, C1, C6, C15, C18, C14, C8 and C13), 60.9, 59.1, 58.0 and 56.2 (OCH$_3$ at C16, C18, C6 and C1), 55.4 (OCH$_3$ of anisoyl group), 42.3 (CH$_3$ at the nitrogen atom).

6) Analysis of Mass spectra
   m/z: 599 (M$^+$).

(23) Physicochemical parameters and analytical data of 3,8-dideoxy-14-O-anisoylmesaconine 1) Property and solubility
   Colorless and amorphous powder. Soluble in ether, chloroform, benzene, ethanol, methanol, ethylacetate, pyridine and dimethyl sulfoxide. Insoluble in hexane and water.

2) Analysis of IR spectra (KBr)
   IR $\nu_{max}^{KBR}$: 3450, 1710 cm$^{-1}$.

3) Analysis of UV spectra (ethanol)
   UV $\lambda_{max}^{EtOH}$ (log ε) nm: 257 (4.01).

4) Analysis of $^1$H-NMR spectra (CDCl$_3$)
   The following signals are shown (δ, ppm). 7.99 and 6.92 (each 2H, d, J=8.9, anisoyl group), 4.47 (1H, d, J=5.0, C14-β-H), 3.88 (3H, s, OCH$_3$ of anisoyl group), 3.70, 3.30, 3.27 and 3.16 (each 3H, s, OCH$_3$ at C1, C6, C16 and C18), 2.34 (3H, s, CH$_3$ at the nitrogen atom).

5) Analysis of $^{13}$C-NMR spectra (CDCl$_3$)
   The following signals are shown (δ, ppm). 165.9 (carbonyl of anisoyl group), 163.5, 131.8, 122.2 and 113.8 (anisoyl group), 94.1, 85.2, 84.3, 80.1, 80.0, 74.3 and 72.7 (C16, C1, C6, C18, C14, C13 and C15), 61.7, 59.0, 57.9 and 56.1 (OCH$_3$ at C16, C18, C6 and C1), 55.4 (OCH$_3$ of anisoyl group), 42.4 (CH$_3$ at the nitrogen atom).

6) Analysis of Mass spectra
   m/z: 587 (M$^+$).

(24) Physicochemical parameters and analytical data of 3,13-dideoxy-14-O-anisoylmesaconine 1) Property and solubility
   Colorless and amorphous powder. Soluble in ether, chloroform, benzene, ethanol, methanol, ethylacetate, pyridine and dimethyl sulfoxide. Insoluble in hexane and water.

2) Analysis of IR spectra (KBr)
   IR $\nu_{max}^{KBR}$: 3450, 1710 cm$^{-1}$.

3) Analysis of UV spectra (ethanol)
   UV $\lambda_{max}^{EtOH}$ (log ε) nm: 257 (4.00).

4) Analysis of $^1$H-NMR spectra (CDCl$_3$)
   The following signals are shown (δ, ppm). 7.95 and 6.92 (each 2H, d, J=8.1, anisoyl group), 5.02 (1H, t, J=5.0, C14-β-H), 3.87 (3H, s, OCH$_3$ of anisoyl group), 3.60, 3.31, 3.28 and 3.16 (each 3H, s, OCH$_3$ at C1, C6, C16 and C18), 2.33 (3H, s, CH$_3$ at the nitrogen atom).

5) Analysis of $^{13}$C-NMR spectra (CDCl$_3$)

The following signals are shown (δ, ppm). 166.0 (carbonyl of anisoyl group), 163.4, 131.9, 122.1 and 113.5 (anisoyl group), 89.4, 85.3, 83.4, 81.6, 80.1, 79.3 and 78.7 (C16, C1, C6, C15, C18, C14 and C8), 59.2, 58.1, 57.9 and 56.0 (OCH$_3$ at C18, C16, C6 and C1), 55.4 (OCH$_3$ of anisoyl group), 42.3 (CH$_3$ at the nitrogen atom).

6) Analysis of Mass spectra m/z: 583 (M$^+$).

(25) Physicochemical parameters and analytical data of 3,8,13-trideoxy-14-O-anisoylmesaconine 1) Property and solubility Colorless and amorphous powder. Soluble in ether, chloroform, benzene, ethanol, methanol, ethylacetate, pyridine and dimethyl sulfoxide. Insoluble in hexane and water.

2) Analysis of IR spectra (KBr)

IR $v_{max}^{KBR}$: 3500, 1710 cm$^{-1}$.

3) Analysis of UV spectra (ethanol)

UV $\lambda_{max}^{EtOH}$ (log ε) nm: 258 (4.01).

4) Analysis of $^1$H-NMR spectra (CDCl$_3$)

The following signals are shown (δ, ppm). 7.98 and 6.93 (each 2H, d, J=8.9, anisoyl group), 5.01 (1H, t, J=4.5, C14-β-H), 3.88 (3H, s, OCH$_3$ of anisoyl group), 3.60, 3.30, 3.28 and 3.16 (each 3H, s, OCH$_3$ at C1, C6, C16 and C18), 2.34 (3H, s, CH$_3$ at the nitrogen atom).

5) Analysis of $^{13}$C-NMR spectra (CDCl$_3$)

The following signals are shown (δ, ppm). 166.0 (carbonyl of anisoyl group), 163.4, 131.5, 122.1 and 113.8 (anisoyl group), 93.3, 85.3, 84.5, 80.3, 80.1 and 72.2 (C16, C1, C6, C18, C14 and C15), 59.2, 58.0, 57.8 and 56.1 (OCH$_3$ at C16, C18, C6 and C1), 55.3 (OCH$_3$ of anisoyl group), 42.3 (CH$_3$ at the nitrogen atom).

6) Analysis of Mass spectra m/z: 571 (M$^+$).

(26) Physicochemical parameters and analytical data of 16-epi-8-deoxy-14-O-anisoylaconine 1) Property and solubility Colorless and amorphous powder. Soluble in ether, chloroform, benzene, ethanol, methanol, ethylacetate, pyridine and dimethyl sulfoxide. Insoluble in hexane and water.

2) Analysis of IR spectra (KBr)

IR $v_{max}^{KBR}$: 3500, 1711 cm$^{-1}$.

3) Analysis of UV spectra (ethanol)

UV $\lambda_{max}^{EtOH}$ (log ε) nm: 257 (4.02).

4) Analysis of $^1$H-NMR spectra (CDCl$_3$)

The following signals are shown (δ, ppm). 7.99 and 6.93 (each 2H, d, J=8.9, anisoyl group), 4.68 (1H, d, J=5.0, C14-β-H), 3.87 (3H, s, OCH$_3$ of anisoyl group), 3.84, 3.30, 3.28 and 3.25 (each 3H, s, OCH$_3$ at C1, C6, C16 and C18), 1.13 (3H, t, J=6.9, CH$_3$ of C$_2$H$_5$ at the nitrogen atom).

5) Analysis of $^{13}$C-NMR spectra (CDCl$_3$)

The following signals are shown (δ, ppm). 164.9 (carbonyl of anisoyl group), 163.6, 131.8, 122.2 and 113.7 (anisoyl group), 91.3, 85.2, 83.7, 79.2, 77.4, 75.9, 72.4 and 72.0 (C16, C6, C1, C14, C18, C13, C15 and C3), 62.2, 59.1, 57.9 and 56.1 (OCH$_3$ at C16, C18, C6 and C1), 55.4 (OCH$_3$ of anisoyl group), 49.1 (CH$_2$ of C$_2$H$_5$ at the nitrogen atom), 13.4 (CH$_3$ of C$_2$H$_5$ at the nitrogen atom).

6) Analysis of Mass spectra m/z: 617 (M$^+$).

(27) Physicochemical parameters and analytical data of 16-epi-3,8-dideoxy-14-O-anisoylaconine 1) Property and solubility Colorless and amorphous powder. Soluble in ether, chloroform, benzene, ethanol, methanol, ethylacetate, pyridine and dimethyl sulfoxide. Insoluble in hexane and water.

2) Analysis of IR spectra (KBr)

IR $v_{max}^{KBR}$: 3500, 1710 cm$^{-1}$.

3) Analysis of UV spectra (ethanol)

UV $\lambda_{max}^{EtOH}$ (log ε) nm: 258 (4.01).

4) Analysis of $^1$H-NMR spectra (CDCl$_3$)

The following signals are shown (δ, ppm). 7.98 and 6.92 (each 2H, d, J=8.9, anisoyl group), 4.68 (1H, d, J=5.0, C14-β-H), 3.87 (3H, s, OCH$_3$ of anisoyl group), 3.86, 3.30, 3.28 and 3.18 (each 3H, s, OCH$_3$ at C1, C6, C16 and C18), 1.11 (3H, t, J=7.0, CH$_3$ of C$_2$H$_5$ at the nitrogen atom).

5) Analysis of $^{13}$C-NMR spectra (CDCl$_3$)

The following signals are shown (δ, ppm). 164.9 (carbonyl of anisoyl group), 163.5, 131.7, 122.2 and 113.8 (anisoyl group), 91.4, 85.3, 84.2, 80.2, 79.0, 75.8 and 72.4 (C16, C1, C6, C18, C14, C13 and C15), 61.2, 59.1, 57.9 and 56.1 (OCH$_3$ at C16, C18, C6 and C1), 55.4 (OCH$_3$ of anisoyl group), 49.1 (CH$_2$ of C$_2$H$_5$ at the nitrogen atom), 13.4 (CH$_3$ of C$_2$H$_5$ at the nitrogen atom).

6) Analysis of Mass spectra m/z: 601 (M$^+$).

(28) Physicochemical parameters and analytical data of 16-epi-3,8,13-trideoxy-14-O-anisoylaconine 1) Property and solubility Colorless and amorphous powder. Soluble in ether, chloroform, benzene, ethanol, methanol, ethylacetate, pyridine and dimethyl sulfoxide. Insoluble in hexane and water.

2) Analysis of IR spectra (KBr)

IR $v_{max}^{KBR}$: 3500, 1711 cm$^{-1}$.

3) Analysis of UV spectra (ethanol)

UV $\lambda_{max}^{EtOH}$ (log ε) nm: 258 (4.00).

4) Analysis of $^1$H-NMR spectra (CDCl$_3$)

The following signals are shown (δ, ppm). 7.98 and 6.93 (each 2H, d, J=8.9, anisoyl group), 5.26 (1H, t, J=4.5, C14-β-H), 3.87 (3H, s, OCH$_3$ of anisoyl group), 3.80, 3.30, 3.28 and 3.16 (each 3H, s, OCH$_3$ at C1, C6, C16 and C18), 1.10 (3H, t, J=7.0, CH$_3$ of C$_2$H$_5$ at the nitrogen atom).

5) Analysis of $^{13}$C-NMR spectra (CDCl$_3$)

The following signals are shown (δ, ppm). 165.0 (carbonyl of anisoyl group), 163.5, 131.6, 122.1 and 113.8 (anisoyl group), 90.2, 85.1, 84.5, 79.9, 78.9 and 72.0 (C16, C1, C6, C18, C14 and C15), 59.5, 58.3, 58.0 and 56.1 (OCH$_3$ at C16, C18, C6 and C1), 55.3 (OCH$_3$ of anisoyl group), 49.1 (CH$_2$ of C$_2$H$_5$ at the nitrogen atom), 13.4 (CH$_3$ of C$_2$H$_5$ at the nitrogen atom).

6) Analysis of Mass spectra m/z: 585 (M$^+$).

(29) Physicochemical parameters and analytical data of 16-epi-8-deoxy-14-O-benzoylaconine 1) Property and solubility Colorless and amorphous powder. Soluble in ether, chloroform, benzene, ethanol, methanol, ethylacetate, pyridine and dimethyl sulfoxide. Insoluble in hexane and water.

2) Analysis of IR spectra (KBr)

IR $v_{max}^{KBR}$: 3500, 1710 cm$^{-1}$.

3) Analysis of UV spectra (ethanol)

UV $\lambda_{max}^{EtOH}$ (log ε) nm: 229.5 (4.01).

4) Analysis of $^1$H-NMR spectra (CDCl$_3$)

The following signals are shown (δ, ppm). 7.40–8.12 (5H, m, benzoyl group), 4.72 (1H, d, J=5.0, C14-β-H), 3.85, 3.28, 3.28 and 3.18 (each 3H, s, OCH$_3$ at C1, C6, C16 and C18), 1.09 (3H, t, J=7.0, CH$_3$ of C$_2$H$_5$ at the nitrogen atom).

5) Analysis of $^{13}$C-NMR spectra (CDCl$_3$)

The following signals are shown (δ, ppm). 164.8 (carbonyl of benzoyl group), 133.2, 130.0, 129.6 and 128.6 (benzoyl group), 91.2, 85.2, 83.7, 79.1, 77.5, 76.2, 72.4 and 71.9 (C16, C6, C1, C14, C18, C13, C15 and C3), 61.3, 59.0, 57.9 and 56.1 (OCH$_3$ at C16, C18, C6 and C1), 49.0 (CH$_2$ of C$_2$H$_5$ at the nitrogen atom), 13.5 (CH$_3$ of C$_2$H$_5$ at the nitrogen atom).

6) Analysis of Mass spectra m/z: 587 (M$^+$).

(30) Physicochemical parameters and analytical data of 16-epi-3,8-dideoxy-14-O-benzoylaconine 1) Property and solubility Colorless and amorphous powder. Soluble in ether, chloroform, benzene, ethanol, methanol, ethylacetate, pyridine and dimethyl sulfoxide. Insoluble in hexane and water.

2) Analysis of IR spectra (KBr)

IR $v_{max}^{KBR}$: 3500, 1715 cm$^{-1}$.

3) Analysis of UV spectra (ethanol)

UV $\lambda_{max}^{EtOH}$ (log $\epsilon$) nm: 231 (3.98).

4) Analysis of $^1$H-NMR spectra (CDCl$_3$)

The following signals are shown ($\delta$, ppm). 7.40–8.15 (5H, m, benzoyl group), 4.73 (1H, d, J=5.0, C14-$\beta$-H), 3.87, 3.29, 3.29 and 3.18 (each 3H, s, OCH$_3$ at C1, C6, C16 and C18), 1.10 (3H, t, J=7.0, CH$_3$ of C$_2$H$_5$ at the nitrogen atom).

5) Analysis of $^{13}$C-NMR spectra (CDCl$_3$)

The following signals are shown ($\delta$, ppm). 164.9 (carbonyl of benzoyl group), 133.1, 130.0, 129.6 and 128.6 (benzoyl group), 91.2, 85.2, 84.2, 80.2, 79.0 and 72.6 (C16, C1, C6, C18, C14 and C15), 61.2, 59.0, 57.9 and 56.1 (OCH$_3$ at C16, C18, C6 and C1), 49.0 (CH$_2$ of C$_2$H$_5$ at the nitrogen atom), 13.5 (CH$_3$ of C$_2$H$_5$ at the nitrogen atom).

6) Analysis of Mass spectra m/z: 571 (M$^+$).

(31) Physicochemical parameters and analytical data of 16-epi-3,8,13-trideoxy-14-O-benzoylaconine 1) Property and solubility Colorless and amorphous powder. Soluble in ether, chloroform, benzene, ethanol, methanol, ethylacetate, pyridine and dimethyl sulfoxide. Insoluble in hexane and water.

2) Analysis of IR spectra (KBr)

IR $v_{max}^{KBR}$: 3450, 1710 cm$^{-1}$.

3) Analysis of UV spectra (ethanol)

UV $\lambda_{max}^{EtOH}$ (log $\epsilon$) nm: 230 (3.98).

4) Analysis of $^1$H-NMR spectra (CDCl$_3$)

The following signals are shown ($\delta$, ppm). 7.38–8.15 (5H, m, benzoyl group), 5.25 (1H, t, J=4.5, C14-$\beta$-H), 3.69, 3.28, 3.28 and 3.18 (each 3H, s, OCH$_3$ at C1, C6, C16 and C18), 1.09 (3H, t, J=7.0, CH$_3$ of C$_2$H$_5$ at the nitrogen atom).

5) Analysis of $^{13}$C-NMR spectra (CDCl$_3$)

The following signals are shown ($\delta$, ppm). 165.0 (carbonyl of benzoyl group), 133.1, 130.0, 129.7 and 128.6 (benzoyl group), 90.3, 85.2, 84.4, 80.2, 78.9 and 72.3 (C16, C1, C6, C18, C14 and C15), 59.6, 57.9, 57.6 and 56.0 (OCH$_3$ at C18, C16, C6 and C1), 49.1 (CH$_2$ of C$_2$H$_5$ at the nitrogen atom), 13.4 (CH$_3$ of C$_2$H$_5$ at the nitrogen atom).

6) Analysis of Mass spectra m/z: 555 (M$^+$).

(32) Physicochemical parameters and analytical data of 16-epi-8-deoxy-14-O-benzoylmesaconine 1) Property and solubility Colorless and amorphous powder. Soluble in ether, chloroform, benzene, ethanol, methanol, ethylacetate, pyridine and dimethyl sulfoxide. Insoluble in hexane and water.

2) Analysis of IR spectra (KBr)

IR $v_{max}^{KBR}$: 3500, 1720 cm$^{-1}$.

3) Analysis of UV spectra (ethanol)

UV $\lambda_{max}^{EtOH}$ (log $\epsilon$) nm: 229 (4.01).

4) Analysis of $^1$H-NMR spectra (CDCl$_3$)

The following signals are shown ($\delta$, ppm). 7.40–8.08 (5H, m, benzoyl group), 4.74 (1H, d, J=5.0, C14-$\beta$-H), 3.87, 3.29, 3.29 and 3.17 (each 3H, s, OCH$_3$ at C1, C6, C16 and C18), 2.38 (3H, s, CH$_3$ at the nitrogen atom).

5) Analysis of $^{13}$C-NMR spectra (CDCl$_3$)

The following signals are shown ($\delta$, ppm). 164.8 (carbonyl of benzoyl group), 132.9, 129.3 and 128.3 (benzoyl group), 91.0, 85.2, 83.7, 79.1, 77.5, 74.8 and 72.5 (C16, C6, C1, C14, C18, C13 and C15), 61.1, 58.8, 57.8 and 55.8 (OCH$_3$ at C16, C18, C6 and C1), 42.3 (CH$_3$ at the nitrogen atom).

6) Analysis of Mass spectra m/z: 589 (M$^+$).

(33) Physicochemical parameters and analytical data of 16-epi-3,8,13-trideoxy-14-O-benzoylmesaconine 1) Property and solubility Colorless and amorphous powder. Soluble in ether, chloroform, benzene, ethanol, methanol, ethylacetate, pyridine and dimethyl sulfoxide. Insoluble in hexane and water.

2) Analysis of IR spectra (KBr)

IR $v_{max}^{KBR}$: 3500, 1720 cm$^{-1}$.

3) Analysis of UV spectra (ethanol)

UV $\lambda_{max}^{EtOH}$ (log $\epsilon$) nm: 230 (4.00).

4) Analysis of $^1$H-NMR spectra (CDCl$_3$)

The following signals are shown ($\delta$, ppm). 7.41–8.22 (5H, m, benzoyl group), 5.27 (1H, t, J=4.3, C14-$\beta$-H), 3.70, 3.29, 3.29 and 3.18 (each 3H, s, OCH$_3$ at C1, C6, C16 and C18), 2.36 (3H, s, CH$_3$ at the nitrogen atom).

5) Analysis of $^{13}$C-NMR spectra (CDCl$_3$)

The following signals are shown ($\delta$, ppm). 165.0 (carbonyl of benzoyl group), 133.0, 129.6 and 128.3 (benzoyl group), 90.1, 85.3, 84.4, 80.3, 79.0 and 72.1 (C16, C1, C6, C18, C14 and C15), 59.5, 58.0, 57.7 and 56.5 (OCH$_3$ at C18, C16, C6 and C1), 42.3 (CH$_3$ at the nitrogen atom).

6) Analysis of Mass spectra m/z: 557 (M$^+$).

(34) Physicochemical parameters and analytical data of 16-epi-3,8-dideoxy-14-O-benzoylmesaconine 1) Property and solubility Colorless and amorphous powder. Soluble in ether, chloroform, benzene, ethanol, methanol, ethylacetate, pyridine and dimethyl sulfoxide. Insoluble in hexane and water.

2) Analysis of IR spectra (KBr)

IR $v_{max}^{KBR}$: 3450, 1715 cm$^{-1}$.

3) Analysis of UV spectra (ethanol)

UV $\lambda_{max}^{EtOH}$ (log $\epsilon$) nm: 230 (4.02).

4) Analysis of $^1$H-NMR spectra (CDCl$_3$)

The following signals are shown ($\delta$, ppm). 7.41–8.05 (5H, m, benzoyl group), 4.73 (1H, d, J=5.0, C14-$\beta$-H), 3.86, 3.30, 3.30 and 3.16 (each 3H, s, OCH$_3$ at C1, C6, C16 and C18), 2.37 (3H, s, CH$_3$ at the nitrogen atom).

5) Analysis of $^{13}$C-NMR spectra (CDCl$_3$)

The following signals are shown ($\delta$, ppm). 165.0 (carbonyl of benzoyl group), 133.0, 129.5 and 128.3 (benzoyl group), 91.0, 85.2, 84.2, 80.2, 79.0, 75.0 and 72.6 (C16, C1, C6, C18, C14, C13 and C15), 61.2, 58.9, 57.7 and 55.6 (OCH$_3$ at C16, C18, C6 and C1), 42.5 (CH$_3$ at the nitrogen atom).

6) Analysis of Mass spectra m/z: 573 (M$^+$).

(35) Physicochemical parameters and analytical data of 16-epi-8-deoxy-14-O-anisoylmesaconine 1) Property and solubility Colorless and amorphous powder. Soluble in ether, chloroform, benzene, ethanol, methanol, ethylacetate, pyridine and dimethyl sulfoxide. Insoluble in hexane and water.

2) Analysis of IR spectra (KBr)

IR $v_{max}^{KBR}$: 3450, 1715 cm$^{-1}$.

3) Analysis of UV spectra (ethanol)

UV $\lambda_{max}^{EtOH}$ (log $\epsilon$) nm: 258 (4.00).

4) Analysis of $^1$H-NMR spectra (CDCl$_3$)

The following signals are shown (δ, ppm). 7.99 and 6.93 (each 2H, d, J=8.9, anisoyl group), 4.71 (1H, d, J=5.0, C14-β-H), 3.87 (3H, s, OCH$_3$ of anisoyl group), 3.84, 3.31, 3.27 and 3.24 (each 3H, s, OCH$_3$ at C1, C6, C16 and C18), 2.35 (3H, s, CH$_3$ at the nitrogen atom).

5) Analysis of $^{13}$C-NMR spectra (CDCl$_3$)

The following signals are shown (δ, ppm). 165.0 (carbonyl of anisoyl group), 163.5, 131.8, 122.1 and 113.8 (anisoyl group), 91.1, 85.3, 83.7, 79.2, 77.8, 75.8, 72.6 and 72.0 (C16, C6, C1, C14, C18, C13, C15 and C3), 62.2, 59.1, 58.0 and 56.0 (OCH$_3$ at C16, C18, C6 and C1), 55.4 (OCH$_3$ of anisoyl group), 42.4 (CH$_3$ at the nitrogen atom).

6) Analysis of Mass spectra m/z: 603 (M$^+$).

(36) Physicochemical parameters and analytical data of 16-epi-3,8-dideoxy-14-O-anisoylmesaconine 1) Property and solubility Colorless and amorphous powder. Soluble in ether, chloroform, benzene, ethanol, methanol, ethylacetate, pyridine and dimethyl sulfoxide. Insoluble in hexane and water.

2) Analysis of IR spectra (KBr)

IR $v_{max}^{KBR}$: 3450, 1710 cm$^{-1}$.

3) Analysis of UV spectra (ethanol)

UV $\lambda_{max}^{EtOH}$ (log ε) nm: 257 (4.01).

4) Analysis of $^1$H-NMR spectra (CDCl$_3$)

The following signals are shown (δ, ppm). 7.99 and 6.92 (each 2H, d, J=8.9, anisoyl group), 4.72 (1H, d, J=5.0, C14-β-H), 3.88 (3H, s, OCH$_3$ of anisoyl group), 3.84, 3.30, 3.27 and 3.16 (each 3H, s, OCH$_3$ at C1, C6, C16 and C18), 2.35 (3H, s, CH$_3$ at the nitrogen atom).

5) Analysis of $^{13}$C-NMR spectra (CDCl$_3$)

The following signals are shown (δ, ppm). 165.0 (carbonyl of anisoyl group), 163.5, 131.8, 122.2 and 113.8 (anisoyl group), 91.0, 85.2, 84.3, 80.1, 79.0, 75.1 and 72.7 (C16, C1, C6, C18, C14, C13 and C15), 62.1, 59.0, 57.9 and 56.1 (OCH$_3$ at C16, C18, C6 and C1), 55.4 (OCH$_3$ of anisoyl group), 42.4 (CH$_3$ at the nitrogen atom).

6) Analysis of Mass spectra m/z: 587 (M$^+$).

(37) Physicochemical parameters and analytical data of 16-epi-3,8,13-trideoxy-14-O-anisoylmesaconine 1) Property and solubility Colorless and amorphous powder. Soluble in ether, chloroform, benzene, ethanol, methanol, ethylacetate, pyridine and dimethyl sulfoxide. Insoluble in hexane and water.

2) Analysis of IR spectra (KBr)

IR $v_{max}^{KBR}$: 3500, 1710 cm$^{-1}$.

3) Analysis of UV spectra (ethanol)

UV $\lambda_{max}^{EtOH}$ (log ε) nm: 258 (4.01).

4) Analysis of $^1$H-NMR spectra (CDCl$_3$)

The following signals are shown (δ, ppm). 7.98 and 6.93 (each 2H, d, J=8.9, anisoyl group), 5.25 (1H, t, J=4.5, C14-β-H), 3.88 (3H, s, OCH$_3$ of anisoyl group), 3.77, 3.30, 3.28 and 3.16 (each 3H, s, OCH$_3$ at C1, C6, C16 and C18), 2.35 (3H, s, CH$_3$ at the nitrogen atom).

5) Analysis of $^{13}$C-NMR spectra (CDCl$_3$)

The following signals are shown (δ, ppm). 165.1 (carbonyl of anisoyl group), 163.4, 131.5, 122.1 and 113.8 (anisoyl group), 90.3, 85.3, 84.5, 80.3, 79.1 and 72.2 (C16, C1, C6, C18, C14 and C15), 59.6, 58.0, 57.8 and 56.1 (OCH$_3$ at C16, C18, C6 and C1), 55.3 (OCH$_3$ of anisoyl group), 42.3 (CH$_3$ at the nitrogen atom).

6) Analysis of Mass spectra m/z: 571 (M$^+$).

(38) Physicochemical parameters and analytical data of 8-deoxy-14-O-trimethylgalloylaconine 1) Property and solubility Colorless and amorphous powder. Soluble in ether, chloroform, benzene, ethanol, methanol, ethylacetate, pyridine and dimethyl sulfoxide. Insoluble in hexane and water.

2) Analysis of IR spectra (KBr)

IR $v_{max}^{KBR}$: 1720 cm$^{-1}$.

3) Analysis of UV spectra (ethanol)

UV $\lambda_{max}^{EtOH}$ (log ε) nm: 215 (4.30), 265 (4.05).

4) Analysis of $^1$H-NMR spectra (CDCl$_3$)

The following signals are shown (δ, ppm). 7.35 (2H, s, trimethylgalloyl group), 5.03 (1H, d, J=4.7 Hz, C14 -β-H), 3.88 (9H, s, OCH$_3$ of trimethylgalloyl group), 3.53, 3.31, 3.30 and 3.26 (each 3H, s, OCH$_3$ at C1, C6, C16 and C18), 1.12 (3H, t, J=7.0 Hz, CH$_3$ of C$_2$H$_5$ at the nitrogen atom).

5) Analysis of $^{13}$C-NMR spectra (CDCl$_3$)

The following signals are shown (δ, ppm). 165.9 (carbonyl of trimethylgalloyl group), 124.3, 107.5, 145.2 and 133.8 (trimethylgalloyl group), 94.1, 85.2, 83.7, 80.3, 77.5, 75.2, 72.4 and 72.0 (C16, C6, C1, C14, C18, C13, C15 and C3), 61.9, 59.3, 58.0 and 55.9 (OCH$_3$ at C16, C18, C6 and C1), 55.9 (OCH$_3$ of trimethylgalloyl group), 49.0 (CH$_2$ of C$_2$H$_5$ at the nitrogen atom), 13.5 (CH$_3$ of C$_2$H$_5$ at the nitrogen atom).

6) Analysis of Mass spectra m/z: 677 (M$^+$).

7) Elemental analysis

Calculated for C$_{35}$H$_{51}$NO$_{12}$: C, 62.02; H, 7.58; N, 2.07. Found: C, 62.18; H, 7.69; N, 2.05.

(39) Physicochemical parameters and analytical data of 8-deoxy-14-O-veratroylaconine 1) Property and solubility Colorless and amorphous powder. Soluble in ether, chloroform, benzene, ethanol, methanol, ethylacetate, pyridine and dimethyl sulfoxide. Insoluble in hexane and water.

2) Analysis of IR spectra (KBr)

IR $v_{max}^{KBR}$: 1720 cm$^{-1}$.

3) Analysis of UV spectra (ethanol)

UV $\lambda_{max}^{EtOH}$ (log ε) nm: 221 (4.35), 264 (4.08), 295 (3.84).

4) Analysis of $^1$H-NMR spectra (CDCl$_3$)

The following signals are shown (δ, ppm). 6.87–7.68 (3H, m, veratroyl group), 5.06 (1H, d, J=4.6 Hz, C14-β -H), 3.92 (6H, OCH$_3$ of veratroyl group), 3.54, 3.32, 3.29 and 3.26 (each 3H, s, OCH$_3$ at C1, C6, C16 and C18), 1.12 (3H, t, J=7.0 Hz, CH$_3$ of C$_2$H$_5$ at the nitrogen atom).

5) Analysis of $^{13}$C-NMR spectra (CDCl$_3$)

The following signals are shown (δ, ppm). 166.0 (carbonyl of veratroyl group), 122.5, 110.5, 153.1, 148.1 and 112.3 (veratroyl group), 94.2, 85.0, 83.7, 80.4, 77.4, 75.3, 72.4 and 72.0 (C16, C6, C1, C14, C18, C13, C15 and C3), 61.8, 59.1, 57.9 and 56.0 (OCH$_3$ at C16, C18, C6 and C1), 55.8 (OCH$_3$ of veratroyl group), 49.1 (CH$_2$ of C$_2$H$_5$ at the nitrogen atom), 13.4 (CH$_3$ of C$_2$H$_5$ at the nitrogen atom).

6) Analysis of Mass spectra m/z: 647 (M$^+$).

7) Elemental analysis

Calculated for C$_{34}$H$_{49}$NO$_{11}$: C, 63.04; H, 7.62; N, 2.16. Found: C, 63.21; H, 7.58; N, 2.05.

(40) Physicochemical parameters and analytical data of 8-deoxy-14-O-p-chlorobenzoylaconine 1) Property and solubility Colorless and amorphous powder. Soluble in ether, chloroform, benzene, ethanol, methanol, ethylacetate, pyridine and dimethyl sulfoxide. Insoluble in hexane and water.

2) Analysis of IR spectra (KBr)

IR $v_{max}^{KBR}$: 1715 cm$^{-1}$.

3) Analysis of UV spectra (ethanol)

UV $\lambda_{max}^{EtOH}$ (log ε) nm: 246 (4.08).

4) Analysis of $^1$H-NMR spectra (CDCl$_3$)

The following signals are shown (δ, ppm). 7.97 and 7.43 (each 2H, d, J=8.8 Hz, p-chlorobenzoyl group), 4.90 (1H, d, J=4.8 Hz, C14-β-H), 3.69, 3.30, 3.28 and 3.26 (each 3H, s, OCH$_3$ at C1, C6, C16 and C18), 1.14 (3H, t, J=7.0 Hz, CH$_3$ of C$_2$H$_5$ at the nitrogen atom).

5) Analysis of $^{13}$C-NMR spectra (CDCl$_3$)

The following signals are shown (δ, ppm). 165.2 (carbonyl of p-chlorobenzoyl group), 131.1, 128.8, 128.1 and 139.6 (p-chlorobenzoyl group), 94.1, 85.0, 83.6, 80.7, 77.3, 75.0, 72.4 and 71.9 (C16, C6, C1, C14, C18, C13, C15 and C3), 61.7, 59.1, 57.8 and 56.0 (OCH$_3$ at C16, C18, C6 and C1), 49.0 (CH$_2$ of C$_2$H$_5$ at the nitrogen atom), 13.3 (CH$_3$ of C$_2$H$_5$ at the nitrogen atom).

6) Analysis of Mass spectra m/z: 621, 623 (M$^+$).

7) Elemental analysis

Calculated for C$_{32}$H$_{44}$NO$_9$Cl: C, 61.78; H, 7.13; N, 2.25. Found: C, 61.93; H, 7.30; N 2.11.

(41) Physicochemical parameters and analytical data of 8-deoxy-14-O-m-chlorobenzoylaconine 1) Property and solubility Colorless and amorphous powder. Soluble in ether, chloroform, benzene, ethanol, methanol, ethylacetate, pyridine and dimethyl sulfoxide. Insoluble in hexane and water.

2) Analysis of IR spectra (KBr)

IR $v_{max}^{KBr}$: 1715 cm$^{-1}$.

3) Analysis of UV spectra (ethanol)

UV $\lambda_{max}^{EtOH}$ (log ε) nm: 231 (4.09), 280 (3.28), 289 (3.25).

4) Analysis of $^1$H-NMR spectra (CDCl$_3$)

The following signals are shown (δ, ppm). 8.02-7.35 (5H, m, m-chlorobenzoyl group), 4.90 (1H, d, J=5.1 Hz, C14-β-H), 3.71, 3.31, 3.28 and 3.26 (each 3H, s, OCH$_3$ at C1, C6, C16 and C18), 1.11 (3H, t, J=7.0 Hz, CH$_3$ of C$_2$H$_5$ at the nitrogen atom).

5) Analysis of $^{13}$C-NMR spectra (CDCl$_3$)

The following signals are shown (δ, ppm). 165.0 (carbonyl of m-chlorobenzoyl group), 131.6, 133.0, 129.7, 134.5 and 127.8 (m-chlorobenzoyl group ), 94.1, 85.1, 83.6, 80.9, 77.3, 75.0, 72.4 and 71.9 (C16, C6, C1, C14, C18, C13, C15 and C3), 61.5, 59.1, 57.8 and 56.1 (OCH$_3$ at C16, C8, C6 and C1), 49.0 (CH$_2$ of C$_2$H$_5$ at the nitrogen atom), 13.3 (CH$_3$ of C$_2$H$_5$ at the nitrogen atom).

6) Analysis of Mass spectra m/z: 621, 623 (M$^+$).

7) Elemental analysis

Calculated for C$_{32}$H$_{44}$NO$_9$Cl: C, 61.78; H, 7.13; N, 2.25. Found: C, 61.75; H, 7.23; N, 2.16.

(42) Physicochemical parameters and analytical data of 8-deoxy-14-O-α-methyl-(4-(α-methylacetic acid)-phenyl)acetylaconine 1) Property and solubility Colorless and amorphous powder. Soluble in ether, chloroform, benzene, ethanol, methanol, ethylacetate, pyridine and dimethyl sulfoxide. Insoluble in hexane and water.

2) Analysis of IR spectra (KBr)

IR $v_{max}^{KBr}$: 1715 cm$^{-1}$.

3) Analysis of UV spectra (ethanol)

UV $\lambda_{max}^{EtOH}$ (log ε) nm: 220 (4.03), 256 (3.28).

4) Analysis of $^1$H-NMR spectra (CDCl$_3$)

The following signals are shown (δ, ppm). 7.30 (4H, s, benzene), 4.91 (1H, d, J=4.7 Hz, C14-β-H), 3.70, 3.45, 3.30 and 3.29 (each 3H, s, OCH$_3$ at C1, C6, C16 and C18), 3.63 (2H, q, J=7.0 Hz, CH of α-methylacetyl and α-methylacetic acid), 1.42 (6H, d, J=7.0 Hz, CH$_3$ of α-methylacetyl and α-methylacetic acid), 1.11 (3H, t, J=7.0 Hz, CH$_3$ of C$_2$H$_5$ at the nitrogen atom).

5) Analysis of $^{13}$C-NMR spectra (CDCl$_3$)

The following signals are shown (δ, ppm). 180.5 (carboxyl group), 166.0 (carbonyl group), 140.4, 139.3, 128.2 and 127.0 (benzene), 60.4 and 60.2 (CH of α-methylacetyl and α-methylacetic acid), 18.2 and 18.1 (CH of α-methylacetyl and α-methylacetic acid), 94.5, 85.0, 83.7, 80.4, 77.5, 75.3, 72.4 and 72.0 (C16, C6, C1, C14, C18, C13, C15 and C3), 61.9, 59.2, 58.0 and 56.1 (OCH$_3$ at C16, C8, C6 and C1), 49.0 (CH$_2$ of C$_2$H$_5$ at the nitrogen atom), 13.2 (CH$_3$ of C$_2$H$_5$ at the nitrogen atom).

6) Analysis of Mass spectra m/z: 687 (M$^+$).

7) Elemental analysis

Calculated for C$_{37}$H$_{53}$NO$_{11}$: C, 64.61; H,7.77; N, 2.04. Found: C, 64.68; H, 7.76; N, 2.18.

(43) Physicochemical parameters and analytical data of 8-deoxy-14-O-methylaconine 1) Property and solubility Colorless and amorphous powder. Soluble in ether, chloroform, benzene, ethanol, methanol, ethylacetate, pyridine and dimethyl sulfoxide. Insoluble in hexane and water.

2) Analysis of IR spectra (KBr)

IR $v_{max}^{KBr}$: 3300 cm$^{-1}$.

3) Analysis of $^1$H-NMR spectra (CDCl$_3$)

The following signals are shown (δ, ppm). 3.62, 3.39, 3.38, 3.31 and 3.27 (each 3H, s, OCH$_3$ at C1, C6, C16, C18 and C14), 1.10 (3H, t, J=7.0 Hz, CH$_3$ of C$_2$H$_5$ at the nitrogen atom).

4) Analysis of $^{13}$C-NMR spectra (CDCl$_3$)

The following signals are shown (δ, ppm). 93.4, 84.7, 83.5, 81.3, 77.5, 77.2, 72.4 and 72.0 (C16, C6, C1, C14, C18, C13, C15 and C3), 60.6, 59.2, 58.3, 58.1 and 56.0 (OCH$_3$ at C16, C18, C6, C1 and C14), 49.4 (CH$_2$ of C$_2$H$_5$ at the nitrogen atom), 14.1 (CH$_3$ of C$_2$H$_5$ at the nitrogen atom).

5) Analysis of Mass spectra m/z: 497 (M$^+$).

6) Elemental analysis

Calculated for C$_{26}$H$_{43}$NO$_8$: C, 62.75; H, 8.71; N, 2.81. Found: C, 62.55; H, 8.86; N, 2.65.

(44) Physicochemical parameters and analytical data of 8-deoxy-14-O-benzylaconine 1) Property and solubility Colorless and amorphous powder. Soluble in ether, chloroform, benzene, ethanol, methanol, ethylacetate, pyridine and dimethyl sulfoxide. Insoluble in hexane and water.

2) Analysis of IR spectra (KBr)

IR $v_{max}^{KBr}$: 3300 cm$^{-1}$.

3) Analysis of UV spectra (ethanol)

UV $\lambda_{max}^{EtOH}$ (log ε) nm: 225 (4.10).

4) Analysis of $^1$H-NMR spectra (CDCl$_3$)

The following signals are shown (δ, ppm). 7.28 (5H, s, benzyl group), 4.48 (2H, s, CH$_2$ of benzyl group), 3.64, 3.30, 3.30 and 3.28 (each 3H, s, OCH$_3$ at C1, C6, C16 and C18), 1.08 (3H, t, J=7.0 Hz, CH$_3$ of C$_2$H$_5$ at the nitrogen atom).

5) Analysis of $^{13}$C-NMR spectra (CDCl$_3$)

The following signals are shown (δ, ppm). 126.5, 127.0, 128.3 and 141.5 (benzyl group), 64.1 (CH$_2$ of benzyl group), 93.6, 84.5, 83.1, 81.2, 77.4, 77.3, 72.4 and 72.1 (C16, C6, C1, C14, C18, C13, C15 and C3), 60.3, 59.1, 58.1 and 56.0 (OCH$_3$ at C16, C18, C6 and C1), 49.5 (CH$_2$ of C$_2$H$_5$ at the nitrogen atom), 14.0 (CH$_3$ of C$_2$H$_5$ at the nitrogen atom).

6) Analysis of Mass spectra m/z: 573 (M$^+$).

7) Elemental analysis

Calculated for C$_{32}$H$_{47}$NO$_8$: C, 66.99; H, 8.26; N, 2.44. Found: C, 67.12; H, 8.37; N, 2.45.

(45) Physicochemical parameters and analytical data of 8-deoxy-14-O-crotylaconine 1) Property and solubility Colorless and amorphous powder. Soluble in ether, chloroform, benzene, ethanol, methanol, ethylacetate, pyridine and dimethyl sulfoxide. Insoluble in hexane and water.

2) Analysis of IR spectra (KBr)

IR $\nu_{max}^{KBR}$: 3300 cm$^{-1}$.

3) Analysis of $^1$H-NMR spectra (CDCl$_3$)

The following signals are shown (δ, ppm). 5.70 (2H, m, crotyl group), 4.10 (2H, m, CH$_2$ of crotyl group), 3.68, 3.40, 3.27 and 3.27 (each 3H, s, OCH$_3$ at C1, C6, C16 and C18), 1.70 (3H, d, J=6.3 Hz, CH$_3$ of crotyl group), 1.12 (3H, t, J=7.3 Hz, CH$_3$ of C$_2$H$_5$ at the nitrogen atom).

4) Analysis of $^{13}$C-NMR spectra (CDCl$_3$)

The following signals are shown (δ, ppm). 130.8 and 123.7 (crotyl group), 93.4, 84.6, 83.5, 81.2, 77.5, 77.2, 72.4 and 72.0 (C16, C6, C1, C14, C18, C13, C15 and C3), 60.5, 59.1, 58.0 and 55.5 (OCH$_3$ at C16, C18, C6 and C1), 49.5 (CH$_2$ of C$_2$H$_5$ at the nitrogen atom), 13.9 (CH$_3$ of C$_2$H$_5$ at the nitrogen atom), 12.7 (CH$_3$ of crotyl group).

5) Analysis of Mass spectra m/z: 537 (M$^+$).

6) Elemental analysis

Calculated for C$_{29}$H$_{47}$NO$_8$: C, 64.78; H, 8.81; N, 2.60. Found: C, 65.01; H, 8.93; N, 2.47.

(46) Physicochemical parameters and analytical data of 8-deoxy-14-O-o-chlorobenzoylaconine 1) Property and solubility Colorless and amorphous powder. Soluble in ether, chloroform, benzene, ethanol, methanol, ethylacetate, pyridine and dimethyl sulfoxide. Insoluble in hexane and water.

2) Analysis of IR spectra (KBr)

IR $\nu_{max}^{KBR}$: 1715 cm$^{-1}$.

3) Analysis of UV spectra (ethanol)

UV $\lambda_{max}^{EtOH}$ (log ε) nm: 227 (4.01), 280 (3.20).

4) Analysis of $^1$H-NMR spectra (CDCl$_3$)

The following signals are shown (δ, ppm). 8.00-7.45 (5H, m, o-chlorobenzoyl group), 4.91 (1H, d, J=4.8 Hz, C14-β-H), 3.70, 3.31, 3.28 and 3.26 (each 3H, s, OCH$_3$ at C1, C6, C16 and C18), 1.11 (3H, t, J=7.0 Hz, CH$_3$ of C$_2$H$_5$ at the nitrogen atom).

5) Analysis of $^{13}$C-NMR spectra (CDCl$_3$)

The following signals are shown (δ, ppm). 165.0 (carbonyl of o-chlorobenzoyl group), 129.9, 136.0, 128.7, 133.8 and 126.3 (o-chlorobenzoyl group), 94.1, 85.0, 83.5, 80.8, 77.3, 75.1, 72.5 and 72.0 (C16, C6, C1, C14, C18, C13, C15 and C3), 61.7, 59.1, 57.9 and 56.0 (OCH$_3$ at C16, C18, C6 and C1), 49.0 (CH$_2$ of C$_2$H$_5$ at the nitrogen atom), 13.5 (CH$_3$ of C$_2$H$_5$ at the nitrogen atom).

6) Analysis of Mass spectra m/z: 621, 623 (M$^+$).

7) Elemental analysis

Calculated for C$_{32}$H$_{44}$NO$_9$Cl: C, 61.78; H, 7.13; N, 2.25. Found: C, 61.86; H, 7.40; N, 2.18.

(47) Physicochemical parameters and analytical data of 8-deoxy-14-O-m-anisoylaconine 1) Property and solubility Colorless and amorphous powder. Soluble in ether, chloroform, benzene, ethanol, methanol, ethylacetate, pyridine and dimethyl sulfoxide. Insoluble in hexane and water.

2) Analysis of IR spectra (KBr)

IR $\nu_{max}^{KBR}$: 1715 cm$^{-1}$.

3) Analysis of UV spectra (ethanol)

UV $\lambda_{max}^{EtOH}$ (log ε) nm: 236 (4.07), 296 (2.62).

4) Analysis of $^1$H-NMR spectra (CDCl$_3$)

The following signals are shown (δ, ppm). 7.64-7.26 (5H, m, m-anisoyl group), 4.92 (1H, d, J=4.6 Hz, C14-β -H), 3.87 (3H, s, OCH$_3$ of m-anisoyl group), 3.87, 3.71, 3.30 and 3.30 (each 3H, s, OCH$_3$ at C1, C6, C16 and C18), 1.18 (3H, t, J=7.0 Hz, CH$_3$ of C$_2$H$_5$ at the nitrogen atom).

5) Analysis of $^{13}$C-NMR spectra (CDCl$_3$)

The following signals are, shown (δ, ppm). 165.0 (carbonyl of m-anisoyl group), 131.2, 121.4, 129.5, 118.3, 158.9 and 115.2 (m-anisoyl group), 94.3, 85.1, 83.7, 80.2, 77.5, 75.3, 72.4 and 72.0 (C16, C6, C1, C14, C18, C13, C15 and C3), 55.4 (OCH$_3$ of m-anisoyl group), 61.6, 59.1, 58.0 and 56.1 (OCH$_3$ at C16, C18, C6 and C1), 49.1 (CH$_2$ of C$_2$H$_5$ at the nitrogen atom), 13.5 (CH$_3$ of C$_2$H$_5$ at the nitrogen atom).

6) Analysis of Mass spectra m/z: 617 (M$^+$).

7) Elemental analysis

Calculated for C$_{33}$H$_{47}$NO$_{10}$: C, 64.16; H, 7.67; N, 2.27. Found: C, 64.19; H, 7.62; N, 2.20.

(48) Physicochemical parameters and analytical data of 8-deoxy-14-O-acetylaconine 1) Property and solubility Colorless prism. m.p. 105°–107° C. Soluble in ether, chloroform, benzene, ethanol, methanol, ethylacetate, pyridine and dimethyl sulfoxide. Insoluble in hexane and water.

2) Analysis of IR spectra (KBr)

IR $\nu_{max}^{KBR}$: 1713 cm$^{-1}$.

3) Analysis of $^1$H-NMR spectra (CDCl$_3$)

The following signals are shown (δ, ppm). 4.97 (1H, d, J=5.0 Hz, C14-β-H), 3.65, 3.37, 3.28 and 3.28 (each 3H, s, OCH$_3$ at C1, C6, C16 and C18), 2.05 (3H, s, CH$_3$ of acetyl group), 1.10 (3H, t, J=7.0 Hz, CH$_3$ of C$_2$H$_5$ at the nitrogen atom).

4) Analysis of $^{13}$C-NMR spectra (CDCl$_3$)

The following signals are shown (δ, ppm). 171.4 (carbonyl of acetyl group), 94.3, 85.1, 83.7, 80.2, 76.6, 75.3, 72.4 and 72.0 (C16, C6, C1, C14, C18, C13, C15 and C3), 61.6, 59.0, 57.9 and 56.0 (OCH$_3$ at C16, C18, C6 and C1), 49.1 (CH$_2$ of C$_2$H$_5$ at the nitrogen atom), 13.5 (CH$_3$ of C$_2$H$_5$ at the nitrogen atom), 21.5 (CH$_3$ of acetyl group).

5) Analysis of Mass spectra m/z: 525 (M$^+$).

6) Elemental analysis

Calculated for C$_{27}$H$_{43}$NO$_9$: C, 61.70; H, 8.25; N, 2.66. Found: C, 61.56; H, 8.31; N, 2.54.

(49) Physicochemical parameters and analytical data of 8-deoxy-14-O-(4-methyl)pentylaconine 1) Property and solubility Colorless and amorphous powder. Soluble in ether, chloroform, benzene, ethanol, methanol, ethylacetate, pyridine and dimethyl sulfoxide. Insoluble in hexane and water.

2) Analysis of $^1$H-NMR spectra (CDCl$_3$)

The following signals are shown (δ, ppm). 3.69, 3.40, 3.27 and 3.27 (each 3H, s, OCH$_3$ at C1, C6, C16 and C18), 1.10 (3H, t, J=7.0 Hz, CH$_3$ of C$_2$H$_5$ at the nitrogen atom), 1.02 (6H, d, J=7.0 Hz, CH$_3$ of 4-methylpentyl group).

3) Analysis of $^{13}$C-NMR spectra (CDCl$_3$)

The following signals are shown (δ, ppm). 93.4, 84.6, 83.3, 81.0, 77.4, 77.2, 72.4 and 71.9 (C16, C6, C1, C14, C18, C13, C15 and C3), 60.5, 59.1, 58.0 and 55.5 (OCH$_3$ at C16, C18, C6 and C1), 49.3 (CH$_2$ of C$_2$H$_5$ at the nitrogen atom), 13.9 (CH$_3$ of C$_2$H$_5$ at the nitrogen atom), 21.3 (CH$_3$ of 4-methylpentyl group).

4) Analysis of Mass spectra m/z: 567 (M$^+$).

5) Elemental analysis

Calculated for C$_{31}$H$_{53}$NO$_8$: C, 65.58; H, 9.41; N, 2.47. Found: C, 65.43; H, 9.65; N, 2.36.

(50) Physicochemical parameters and analytical data of de-N-ethyl-8-deoxy-14-O-anisoylaconine 1) Property and solubility Colorless and amorphous powder. Soluble in ether, chloroform, benzene, ethanol, methanol, ethylacetate, pyridine and dimethyl sulfoxide. Insoluble in hexane and water.

2) Analysis of IR spectra (KBr)

IR $\nu_{max}^{KBR}$: 1715 cm$^{-1}$.

3) Analysis of UV spectra (ethanol)

UV $\lambda_{max}^{EtOH}$ (log ε) nm: 258 (4.02).

4) Analysis of $^1$H-NMR spectra (CDCl$_3$)

The following signals are shown (δ, ppm). 7.99 and 6.95 (each 2H, d, J=8.9, anisoyl group), 4.95 (1H, d, J=5.0, C14-β-H), 3.87 (3H, s, OCH$_3$ of anisoyl group), 3.69, 3.30, 3.28 and 3.25 (each 3H, s, OCH$_3$ at C1, C6, C16 and C18).

5) Analysis of $^{13}$C-NMR spectra (CDCl$_3$)

The following signals are shown (δ, ppm). 166.0 (carbonyl of anisoyl group), 163.5, 131.8, 113.7 and 122.1 (anisoyl group), 94.3, 85.2, 83.7, 80.2, 77.4, 75.1, 72.4 and 72.0 (C16, C6, C1, C14, C18, C13, C15 and C3), 61.9, 59.0, 57.9 and 56.1 (OCH$_3$ at C16, C18, C6 and C1), 55.4 (OCH$_3$ of anisoyl group).

6) Analysis of Mass spectra m/z: 589 (M$^+$).

7) Elemental analysis

Calculated for C$_{31}$H$_{43}$NO$_{10}$: C, 63.14; H, 7.35; N, 2.38. Found: C, 63.39; H, 7.33; N, 2.02.

(51) Physicochemical parameters and analytical data of de-N-ethyl-N-amyl-8-deoxy-14-O-anisoylaconine 1) Property and solubility Colorless and amorphous powder. Soluble in ether, chloroform, benzene, ethanol, methanol, ethylacetate, pyridine and dimethyl sulfoxide. Insoluble in hexane and water.

2) Analysis of IR spectra (KBr)

IR $\nu_{max}^{KBR}$: 1715 cm$^{-1}$.

3) Analysis of UV spectra (ethanol)

UV $\lambda_{max}^{EtOH}$ (log ε) nm: 257 (4.02).

4) Analysis of $^1$H-NMR spectra (CDCl$_3$)

The following signals are shown (δ, ppm). 8.01 and 6.93 (each 2H, d, J=8.9, anisoyl group), 4.95 (1H, d, J=5.0, C14-β-H), 3.87 (3H, s, OCH$_3$ of anisoyl group), 3.70, 3.30, 3.28 and 3.25 (each 3H, s, OCH$_3$ at C1, C6, C16 and C18), 0.98 (3H, t, J=7.0, CH$_3$ of amyl group at the nitrogen atom).

5) Analysis of $^{13}$C-NMR spectra (CDCl$_3$)

The following signals are shown (δ, ppm). 166.0 (carbonyl of anisoyl group), 163.8, 131.8, 113.5 and 122.2 (anisoyl group), 94.3, 85.3, 83.6, 80.0, 77.6, 75.1, 72.5 and 72.0 (C16, C6, C1, C14, C18, C13, C15 and C3), 61.8, 59.1, 57.8 and 56.0 (OCH$_3$ at C16, C18, C6 and C1), 55.4 (OCH$_3$ of anisoyl group), 13.1 (CH$_3$ of amyl group at the nitrogen atom).

6) Analysis of Mass spectra m/z: 659 (M$^+$).

7) Elemental analysis

Calculated for C$_{36}$H$_{53}$NO$_{10}$: C, 65.53; H, 8.10; N, 2.12. Found: C, 65.81; H, 8.09; N, 2.18.

(52) Physicochemical parameters and analytical data of de-N-ethyl-N-propyl-8-deoxy-14-O-anisoylaconine 1) Property and solubility Colorless and amorphous powder. Soluble in ether, chloroform, benzene, ethanol, methanol, ethylacetate, pyridine and dimethyl sulfoxide. Insoluble in hexane and water.

2) Analysis of IR spectra (KBr)

IR $\nu_{max}^{KBR}$: 1715 cm$^{-1}$.

3) Analysis of UV spectra (ethanol)

UV $\lambda_{max}^{EtOH}$ (log ε) nm: 258 (4.02).

4) Analysis of $^1$H-NMR spectra (CDCl$_3$)

The following signals are shown (δ, ppm). 7.99 and 8.94 (each 2H, d, J=8.9, anisoyl group), 4.98 (1H, d, J=5.0, C14-β-H), 3.87 (3H, s, OCH$_3$ of anisoyl group), 3.68, 3.30, 3.29 and 3.24 (each 3H, s, OCH$_3$ at C1, C6, C16 and C18), 1.10 (3H, t, J=7.0, CH$_3$ of propyl group at the nitrogen atom).

5) Analysis of $^{13}$C-NMR spectra (CDCl$_3$)

The following signals are shown (δ, ppm). 165.9 (carbonyl of anisoyl group), 163.6, 131.8, 122.2 and 113.7 (anisoyl group), 94.3, 85.3, 83.7, 80.2, 77.5, 75.0, 72.3 and 71.9 (C16, C6, C1, C14, C18, C13, C15 and C3), 61.8, 59.1, 57.8 and 56.1 (OCH$_3$ at C16, C18, C6 and C1), 55.4 (OCH$_3$ of anisoyl group), 13.1 (CH$_3$ of propyl group at the nitrogen atom).

6) Analysis of Mass spectra m/z: 631 (M$^+$).

7) Elemental analysis

Calculated for C$_{34}$H$_{49}$NO$_{10}$: C, 64.64; H, 7.82; N, 2.22. Found: C, 64.85; H, 7.66; N, 2.01.

(53) Physicochemical parameters and analytical data of de-N-ethyl-N-(4-methyl)pentyl-8-deoxy-14-O-anisoylaconine 1) Property and solubility Colorless and amorphous powder. Soluble in ether, chloroform, benzene, ethanol, methanol, ethylacetate, pyridine and dimethyl sulfoxide. Insoluble in hexane and water.

2) Analysis of IR spectra (KBr)

IR $\nu_{max}^{KBR}$: 1715 cm$^{-1}$.

3) Analysis of UV spectra (ethanol)

UV $\lambda_{max}^{EtOH}$ (log ε) nm: 258 (4.01).

4) Analysis of $^1$H-NMR spectra (CDCl$_3$)

The following signals are shown (δ, ppm). 8.01 and 6.94 (each 2H, d, J=8.9, anisoyl group), 4.94 (1H, d, J=5.0 C14-β-H), 3.88 (3H, s, OCH$_3$ of anisoyl group), 3.69, 3.29, 3.28 and 3.25 (each 3H, s, OCH$_3$ at C1, C6, C16 and C18), 1.02 (6H, d, J=7.0 Hz, CH$_3$ of 4-methylpentyl group at the nitrogen atom).

5) Analysis of $^{13}$C-NMR spectra (CDCl$_3$)

The following signals are shown (δ, ppm). 166.0 (carbonyl of anisoyl group), 163.6, 131.7, 113.4 and 122.1 (anisoyl group), 94.5, 85.3, 83.5, 80.0, 77.6, 75.0, 72.5 and 71.9 (C16, C6, C1, C14, C18, C13, C15 and C3), 61.8, 59.1, 57.8 and 56.0 (OCH$_3$ at C16, C18, C6 and C1), 55.4 (OCH$_3$ of anisoyl group), 21.5 (CH$_3$ of 4-methylpentyl group at the nitrogen atom).

6) Analysis of Mass spectra m/z: 673 (M$^+$).

7) Elemental analysis

Calculated for C$_{37}$H$_{55}$NO$_{10}$: C, 65.95; H, 8.23; N, 2.08. Found: C, 66.17; H, 8.29; N, 2.05.

(54) Physicochemical parameters and analytical data of de-N-ethyl-N-acetyl-8-deoxy-14-O-anisoylaconine 1) Property and solubility Colorless and amorphous powder. Soluble in ether, chloroform, benzene, ethanol, methanol, ethylacetate, pyridine and dimethyl sulfoxide. Insoluble in hexane and water.

2) Analysis of IR spectra (KBr)

IR $\nu_{max}^{KBR}$: 1715, 1655 cm$^{-1}$.

3) Analysis of UV spectra (ethanol)

UV $\lambda_{max}^{EtOH}$ (log ε) nm: 258 (4.02).

4) Analysis of $^1$H-NMR spectra (CDCl$_3$)

The following signals are shown (δ, ppm). 7.99 (2H, d, J=8.9 Hz, anisoyl group), 6.94 (2H, d, J=8.9, anisoyl group), 4.93 (1H, d, J=5.0, C14-β-H), 3.87 (3H, s, OCH$_3$ of anisoyl group), 3.69, 3.30, 3.28 and 3.25 (each 3H, s, OCH$_3$ at C1, C6, C16 and C18), 2.34 (3H, s, CH$_3$ of acetyl group at the nitrogen atom).

5) Analysis of $^{13}$C-NMR spectra (CDCl$_3$)

The following signals are shown (δ, ppm). 170.8 (carbonyl of acetyl group at the nitrogen atom), 165.9 (carbonyl of anisoyl group), 163.6, 131.8, 113.7 and 122.2 (anisoyl group), 94.3, 83.7, 80.2, 79.9, 77.4, 75.1, 72.4 and 72.0 (C16, C6, C14, C1, C18, C13, C15 and C3), 61.8, 59.1, 57.9 and 56.1 (OCH$_3$ at C16, C18, C6 and C1), 55.4 (OCH$_3$ of anisoyl group), 22.4 (CH$_3$ of acetyl group at the nitrogen atom).

6) Analysis of Mass spectra m/z: 631 (M$^+$).

7) Elemental analysis

Calculated for C$_{33}$H$_{45}$NO$_{11}$: C, 62.74; H, 7.18; N, 2.22. Found: C, 62.62; H, 7.10; N, 2.18.

(55) Physicochemical parameters and analytical data of de-N-ethyl-N-benzoyl-8-deoxy-14-O-anisoylaconine 1) Property and solubility Colorless and amorphous powder. Soluble in ether, chloroform, benzene, ethanol, methanol, ethylacetate, pyridine and dimethyl sulfoxide. Insoluble in hexane and water.

2) Analysis of IR spectra (KBr)

IR $v_{max}^{KBR}$: 1711, 1653 cm$^{-1}$.

3) Analysis of UV spectra (ethanol)

UV $\lambda_{max}^{EtOH}$ (log ε) nm: 232 (4.10), 258 (4.03).

4) Analysis of $^1$H-NMR spectra (CDCl$_3$)

The following signals are shown (δ, ppm). 7.82-7.10 (5H, m, benzoyl group at the nitrogen atom), 7.99 (2H, d, J=8.9 Hz, anisoyl group), 6.93 (2H, d, J=8.9, anisoyl group), 4.95 (1H, d, J=5.0, C14-β-H), 3.87 (3H, s, OCH$_3$ of anisoyl group), 3.70, 3.31, 3.27 and 3.25 (each 3H, s, OCH$_3$ at C1, C6, C16 and C18).

5) Analysis of $^{13}$C-NMR spectra (CDCl$_3$)

The following signals are shown (δ, ppm). 165.9 and 165.7 (benzoyl group at the nitrogen atom), 163.7, 131.7, 113.6 and 122.1 (anisoyl group), 133.9, 133.5, 128.6, 128.6, 128.2 and 127.6 (benzoyl group), 94.4, 83.7, 80.1, 79.8, 77.5, 75.1, 72.4 and 71.9 (C16, C6, C14, C1, C18, C13, C15 and C3), 61.8, 59.1, 57.8 and 56.0 (OCH$_3$ at C16, C18, C6 and C1), 55.4 (OCH$_3$ of anisoyl group).

6) Analysis of Mass spectra m/z: 693 (M$^+$).

7) Elemental analysis

Calculated for C$_{38}$H$_{47}$NO$_{11}$: C, 65.79; H, 6.83; N, 2.02. Found: C, 65.91; H, 6.79; N, 2.15.

(56) Physicochemical parameters and analytical data of 16-epi-8-deoxy-14-O-trimethylgalloylaconine 1) Property and solubility Colorless and amorphous powder. Soluble in ether, chloroform, benzene, ethanol, methanol, ethylacetate, pyridine and dimethyl sulfoxide. Insoluble in hexane and water.

2) Analysis of IR spectra (KBr)

IR $v_{max}^{KBR}$: 1720 cm$^{-1}$.

3) Analysis of UV spectra (ethanol)

UV $\lambda_{max}^{EtOH}$ (log ε) nm: 215 (4.30), 265 (4.05).

4) Analysis of $^1$H-NMR spectra (CDCl$_3$)

The following signals are shown (δ, ppm). 7.35 (2H, s, trimethylgalloyl group), 5.03 (1H, d, J=4.7 Hz, C14-β-H), 3.88 (9H, s, OCH$_3$ of trimethylgalloyl group), 3.75, 3.31, 3.30 and 3.26 (each 3H, s, OCH$_3$ at C1, C6, C16 and C18), 1.12 (3H, t, J=7.0 Hz, CH$_3$ of C$_2$H$_5$ at the nitrogen atom).

5) Analysis of $^{13}$C-NMR spectra (CDCl$_3$)

The following signals are shown (δ, ppm). 165.9 (carbonyl of trimethylgalloyl group), 124.3, 107.5, 145.2 and 133.8 (trimethylgalloyl group), 91.1, 85.2, 83.7, 80.3, 77.5, 75.2, 72.4 and 72.0 (C16, C6, C1, C14, C18, C13, C15 and C3), 55.9 (OCH$_3$ of trimethylgalloyl group), 61.9, 59.3, 58.0 and 56.1 (OCH$_3$ at C16, C18, C6 and C1), 49.0 (CH$_2$ of C$_2$H$_5$ at the nitrogen atom), 13.5 (CH$_3$ of C$_2$H$_5$ at the nitrogen atom).

6) Analysis of Mass spectra m/z: 677 (M$^+$).

(57) Physicochemical parameters and analytical data of 16-epi-8-deoxy-14-O-veratroylaconine 1) Property and solubility Colorless and amorphous powder. Soluble in ether, chloroform, benzene, ethanol, methanol, ethylacetate, pyridine and dimethyl sulfoxide. Insoluble in hexane and water.

2) Analysis of IR spectra (KBr)

IR $v_{max}^{KBR}$: 1720 cm$^{-1}$.

3) Analysis of UV spectra (ethanol)

UV $\lambda_{max}^{EtOH}$ (log ε) nm: 221 (4.35), 264 (4.08), 295 (3.84).

4) Analysis of $^1$H-NMR spectra (CDCl$_3$)

The following signals are shown (δ, ppm). 6.87-7.68 (3H, m, veratroyl group), 5.06 (1H, d, J=4.6 Hz, C14-β-H), 3.92 (6H, s, OCH$_3$ of veratroyl group), 3.76, 3.32, 3.29 and 3.26 (each 3H, s, OCH$_3$ at C1, C6, C16 and C18), 1.12 (3H, t, J=7.0 Hz, CH$_3$ of C$_2$H$_5$ at the nitrogen atom).

5) Analysis of $^{13}$C-NMR spectra (CDCl$_3$)

The following signals are shown (δ, ppm). 166.0 (carbonyl of veratroyl group), 122.5, 110.5, 153.1, 148.1 and 112.3 (veratroyl group), 91.2, 85.0, 83.7, 80.4, 77.4, 75.3, 72.4 and 72.0 (C16, C6, C1, C14, C18, C13, C15 and C3), 55.8 (OCH$_3$ of veratroyl group), 61.8, 59.1, 57.9 and 56.0 (OCH$_3$ at C16, C18, C6 and C1), 49.1 (CH$_2$ of C$_2$H$_5$ at the nitrogen atom), 13.4 (CH$_3$ of C$_2$H$_5$ at the nitrogen atom).

6) Analysis of Mass spectra m/z: 647 (M$^+$).

(58) Physicochemical parameters and analytical data of 16-epi-8-deoxy-14-O-p-chlorobenzoylaconine 1) Property and solubility Colorless and amorphous powder. Soluble in ether, chloroform, benzene, ethanol, methanol, ethylacetate, pyridine and dimethyl sulfoxide. Insoluble in hexane and water.

2) Analysis of IR spectra (KBr)

IR $v_{max}^{KBR}$: 1715 cm$^{-1}$.

3) Analysis of UV spectra (ethanol)

UV $\lambda_{max}^{EtOH}$ (log ε) nm: 246 (4.08).

4) Analysis of $^1$H-NMR spectra (CDCl$_3$)

The following signals are shown (δ, ppm). 7.91 and 7.38 (each 2H, d, J=8.9, p-chlorobenzoyl group), 5.10 (1H, d, J=4.8 Hz, C14-β-H), 3.85, 3.43, 3.36 and 3.36 (each 3H, s, OCH$_3$ at C1, C6, C16 and C18), 1.11 (3H, t, J=7.0 Hz, CH$_3$ of C$_2$H$_5$ at the nitrogen atom).

5) Analysis of $^{13}$C-NMR spectra (CDCl$_3$)

The following signals are shown (δ, ppm). 165.0 (carbonyl of p-chlorobenzoyl group), 130.5, 130.7, 128.7 and 139.6 (p-chlorobenzoyl group), 91.1, 84.8, 83.5, 80.7, 77.3, 75.2, 73.0 and 72.1 (C16, C6, C1, C14, C18, C13, C15 and C3), 62.2, 59.2, 58.0 and 56.0 (OCH$_3$ at C16, C18, C6 and C1), 49.2 (CH$_2$ of C$_2$H$_5$ at the nitrogen atom), 13.3 (CH$_3$ of C$_2$H$_5$ at the nitrogen atom).

6) Analysis of Mass spectra m/z: 621, 623 (M$^+$).

(59) Physicochemical parameters and analytical data of 16-epi-8-deoxy-14-O-m-chlorobenzoylaconine 1) Property and solubility Colorless and amorphous powder. Soluble in ether, chloroform, benzene, ethanol, methanol, ethylacetate, pyridine and dimethyl sulfoxide. Insoluble in hexane and water.

2) Analysis of IR spectra (KBr)

IR $v_{max}^{KBR}$: 1715 cm$^{-1}$.

3) Analysis of UV spectra (ethanol)

UV $\lambda_{max}^{EtOH}$ (log ε) nm: 231 (4.09), 280 (3.28), 289 (3.25).

4) Analysis of $^1$H-NMR spectra (CDCl$_3$)

The following signals are shown (δ, ppm). 7.98–7.30 (5H, m, m-chlorobenzoyl group), 5.05 (1H, d, J=4.7 Hz, C14-β-H), 3.86, 3.32, 3.30 and 3.30 (each 3H, s, OCH$_3$ at C1, C6, C16 and C18), 1.12 (3H, t, J=7.0 Hz, CH$_3$ of C$_2$H$_5$ at the nitrogen atom).

5) Analysis of $^{13}$C-NMR spectra (CDCl$_3$)

The following signals are shown (δ, ppm). 165.2 (carbonyl of m-chlorobenzoyl group), 131.6, 129.8, 129.5, 135.0 and 128.4 (m-chlorobenzoyl group), 91.4, 84.9, 83.4, 80.6, 77.2, 75.3, 73.0 and 72.1 (C16, C6, C1, C14, C18, C13, C15 and C3), 62.2, 59.2, 58.1 and 56.0 (OCH$_3$ at C16, C18, C6 and C1), 49.1 (CH$_2$ of C$_2$H$_5$ at the nitrogen atom), 13.3 (CH$_3$ of C$_2$H$_5$ at the nitrogen atom).

6) Analysis of Mass spectra m/z: 621, 623 (M$^+$).

(60) Physicochemical parameters and analytical data of 16-epi-8-deoxy-14-O-α-methyl-(4-(α-methylacetic acid-)phenyl)acetylaconine 1) Property and solubility Colorless and amorphous powder. Soluble in ether, chloroform, benzene, ethanol, methanol, ethylacetate, pyridine and dimethyl sulfoxide. Insoluble in hexane and water.

2) Analysis of IR spectra (KBr)

IR $v_{max}^{KBR}$: 1715 cm$^{-1}$.

3) Analysis of UV spectra (ethanol)

UV $\lambda_{max}^{EtOH}$ (log ε) nm: 220 (4.03), 256 (3.88).

4) Analysis of $^1$H-NMR spectra (CDCl$_3$)

The following signals are shown (δ, ppm). 7.30 (4H, s, benzene), 4.91 (1H, d, J=4.7 Hz, C14-β-H), 3.86, 3.45, 3.30 and 3.29 (each 3H, s, OCH$_3$ at C1, C6, C16 and C18), 3.63 (2H, q, J=7.0 Hz, CH of α-methylacetyl and α-methylacetic acid), 1.42 (6H, d, J=7.0 Hz, CH$_3$ of α-methylacetyl and α-methylacetic acid), 1.11 (3H, t, J=7.0 Hz, CH$_3$ of C$_2$H$_5$ at the nitrogen atom).

5) Analysis of $^{13}$C-NMR spectra (CDCl$_3$)

The following signals are shown (δ, ppm). 180.5 (carboxyl), 166.0 (carbonyl), 140.4, 139.3, 128.2 and 127.0 (benzene), 60.4 and 60.2 (CH of α-methylacetyl and α-methylacetic acid), 18.2 and 18.1 (CH$_3$ of α-methylacetyl and α-methylacetic acid), 90.5, 85.0, 83.7, 80.4, 77.5, 75.3, 72.4 and 72.0 (C16, C6, C1, C14, C18, C13, C15 and C3), 61.9, 59.2, 58.0 and 56.1 (OCH$_3$ at C16, C18, C6 and C1), 49.0 (CH$_2$ of C$_2$H$_5$ at the nitrogen atom), 13.2 (CH$_3$ of C$_2$H$_5$ at the nitrogen atom).

6) Analysis of Mass spectra m/z: 687 (M$^+$).

(61) Physicochemical parameters and analytical data of 16-epi-8-deoxy-14-O-methylaconine 1) Property and solubility Colorless and amorphous powder. Soluble in ether, chloroform, benzene, ethanol, methanol, ethylacetate, pyridine and dimethyl sulfoxide. Insoluble in hexane and water.

2) Analysis of IR spectra (KBr)

IR $v_{max}^{KBR}$: 3300 cm$^{-1}$.

3) Analysis of $^1$H-NMR spectra (CDCl$_3$)

The following signals are shown (δ, ppm). 3.80, 3.39, 3.38, 3.31 and 3.27 (each 3H, s, OCH$_3$ at C1, C6, C16, C14 and C18), 1.10 (3H, t, J=7.0 Hz, CH$_3$ of C$_2$H$_5$ at the nitrogen atom).

4) Analysis of $^{13}$C-NMR spectra (CDCl$_3$)

The following signals are shown (δ, ppm). 90.3, 84.7, 83.5, 81.3, 77.5, 77.2, 72.4 and 72.0 (C16, C6, C14, C18, C13, C15 and C3), 60.6, 59.2, 58.3, 58.1 and 56.0 (C16, C18, C14, C6 and C1), 49.4 (CH$_2$ of C$_2$H$_5$ at the nitrogen atom), 14.1 (CH$_3$ of C$_2$H$_5$ at the nitrogen atom).

5) Analysis of Mass spectra m/z: 497 (M$^+$).

(62) Physicochemical parameters and analytical data of 16-epi-8-deoxy-14-O-benzylaconine 1) Property and solubility Colorless and amorphous powder. Soluble in ether, chloroform, benzene, ethanol, methanol, ethylacetate, pyridine and dimethyl sulfoxide. Insoluble in hexane and water.

2) Analysis of IR spectra (KBr)

IR $v_{max}^{KBR}$: 3300 cm$^{-1}$.

3) Analysis of UV spectra (ethanol)

UV $\lambda_{max}^{EtOH}$ (log ε) nm: 225 (4.10).

4) Analysis of $^1$H-NMR spectra (CDCl$_3$)

The following signals are shown (δ, ppm). 7.28 (5H, s, benzyl group), 4.48 (2H, s, CH$_2$ of benzyl group), 3.80, 3.30, 3.30 and 3.28 (each 3H, s, OCH$_3$ at C1, C6, C16 and C18), 1.08 (3H, t, J=7.0 Hz, CH$_3$ of C$_2$H$_5$ at the nitrogen atom).

5) Analysis of $^{13}$C-NMR spectra (CDCl$_3$)

The following signals are shown (δ, ppm). 126.5, 127.0, 128.3 and 141.5 (benzyl group), 64.1 (CH$_2$ of benzyl group), 90.5, 84.5, 83.1, 81.2, 77.4, 77.3, 72.4 and 72.1 (C16, C6, C1, C14, C18, C13, C15 and C3), 60.3, 59.1, 58.1 and 56.0 (OCH$_3$ at C16, C18, C6 and C1), 49.5 (CH$_2$ of C$_2$H$_5$ at the nitrogen atom), 14.0 (CH$_3$ of C$_2$H$_5$ at the nitrogen atom).

6) Analysis of Mass spectra m/z: 573 (M$^+$).

(63) Physicochemical parameters and analytical data of 16-epi-8-deoxy-14-O-crotylaconine 1) Property and solubility Colorless and amorphous powder. Soluble in ether, chloroform, benzene, ethanol, methanol, ethylacetate, pyridine and dimethyl sulfoxide. Insoluble in hexane and water.

2) Analysis of IR spectra (KBr)

IR $v_{max}^{KBR}$: 3300 cm$^{-1}$.

3) Analysis of $^1$H-NMR spectra (CDCl$_3$)

The following signals are shown (δ, ppm). 5.70 (2H, m, crotyl group), 4.10 (2H, m, CH$_2$ of crotyl group), 3.82, 3.40, 3.27 and 3.27 (each 3H, s, OCH$_3$ at C1, C6, C16 and C18), 1.70 (3H, d, J=6.3 Hz, CH$_3$ of crotyl group), 0.88 (3H, t, J=7.3 Hz, CH$_3$ of C$_2$H$_5$ at the nitrogen atom), 4) Analysis of $^{13}$C-NMR spectra (CDCl$_3$)

The following signals are shown (δ, ppm). 130.8 and 123.7 (crotyl group), 90.4, 84.6, 83.5, 81.2, 77.5, 77.2, 72.4 and 72.0 (C16, C6, C1, C14, C18, C13, C15 and C3), 60.5, 59.1, 58.0 and 55.5 (OCH$_3$ at C16, C18, C6 and C1), 49.5 (CH$_2$ of C$_2$H$_5$ at the nitrogen atom), 13.9 (CH$_3$ of C$_2$H$_5$ at the nitrogen atom), 12.7 (CH$_3$ of crotyl group).

5) Analysis of Mass spectra m/z: 537 (M$^+$).

(64) Physicochemical parameters and analytical data of 16-epi-8-deoxy-14-O-o-chlorobenzoylaconine 1) Property and solubility Colorless and amorphous powder. Soluble in ether, chloroform, benzene, ethanol, methanol, ethylacetate, pyridine and dimethyl sulfoxide. Insoluble in hexane and water.

2) Analysis of IR spectra (KBr)

IR $v_{max}^{KBR}$: 1715 cm$^{-1}$.

3) Analysis of UV spectra (ethanol)

UV $\lambda_{max}^{EtOH}$ (log ε) nm: 227 (4.01), 280 (3.20).

4) Analysis of $^1$H-NMR spectra (CDCl$_3$)

The following signals are shown (δ, ppm). 8.00–7.45 (5H, m, o-chlorobenzoyl group), 5.02 (1H, d, J=4.8 Hz, C14-β-H), 3.85, 3.45, 3.40 and 3.40 (each 3H, s, OCH$_3$ at C1, C6, C16 and C18), 0.88 (3H, t, J=7.0 Hz, CH$_3$ of C$_2$H$_5$ at the nitrogen atom).

5) Analysis of $^{13}$C-NMR spectra (CDCl$_3$)

The following signals are shown (δ, ppm). 166.0 (carbonyl of o-chlorobenzoyl group), 129.9, 136.0, 128.7, 133.8 and 126.3 (o-chlorobenzoyl group), 90.3, 84.9, 83.5, 80.4, 77.7, 75.1, 72.6 and 72.0 (C16, C6, C1, C14, C18, C13, C15 and C3), 61.8, 59.1, 57.9 and 56.0 (OCH$_3$ at C16, C18, C6 and C1), 49.0 (CH$_2$ of C$_2$H$_5$ at the nitrogen atom), 13.5 (CH$_3$ of C$_2$H$_5$ at the nitrogen atom).

6) Analysis of Mass spectra
 m/z: 621, 623 (M$^+$).

(65) Physicochemical parameters and analytical data of 16-epi-8-deoxy-14-O-m-anisoylaconine 1) Property and solubility
Colorless and amorphous powder. Soluble in ether, chloroform, benzene, ethanol, methanol, ethylacetate, pyridine and dimethyl sulfoxide. Insoluble in hexane and water.

2) Analysis of IR spectra (KBr)
 IR $v_{max}^{KBR}$: 1715 cm$^{-1}$.

3) Analysis of UV spectra (ethanol)
 UV $\lambda_{max}^{EtOH}$ (log ε) nm: 236 (4.07), 296 (2.62).

4) Analysis of $^1$H-NMR spectra (CDCl$_3$)
The following signals are shown (δ, ppm). 7.64-7.26 (5H, m, m-anisoyl group), 4.92 (1H, d, J=4.6 Hz, C14 -β-H), 3.71, 3.30, 3.30 and 3.89 (each 3H, s, OCH$_3$ at C1, C6, C16 and C18), 3.91 (3H, s, OCH$_3$ of m-anisoyl group), 1.18 (3H, t, J=7.0 Hz, CH$_3$ of C$_2$H$_5$ at the nitrogen atom).

5) Analysis of $^{13}$C-NMR spectra (CDCl$_3$)
The following signals are shown (δ, ppm). 165.0 (carbonyl of m-anisoyl group), 131.2, 121.4, 129.5, 118.3, 158.9 and 115.2 (m-anisoyl group), 90.2, 85.1, 83.7, 80.2, 77.5, 75.3, 72.4 and 72.0 (C16, C6, C1, C14, C18, C13, C15 and C3), 55.4 (OCH$_3$ of m-anisoyl group), 61.6, 59.1, 58.0 and 56.1 (OCH$_3$ at C16, C18, C6 and C1), 49.1 (CH$_2$ of C$_2$H$_5$ at the nitrogen atom), 13.5 (CH$_3$ of C$_2$H$_5$ at the nitrogen atom).

6) Analysis of Mass spectra
 m/z: 617 (M$^+$).

(66) Physicochemical parameters and analytical data of 16-epi-de-N-ethyl-8-deoxy-14-O-anisoylaconine 1) Property and solubility
Colorless and amorphous powder. Soluble in ether, chloroform, benzene, ethanol, methanol, ethylacetate, pyridine and dimethyl sulfoxide. Insoluble in hexane and water.

2) Analysis of IR spectra (KBr)
 IR $v_{max}^{KBR}$: 1715 cm$^{-1}$.

3) Analysis of UV spectra (ethanol)
 UV $\lambda_{max}^{EtOH}$ (log ε) nm: 258 (4.02).

4) Analysis of $^1$H-NMR spectra (CDCl$_3$)
The following signals are shown (δ, ppm). 7.99 and 6.94 (each 2H, d, J=8.9 Hz, anisoyl group), 5.15 (1H, d, J=5.0 Hz, C14-β-H), 3.84, 3.30, 3.28 and 3.25 (each 3H, s, OCH$_3$ at C1, C6, C16 and C18), 3.87 (3H, s, OCH$_3$ of anisoyl group).

5) Analysis of $^{13}$C-NMR spectra (CDCl$_3$)
The following signals are shown (δ, ppm). 166.0 (carbonyl of anisoyl group), 163.5, 131.8, 113.7 and 122.1 (anisoyl group), 91.2, 85.1, 83.7, 80.2, 77.4, 75.9, 72.4 and 72.0 (C16, C6, C1, C14, C18, C13, C15 and C3), 55.4 (OCH$_3$ of anisoyl group), 62.2, 59.0, 57.9 and 56.1 (OCH$_3$ at C16, C18, C6 and C1).

6) Analysis of Mass spectra
 m/z: 573 (M$^+$).

(67) Physicochemical parameters and analytical data of 16-epi-de-N-ethyl-N-amyl-8-deoxy-14-O-anisoylaconine 1) Property and solubility
Colorless and amorphous powder. Soluble in ether, chloroform, benzene, ethanol, methanol, ethylacetate, pyridine and dimethyl sulfoxide. Insoluble in hexane and water.

2) Analysis of IR spectra (KBr)
 IR $v_{max}^{KBR}$: 1715 cm$^{-1}$.

3) Analysis of UV spectra (ethanol)
 UV $\lambda_{max}^{EtOH}$ (log ε) nm: 257 (4.02).

4) Analysis of $^1$H-NMR spectra (CDCl$_3$)
The following signals are shown (δ, ppm). 8.01 and 6.93 (each 2H, d, J=8.9 Hz, anisoyl group), 5.14 (1H, d, J=5.0 Hz, C14-β-H), 3.83, 3.30, 3.28 and 3.25 (each 3H, s, OCH$_3$ at C1, C6, C16 and C18), 3.87 (3H, s, OCH$_3$ of anisoyl group), 0.98 (3H, t, J=7.0 Hz, CH$_3$ of amyl group at the nitrogen atom).

5) Analysis of $^{13}$C-NMR spectra (CDCl$_3$)
The following signals are shown (δ, ppm). 166.0 (carbonyl of anisoyl group), 163.8, 131.8, 113.5 and 122.2 (anisoyl group), 91.2, 85.3, 83.6, 80.0, 77.6, 76.0, 72.5 and 72.0 (C16, C6, C1, C14, C18, C13, C15 and C3), 55.4 (OCH$_3$ of anisoyl group), 62.2, 59.1, 57.8 and 56.0 (OCH$_3$ at C16, C18, C6 and C1), 13.1 (CH$_3$ of amyl group at the nitrogen atom).

6) Analysis of Mass spectra
 m/z: 671 (M$^+$).

(68) Physicochemical parameters and analytical data of 16-epi-de-N-ethyl-N-propyl-8-deoxy-14-O-anisoylaconine 1) Property and solubility
Colorless and amorphous powder. Soluble in ether, chloroform, benzene, ethanol, methanol, ethylacetate, pyridine and dimethyl sulfoxide. Insoluble in hexane and water.

2) Analysis of IR spectra (KBr)
 IR $v_{max}^{KBR}$: 1715 cm$^{-1}$.

3) Analysis of UV spectra (ethanol)
 UV $\lambda_{max}^{EtOH}$ (log ε) nm: 258 (4.02).

4) Analysis of $^1$H-NMR spectra (CDCl$_3$)
The following signals are shown (δ, ppm). 8.99 and 6.94 (each 2H, d, J=8.9 Hz, anisoyl group), 5.12 (1H, d, J=5.0 Hz, C14-β-H), 3.84, 3.30, 3.29 and 3.24 (each 3H, s, OCH$_3$ at C1, C6, C16 and C18), 3.87 (3H, s, OCH$_3$ of anisoyl group), 1.10 (3H, t, J=7.0 Hz, CH$_3$ of propyl group at the nitrogen atom).

5) Analysis of $^{13}$C-NMR spectra (CDCl$_3$)
The following signals are shown (δ, ppm). 165.9 (carbonyl of anisoyl group), 163.6, 131.8, 122.2 and 113.7 (anisoyl group), 91.2, 85.2, 83.7, 80.2, 77.5, 76.0, 72.3 and 71.9 (C16, C6, C1, C14, C18, C13, C15 and C3), 55.4 (OCH$_3$ of anisoyl group), 62.2, 59.1, 57.9 and 56.1 (OCH$_3$ at C16, C18, C6 and C1), 13.0 (CH$_3$ of propyl group at the nitrogen atom).

6) Analysis of Mass spectra
 m/z: 643 (M$^+$).

(69) Physicochemical parameters and analytical data of 16-epi-de-N-ethyl-N-(4-methyl)pentyl-8-deoxy-14-O-anisoylaconine 1) Property and solubility
Colorless and amorphous powder. Soluble in ether, chloroform, benzene, ethanol, methanol, ethylacetate, pyridine and dimethyl sulfoxide. Insoluble in hexane and water.

2) Analysis of IR spectra (KBr)
 IR $v_{max}^{KBR}$: 1715 cm$^{-1}$.

3) Analysis of UV spectra (ethanol)
 UV $\lambda_{max}^{EtOH}$ (log ε) nm: 258 (4.01).

4) Analysis of $^1$H-NMR spectra (CDCl$_3$)
The following signals are shown (δ, ppm). 8.01 and 6.94 (each 2H, d, J=8.9 Hz, anisoyl group), 5.12 (1H, d, J=5.0 Hz, C14-β-H), 3.84, 3.29, 3.28 and 3.25 (each 3H, s, OCH$_3$ at C1, C6, C16 and C18), 3.88 (3H, s, OCH$_3$ of anisoyl group), 1.02 (6H, d, J=7.0 Hz, CH$_3$ of 4-methylpentyl group at the nitrogen atom).

5) Analysis of $^{13}$C-NMR spectra (CDCl$_3$)

The following signals are shown (δ, ppm). 166.0 (carbonyl of anisoyl group), 163.9, 131.7, 122.1 and 113.4 (anisoyl group), 91.3, 85.2, 83.5, 80.0, 77.6, 76.0, 72.5 and 71.9 (C16, C6, C1, C14, C18, C13, C15 and C3), 55.4 ($OCH_3$ of anisoyl group), 62.2, 59.1, 57.8 and 56.0 ($OCH_3$ at C16, C18, C6 and C1), 21.5 ($CH_3$ of 4-methylpentyl group at the nitrogen atom).

6) Analysis of Mass spectra
m/z: 685 ($M^+$).

(70) Physicochemical parameters and analytical data of 16-epi-de-N-ethyl-N-acetyl-8-deoxy-14-O-anisoylaconine 1) Property and solubility
Colorless and amorphous powder. Soluble in ether, chloroform, benzene, ethanol, methanol, ethylacetate, pyridine and dimethyl sulfoxide. Insoluble in hexane and water.

2) Analysis of IR spectra (KBr)
IR $v_{max}^{KBR}$: 1715, 1655 $cm^{-1}$.

3) Analysis of UV spectra (ethanol)
UV $\lambda_{max}^{EtOH}$ (log ε) nm: 258 (4.02).

4) Analysis of $^1$H-NMR spectra ($CDCl_3$)
The following signals are shown (δ, ppm). 7.99 and 6.94 (each 2H, d, J=8.9 Hz, anisoyl group), 5.15 (1H, d, J=5.0 Hz, C14-β-H), 3.84, 3.30, 3.28 and 3.25 (each 3H, s, $OCH_3$ at C1, C6, C16 and C18), 3.87 (3H, s, $OCH_3$ of anisoyl group), 2.34 (3H, s, $CH_3$ of acetyl group at the nitrogen atom).

5) Analysis of $^{13}$C-NMR spectra ($CDCl_3$)
The following signals are shown (δ, ppm). 170.9 (carboxyl of acetyl group at the nitrogen atom), 165.9 (carbonyl of anisoyl group), 163.6, 131.8, 113.7 and 122.2 (anisoyl group), 91.2, 83.7, 80.2, 79.8, 77.5, 76.0, 72.4 and 72.0 (C16, C6, C14, C1, C18, C13, C15 and C3), 62.2, 59.1, 57.9 and 56.1 ($OCH_3$ at C16, C18, C6 and C1), 55.4 ($OCH_3$ of anisoyl group), 22.4 ($CH_3$ of acetyl group at the nitrogen atom).

6) Analysis of Mass spectra
m/z: 643 ($M^+$).

(71) Physicochemical parameters and analytical data of 16-epi-de-N-ethyl-N-benzoyl-8-deoxy-14-O-anisoylaconine 1) Property and solubility
Colorless and amorphous powder. Soluble in ether, chloroform, benzene, ethanol, methanol, ethylacetate, pyridine and dimethyl sulfoxide. Insoluble in hexane and water.

2) Analysis of IR spectra (KBr)
IR $v_{max}^{KBR}$: 1711, 1653 $cm^{-1}$.

3) Analysis of UV spectra (ethanol)
UV $\lambda_{max}^{EtOH}$ (log ε) nm: 232 (4.10), 258 (4.03).

4) Analysis of $^1$H-NMR spectra ($CDCl_3$)
The following signals are shown (δ, ppm). 7.82-7.10 (5H, m, benzoyl group), 7.99 and 6.93 (each 2H, d, J=8.9 Hz, anisoyl group), 5.14 (1H, d, J=5.0 Hz, C14-β-H), 3.84, 3.31, 3.27 and 3.25 (each 3H, s, $OCH_3$ at C1, C6, C16 and C18), 3.87 (3H, s, $OCH_3$ of anisoyl group).

5) Analysis of $^{13}$C-NMR spectra ($CDCl_3$)
The following signals are shown (δ, ppm). 165.9 and 165.7 (carbonyl group), 163.7, 131.7, 113.6 and 122.1 (anisoyl group), 133.9, 133.5, 128.6, 128.2 and 127.6 (benzoyl group), 91.3, 83.7, 80.1, 79.9, 77.5, 76.0, 72.4 and 71.9 (C16, C6, C14, C1, C18, C13, C15 and C3), 62.2, 59.1, 57.8 and 56.0 ($OCH_3$ at C16, C18, C6 and C1), 55.4 ($OCH_3$ of anisoyl group).

6) Analysis of Mass spectra
m/z: 705 ($M^+$).

(72) Physicochemical parameters and analytical data of 8-deoxy-14-O-p-methoxybenzylaconine 1) Property and solubility
Colorless and amorphous powder. Soluble in ether, chloroform, benzene, ethanol, methanol, ethylacetate, pyridine and dimethyl sulfoxide. Insoluble in hexane and water.

2) Analysis of IR spectra (KBr)
IR $v_{max}^{KBR}$: 3300 $cm^{-1}$.

3) Analysis of UV spectra (ethanol)
UV $\lambda_{max}^{EtOH}$ (log ε) nm: 224 (4.19), 275 (3.60), 280 (3.53).

4) Analysis of $^1$H-NMR spectra ($CDCl_3$)
The following signals are shown (δ, ppm). 7.10 and 6.73 (each 2H, d, J=8.9 Hz, benzene of p-methoxybenzyl group), 3.65, 3.39, 3.31 and 3.28 (each 3H, s, $OCH_3$ at C1, C6, C16 and C18), 3.91 (3H, s, $OCH_3$ of p-methoxybenzyl group), 4.45 (2H, s, $CH_2$ of p-methoxybenzyl group), 1.09 (3H, t, J=7.0 Hz, $CH_3$ of $C_2H_5$ at the nitrogen atom).

5) Analysis of $^{13}$C-NMR spectra ($CDCl_3$)
The following signals are shown (δ, ppm). 133.6, 128.2, 113.8 and 157.7 (p-methoxybenzyl group), 64.0 ($CH_2$ of p-methoxybenzyl group), 93.7, 84.4, 83.2, 81.0, 77.4, 77.2, 72.3 and 72.0 (C16, C6, C14, C18, C13, C15 and C3), 60.2, 59.1, 58.1 and 56.0 ($OCH_3$ at C16, C18, C6 and C1), 55.8 ($OCH_3$ of p-methoxybenzyl group), 49.4 ($CH_2$ of $C_2H_5$ at the nitrogen atom), 14.0 ($CH_3$ of $C_2H_5$ at the nitrogen atom).

6) Analysis of Mass spectra
m/z: 603 ($M^+$).

7) Elemental analysis
Calculated for $C_{33}H_{49}NO_9$: C, 65.65; H, 8.18; N, 2.32. Found: C, 65.73; H, 8.29; N, 2.12.

(73) Physicochemical parameters and analytical data of 8-deoxy-14-O-amylaconine

1) Property and solubility
Colorless and amorphous powder. Soluble in ether, chloroform, benzene, ethanol, methanol, ethylacetate, pyridine and dimethyl sulfoxide. Insoluble in hexane and water.

2) Analysis of IR spectra (KBr)
IR $v_{max}^{KBR}$: 3300 $cm^{-1}$.

3) Analysis of $^1$H-NMR spectra ($CDCl_3$)
The following signals are shown (δ, ppm). 3.64, 3.33, 3.31 and 3.28 (each 3H, s, $OCH_3$ at C1, C6, C16 and C18), 0.92 (3H, t, J=7.4 Hz, $CH_3$ of $C_2H_5$ at the nitrogen atom), 0.90 (3H, t, J=10.1 Hz, $CH_3$ of amyl group).

4) Analysis of $^{13}$C-NMR spectra ($CDCl_3$)
The following signals are shown (δ, ppm). 93.5, 84.6, 83.5, 81.2, 77.5, 77.2, 72.5 and 72.1 (C16, C6, C14, C18, C13, C15 and C3), 60.5, 59.1, 58.0 and 55.6 ($OCH_3$ at C16, C18, C6 and C1), 49.4 ($CH_2$ of $C_2H_5$ at the nitrogen atom), 14.0 ($CH_3$ of $C_2H_5$ at the nitrogen atom), 13.5 ($CH_3$ of amyl group).

5) Analysis of Mass spectra
m/z: 553 ($M^+$).

6) Elemental analysis
Calculated for $C_{30}H_{51}NO_8$: C, 65.07; H, 9.28; N, 2.53. Found: C, 64.99; H, 9.35; N, 2.49.

(74) Physicochemical parameters and analytical data of 8-deoxy-14-O-m-bromobenzoylaconine 1) Property and solubility
Colorless and amorphous powder. Soluble in ether, chloroform, benzene, ethanol, methanol, ethylacetate, pyridine and dimethyl sulfoxide. Insoluble in hexane and water.

2) Analysis of IR spectra (KBr)
IR $v_{max}^{KBR}$: 1723 $cm^{-1}$.

3) Analysis of UV spectra (ethanol)
UV $\lambda_{max}^{EtOH}$ (log ε) nm: 225 (4.15), 280 (3.14), 289 (3.12).

4) Analysis of $^1$H-NMR spectra ($CDCl_3$)
8.18-7.34 (4H, m, m-bromobenzoyl group), 5.00 (1H, d, J=5.0 Hz, C14-β-H), 3.71, 3.30, 3.29 and 3.27 (each 3H, s, $OCH_3$ at C1, C6, C16 and C18), 1.13 (3H, t, J=7.1 Hz, $CH_3$ of $C_2H_5$ at the nitrogen atom).

5) Analysis of $^{13}$C-NMR spectra ($CDCl_3$)

The following signals are shown (δ, ppm). 165.0 (carbonyl of m-bromobenzoyl group), 136.4, 136.1, 132.0, 130.1, 128.3 and 122.6 (m-bromobenzoyl group), 94.1, 85.1, 83.5, 81.0, 77.2, 75.1, 72.4 and 71.9 (C16, C6, C1, C14, C18, C13, C15 and C3), 59.2, 59.0 and 56.1 (OCH$_3$ at C16, C18, C6 and C1), 49.2 (CH$_2$ of C$_2$H$_5$ at the nitrogen atom), 13.3 (CH$_3$ of C$_2$H$_5$ at the nitrogen atom).

6) Analysis of Mass spectra
MS m/z: 665, 667 (M$^+$).

7) Elemental analysis
Calculated for C$_{32}$H$_{44}$NO$_9$: C, 57.66; H, 6.65; N, 2.10.
Found: C, 57.48; H, 6.91; N 2.00.

(75) Physicochemical parameters and analytical data of 8-deoxy-14-O-m-fluorobenzoylaconine 1) Property and solubility
Colorless and amorphous powder. Soluble in ether, chloroform, benzene, ethanol, methanol, ethylacetate, pyridine and dimethyl sulfoxide. Insoluble in hexane and water.

2) Analysis of IR spectra (KBr)
IR $v_{max}^{KBR}$: 1725 cm$^{-1}$.

3) Analysis of UV spectra (ethanol)
UV $\lambda_{max}^{EtOH}$ (log ε) nm: 228 (4.18), 278 (3.39), 285 (3.33).

4) Analysis of $^1$H-NMR spectra (CDCl$_3$)
7.95–7.40 (4H, m, m-fluorobenzoyl group), 5.01 (1H, d, J=5.1 Hz, C14-β-H), 3.94, 3.32, 3.31 and 3.19 (each 3H, s, OCH$_3$ at C1, C6, C16 and C18), 1.26 (3H, t, J=7.0 Hz, CH$_3$ of C$_2$H$_5$ at the nitrogen atom).

5) Analysis of $^{13}$C-NMR spectra (CDCl$_3$)
164.4 (carbonyl of m-fluorobenzoyl group), 160.5, 130.3, 130.2, 125.6, 120.5 and 116.7 (m-fluorobenzoyl group), 93.9, 84.9, 83.7, 80.6, 77.2, 75.0, 72.0 and 71.8 (C16, C6, C1, C14, C18, C13, C15 and C3), 59.2, 58.1, 57.7 and 56.2 (OCH$_3$ at C16, C18, C6 and C1), 49.4 (CH$_2$ of C$_2$H$_5$ at the nitrogen atom), 12.8 (CH$_3$ of C$_2$H$_5$ at the nitrogen atom).

6) Analysis of Mass spectra
m/z: 605 (M$^+$).

7) Elemental analysis
Calculated for C$_{32}$H$_{44}$NO$_9$: C, 63.46; H, 7.32; N 2.31.
Found: C, 63.41; H, 7.29; N, 2.41.

(76) Physicochemical parameters and analytical data of 3,8,13-trideoxy-14-O-veratroylaconine 1) Property and solubility
Colorless and amorphous powder. Soluble in ether, chloroform, benzene, ethanol, methanol, ethylacetate, pyridine and dimethyl sulfoxide. Insoluble in hexane and water.

2) Analysis of IR spectra (KBr)
IR $v_{max}^{KBR}$: 1720 cm$^{-1}$.

3) Analysis of UV spectra (ethanol)
UV $\lambda_{max}^{EtOH}$ (log ε) nm: 221 (4.35), 264 (4.08), 295 (3.84).

4) Analysis of $^1$H-NMR spectra (CDCl$_3$)
The following signals are shown (δ, ppm). 6.88–7.68 (3H, m, veratroyl group), 5.20 (1H, t, J=4.6 Hz, C14-β -H), 3.92 (6H, s, OCH$_3$ of veratroyl group), 3.36, 3.30, 3.28 and 3.26 (each 3H, s, OCH$_3$ at C1, C6, C16 and C18), 1.10 (3H, t, J=7.0 Hz, CH$_3$ of C$_2$H$_5$ at the nitrogen atom).

5) Analysis of $^{13}$C-NMR spectra (CDCl$_3$)
The following signals are shown (δ, ppm). 166.0 (carbonyl of veratroyl group), 122.5, 110.5, 153.1, 148.2 and 112.3 (veratroyl group), 93.0, 86.0, 85.1, 81.9, 78.4 and 72.4 (C16, C1, C6, C18, C14 and C15), 55.8 (OCH$_3$ of veratroyl group), 59.1, 58.7, 57.9 and 56.0 (OCH$_3$ at C18, C16, C6 and C1), 49.0 (CH$_2$ of C$_2$H$_5$ at the nitrogen atom), 13.4 (CH$_3$ of C$_2$H$_5$ at the nitrogen atom).

6) Analysis of Mass spectra
m/z: 615 (M$^+$).

7) Elemental analysis
Calculated for C$_{34}$H$_{49}$NO$_9$: C, 66.32; H, 8.02; N, 2.27.
Found: C, 66.51; H, 7.96; N, 2.36.

(77) Physicochemical parameters and analytical data of 3,8,13-trideoxy-14-O-acetylaconine 1) Property and solubility
Colorless and amorphous powder. Soluble in ether, chloroform, benzene, ethanol, methanol, ethylacetate, pyridine and dimethyl sulfoxide. Insoluble in hexane and water.

2) Analysis of IR spectra (KBr)
IR $v_{max}^{KBr}$: 1713 cm$^{-1}$.

3) Analysis of $^1$H-NMR spectra (CDCl$_3$)
5.05 (1H, t, J=5.0 Hz, C14-β-H), 3.36, 3.30, 3.27 and 3.23 (each 3H, s, OCH$_3$ at C1, C6, C16 and C18), 2.03 (3H, s, CH$_3$ of acetyl group), 1.10 (3H, t, J=7.0 Hz, CH$_3$ of C$_2$H$_5$ at the nitrogen atom).

4) Analysis of $^{13}$C-NMR spectra (CDCl$_3$)
The following signals are shown (δ, ppm). 171.5 (carbonyl of acetyl group), 93.0, 86.0, 85.1, 81.7, 77.4 and 72.4 (C16, C1, C6, C18, C14 and C15), 59.2, 58.8, 57.7 and 56.1 (OCH$_3$ at C18, C16, C6 and C1), 49.1 (CH$_2$ of C$_2$H$_5$ at the nitrogen atom), 13.4 (CH$_3$ of C$_2$H$_5$ at the nitrogen atom), 21.4 (CH$_3$ of acetyl group).

5) Analysis of Mass spectra
m/z: 493 (M$^+$).

6) Elemental analysis
Calculated for C$_{27}$H$_{43}$NO$_7$: C, 65.69; H, 8.78; N, 2.84.
Found: C, 65.81; H, 8.67; N, 2.63.

(78) Physicochemical parameters and analytical data of 3,8,13-trideoxy-14-O-m-chlorobenzoylaconine 1) Property and solubility
Colorless and amorphous powder. Soluble in ether, chloroform, benzene, ethanol, methanol, ethylacetate, pyridine and dimethyl sulfoxide. Insoluble in hexane and water.

2) Analysis of IR spectra (KBr)
IR $v_{max}^{KBr}$: 1715 cm$^{-1}$.

3) Analysis of UV spectra (ethanol)
UV $\lambda_{max}^{EtOH}$ (log ε) nm: 231 (4.09), 280 (3.28), 289 (3.25).

4) Analysis of $^1$H-NMR spectra (CDCl$_3$)
The following signals are shown (δ, ppm). 7.78–7.30 (5H, m, m-chlorobenzoyl group), 5.06 (1H, t, J=4.7 Hz, C14-β-H), 3.51, 3.32, 3.28 and 3.25 (each 3H, s, OCH$_3$ at C1, C6, C16 and C18), 1.12 (3H, t, J=7.0 Hz, CH$_3$ of C$_2$H$_5$ at the nitrogen atom).

5) Analysis of $^{13}$C-NMR spectra (CDCl$_3$)
The following signals are shown (δ, ppm). 165.0 (carbonyl of m-chlorobenzoyl group), 131.6, 130.0, 129.5, 135.0 and 128.4 (m-chlorobenzoyl group), 93.1, 86.0, 85.3, 82.0, 78.3 and 72.5 (C16, C1, C6, C18, C14 and C15), 59.0, 58.7, 58.0 and 56.0 (OCH$_3$ at C18, C16, C6 and C1), 49.2 (CH$_2$ of C$_2$H$_5$ at the nitrogen atom), 13.1 (CH$_3$ of C$_2$H$_5$ at the nitrogen atom).

6) Analysis of Mass spectra
m/z: 589, 591 (M$^+$).

7) Elemental analysis
Calculated for C$_{32}$H$_{44}$NO$_7$Cl: C, 65.13; H, 7.51; N, 2.37.
Found: C, 65.41; H, 7.66; N, 2.14.

(79) Physicochemical parameters and analytical data of 3,8,13-trideoxy-14-O-benzylaconine 1) Property and solubility
Colorless and amorphous powder. Soluble in ether, chloroform, benzene, ethanol, methanol, ethylacetate, pyridine and dimethyl sulfoxide. Insoluble in hexane and water.

2) Analysis of IR spectra (KBr)
IR $v_{max}^{KBr}$: 3450 cm$^{-1}$.

3) Analysis of UV spectra (ethanol)

UV $\lambda_{max}^{EtOH}$ (log ε) nm: 225 (4.09).

4) Analysis of $^1$H-NMR spectra (CDCl$_3$)

The following signals are shown (δ, ppm). 7.29 (5H, s, benzyl group), 4.48 (2H, s, CH$_2$ of benzyl group), 3.47, 3.31, 3.31 and 3.28 (each 3H, s, OCH$_3$ at C1, C6, C16 and C18), 1.09 (3H, t, J=7.0 Hz).

5) Analysis of $^{13}$C-NMR spectra (CDCl$_3$)

The following signals are shown (δ, ppm). 126.3, 127.3, 128.0 and 141.8 (benzyl group), 64.3 (CH$_2$ of benzyl group), 92.5, 86.1, 84.3, 82.0, 81.1 and 72.5 (C16, C1, C6, C18, C14 and C15), 59.2, 58.0, 57.2 and 56.0 (C16, C6, C18 and C1), 49.2 (CH$_2$ of C$_2$H$_5$ at the nitrogen atom), 13.1 (CH$_3$ of C$_2$H$_5$ at the nitrogen atom).

6) Analysis of Mass spectra m/z: 541 (M$^+$).

7) Elemental analysis

Calculated for C$_{32}$H$_{47}$NO$_6$: C, 70.95; H, 8.74; N, 2.59. Found: C, 70.77; H, 8.84; N, 2.65.

(80) Physicochemical parameters and analytical data of 3,8,13-trideoxy-14-O-(4-methyl)pentylaconine 1) Property and solubility Colorless and amorphous powder. Soluble in ether, chloroform, benzene, ethanol, methanol, ethylacetate, pyridine and dimethyl sulfoxide. Insoluble in hexane and water.

2) Analysis of $^1$H-NMR spectra (CDCl$_3$)

The following signals are shown (δ, ppm). 3.50, 3.37, 3.28 and 3.28 (each 3H, s, OCH$_3$ at C1, C6, C16 and C18), 1.02 (6H, d, J=7.0 Hz, CH$_3$ of 4-methylpentyl group), 1.10 (3H, t, J=7.0, CH$_3$ of C$_2$H$_5$ at the nitrogen atom).

3) Analysis of $^{13}$C-NMR spectra (CDCl$_3$)

The following signals are shown (δ, ppm). 92.4, 86.0, 83.2, 80.3, 77.3 and 73.0 (C16, C1, C6, C18, C14 and C15), 59.2, 58.7, 57.9 and 56.0 (C18, C16, C6 and C1), 49.0 (CH$_2$ of C$_2$H$_5$ at the nitrogen atom), 13.1 (CH$_3$ of C$_2$H$_5$ at the nitrogen atom), 21.2 (CH$_3$ of 4-methylpentyl group).

4) Analysis of Mass spectra m/z: 535 (M$^+$).

5) Elemental analysis

Calculated for C$_{31}$H$_{53}$NO$_6$: C, 69.50; H, 9.97; N, 2.61. Found: C, 69.76; H, 10.05; N, 2.46.

(81) Physicochemical parameters and analytical data of 3,8,13-trideoxy-14-O-crotylaconine 1) Property and solubility Colorless and amorphous powder. Soluble in ether, chloroform, benzene, ethanol, methanol, ethylacetate, pyridine and dimethyl sulfoxide. Insoluble in hexane and water.

2) Analysis of IR spectra (KBr)

IR $\nu_{max}^{KBr}$: 3300 cm$^{-1}$.

3) Analysis of $^1$H-NMR spectra (CDCl$_3$)

The following signals are shown (δ, ppm). 5.72 (2H, m, crotyl group), 4.08 (2H, m, CH$_2$ of crotyl group), 3.51, 3.40, 3.28 and 3.28 (each 3H, s, OCH$_3$ at C1, C6, C16 and C18), 1.71 (3H, d, J=6.3 Hz, CH$_3$ of crotyl group), 0.91 (3H, t, J=7.3 Hz, CH$_3$ of C$_2$H$_5$ at the nitrogen atom).

4) Analysis of $^{13}$C-NMR spectra (CDCl$_3$)

The following signals are shown (δ, ppm). 130.8 and 123.8 (crotyl group), 92.3, 86.2, 84.6, 81.5, 81.3 and 72.5 (C16, C1, C6, C18, C14 and C15), 59.0, 58.1, 57.8 and 55.8 (OCH$_3$ at C18, C6, C16 and C1), 49.4 (CH$_2$ of C$_2$H$_5$ at the nitrogen atom), 13.9 (CH$_3$ of C$_2$H$_5$ at the nitrogen atom), 12.6 (CH$_3$ of crotyl group).

5) Analysis of Mass spectra m/z: 505 (M$^+$).

6) Elemental analysis

Calculated for C$_{29}$H$_{47}$NO$_6$: C, 68.88; H, 9.37; N, 2.77. Found: C, 68.91; H, 9.36; N, 2.68.

(82) Physicochemical parameters and analytical data of 3,8-dideoxy-14-O-veratroylaconine 1) Property and solubility Colorless and amorphous powder. Soluble in ether, chloroform, benzene, ethanol, methanol, ethylacetate, pyridine and dimethyl sulfoxide. Insoluble in hexane and water.

2) Analysis of IR spectra (KBr)

IR $\nu_{max}^{KBr}$: 1720 cm$^{-1}$.

3) Analysis of UV spectra (ethanol)

UV $\lambda_{max}^{EtOH}$ (log ε) nm: 221 (4.35), 264 (4.08), 295 (3.84).

4) Analysis of $^1$H-NMR spectra (CDCl$_3$)

The following signals are shown (δ, ppm). 6.69–7.67 (3H, m, veratroyl group), 5.07 (1H, d, J=4.6 Hz, C14-β-H), 3.92 (6H, s, OCH$_3$ of veratroyl group), 3.53, 3.32, 3.29 and 3.26 (each 3H, s, OCH$_3$ at C1, C6, C16 and C18), 1.11 (3H, t, J=7.0 Hz, CH$_3$ of C$_2$H$_5$ at the nitrogen atom).

5) Analysis of $^{13}$C-NMR spectra (CDCl$_3$)

The following signals are shown (δ, ppm). 165.9 (carbonyl of veratroyl group), 122.6, 110.5, 153.1, 148.1 and 112.3 (veratroyl group), 94.1, 86.0, 85.1, 80.3, 81.9, 75.3 and 72.4 (C16, C1, C6, C14, C18, C13 and C15), 55.8 (OCH$_3$ of veratroyl group), 61.8, 59.0, 58.0 and 56.0 (OCH$_3$ at C16, C18, C6 and C1), 49.0 (CH$_2$ of C$_2$H$_5$ at the nitrogen atom), 13.4 (CH$_3$ of C$_2$H$_5$ at the nitrogen atom).

6) Analysis of Mass spectra m/z: 631 (M$^+$).

7) Elemental analysis

Calculated for C$_{34}$H$_{49}$NO$_{10}$: C, 64.64; H, 7.82; N 2.22. Found: C, 64.83; H, 8.01; N, 2.08.

(83) Physicochemical parameters and analytical data of 3,8-dideoxy-14-O-acetylaconine 1) Property and solubility Colorless and amorphous powder. Soluble in ether, chloroform, benzene, ethanol, methanol, ethylacetate, pyridine and dimethyl sulfoxide. Insoluble in hexane and water.

2) Analysis of IR spectra (KBr)

IR $\nu_{max}^{KBr}$: 1713 cm$^{-1}$.

3) Analysis of $^1$H-NMR spectra (CDCl$_3$)

The following signals are shown (δ, ppm). 4.95 (1H, d, J=5.0 Hz, C14-β-H), 3.65, 3.31, 3.28 and 3.28 (each 3H, s, OCH$_3$ at C1, C6, C16 and C18), 2.06 (3H, s, CH$_3$ of acetyl group), 1.10 (3H, t, J=7.0 Hz, CH$_3$ of C$_2$H$_5$ at the nitrogen atom).

4) Analysis of $^{13}$C-NMR spectra (CDCl$_3$)

The following signals are shown (δ, ppm). 171.5 (carbonyl of acetyl group), 94.1, 85.4, 83.3, 80.2, 77.3, 75.3 and 72.4 (C16, C1, C6, C18, C14, C13 and C15), 61.6, 59.0, 57.9 and 56.0 (OCH$_3$ at C16, C18, C6 and C1), 49.0 (CH$_2$ of C$_2$H$_5$ at the nitrogen atom), 13.5 (CH$_3$ of C$_2$H$_5$ at the nitrogen atom), 21.6 (CH$_3$ of acetyl group).

5) Analysis of Mass spectra m/z: 509 (M$^+$).

6) Elemental analysis

Calculated for C$_{27}$H$_{43}$NO$_8$: C, 63.63; H, 8.50; N, 2.75. Found: C, 63.39; H, 8.71; N, 2.54.

(84) Physicochemical parameters and analytical data of 3,8-dideoxy-14-O-m-chlorobenzoylaconine 1) Property and solubility Colorless and amorphous powder. Soluble in ether, chloroform, benzene, ethanol, methanol, ethylacetate, pyridine and dimethyl sulfoxide. Insoluble in hexane and water.

2) Analysis of IR spectra (KBr)

IR $\nu_{max}^{KBr}$: 1715 cm$^{-1}$.

3) Analysis of UV spectra (ethanol)

UV $\lambda_{max}^{EtOH}$ (log ε) nm: 231 (4.09), 280 (3.28), 289 (3.25).

4) Analysis of $^1$H-NMR spectra (CDCl$_3$)

The following signals are shown (δ, ppm). 7.98–7.30 (5H, m, m-chlorobenzoyl group), 4.90 (1H, d, J=4.7 Hz, C14-β-H), 3.70, 3.32, 3.28 and 3.26 (each 3H, s, $OCH_3$ at C1, C6, C16 and C18), 1.11 (3H, t, J=7.0 Hz, $CH_3$ of $C_2H_5$ at the nitrogen atom).

5) Analysis of $^{13}C$-NMR spectra ($CDCl_3$)

The following signals are shown (δ, ppm). 165.0 (carbonyl of m-chlorobenzoyl group), 131.5, 129.9, 129.5, 135.0 and 128.4 (m-chlorobenzoyl group), 94.4, 86.2, 85.0, 82.5, 80.3, 75.3 and 72.6 (C16, C1, C6, C18, C14, C13 and C15), 61.8, 59.1, 58.1 and 56.0 ($OCH_3$ at C16, C18, C6 and C1), 49.1 ($CH_2$ of $C_2H_5$ at the nitrogen atom), 13.2 ($CH_3$ of $C_2H_5$ at the nitrogen atom).

6) Analysis of Mass spectra m/z: 605, 607 ($M^+$).

7) Elemental analysis

Calculated for $C_{32}H_{44}NO_8Cl$: C, 63.41; H, 7.32; N, 2.31. Found: C, 63.66; H, 7.51; N, 2.25.

(85) Physicochemical parameters and analytical data of 3,8-dideoxy-14-O-benzylaconine 1) Property and solubility Colorless and amorphous powder. Soluble in ether, chloroform, benzene, ethanol, methanol, ethylacetate, pyridine and dimethyl sulfoxide. Insoluble in hexane and water.

2) Analysis of IR spectra (KBr)

IR $v_{max}^{KBr}$: 3300 $cm^{-1}$.

3) Analysis of UV spectra (ethanol)

UV $\lambda_{max}^{EtOH}$ (log ε) nm: 225 (4.10).

4) Analysis of $^1H$-NMR spectra ($CDCl_3$)

The following signals are shown (δ, ppm). 7.28 (5H, s, benzyl group), 4.47 (2H, s, $CH_2$ of benzyl group), 3.65, 3.31, 3.31 and 3.28 (each 3H, s, $OCH_3$ at C1, C6, C16 and C18), 1.08 (3H, t, J=7.0 Hz, $CH_3$ of $C_2H_5$ at the nitrogen atom).

5) Analysis of $^{13}C$-NMR spectra ($CDCl_3$)

The following signals are shown (δ, ppm). 126.3, 127.2, 128.3 and 141.6 (benzyl group), 64.2 ($CH_2$ of benzyl group), 93.5, 86.1, 84.3, 81.9, 81.1, 77.3 and 72.4 (C16, C1, C6, C18, C14, C13 and C15), 60.2, 59.1, 58.0 and 56.0 ($OCH_3$ at C16, C18, C6 and C1), 49.2 ($CH_2$ of $C_2H_5$ at the nitrogen atom), 13.0 ($CH_3$ of $C_2H_5$ at the nitrogen atom).

6) Analysis of Mass spectra m/z: 557 ($M^+$).

7) Elemental analysis

Calculated for $C_{32}H_{47}NO_7$: C, 68.91; H, 8.49; N, 2.51. Found: C, 69.14; H, 8.69; N, 2.55.

(86) Physicochemical parameters and analytical data of 3,8-dideoxy-14-O-(4-methyl)pentylaconine 1) Property and solubility Colorless and amorphous powder. Soluble in ether, chloroform, benzene, ethanol, methanol, ethylacetate, pyridine and dimethyl sulfoxide. Insoluble in hexane and water.

2) Analysis of $^1H$-NMR spectra ($CDCl_3$)

The following signals are shown (δ, ppm). 3.68, 3.37, 3.28 and 3.28 (each 3H, s, $OCH_3$ at C1, C6, C16 and C18), 1.10 (3H, t, J=7.0 Hz, $CH_3$ of $C_2H_5$ at the nitrogen atom), 1.02 (6H, d, J=7.0 Hz, $CH_3$ of 4-methylpentyl group).

3) Analysis of $^{13}C$-NMR spectra ($CDCl_3$)

The following signals are shown (δ, ppm). 93.4, 85.3, 83.2, 80.3, 77.4, 75.5 and 72.4 (C16, C1, C6, C18, C14, C13 and C15), 60.3, 59.0, 58.2 and 56.0 ($OCH_3$ at C16, C18, C6 and C1), 49.3 ($CH_2$ of $C_2H_5$ at the nitrogen atom), 13.8 ($CH_3$ of $C_2H_5$ at the nitrogen atom), 21.2 ($CH_3$ of 4-methylpentyl group).

4) Analysis of Mass spectra m/z: 551 ($M^+$).

5) Elemental analysis

Calculated for $C_{31}H_{53}NO_7$: C, 67.48; H, 9.68; N, 2.54. Found: C, 67.21; H, 9.76; N, 2.22.

(87) Physicochemical parameters and analytical data of 3,8-dideoxy-14-O-crotylaconine 1) Property and solubility Colorless and amorphous powder. Soluble in ether, chloroform, benzene, ethanol, methanol, ethylacetate, pyridine and dimethyl sulfoxide. Insoluble in hexane and water.

2) Analysis of IR spectra (KBr)

IR $v_{max}^{KBr}$: 3300 $cm^{-1}$.

3) Analysis of $^1H$-NMR spectra ($CDCl_3$)

The following signals are shown (δ, ppm). 5.71 (2H, m, crotyl group), 4.09 (2H, m, $CH_2$ of crotyl group), 3.69, 3.40, 3.27 and 3.27 (each 3H, s, $OCH_3$ at C1, C6, C16 and C18), 1.70 (3H, d, J=6.3 Hz, $CH_3$ of crotyl group), 0.89 (3H, t, J=7.3 Hz, $CH_3$ of $C_2H_5$ at the nitrogen atom).

4) Analysis of $^{13}C$-NMR spectra ($CDCl_3$)

The following signals are shown (δ, ppm). 130.8 and 123.7 (crotyl group), 93.5, 86.2, 84.6, 81.6, 81.3, 77.2 and 72.4 (C16, C1, C6, C18, C14, C13 and C15), 49.5 ($CH_2$ of $C_2H_5$ at the nitrogen atom), 14.0 ($CH_3$ of $C_2H_5$ at the nitrogen atom), 12.7 ($CH_3$ of crotyl group), 60.5, 59.0, 58.1 and 55.8 ($OCH_3$ at C16, C18, C6 and C1).

5) Analysis of Mass spectra m/z: 521 ($M^+$).

6) Elemental analysis

Calculated for $C_{29}H_{47}NO_7$: C, 66.77; H, 9.08; N 2.68. Found: C, 66.91; H, 9.21; N, 2.55.

(88) Physicochemical parameters and analytical data of 14-O-veratroylaconine

1) Property and solubility

Colorless and amorphous powder. Soluble in ether, chloroform, benzene, ethanol, methanol, ethylacetate, pyridine and dimethyl sulfoxide. Insoluble in hexane and water.

2) Analysis of IR spectra (KBr)

IR $v_{max}^{KBr}$: 1720 $cm^{-1}$.

3) Analysis of UV spectra (ethanol)

UV $\lambda_{max}^{EtOH}$ (log ε) nm: 221 (4.35), 264 (4.05), 295 (3.84).

4) Analysis of $^1H$-NMR spectra ($CDCl_3$)

The following signals are shown (δ, ppm). 6.89–7.68 (3H, m, veratroyl group), 4.97 (1H, d, J=5.0 Hz, C14 -β-H), 3.92 (6H, s, $OCH_3$ of veratroyl group), 3.71, 3.31, 3.29 and 3.25 (each 3H, s, $OCH_3$ at C1, C6, C16 and C18), 1.10 (3H, t, J=7.0 Hz, $CH_3$ of $C_2H_5$ at the nitrogen atom).

5) Analysis of $^{13}C$-NMR spectra ($CDCl_3$)

The following signals are shown (δ, ppm). 166.0 (carbonyl of veratroyl group), 122.5, 110.6, 153.1, 148.3 and 112.3 (veratroyl group), 90.8, 83.5, 82.4, 81.9, 79.5, 78.6, 77.3, 74.8 and 71.9 (C16, C6, C1, C15, C14, C8, C18, C13 and C3), 55.8 ($OCH_3$ of veratroyl group), 60.9, 59.1, 58.0 and 55.6 ($OCH_3$ at C16, C18, C6 and C1), 48.4 ($CH_2$ of $C_2H_5$ at the nitrogen atom), 13.5 ($CH_3$ of $C_2H_5$ at the nitrogen atom).

6) Analysis of Mass spectra m/z: 663 ($M^+$).

7) Elemental analysis

Calculated for $C_{34}H_{49}NO_{12}$: C, 61.52; H, 7.44; N, 2.11. Found: C, 61.80; H, 7.56; N, 2.09.

(89) Physicochemical parameters and analytical data of 14-O-acetylaconine

1) Property and solubility

Colorless and amorphous powder. Soluble in ether, chloroform, benzene, ethanol, methanol, ethylacetate, pyridine and dimethyl sulfoxide. Insoluble in hexane and water.

2) Analysis of IR spectra (KBr)

IR $v_{max}^{KBr}$: 1713 $cm^{-1}$.

3) Analysis of $^1H$-NMR spectra ($CDCl_3$)

The following signals are shown (δ, ppm). 4.95 (1H, d, J=4.8 Hz, C14-β-H), 3.71, 3.71, 3.31, 3.29 and 3.25 (each 3H, s, $OCH_3$ at C1, C6, C16 and C18), 2.01 (3H, s, $CH_3$ of acetyl group), 1.10 (3H, t, J=7.0 Hz, $CH_3$ of $C_2H_5$ at the nitrogen atom).

4) Analysis of $^{13}$C-NMR spectra ($CDCl_3$)

The following signals are shown (δ, ppm). 171.5 (carbonyl of acetyl group), 90.7, 83.5, 82.4, 79.9, 79.5, 78.6, 77.3, 74.8 and 71.9 (C16, C6, C1, C15, C14, C8, C18, C13 and C3), 60.9, 59.1, 58.0 and 55.6 ($OCH_3$ at C16, C18, C6 and C1), 49.0 ($CH_2$ of $C_2H_5$ at the nitrogen atom), 13.3 ($CH_3$ of $C_2H_5$ at the nitrogen atom), 21.5 ($CH_3$ of acetyl group).

5) Analysis of Mass spectra m/z: 541 ($M^+$).

6) Elemental analysis

Calculated for $C_{27}H_{43}NO_{10}$: C, 59.87; H, 8.00; N 2.59. Found: C, 60.05; H, 8.08; N, 2.44.

(90) Physicochemical parameters and analytical data of 14-O-m-chlorobenzoylaconine 1) Property and solubility Colorless and amorphous powder. Soluble in ether, chloroform, benzene, ethanol, methanol, ethylacetate, pyridine and dimethyl sulfoxide. Insoluble in hexane and water.

2) Analysis of IR spectra (KBr)

IR $v_{max}^{KBr}$: 1715 $cm^{-1}$.

3) Analysis of UV spectra (ethanol)

UV $\lambda_{max}^{EtOH}$ (log ε) nm: 231 (4.09), 280 (3.28), 289 (3.25).

4) Analysis of $^1$H-NMR spectra ($CDCl_3$)

The following signals are shown (δ, ppm). 7.98-7.31 (5H, m, m-chlorobenzoyl group), 4.89 (1H, d, J=5.0 Hz, C14-β-H), 3.71, 3.31, 3.28 and 3.24 (each 3H, s, $OCH_3$ at C1, C6, C16 and C18), 1.02 (3H, t, J=7.0 Hz, $CH_3$ of $C_2H_5$ at the nitrogen atom).

5) Analysis of $^{13}$C-NMR spectra ($CDCl_3$)

166.0 (carbonyl of m-chlorobenzoyl group), 131.5, 130.0, 129.5, 135.1 and 128.3 (m-chlorobenzoyl group), 90.7, 83.4, 82.3, 82.0, 79.4, 78.6, 77.3, 74.7 and 72.0 (C16, C6, C1, C15, C14, C8, C18, C13 and C3), 60.9, 59.1, 57.9 and 55.6 ($OCH_3$ at C16, C8, C6 and C1), 48.8 ($CH_2$ of $C_2H_5$ at the nitrogen atom), 13.0 ($CH_3$ of $C_2H_5$ at the nitrogen atom).

6) Analysis of Mass spectra m/z: 637, 639 ($M^+$).

7) Elemental analysis

Calculated for $C_{32}H_{44}NO_{10}Cl$: C, 60.23; H, 6.95; N, 2.19. Found: C 60.33; H, 7.11; N 1.97.

(91) Physicochemical parameters and analytical data of 14-O-benzylaconine

1) Property and solubility

Colorless and amorphous powder. Soluble in ether, chloroform, benzene, ethanol, methanol, ethylacetate, pyridine and dimethyl sulfoxide. Insoluble in hexane and water.

2) Analysis of IR spectra (KBr)

IR $v_{max}^{KBr}$: 3300 $cm^{-1}$.

3) Analysis of UV spectra (ethanol)

UV $\lambda_{max}^{EtOH}$ (log ε) nm: 225 (4.10).

4) Analysis of $^1$H-NMR spectra ($CDCl_3$)

The following signals are shown (δ, ppm). 7.28 (5H, s, benzyl group), 4.50 (2H, s, $CH_2$ of benzyl group), 3.70, 3.31, 3.29 and 3.25 (each 3H, s, $OCH_3$ at C1, C6, C16 and C18), 1.09 (3H, t, J=7.0 Hz, $CH_3$ of $C_2H_5$ at the nitrogen atom).

5) Analysis of $^{13}$C-NMR spectra ($CDCl_3$)

The following signals are shown (δ, ppm). 126.7, 127.0, 128.6 and 141.7 (benzyl group), 64.0 ($CH_2$ of benzyl group), 90.8, 83.4, 82.1, 81.9, 79.5, 78.8, 77.3, 74.6 and 71.9 (C16, C6, C1, C15, C14, C8, C18, C13 and C3), 60.9, 59.1, 57.9 and 55.6 ($OCH_3$ at C16, C18, C6 and C1), 49.0 ($CH_2$ of $C_2H_5$ at the nitrogen atom), 13.1 ($CH_3$ of $C_2H_5$ at the nitrogen atom).

6) Analysis of Mass spectra m/z: 589 ($M^+$).

7) Elemental analysis

Calculated for $C_{32}H_{47}NO_9$: C, 65.17; H, 8.03; N, 2.38. Found: C, 64.92; H, 7.97; N, 2.18.

(92) Physicochemical parameters and analytical data of 14-O-(4-methyl)pentylaconine 1) Property and solubility Colorless and amorphous powder. Soluble in ether, chloroform, benzene, ethanol, methanol, ethylacetate, pyridine and dimethyl sulfoxide. Insoluble in hexane and water.

2) Analysis of $^1$H-NMR spectra ($CDCl_3$)

The following signals are shown (δ, ppm). 3.70, 3.30, 3.28 and 3.25 (each 3H, s, $OCH_3$ at C1, C6, C16 and C18), 1.09 (3H, t, J=7.0 Hz, $CH_3$ of $C_2H_5$ at the nitrogen atom), 1.02 (6H, d, J=7.0 Hz, $CH_3$ of 4-methylpentyl group).

3) Analysis of $^{13}$C-NMR spectra ($CDCl_3$)

The following signals are shown (δ, ppm). 90.8, 83.4, 82.1, 81.9, 79.5, 78.9, 77.4, 74.5 and 72.0 (C16, C6, C1, C15, C14, C8, C18, C13 and C3), 60.8, 59.0, 58.0 and 55.5 ($OCH_3$ at C16, C18, C6 and C1), 49.0 ($CH_2$ of $C_2H_5$ at the nitrogen atom), 13.1 ($CH_3$ of $C_2H_5$ at the nitrogen atom), 21.1 ($CH_3$ of 4-methylpentyl group).

4) Analysis of Mass spectra m/z: 583 ($M^+$).

5) Elemental analysis

Calculated for $C_{31}H_{53}NO_9$: C, 63.78; H, 9.15; N 2.40. Found: C, 63.61; H, 9.02; N, 2.36.

(93) Physicochemical parameters and analytical data of 14-O-crotylaconine

1) Property and solubility

Colorless and amorphous powder. Soluble in ether, chloroform, benzene, ethanol, methanol, ethylacetate, pyridine and dimethyl sulfoxide. Insoluble in hexane and water.

2) Analysis of IR spectra (KBr)

IR $v_{max}^{KBr}$: 3300 $cm^{-1}$.

3) Analysis of $^1$H-NMR spectra ($CDCl_3$)

The following signals are shown (δ, ppm). 5.68 (2H, m, CH=CH of crotyl group), 4.10 (2H, m, $CH_2$ of crotyl group), 3.70, 3.35, 3.29 and 3.25 (each 3H, s, $OCH_3$ at C1, C6, C16 and C18), 1.70 (3H, d, J=6.3 Hz, $CH_3$ of crotyl group), 0.90 (3H, t, J=7.0 Hz, $CH_3$ of $C_2H_5$ at the nitrogen atom).

4) Analysis of $^{13}$C-NMR spectra ($CDCl_3$)

The following signals are shown (δ, ppm). 130.7 and 123.5 (CH=CH of crotyl group), 90.7, 83.5, 82.3, 82.0, 79.4, 78.8, 77.5, 74.6 and 72.0 (C16, C6, C1, C15, C14, C8, C18, C13 and C3), 60.8, 59.0, 58.1 and 55.6 ($OCH_3$ at C16, C18, C6 and C1), 49.1 ($CH_2$ of $C_2H_5$ at the nitrogen atom), 13.9 ($CH_3$ of $C_2H_5$ at the nitrogen atom), 12.9 ($CH_3$ of crotyl group).

5) Analysis of Mass spectra m/z: 553 ($M^+$).

6) Elemental analysis

Calculated for $C_{29}H_{47}NO_9$: C, 62.91; H, 8.56; N, 2.53. Found: C, 63.14; H, 8.44; N 2.37.

(94) Physicochemical parameters and analytical data of 3,13-dideoxy-14-O-veratroylaconine 1) Property and solubility Colorless and amorphous powder. Soluble in ether, chloroform, benzene, ethanol, methanol, ethylacetate, pyridine and dimethyl sulfoxide. Insoluble in hexane and water.

2) Analysis of IR spectra (KBr)

IR $v_{max}^{KBr}$: 1720 $cm^{-1}$.

3) Analysis of UV spectra (ethanol)

UV $\lambda_{max}^{EtOH}$ (log ε) nm: 221 (4.35), 264 (4.07), 295 (3.80).

4) Analysis of $^1$H-NMR spectra (CDCl$_3$)

The following signals are shown (δ, ppm). 6.89–7.70 (3H, m, veratroyl group), 5.03 (1H, t, J=4.8 Hz, C14-β -H), 3.92 (6H, s, veratroyl group), 3.58, 3.29, 3.27 and 3.21 (each 3H, s, OCH$_3$ at C1, C6, C16 and C18), 1.10 (3H, t, J=7.0 Hz, CH$_3$ of C$_2$H$_5$ at the nitrogen atom).

5) Analysis of $^{13}$C-NMR spectra (CDCl$_3$)

The following signals are shown (δ, ppm). 166.0 (carbonyl of veratroyl group), 122.7, 110.4, 153.2, 148.1 and 112.4 (veratroyl group), 89.7, 85.2, 83.6, 81.7, 79.9, 78.6 and 77.5 (C16, C1, C6, C18, C15, C8 and C14), 55.8 (OCH$_3$ of veratroyl group), 59.1, 57.9, 57.6 and 55.6 (OCH$_3$ at C18, C16, C6 and C1), 49.0 (CH$_2$ of C$_2$H$_5$ at the nitrogen atom), 13.2 (CH$_3$ of C$_2$H$_5$ at the nitrogen atom).

6) Analysis of Mass spectra m/z: 631 (M$^+$).

7) Elemental analysis

Calculated for C$_{34}$H$_{49}$NO$_{10}$: C, 64.64; H, 7.82; N, 2.22. Found: C, 64.45; H, 7.93; N, 2.21.

(95) Physicochemical parameters and analytical data of 3,13-dideoxy-14-O-acetylaconine 1) Property and solubility Colorless and amorphous powder. Soluble in ether, chloroform, benzene, ethanol, methanol, ethylacetate, pyridine and dimethyl sulfoxide. Insoluble in hexane and water.

2) Analysis of IR spectra (KBr)

IR $v_{max}^{KBr}$: 1715 cm$^{-1}$.

3) Analysis of $^1$H-NMR spectra (CDCl$_3$)

The following signals are shown (δ, ppm). 4.93 (1H, t, J=4.8 Hz, C14-β-H), 3.59, 3.30, 3.27 and 3.21 (each 3H, s, OCH$_3$ at C1, C6, C16 and C18), 2.02 (3H, s, CH$_3$ of acetyl group), 1.10 (3H, t, J=7.0 Hz, CH$_3$ of C$_2$H$_5$ at the nitrogen atom).

4) Analysis of $^{13}$C-NMR spectra (CDCl$_3$)

171.4 (carbonyl of acetyl group), 89.8, 85.2, 83.6, 81.7, 79.9, 78.6 and 77.5 (C16, C1, C6, C18, C15, C8 and C14), 59.2, 57.8, 57.6 and 55.5 (OCH$_3$ at C18, C16, C6 and C1), 49.0 (CH$_2$ of C$_2$H$_5$ at the nitrogen atom), 13.2 (CH$_3$ of C$_2$H$_5$ at the nitrogen atom), 21.4 (CH$_3$ of acetyl group).

5) Analysis of Mass spectra m/z: 509 (M$^+$).

6) Elemental analysis

Calculated for C$_{27}$H$_{43}$NO$_8$: C, 63.63; H, 8.50; N, 2.75. Found: C, 63.81; H, 8.65; N, 2.63.

(96) Physicochemical parameters and analytical data of 3,13-dideoxy-14-O-m-chlorobenzoylaconine 1) Property and solubility Colorless and amorphous powder. Soluble in ether, chloroform, benzene, ethanol, methanol, ethylacetate, pyridine and dimethyl sulfoxide. Insoluble in hexane and water.

2) Analysis of IR spectra (KBr)

IR $v_{max}^{KBr}$: 1715 cm$^{-1}$.

3) Analysis of UV spectra (ethanol)

UV $\lambda_{max}^{EtOH}$ (log ε) nm: 221 (4.05), 281 (3.25), 289 (3.25).

4) Analysis of $^1$H-NMR spectra (CDCl$_3$)

The following signals are shown (δ, ppm). 7.95-7.28 (5H, m, m-chlorobenzoyl group), 5.01 (1H, t, J=4.9 Hz, C14-β-H), 3.59, 3.30, 3.27 and 3.21 (each 3H, s, OCH$_3$ at C1, C6, C16 and C18), 1.12 (3H, t, J=7.0 Hz, CH$_3$ of C$_2$H$_5$ at the nitrogen atom).

5) Analysis of $^{13}$C-NMR spectra (CDCl$_3$)

The following signals are shown (δ, ppm). 165.5 (carbonyl of m-chlorobenzoyl group), 131.4, 130.0, 129.5, 135.1 and 128.4 (m-chlorobenzoyl group), 89.6, 85.0, 83.6, 81.8, 80.0, 78.5 and 77.5 (C16, C1, C6, C18, C15, C8 and C14), 59.0, 57.8, 57.6 and 55.6 (OCH$_3$ at C18, C16, C6 and C1), 49.1 (CH$_2$ of C$_2$H$_5$ at the nitrogen atom), 13.0 (CH$_3$ of C$_2$H$_5$ at the nitrogen atom).

6) Analysis of Mass spectra m/z: 605, 607 (M$^+$).

7) Elemental analysis

Calculated for C$_{32}$H$_{44}$NO$_8$Cl: C, 63.41; H, 7.32; N, 2.31. Found: C, 63.28; H, 7.55; N, 2.15.

(97) Physicochemical parameters and analytical data of 3,13-dideoxy-14-O-benzylaconine 1) Property and solubility Colorless and amorphous powder. Soluble in ether, chloroform, benzene, ethanol, methanol, ethylacetate, pyridine and dimethyl sulfoxide. Insoluble in hexane and water.

2) Analysis of IR spectra (KBr)

IR $v_{max}^{KBr}$: 3300 cm$^{-1}$.

3) Analysis of UV spectra (ethanol)

UV $\lambda_{max}^{EtOH}$ (log ε) nm: 225 (4.09).

4) Analysis of $^1$H-NMR spectra (CDCl$_3$)

The following signals are shown (δ, ppm). 7.28 (5H, s, benzyl group), 4.50 (2H, s, CH$_2$ of benzyl group), 3.61, 3.31, 3.28 and 3.26 (each 3H, s, OCH$_3$ at C1, C6, C16 and C18), 1.09 (3H, t, J=7.0 Hz, CH$_3$ of C$_2$H$_5$ at the nitrogen atom).

5) Analysis of $^{13}$C-NMR spectra (CDCl$_3$)

The following signals are shown (δ, ppm). 126.7, 127.0, 128.6 and 141.6 (benzyl group), 64.1 (CH$_2$ of benzyl group), 89.8, 85.3, 83.7, 81.8, 79.7, 78.5 and 77.4 (C16, C1, C6, C18, C15, C8 and C14), 59.3, 58.0, 57.6 and 55.5 (OCH$_3$ at C18, C16, C6 and C1), 49.3 (CH$_2$ of C$_2$H$_5$ at the nitrogen atom), 14.0 (CH$_3$ of C$_2$H$_5$ at the nitrogen atom).

6) Analysis of Mass spectra m/z: 557 (M$^+$).

7) Elemental analysis

Calculated for C$_{32}$H$_{47}$NO$_7$: C, 68.91; H, 8.49; N, 2.51. Found: C, 68.76; H, 8.58; N, 2.42.

(98) Physicochemical parameters and analytical data of 3,13-dideoxy-14-O-(4-methyl)pentylaconine 1) Property and solubility Colorless and amorphous powder. Soluble in ether, chloroform, benzene, ethanol, methanol, ethylacetate, pyridine and dimethyl sulfoxide. Insoluble in hexane and water.

2) Analysis of IR spectra (KBr)

IR $v_{max}^{KBr}$: 3450 cm$^{-1}$.

3) Analysis of $^1$H-NMR spectra (CDCl$_3$)

The following signals are shown (δ, ppm). 3.61, 3.30, 3.29 and 3.26 (each 3H, s, OCH$_3$ at C1, C6, C16 and C18), 1.10 (3H, t, J=7.0 Hz, CH$_3$ of C$_2$H$_5$ at the nitrogen atom), 1.02 (6H, d, J=7.0 Hz, CH$_3$ of 4-methylpentyl group).

3) Analysis of $^{13}$C-NMR spectra (CDCl$_3$)

The following signals are shown (δ, ppm). 89.7, 85.2, 83.5, 81.7, 79.8, 78.6 and 77.3 (C16, C1, C6, C18, C15, C8 and C14), 59.3, 58.0, 57.6 and 55.4 (OCH$_3$ at C18, C16, C6 and C1), 49.3 (CH$_2$ of C$_2$H$_5$ at the nitrogen atom), 14.0 (CH$_3$ of C$_2$H$_5$ at the nitrogen atom), 21.3 (CH$_3$ of 4-methylpentyl group).

5) Analysis of Mass spectra m/z: 551 (M$^+$).

6) Elemental analysis

Calculated for C$_{31}$H$_{53}$NO$_7$: C, 67.48; H, 9.68; N, 2.54. Found: C, 67.66; H, 9.81; N, 2.32.

(99) Physicochemical parameters and analytical data of 3,13-dideoxy-14-O-crotylaconine 1) Property and solubility Colorless and amorphous powder. Soluble in ether, chloroform, benzene, ethanol, methanol, ethylacetate, pyridine and dimethyl sulfoxide. Insoluble in hexane and water.

2) Analysis of IR spectra (KBr)

IR $v_{max}^{KBr}$: 3300 cm$^{-1}$.

3) Analysis of $^1$H-NMR spectra (CDCl$_3$)

The following signals are shown (δ, ppm). 5.68 (2H, m, CH=CH of crotyl group), 4.09 (2H, m, CH$_2$ of crotyl group), 3.58, 3.30, 3.27 and 3.23 (each 3H, s, OCH$_3$ at C1, C6, C16 and C18), 1.72 (3H, d, J=6.3 Hz, CH$_3$ of crotyl group), 0.90 (3H, t, J=7.0 Hz, CH$_3$ of C$_2$H$_5$ at the nitrogen atom).

4) Analysis of $^{13}$C-NMR spectra (CDCl$_3$)

The following signals are shown (δ, ppm). 130.8 and 123.6 (CH=CH of crotyl group), 89.7, 85.0, 83.5, 81.5, 79.8, 78.7 and 77.5 (C16, C1, C6, C18, C15, C8 and C14), 59.1, 58.1, 57.7 and 55.6 (OCH$_3$ at C18, C16, C6 and C1), 49.2 (CH$_2$ of C$_2$H$_5$ at the nitrogen atom), 14.0 (CH$_3$ of C$_2$H$_5$ at the nitrogen atom), 12.8 (CH$_3$ of crotyl group).

5) Analysis of Mass spectra m/z: 521 (M$^+$).

6) Elemental analysis

Calculated for C$_{29}$H$_{47}$NO$_7$: C, 66.77; H, 9.08; N, 2.68. Found: C, 66.91; H, 9.15; N, 2.81.

(100) Physicochemical parameters and analytical data of 3-deoxy-14-O-veratroylaconine 1) Property and solubility Colorless and amorphous powder. Soluble in ether, chloroform, benzene, ethanol, methanol, ethylacetate, pyridine and dimethyl sulfoxide. Insoluble in hexane and water.

2) Analysis of IR spectra (KBr)

IR $v_{max}^{KBr}$: 1720 cm$^{-1}$.

3) Analysis of UV spectra (ethanol)

UV $\lambda_{max}^{EtOH}$ (log ε) nm: 221 (4.34), 264 (4.08), 295 (3.84).

4) Analysis of $^1$H-NMR spectra (CDCl$_3$)

The following signals are shown (δ, ppm). 6.88–7.68 (3H, m, veratroyl group), 4.98 (1H, d, J=4.7 Hz, C14-β -H), 3.92 (6H, s, OCH$_3$ of veratroyl group), 3.70, 3.31, 3.29 and 3.24 (each 3H, s, OCH$_3$ at C1, C6, C16 and C18), 1.10 (3H, t, J=7.0 Hz, CH$_3$ of C$_2$H$_5$ at the nitrogen atom).

5) Analysis of $^{13}$C-NMR spectra (CDCl$_3$)

The following signals are shown (δ, ppm). 165.9 (carbonyl of veratroyl group), 122.5, 110.5, 153.1, 148.2 and 112.3 (veratroyl group), 90.8, 85.2, 83.6, 81.9, 81.7, 79.5, 78.6 and 74.8 (C16, C1, C6, C15, C18, C14, C8 and C13), 55.8 (OCH$_3$ of veratroyl group), 60.9, 59.1, 58.0 and 55.7 (OCH$_3$ at C16, C18, C6 and C1), 49.0 (CH$_2$ of C$_2$H$_5$ at the nitrogen atom), 13.2 (CH$_3$ of C$_2$H$_5$ at the nitrogen atom).

6) Analysis of Mass spectra m/z: 647 (M$^+$).

7) Elemental analysis

Calculated for C$_{34}$H$_{49}$NO$_{11}$: C, 63.04; H, 7.62; N, 2.16. Found: C, 63.22; H, 7.59; N, 2.13.

(101) Physicochemical parameters and analytical data of 3-deoxy-14-O-acetylaconine 1) Property and solubility Colorless and amorphous powder. Soluble in ether, chloroform, benzene, ethanol, methanol, ethylacetate, pyridine and dimethyl sulfoxide. Insoluble in hexane and water.

2) Analysis of IR spectra (KBr)

IR $v_{max}^{KBr}$: 1713 cm$^{-1}$.

3) Analysis of $^1$H-NMR spectra (CDCl$_3$)

The following signals are shown (δ, ppm). 4.96 (1H, d, J=4.8 Hz, C14-β-H), 3.70, 3.31, 3.29 and 3.24 (each 3H, s, OCH$_3$ at C1, C6, C16 and C18), 2.02 (3H, s, CH$_3$ of acetyl group).

4) Analysis of $^{13}$C-NMR spectra (CDCl$_3$)

The following signals are shown (δ, ppm). 171.6 (carbonyl of acetyl group), 90.8, 85.2, 83.3, 81.8, 81.6, 79.5, 78.6 and 74.8 (C16, C1, C6, C15, C18, C14, C8 and C13), 60.9 59.0, 58.1 and 55.6 (OCH$_3$ at C16, C18, C6 and C1), 49.0 (CH$_2$ of C$_2$H$_5$ at the nitrogen atom), 13.2 (CH$_3$ of C$_2$H$_5$ at the nitrogen atom), 21.5 (CH$_3$ of acetyl group).

5) Analysis of Mass spectra m/z 525 (M$^+$).

6) Elemental analysis

Calculated for C$_{27}$H$_{43}$NO$_9$: C 61.70; H 8.25; N, 2.66. Found: C, 61.79; H, 8.18; N, 2.48.

(102) Physicochemical parameters and analytical data of 3-deoxy-14-O-m-chlorobenzoylaconine 1) Property and solubility Colorless and amorphous powder, Soluble in ether, chloroform, benzene, ethanol, methanol, ethylacetate, pyridine and dimethyl sulfoxide. Insoluble in hexane and water.

2) Analysis of IR spectra (KBr)

IR $v_{max}^{KBr}$: 1715 cm$^{-1}$.

3) Analysis of UV spectra (ethanol)

UV $\lambda_{max}^{EtOH}$ (log ε) nm: 231 (4.09), 280 (3.28), 289 (3.25).

4) Analysis of $^1$H-NMR spectra (CDCl$_3$)

The following signals are shown (δ, ppm). 7.98-7.30 (5H, m, m-chlorobenzoyl group), 4.87 (1H, d, J=5.0 Hz, C14-β-H), 3.71, 3.31, 3.29 and 3.25 (each 3H, s, OCH$_3$ at C1, C6, C16 and C18), 1.11 (3H, t, J=7.0 Hz, CH$_3$ of C$_2$H$_5$ at the nitrogen atom).

5) Analysis of $^{13}$C-NMR spectra (CDCl$_3$)

The following signals are shown (δ, ppm). 165.3 (carbonyl of m-chlorobenzoyl group) 131.5, 129.9, 129.4, 135.1 and 128.4 (m-chlorobenzoyl group), 90.7, 85.2, 83.6, 82.0, 81.6, 79.5, 78.6 and 74.8 (C16, C1, C6, C15, C18, C14, C8 and C13), 60.9, 59.2, 58.1 and 55.6 (OCH$_3$ at C16, C18, C6 and C1), 49.1 (CH$_2$ of C$_2$H$_5$ at the nitrogen atom), 13.0 (CH$_3$ of C$_2$H$_5$ at the nitrogen atom).

6) Analysis of Mass spectra m/z: 621, 623 (M$^+$).

7) Elemental analysis

Calculated for C$_{32}$H$_{44}$NO$_9$Cl: C, 61.78; H, 7.13; N, 2.25. Found: C, 61.91; H, 7.32; N, 2.28.

(103) Physicochemical parameters and analytical data of 3-deoxy-14-O-benzylaconine 1) Property and solubility Colorless and amorphous powder. Soluble in ether, chloroform, benzene, ethanol, methanol, ethylacetate, pyridine and dimethyl sulfoxide. Insoluble in hexane and water.

2) Analysis of IR spectra (KBr)

IR $v_{max}^{KBr}$: 3300 cm$^{-1}$.

3) Analysis of UV spectra (ethanol)

UV $\lambda_{max}^{EtOH}$ (log ε) nm: 225 (4.10).

4) Analysis of $^1$H-NMR spectra (CDCl$_3$)

The following signals are shown (δ, ppm). 7.28 (5H, s, benzyl group), 4.49 (2H, s, CH$_2$ of benzyl group), 3.70, 3.31, 3.29 and 3.27 (each 3H, s, OCH$_3$ at C1, C6, C16 and C18), 1.10 (3H, t, J=7.0 Hz, CH$_3$ of C$_2$H$_5$ at the nitrogen atom).

5) Analysis of $^{13}$C-NMR spectra (CDCl$_3$)

The following signals are shown (δ, ppm). 126.6, 127.0, 128.5 and 141.7 (benzyl group), 64.0 (CH$_2$ of benzyl group), 90.8, 85.3, 83.7, 81.8, 81.6, 79.5, 78.6 and 74.9 (C16, C1, C6, C15, C18, C14, C8 and C13), 60.7, 59.1, 58.0 and 55.6 (OCH$_3$ at C16, C18, C6 and C1), 49.4 (CH$_2$ of C$_2$H$_5$ at the nitrogen atom), 14.0 (CH$_3$ of C$_2$H$_5$ at the nitrogen atom).

6) Analysis of Mass spectra m/z: 573 (M$^+$).

7) Elemental analysis

Calculated for C$_{32}$H$_{47}$NO$_8$: C, 66.99; H, 8.26; N, 2.44. Found: C, 67.15; H, 8.41; N, 2.38.

(104) Physicochemical parameters and analytical data of 3-deoxy-14-O-(4-methyl)pentylaconine 1) Property and solubility Colorless and amorphous powder. Soluble in ether, chloroform, benzene, ethanol, methanol, ethylacetate, pyridine and dimethyl sulfoxide. Insoluble in hexane and water.

2) Analysis of $^1$H-NMR spectra (CDCl$_3$)

The following signals are shown (δ, ppm). 3.71, 3.30, 3.28 and 3.25 (each 3H, s, OCH$_3$ at C1, C6, C16 and C18), 1.09 (3H, t, J=7.0 Hz, CH$_3$ of C$_2$H$_5$ at the nitrogen atom), 1.02 (6H, d, J=7.0 Hz, CH$_3$ of 4-methylpentyl group).

3) Analysis of $^{13}$C-NMR spectra (CDCl$_3$)

The following signals are shown (δ, ppm). 90.7, 85.4, 83.7, 81.7, 81.5, 79.2, 78.5 and 74.8 (C16, C1, C6, C15, C18, C14 C8 and C13), 60.8, 59.1, 58.0 and 55.5 (OCH$_3$ at C16, C18, C6 and C1), 49.4 (CH$_2$ of C$_2$H$_5$ at the nitrogen atom), 13.5 (CH$_3$ of C$_2$H$_5$ at the nitrogen atom), 21.0 (CH$_3$ of 4-methylpentyl group).

4) Analysis of Mass spectra m/z: 567 (M$^+$).

5) Elemental analysis

Calculated for C$_{31}$H$_{53}$NO$_8$: C, 65.58; H, 9.41; N, 2.47. Found: C, 65.61; H, 9.53; N, 2.38.

(105) Physicochemical parameters and analytical data of 3-deoxy-14-O-crotylaconine 1) Property and solubility Colorless and amorphous powder. Soluble in ether, chloroform, benzene, ethanol, methanol, ethylacetate, pyridine and dimethyl sulfoxide. Insoluble in hexane and water.

2) Analysis of IR spectra (KBr)

IR $v_{max}^{KBr}$: 3300 cm$^{-1}$.

3) Analysis of $^1$H-NMR spectra (CDCl$_3$)

The following signals are shown (δ, ppm). 5.69 (2H, m, CH=CH of crotyl group), 4.10 (2H, m, CH$_2$ of crotyl group), 3.68, 3.40, 3.29 and 3.25 (each 3H, s, OCH$_3$ at C1, C6, C16 and C18), 1.71 (3H, d, J=6.3 Hz, CH$_3$ of crotyl group), 0.89 (3H, t, J=7.0 Hz, CH$_3$ of C$_2$H$_5$ at the nitrogen atom).

4) Analysis of $^{13}$C-NMR spectra (CDCl$_3$)

The following signals are shown (δ, ppm). 130.8 and 123.6 (CH=CH of crotyl group), 90.6, 85.0, 83.5, 82.0, 81.7, 79.5, 78.6 and 74.8 (C16, C1, C6, C15, C18, C14 C8 and C13), 60.9, 59.2, 57.9 and 55.7 (OCH$_3$ at C16, C18, C6 and C1), 49.3 (CH$_2$ of C$_2$H$_5$ at the nitrogen atom), 13.9 (CH$_3$ of C$_2$H$_5$ at the nitrogen atom), 12.7 (CH$_3$ of crotyl group).

5) Analysis of Mass spectra m/z: 537 (M$^+$).

6) Elemental analysis

Calculated for C$_{29}$H$_{47}$NO$_8$: C, 64.78; H, 8.81; N, 2.60. Found: C, 64.51; H, 8.66; N, 2.39.

(106) Physicochemical parameters and analytical data of 16-epi-8-deoxy-14-O-(p-methoxy)benzylaconine 1) Property and solubility Colorless and amorphous powder. Soluble in ether, chloroform, benzene, ethanol, methanol, ethylacetate, pyridine and dimethyl sulfoxide. Insoluble in hexane and water.

2) Analysis of IR spectra (KBr)

IR $v_{max}^{KBr}$: 3300 cm$^{-1}$.

3) Analysis of UV spectra (ethanol)

UV $\lambda_{max}^{EtOH}$ (log ε) nm: 224 (4.19), 275 (3.60), 280 (3.53).

4) Analysis of $^1$H-NMR spectra (CDCl$_3$)

The following signals are shown (δ, ppm). 7.10 and 6.71 (each 2H, d, J=8.9 Hz, p-methoxybenzyl group), 3.82, 3.39, 3.31 and 3.28 (each 3H, s, OCH$_3$ at C1, C6, C16 and C18), 3.91 (3H, , OCH$_3$ of benzyl group), 4.45 (2H, s CH$_2$ of benzyl group), 1.09 (3H, t, J=7.0 Hz, CH$_3$ of C$_2$H$_5$ at the nitrogen atom).

5) Analysis of $^{13}$C-NMR spectra (CDCl$_3$)

The following signals are shown (δ, ppm). 133.6, 128.2, 113.8 and 157.7 (benzyl group), 64.0 (CH$_2$ of benzyl group), 90.3, 84.4, 83.2, 81.0, 77.4, 77.2, 72.3 and 72.0 (C16, C6, C14, C18, C13, C15 and C3), 60.2, 59.1, 58.1 and 56.0 (OCH$_3$ at C16, C18, C6 and C1), 55.8 (OCH$_3$ of p-methoxybenzyl group), 49.4 (CH$_2$ of C$_2$H$_5$ at the nitrogen atom), 14.0 (CH$_3$ of C$_2$H$_5$ at the nitrogen atom).

6) Analysis of Mass spectra m/z: 603 (M$^+$).

(107) Physicochemical parameters and analytical data of 16-epi-8-deoxy-14-O-amylaconine 1) Property and solubility Colorless and amorphous powder. Soluble in ether, chloroform, benzene, ethanol, methanol, ethylacetate, pyridine and dimethyl sulfoxide. Insoluble in hexane and water.

2) Analysis of IR spectra (KBr)

IR $v_{max}^{KBr}$: 3300 cm$^{-1}$.

3) Analysis of $^1$H-NMR spectra (CDCl$_3$)

The following signals are shown (δ, ppm). 3.82, 3.33, 3.21 and 3.28 (each 3H, s, OCH$_3$ at C1, C6, C16 and C18), 0.92 (3H, t, J=7.4 Hz, CH$_3$ of C$_2$H$_5$ at the nitrogen atom), 0.90 (3H, t, J=10.1 Hz, CH$_3$ of amyl group).

4) Analysis of $^{13}$C-NMR spectra (CDCl$_3$)

The following signals are shown (δ, ppm). 90.2, 84.6, 83.5, 81.2, 77.5, 77.2, 72.5 and 72.1 (C16, C6, C14, C18, C13, C15 and C3), 60.5, 59.1, 58.0 and 55.6 (OCH$_3$ at C16, C18, C6 and C1), 49.4 (CH$_2$ of C$_2$H$_5$ at the nitrogen atom), 14.0 (CH$_3$ of C$_2$H$_5$ at the nitrogen atom), 13.5 (CH$_3$ of amyl group).

5) Analysis of Mass spectra m/z: 553 (M$^+$).

(108) Physicochemical parameters and analytical data of 16-epi-3,8,13-trideoxy-14-O-veratroylaconine 1) Property and solubility Colorless and amorphous powder. Soluble in ether, chloroform, benzene, ethanol, methanol, ethylacetate, pyridine and dimethyl sulfoxide. Insoluble in hexane and water.

2) Analysis of IR spectra (KBr)

IR $v_{max}^{KBr}$: 1720 cm$^{-1}$.

3) Analysis of UV spectra (ethanol)

UV $\lambda_{max}^{EtOH}$ (log ε) nm: 221 (4.35), 264 (4.08), 295 (3.84).

4) Analysis of $^1$H-NMR spectra (CDCl$_3$)

The following signals are shown (δ, ppm). 6.88–7.68 (3H, m, veratroyl group), 5.20 (1H, t, J=4.6, Hz, C14-β -H), 3.92 (6H, s, OCH$_3$ of veratroyl group), 3.56, 3.30, 3.28 and 3.26 (each 3H, s, OCH$_3$ at C1, C6, C16 and C18), 1.10 (3H, t, J=7.0 Hz, CH$_3$ of C$_2$H$_5$ at the nitrogen atom).

5) Analysis of $^{13}$C-NMR spectra (CDCl$_3$)

The following signals are shown (δ, ppm). 166.0 (carbonyl of veratroyl group), 122.5, 110.5, 153.1, 148.2 and 112.3 (veratroyl group), 90.2, 86.0, 85.1, 81.9, 78.4 and 72.4 (C16, C1, C6, C18, C14 and C15), 55.8 (OCH$_3$ of veratroyl group), 59.1, 58.7, 57.9 and 56.0 (OCH$_3$ at C18, C16, C6 and C1), 49.0 (CH$_2$ of C$_2$H$_5$ at the nitrogen atom), 13.4 (CH$_3$ of C$_2$H$_5$ at the nitrogen atom).

6) Analysis of Mass spectra m/z: 615 (M$^+$).

(109) Physicochemical parameters and analytical data of 16-epi-3,8,13-trideoxy-14-O-m-chlorobenzoylaconine 1) Property and solubility Colorless and amorphous powder. Soluble in ether, chloroform, benzene, ethanol, methanol, ethylacetate, pyridine and dimethyl sulfoxide. Insoluble in hexane and water.

2) Analysis of IR spectra (KBr)

IR $v_{max}^{KBr}$: 1715 cm$^{-1}$.

3) Analysis of UV spectra (ethanol)

UV $\lambda_{max}^{EtOH}$ (log ε) nm: 231 (4.09), 280 (3.28), 289 (3.25).

4) Analysis of $^1$H-NMR spectra (CDCl$_3$)

The following signals are shown (δ, ppm). 7.98-7.30 (5H, m, m-chlorobenzoyl group), 5.06 (1H, t, J=4.7 Hz, C14-β-H), 3.75, 3.32, 3.28 and 3.26 (each 3H, s, OCH$_3$ at C1, C6, C16 and C18), 1.12 (3H, t, J=7.0 Hz, CH$_3$ of C$_2$H$_5$ at the nitrogen atom).

5) Analysis of $^{13}$C-NMR spectra (CDCl$_3$)

The following signals are shown (δ, ppm). 165.0 (carbonyl of m-chlorobenzoyl group), 131.6, 130.0, 129.5, 135.0 and 128.4 (m-chlorobenzoyl group), 90.1, 86.0, 85.3, 82.0, 78.3 and 72.5 (C16, C1, C6, C18, C14 and C15), 59.0, 58.7, 58.0 and 56.0 (OCH$_3$ at C18, C16, C6 and C1), 49.2 (CH$_2$ of C$_2$H$_5$ at the nitrogen atom), 13.1 (CH$_3$ of C$_2$H$_5$ at the nitrogen atom).

6) Analysis of Mass spectra m/z: 589, 591 (M$^+$).

(110) Physicochemical parameters and analytical data of 16-epi-3,8,13-trideoxy-14-O-benzylaconine 1) Property and solubility Colorless and amorphous powder. Soluble in ether, chloroform, benzene, ethanol, methanol, ethylacetate, pyridine and dimethyl sulfoxide. Insoluble in hexane and water.

2) Analysis of IR spectra (KBr)

IR $v_{max}^{KBr}$: 3450 cm$^{-1}$.

3) Analysis of UV spectra (ethanol)

UV $\lambda_{max}^{EtOH}$ (log ε) nm: 225 (4.09).

4) Analysis of $^1$H-NMR spectra (CDCl$_3$)

The following signals are shown (δ, ppm). 7.29 (5H, s, benzyl group), 4.48 (2H, s, CH$_2$ of benzyl group), 3.68, 3.31, 3.31 and 3.28 (each 3H, s, OCH$_3$ at C1, C6, C16 and C18), 1.09 (3H, t, J= 7.0 Hz ).

5) Analysis of $^{13}$C-NMR spectra (CDCl$_3$)

The following signals are shown (δ, ppm). 126.3, 127.3, 128.0 and 141.8 (benzyl group) 64.3 (CH$_2$ of benzyl group), 90.0, 86.1, 84.3, 82.0, 81.1 and 72.5 (C16, C1, C6, C18, C14 and C15) 59.2, 58.0, 57.2 and 56.0 (OCH$_3$ at C18 C6, C16 and C1), 49.2 (CH$_2$ of C$_2$H$_5$ at the nitrogen atom), 13.1 (CH$_3$ of C$_2$H$_5$ at the nitrogen atom).

6) Analysis of Mass spectra m/z: 541 (M$^+$).

(111) Physicochemical parameters and analytical data of 16-epi-3,8,13-trideoxy-14-O-crotylaconine 1) Property and solubility Colorless and amorphous powder. Soluble in ether, chloroform, benzene, ethanol, methanol, ethylacetate, pyridine and dimethyl sulfoxide. Insoluble in hexane and water.

2) Analysis of IR spectra (KBr)

IR $v_{max}^{KBr}$: 3300 cm$^{-1}$.

3) Analysis of $^1$H-NMR spectra (CDCl$_3$)

The following signals are shown (δ, ppm). 5.72 (2H, m, CH=CH of crotyl group), 4.08 (2H, m, CH$_2$ of crotyl group), 3.73, 3.40, 3.28 and 3.28 (each 3H, s, OCH$_3$ at C1, C6, C16 and C18), 1.71 (3H, d, J=6.3 Hz, CH$_3$ of crotyl group), 0.91 (3H, t, J=7.3 Hz, CH$_3$ of C$_2$H$_5$ at the nitrogen atom).

4) Analysis of $^{13}$C-NMR spectra (CDCl$_3$)

The following signals are shown (δ, ppm). 130.8 and 123.8 (CH=CH of crotyl group), 90.1, 86.2, 84.6, 81.5, 81.3 and 72.5 (C16, C1, C6, C18, C14 and C15), 59.0, 58.1, 57.8 and 55.8 (OCH$_3$ at C18, C6, C16 and C1), 49.4 (CH$_2$ of C$_2$H$_5$ at the nitrogen atom), 13.9 (CH$_3$ of C$_2$H$_5$ at the nitrogen atom), 12.6 (CH$_3$ of crotyl group).

5) Analysis of Mass spectra m/z: 505 (M$^+$).

(112) Physicochemical parameters and analytical data of 16-epi-3,8-dideoxy-14-O-veratroylaconine 1) Property and solubility Colorless and amorphous powder. Soluble in ether, chloroform, benzene, ethanol, methanol, ethylacetate, pyridine and dimethyl sulfoxide. Insoluble in hexane and water.

2) Analysis of IR spectra (KBr)

IR $v_{max}^{KBr}$: 1720 cm$^{-1}$.

3) Analysis of UV spectra (ethanol)

UV $\lambda_{max}^{EtOH}$ (log ε) nm: 221 (4.35), 264 (4.08), 295 (3.84).

4) Analysis of $^1$H-NMR spectra (CDCl$_3$)

The following signals are shown (δ, ppm). 6.69–7.67 (3H, m, veratroyl group), 5.07 (1H, d, J=4.6 Hz, C14-β -H), 3.92 (6H, s, OCH$_3$ of veratroyl group), 3.80, 3.32, 3.29 and 3.26 (each 3H, s, OCH$_3$ at C1, C6, C16 and C18), 1.11 (3H, t, J=7.0 Hz, CH$_3$ of C$_2$H$_5$ at the nitrogen atom).

5) Analysis of $^{13}$C-NMR spectra (CDCl$_3$)

The following signals are shown (δ, ppm). 165.9 (carbonyl of veratroyl group), 122.6, 110.5, 153.1, 148.1 and 112.3 (veratroyl group), 90.1, 86.0, 85.1, 80.3, 81.9, 75.3 and 72.4 (C16, C1, C6, C14, C18, C13 and C15), 55.8 (OCH$_3$ of veratroyl group), 61.8, 59.0, 58.0 and 56.0 (OCH$_3$ at C16, C18, C6 and C1), 49.0 (CH$_2$ of C$_2$H$_5$ at the nitrogen atom),13.4 (CH$_3$ of C$_2$H$_5$ at the nitrogen atom).

6) Analysis of Mass spectra m/z: 631 (M$^+$).

(113) Physicochemical parameters and analytical data of 16-epi-3,8-dideoxy-14-O-m-chlorobenzoylaconine 1) Property and solubility Colorless and amorphous powder. Soluble in ether, chloroform, benzene, ethanol, methanol, ethylacetate, pyridine and dimethyl sulfoxide. Insoluble in hexane and water.

2) Analysis of IR spectra (KBr)

IR $v_{max}^{KBr}$: 1715 cm$^{-1}$.

3) Analysis of UV spectra (ethanol)

UV $\lambda_{max}^{EtOH}$ (log ε) nm: 231 (4.09), 280 (3.28), 289 (3.25).

4) Analysis of $^1$H-NMR spectra (CDCl$_3$)

The following signals are shown (δ, ppm). 7.98-7.30 (5H, m, m-chlorobenzoyl group), 4.90 (1H, d, J=4.7 Hz, C14-β-H), 3.85, 3.32, 3.28 and 3.26 (each 3H s, OCH$_3$ at C1, C6, C16 and C18), 1.11 (3H, t, J=7.0 Hz, CH$_3$ of C$_2$H$_5$ at the nitrogen atom).

5) Analysis of $^{13}$C-NMR spectra (CDCl$_3$)

The following signals are shown (δ, ppm). 165.1 (carbonyl of m-chlorobenzoyl group), 131.5, 129.9, 129.5, 135.0 and 128.4 (m-chlorobenzoyl group), 90.4, 86.2, 85.0, 82.5, 80.3, 75.3 and 72.6 (C16, C1, C6, C18, C14, C13 and C15), 61.8, 59.1, 58.1 and 56.0 (OCH$_3$ at C16, C18, C6 and C1), 49.1 (CH$_2$ of C$_2$H$_5$ at the nitrogen atom), 13.2 (CH$_3$ of C$_2$H$_5$ at the nitrogen atom).

6) Analysis of Mass spectra m/z: 605, 607 (M$^+$).

(114) Physicochemical parameters and analytical data of 16-epi-3,8-dideoxy-14-O-benzylaconine 1) Property and solubility Colorless and amorphous powder. Soluble in ether, chloroform, benzene, ethanol, methanol, ethylacetate, pyridine and dimethyl sulfoxide. Insoluble in hexane and water.

2) Analysis of IR spectra (KBr)

IR $v_{max}^{KBr}$: 3300 cm$^{-1}$.

3) Analysis of UV spectra (ethanol)

UV $\lambda_{max}^{EtOH}$ (log ε) nm: 225 (4.10).

4) Analysis of $^1$H-NMR spectra (CDCl$_3$)

The following signals are shown (δ, ppm). 7.28 (5H, benzyl group ), 4 47 (2H, s, CH$_2$ of benzyl group), 3.83, 3.31, 3.31 and 3.28 (each 3H, s, OCH$_3$ at C1, C6, C16 and C18), 1.08 (3H, t, J=7.0 Hz, CH$_3$ of C$_2$H$_5$ at the nitrogen atom).

5) Analysis of $^{13}$C-NMR spectra (CDCl$_3$)

The following signals are shown (δ, ppm). 126.3, 127.2, 128.3 and 141.6 (benzyl group), 64.2 (CH$_2$ of benzyl group) 90.0, 86.1, 84.3, 81.9, 81.1, 77.3 and 72.4 (C16, C1, C6, C18, C14, C13 and C15) 60.2, 59.1, 58.0 and 56.0 (OCH$_3$ at C16, C18, C6 and C1), 49.2 (CH$_2$ of C$_2$H$_5$ at the nitrogen atom), 13.0 (CH$_3$ of C$_2$H$_5$ at the nitrogen atom).

6) Analysis of Mass spectra
m/z: 557 (M⁺).

(115) Physicochemical parameters and analytical data of 16-epi-3,8-dideoxy-14-O-crotylaconine 1) Property and solubility Colorless and amorphous powder. Soluble in ether, chloroform, benzene, ethanol, methanol, ethylacetate, pyridine and dimethyl sulfoxide. Insoluble in hexane and water.

2) Analysis of IR spectra (KBr)
IR $\nu_{max}^{KBr}$: 3300 cm$^{-1}$.

3) Analysis of $^1$H-NMR spectra (CDCl$_3$)

The following signals are shown (δ, ppm). 5.71 (2H, m, CH=CH of crotyl group), 4.09 (2H, m, CH$_2$ of crotyl group), 3.82, 3.40, 3.27 and 3.27 (each 3H, s, OCH$_3$ at C1, C6, C16 and C18), 1.70 (3H, d, J=6.3 Hz, CH$_3$ of crotyl group), 0.89 (3H, t, J=7.3 Hz, CH$_3$ of C$_2$H$_5$ at the nitrogen atom).

4) Analysis of $^{13}$C-NMR spectra (CDCl$_3$)

The following signals are shown (δ, ppm). 130.8 and 123.7 (CH=CH of crotyl group), 90.2, 86.2, 84.6, 81.6, 81.3, 77.2 and 72.4 (C16, C1, C6, C18, C14, C13 and C15), 49.5 (CH$_2$ of C$_2$H$_5$ at the nitrogen atom), 14.0 (CH$_3$ of C$_2$H$_5$ at the nitrogen atom), 12.7 (CH$_3$ of crotyl group), 60.5, 59.0, 58.1 and 55.8 (OCH$_3$ at C16, C18, C6 and C1).

5) Analysis of Mass spectra
m/z. 521 (M⁺).

(116) Physicochemical parameters and analytical data of de-N-ethyl-3,8-dideoxy-14-O-anisoylaconine 1) Property and solubility Colorless and amorphous powder. Soluble in ether, chloroform, benzene, ethanol, methanol, ethylacetate, pyridine and dimethyl sulfoxide. Insoluble in hexane and water.

2) Analysis of IR spectra (KBr)
IR $\nu_{max}^{KBr}$: 1715 cm$^{-1}$.

3) Analysis of UV spectra (ethanol)
UV $\lambda_{max}^{EtOH}$ (log ε) nm: 258 (4.02).

4) Analysis of $^1$H-NMR spectra (CDCl$_3$)

The following signals are shown (δ, ppm). 7.98 and 6.95 (each 2H, d, J=8.9 Hz, anisoyl group), 4.95 (1H, d, J=5.0 Hz, C14-β-H), 3.69, 3.30, 3.28 and 3.25 (each 3H, s, OCH$_3$ at C1, C6, C16 and C18), 3.87 (3H, s, OCH$_3$ of anisoyl group).

5) Analysis of $^{13}$C-NMR spectra (CDCl$_3$)

The following signals are shown (δ, ppm). 166.0 (carbonyl of anisoyl group), 163.8, 131.4, 113.5 and 122.2 (anisoyl group), 94.4, 86.2, 85.0, 82.5, 80.1, 75.0 and 72.3 (C16, C1, C6, C18, C14, C13 and C15) 61.9, 59.1 58.0 and 56.0 (OCH$_3$ at C16, C18, C6 and C1), 55.4 (OCH$_3$ of anisoyl group).

6) Analysis of Mass spectra
m/z: 573 (M⁺).

7) Elemental analysis

Calculated for C$_{31}$H$_{43}$NO$_9$: C 64.90; H, 7.55; N, 9.44. Found: C, 64.85; H, 7.41; N, 2.22.

(117) Physicochemical parameters and analytical data of de-N-ethyl-N-amyl-3,8-dideoxy-14-O-anisoylaconine 1) Property and solubility Colorless and amorphous powder. Soluble in ether, chloroform, benzene, ethanol, methanol, ethylacetate, pyridine and dimethyl sulfoxide. Insoluble in hexane and water.

2) Analysis of IR spectra (KBr)
IR $\nu_{max}^{KBr}$: 1715 cm$^{-1}$.

3) Analysis of UV spectra (ethanol)
UV $\lambda_{max}^{EtOH}$ (log ε) nm: 257 (4.02).

4) Analysis of $^1$H-NMR spectra (CDCl$_3$)

The following signals are shown (δ, ppm). 8.00 and 6.93 (each 2H, d, J=8.9 Hz, anisoyl group), 4.96 (1H, d, J=5.0 Hz, C14-β-H), 3.87 (6H, s, OCH$_3$ of anisoyl group), 3.69, 3.31, 3.27 and 3.24 (each 3H, s, OCH$_3$ at C1, C6, C16 and C18), 0.99 (3H, t, J=7.0 Hz, CH$_3$ of amyl group at the nitrogen atom).

5) Analysis of $^{13}$C-NMR spectra (CDCl$_3$)

The following signals are shown (δ, ppm). 166.0 (carbonyl of anisoyl group), 163.8, 131.8, 113.6 and 122.1 (anisoyl group), 94.2, 86.0, 85.1, 82.3, 80.2, 75.1 and 72.4 (C16, C1, C6, C18, C14, C13 and C15), 55.4 (OCH$_3$ of anisoyl group), 61.8, 59.1, 57.8 and 56.0 (OCH$_3$ at C16, C18, C6 and C1), 13.1 (CH$_3$ of amyl group at the nitrogen atom).

6) Analysis of Mass spectra
m/z: 643 (M⁺).

(118) Physicochemical parameters and analytical data of de-N-ethyl-N-propyl-3,8-dideoxy-14-O-anisoylaconine 1) Property and solubility Colorless and amorphous powder. Soluble in ether, chloroform, benzene, ethanol, methanol, ethylacetate, pyridine and dimethyl sulfoxide. Insoluble in hexane and water.

2) Analysis of IR spectra (KBr)
IR $\nu_{max}^{KBr}$: 1715 cm$^{-1}$.

3) Analysis of UV spectra (ethanol)
UV $\lambda_{max}^{EtOH}$ (log ε) nm: 258 (4.02).

4) Analysis of $^1$H-NMR spectra (CDCl$_3$)

The following signals are shown (δ, ppm). 7.99 and 6.94 (each 2H, d, J=8.9 Hz, anisoyl group), 4.94 (1H, d, J=5.0 Hz, C14-β-H), 3.69, 3.30, 3.29 and 3.24 (each 3H, s, OCH$_3$ at C1, C6, C16 and C18), 3.87 (3H, s, CH$_3$ of anisoyl group), 1.10 (3H, t, J=7.0 Hz, CH$_3$ of propyl group).

5) Analysis of $^{13}$C-NMR spectra (CDCl$_3$)

The following signals are shown (δ, ppm). 165.9 (carboxyl of anisoyl group), 163.6, 131.8, 122.2 and 113.7 (anisoyl group), 94.3, 86.2, 85.0, 82.1, 80.1, 75.3 and 72.2 (C16, C1, C6, C18, C14, C13 and C15), 61.8, 59.0, 58.0 and 56.0 (OCH$_3$ at C16, C18, C6 and C1), 55.4 (OCH$_3$ of anisoyl group), 13.0 (CH$_3$ of propyl group at the nitrogen atom).

6) Analysis of Mass spectra
m/z: 615 (M⁺).

7) Elemental analysis

Calculated for C$_{34}$H$_{49}$NO$_9$: C, 66.32; H, 8.02; N, 2.27. Found: C, 66.45; H, 7.98; N, 2.20.

(119) Physicochemical parameters and analytical data of de-N-ethyl-N-(4-methylpentyl)-3,8-dideoxy-14-O-anisoylaconine 1) Property and solubility Colorless and amorphous powder. Soluble in ether, chloroform, benzene, ethanol, methanol, ethylacetate, pyridine and dimethyl sulfoxide. Insoluble in hexane and water.

2) Analysis of IR spectra (KBr)
IR $\nu_{max}^{KBr}$: 1715 cm$^{-1}$.

3) Analysis of UV spectra (ethanol)
UV $\lambda_{max}^{EtOH}$ (log ε) nm: 258 (4.01).

4) Analysis of $^1$H-NMR spectra (CDCl$_3$)

The following signals are shown (δ, ppm). 8.00 and 6.94 (each 2H, d, J=8.9, anisoyl group) 4.94 (1H, d, J=5.0 Hz, C14-β-H), 3.88 (3H, s, OCH$_3$ of anisoyl group), 3.70, 3.30, 3.27 and 3.25 (each 3H, s, OCH$_3$ at C1, C6, C16 and C18), 1.02 (6H, d, J=7.0 Hz, CH$_3$ of 4-methylpentyl group at the nitrogen atom).

5) Analysis of $^{13}$C-NMR spectra (CDCl$_3$)

The following signals are shown (δ, ppm). 166.0 (carbonyl of anisoyl croup), 163.9, 131.7, 113.4 and 122.1 (anisoyl group), 94.3, 86.1, 85.0, 82.2, 80.1, 75.1 and 72.3 (C16, C1, C6, C18, C14, C13 and C15), 61.8, 59.0, 57.9 and 56.0 (OCH$_3$ at C16, C18, C6 and C1), 55.4 (OCH$_3$ of anisoyl group), 21.5 (CH$_3$ of 4-methylpentyl group at the nitrogen atom).

6) Analysis of Mass spectra
m/z: 657 (M⁺).

7) Elemental analysis

Calculated for C$_{37}$H$_{55}$NO$_9$: C, 67.55; H, 8.43; N, 2.13. Found: C, 67.38; H, 8.29; N, 2.26.

(120) Physicochemical parameters and analytical data of de-N-ethyl-N-acetyl-3,8-dideoxy-14-O-anisoylaconine
1) Property and solubility
Colorless and amorphous powder. Soluble in ether, chloroform, benzene, ethanol, methanol, ethylacetate, pyridine and dimethyl sulfoxide. Insoluble in hexane and water.
2) Analysis of IR spectra (KBr)
IR $\nu_{max}^{KBr}$: 1715, 1655 cm$^{-1}$.
3) Analysis of UV spectra (ethanol)
UV $\lambda_{max}^{EtOH}$ (log ε) nm: 258 (4.02).
4) Analysis of $^1$H-NMR spectra (CDCl$_3$)
The following signals are shown (δ, ppm). 7.98 and 6.95 (each 2H, d, J=8.9, anisoyl group), 4.95 (1H, d, J=5.0 Hz, C14-β-H), 3.87 (3H, s, OCH$_3$ of anisoyl group), 3.69, 3.31, 3.28 and 3.25 (each 3H, s, OCH$_3$ at C1, C6, C16 and C18), 2.30 (3H, s, CH$_3$ of acetyl group at the nitrogen atom).
5) Analysis of $^{13}$C-NMR spectra (CDCl$_3$)
The following signals are shown (δ, ppm). 171.0 (carbonyl of acetyl group), 166.0 (carbonyl of anisoyl group), 163.7, 131.6, 113.5 and 122.1 (anisoyl group), 94.4, 85.0, 82.5, 82.3, 80.2, 75.1 and 72.3 (C16, C6, C18, C1, C14, C13 and C15), 61.9, 59.1, 58.0 and 56.0 (OCH$_3$ at C16, C18, C6 and C1), 55.4 (OCH$_3$ of anisoyl group), 21.0 (CH$_3$ of acetyl group at the nitrogen atom).
6) Analysis of Mass spectra
m/z: 615 (M$^+$).
7) Elemental analysis
Calculated for C$_{33}$H$_{45}$NO$_{10}$: C, 64.37; H, 7.37; N, 2.27. Found: C, 64.52; H, 7.16; N, 2.25.

(121) Physicochemical parameters and analytical data of de-N-ethyl-N-benzoyl-3,8-dideoxy-14-O-anisoylaconine
1) Property and solubility
Colorless and amorphous powder. Soluble in ether, chloroform, benzene, ethanol, methanol, ethylacetate, pyridine and dimethyl sulfoxide. Insoluble in hexane and water.
2) Analysis of IR spectra (KBr)
IR $\nu_{max}^{KBr}$: 1710, 1653 cm$^{-1}$.
3) Analysis of UV spectra (ethanol)
UV $\lambda_{max}^{EtOH}$ (log ε) nm: 232 (4.10), 258 (4.03).
4) Analysis of $^1$H-NMR spectra (CDCl$_3$)
The following signals are shown (δ, ppm). 7.81-7.09 (5H, m, benzoyl group), 7.98 and 6.95 (each 2H, d, J=8.9, anisoyl group), 4.93 (1H, d, J=5.0 Hz, C14-β-H), 3.87 (3H, s, OCH$_3$ of anisoyl group), 3.70, 3.31, 3.27 and 3.25 (each 3H, s, OCH$_3$ at C1, C6, C16 and C18).
5) Analysis of $^{13}$C-NMR spectra (CDCl$_3$)
The following signals are shown (δ, ppm). 165.8 and 166.0 (carbonyl group), 163.8, 131.7, 113.6 and 122.0 (anisoyl group), 133.9, 133.4, 128.6, 128.2 and 127.6 (benzoyl group), 94.3, 85.0, 82.4, 82.0, 80.3, 75.0 and 72.5 (C16, C6, C18, C1, C14, C13 and C15), 61.8, 59.1, 57.8 and 56.0 (OCH$_3$ at C16, C18, C6 and C1), 55.4 (OCH$_3$ of anisoyl group).
6) Analysis of Mass spectra
m/z: 677 (M$^+$).
7) Elemental analysis
Calculated for C$_{36}$H$_{47}$NO$_{10}$: C, 67.34; H, 6.99; N 2.07. Found: C, 67.46; H, 7.08; N, 2.01.

(122) Physicochemical parameters and analytical data of de-N-ethyl-3,8,13-trideoxy-14-O-anisoylaconine
1) Property and solubility
Colorless and amorphous powder. Soluble in ether, chloroform, benzene, ethanol, methanol, ethylacetate, pyridine and dimethyl sulfoxide. Insoluble in hexane and water.
2) Analysis of IR spectra (KBr)
IR $\nu_{max}^{KBr}$: 1715 cm$^{-1}$.
3) Analysis of UV spectra (ethanol)
UV $\lambda_{max}^{EtOH}$ (log ε) nm: 258 (4.01).
4) Analysis of $^1$H-NMR spectra (CDCl$_3$)
The following signals are shown (δ, ppm). 7.99 and 6.96 (each 2H, d, J=8.9, anisoyl group), 5.08 (1H, t, J=4.8 Hz, C14-β-H), 3.87 (3H, s, OCH$_3$ of anisoyl group), 3.70, 3.31, 3.28 and 3.25 (each 3H, s, OCH$_3$ at C1, C6, C16 and C18).
5) Analysis of $^{13}$C-NMR spectra (CDCl$_3$)
The following signals are shown (δ, ppm). 165.9 and 166.0 (carbonyl group), 163.7, 131.6, 113.4 and 122.2 (anisoyl group), 94.5, 86.3, 84.9, 82.5, 80.2 and 72.5 (C16, C1, C6, C18, C14 and C15), 59.1, 58.7, 57.9 and 56.0 (OCH$_3$ at C18, C16, C6 and C 1), 55.4 (OCH$_3$ of anisoyl group ).
6) Analysis of Mass spectra
m/z: 557 (M$^+$).
7) Elemental analysis
Calculated for C$_{31}$H$_{43}$NO$_8$: C, 66.77; H, 7.77; N, 2.51. Found: C, 66.70; H, 7.64; N, 2.48.

(123) Physicochemical parameters and analytical data of de-N-ethyl-N-amyl-3,8,13-trideoxy-14-O-anisoylaconine
1) Property and solubility
Colorless and amorphous powder. Soluble in ether, chloroform, benzene, ethanol, methanol, ethylacetate, pyridine and dimethyl sulfoxide. Insoluble in hexane and water.
2) Analysis of IR spectra (KBr)
IR $\nu_{max}^{KBr}$: 1715 cm$^{-1}$.
3) Analysis of UV spectra (ethanol)
UV $\lambda_{max}^{EtOH}$ (log ε) nm: 257 (4.02).
4) Analysis of $^1$H-NMR spectra (CDCl$_3$)
The following signals are shown (δ, ppm). 8.01 and 6.93 (each 2H, d, J=8.9, anisoyl group), 5.09 (1H, t, J=4.8 Hz, C14-β-H), 3.87 (3H, s, OCH$_3$ of anisoyl group), 3.69, 3.31, 3.27 and 3.24 (each 3H, s, OCH$_3$ at C1, C6, C16 and C18), 0.98 (3H, t, J=7.0 Hz, CH$_3$ of amyl group at the nitrogen atom).
5) Analysis of $^{13}$C-NMR spectra (CDCl$_3$)
The following signals are shown (δ, ppm). 166.0 (carbonyl group), 163.7, 131.8, 113.6 and 122.1 (anisoyl group), 94.1, 85.9, 85.1, 82.3, 80.2 and 72.3 (C16, C1, C6, C18, C14 and C15), 59.2, 58.8, 57.9 and 56.0 (OCH$_3$ at C18, C16, C6 and C1), 55.4 (OCH$_3$ of anisoyl group), 13.2 (CH$_3$ of amyl group at the nitrogen atom).
6) Analysis of Mass spectra
m/z: 627 (M$^+$).
7) Elemental analysis
Calculated for C$_{36}$H$_{53}$NO$_8$: C, 68.87; H, 8.51; N, 2.23. Found: C, 68.92; H, 8.50; N, 2.18.

(124) Physicochemical parameters and analytical data of de-N-ethyl-N-propyl-3,8,13-trideoxy-14-O-anisoylaconine
1) Property and solubility
Colorless and amorphous powder. Soluble in ether, chloroform, benzene, ethanol, methanol, ethylacetate, pyridine and dimethyl sulfoxide. Insoluble in hexane and water.
2) Analysis of IR spectra (KBr)
IR $\nu_{max}^{KBr}$: 1715 cm$^{-1}$.
3) Analysis of UV spectra (ethanol)
UV $\lambda_{max}^{EtOH}$ (log ε) nm: 258 (4.02).
4) Analysis of $^1$H-NMR spectra (CDCl$_3$)
The following signals are shown (δ, ppm). 7.99 and 6.95 (each 2H, d, J=8.9, anisoyl group), 5.06 (1H, t, J=4.8 Hz, C14-β-H), 3.69, 3.30, 3.29 and 3.24 (each 3H, s, OCH$_3$ at C1, C6, C16 and C18), 1.10 (3H, t, J=7.0 Hz, CH$_3$ of propyl group at the nitrogen atom).
5) Analysis of $^{13}$C-NMR spectra (CDCl$_3$)
The following signals are shown (δ, ppm). 166.0 (carbonyl group), 163.6, 131.8, 122.2 and 113.7 (anisoyl group), 94.3, 86.2, 85.1, 82.0, 80.1 and 72.1 (C16, C1, C6, C18, C14 and C15), 59.2, 58.8, 57.9 and 56.0 (OCH$_3$ at C18, C16, C6 and C1), 55.4 (OCH$_3$ of anisoyl group), 13.0 (CH$_3$ of propyl group at the nitrogen atom).

6) Analysis of Mass spectra
m/z: 599 (M$^+$).

7) Elemental analysis
Calculated for $C_{34}H_{49}NO_8$: C, 68.09; H, 8.23; N, 2.34.
Found: C, 68.17; H, 8.35; N, 2.30.

(125) Physicochemical parameters and analytical data of de-N-ethyl-N-(4-methyl)pentyl-3,8,13-trideoxy-14-O-anisoylaconine 1) Property and solubility
Colorless and amorphous powder. Soluble in ether, chloroform, benzene, ethanol, methanol, ethylacetate, pyridine and dimethyl sulfoxide. Insoluble in hexane and water.

2) Analysis of IR spectra (KBr)
IR $v_{max}^{KBr}$: 1715 cm$^{-1}$.

3) Analysis of UV spectra (ethanol)
UV $\lambda_{max}^{EtOH}$ (log ε) nm: 258 (4.01).

4) Analysis of $^1$H-NMR spectra (CDCl$_3$)
The following signals are shown (δ, ppm). 8.01 and 6.95 (each 2H, d, J=8.9 Hz, anisoyl group), 5.10 (1H, t, J=4.8 Hz, C14-β-H), 3.69, 3.30, 3.27 and 3.25 (each 3H, s, OCH$_3$ at C1, C6, C16 and C18), 3.88 (3H, s, OCH$_3$ of anisoyl group), 1.02 (6H, d, J=7.0 Hz, CH$_3$ of 4-methylpentyl group at the nitrogen atom).

5) Analysis of $^{13}$C-NMR spectra (CDCl$_3$)
The following signals are shown (δ, ppm). 166.0 (carbonyl of anisoyl group) 163.8, 131.7, 113.4 and 122.0 (anisoyl group), 94.3, 86.1, 85.0, 82.2, 80.1 and 72.5 (C16, C1, C6, C18, C14 and C15), 59.3, 58.8, 57.9 and 56.0 (OCH$_3$ at C18, C16, C6 and C1), 55.4 (OCH$_3$ of anisoyl group), 21.5 (CH$_3$ of 4-methylpentyl group at the nitrogen atom).

6) Analysis of Mass spectra
m/z: 641 (M$^+$).

7) Elemental analysis
Calculated for $C_{37}H_{55}NO_8$: C 69.24; H 8.64; N 2.18.
Found: C, 69.46; H, 8.53; N, 2.09.

(126) Physicochemical parameters and analytical data of de-N-ethyl-N-acetyl-3,8,13-trideoxy-14-O-anisoylaconine 1) Property and solubility
Colorless and amorphous powder. Soluble in ether, chloroform, benzene, ethanol, methanol, ethylacetate, pyridine and dimethyl sulfoxide. Insoluble in hexane and water.

2) Analysis of IR spectra (KBr)
IR $v_{max}^{KBr}$: 1715, 1655 cm$^{-1}$.

3) Analysis of UV spectra (ethanol)
UV $\lambda_{max}^{EtOH}$ (log ε) nm: 258 (4.02).

4) Analysis of $^1$H-NMR spectra (CDCl$_3$)
The following signals are shown (δ, ppm). 7.99 and 6.95 (each 2H, d, J=8.9 anisoyl group) 5.08 (1H, t, J=4.8 Hz, C14-β-H) 3.87 (3H, s, OCH$_3$ of anisoyl group) 3.70, 3.31, 3.28 and 3.25 (each 3H, s, OCH$_3$ C1, C6, C15 and C18), 2.30 (3H, s, CH$_3$ of acetyl group at the nitrogen atom).

5) Analysis of $^{13}$C-NMR spectra (CDCl$_3$)
The following signals are shown (δ, ppm). 170.9 (carbonyl of acetyl group), 166.0 (carbonyl of anisoyl group), 163.7, 131.6, 113.4 and 122.2 (anisoyl group), 94.5, 84.9, 82.5, 81.9, 80.2 and 72.4 (C16, C6, C18, C1, C14, and C15), 59.1, 58.7, 57.9, and 56.0 (OCH$_3$ at C18, C16, C6 and C1), 55.4 (OCH$_3$ of anisoyl group), 21.0 (CH$_3$ of acetyl group at the nitrogen atom).

6) Analysis of Mass spectra
m/z: 599 (M$^+$).

7) Elemental analysis
Calculated for $C_{33}H_{45}NO_9$: C, 66.09; H, 7.56; N, 2.34.
Found: C, 65.87; H, 7.43; N, 2.28.

(127) Physicochemical parameters and analytical data of de-N-ethyl-N-benzoyl-3,8,13-trideoxy-14-O-anisoylaconine 1) Property and solubility
Colorless and amorphous powder. Soluble in ether, chloroform, benzene, ethanol, methanol, ethylacetate, pyridine and dimethyl sulfoxide. Insoluble in hexane and water.

2) Analysis of IR spectra (KBr)
IR $v_{max}^{KBr}$: 1710, 1653 cm$^{-1}$.

3) Analysis of UV spectra (ethanol)
UV $\lambda_{max}^{EtOH}$ (log ε) nm: 232 (4.10), 258 (4.03).

4) Analysis of $^1$H-NMR spectra (CDCl$_3$)
The following signals are shown (δ, ppm). 7.82-7 09 (5H, m, benzoyl group), 7.98 and 6.96 (each 2H, d, J=8.9, anisoyl group), 5.06 (1H, t, J=4.8 Hz, C14-β-H), 3.88 (3H, s, OCH$_3$ of anisoyl group), 3.69, 3.30, 3.27 and 3.24 (each 3H, s, OCH$_3$ at C1, C6, C16 and C18).

5) Analysis of $^{13}$C-NMR spectra (CDCl$_3$)
The following signals are shown (δ, ppm). 166.0 and 165.8 (carbonyl group), 163.8, 131.7, 113.6 and 122.0 (anisoyl group), 133.9, 133.4, 128.6 and 128.2 (benzoyl group), 94.2, 85.0, 82.4, 81.8, 80.3 and 72.6 (C16, C6, C18, C1, C14 and C15), 59.2, 58.8, 57.9 and 56.0 (OCH$_3$ at C18, C16, C6 and C1), 55.4 (OCH$_3$ of anisoyl group).

6) Analysis of Mass spectra
m/z: 661 (M$^+$).

7) Elemental analysis
Calculated for $C_{38}H_{47}NO_9$: C, 68.97; H 7.16; N 2.12.
Found: C, 69.11; H, 7.02; N, 2.31.

(128) Physicochemical parameters and analytical data of de-N-ethyl-14-O-anisoylaconine 1) Property and solubility
Colorless and amorphous powder. Soluble in ether, chloroform, benzene, ethanol, methanol, ethylacetate, pyridine and dimethyl sulfoxide. Insoluble in hexane and water.

2) Analysis of IR spectra (KBr)
IR $v_{max}^{KBr}$: 1715 cm$^{-1}$.

3) Analysis of UV spectra (ethanol)
UV $\lambda_{max}^{EtOH}$ (log ε) nm: 258 (4.02).

4) Analysis of $^1$H-NMR spectra (CDCl$_3$)
The following signals are shown (δ, ppm). 7.99 and 6.94 (each 2H, d, J=8.9, anisoyl group), 4.96 (1H, d, J=5.0 Hz, C14-β-H), 3.87 (3H, s, OCH$_3$ of anisoyl group), 3.70, 3.30, 3.28 and 3.25 (each 3H, s, OCH$_3$ at C1, C6, C16 and C18).

5) Analysis of $^{13}$C-NMR spectra (CDCl$_3$)
The following signals are shown (δ, ppm). 166.0 (carbonyl group), 163.6, 131.8, 113.7 and 122.2 (anisoyl group), 90.8, 83.6, 82.4, 81.9, 79.5, 78.6, 77.3, 74.7 and 72.0 (C16, C6, C1, C15, C14, C8, C18, C13 and C3), 60.9, 59.1, 58.0 and 55.6 (OCH$_3$ at C16, C18, C6 and C1), 55.4 (OCH$_3$ of anisoyl group).

6) Analysis of Mass spectra
m/z: 605 (M$^+$).

7) Elemental analysis
Calculated for $C_{31}H_{43}NO_{11}$: C, 61.47; H, 7.16; N, 2.31.
Found: C, 61.45; H, 7.02; N, 2.28.

(129) Physicochemical parameters and analytical data of de-N-ethyl-N-amyl-14-O-anisoylaconine 1) Property and solubility
Colorless and amorphous powder. Soluble in ether, chloroform, benzene, ethanol, methanol, ethylacetate, pyridine and dimethyl sulfoxide. Insoluble in hexane and water.

2) Analysis of IR spectra (KBr)
IR $v_{max}^{KBr}$: 1715 cm$^{-1}$.

3) Analysis of UV spectra (ethanol)
UV $\lambda_{max}^{EtOH}$ (log ε) nm: 257 (4.02).

4) Analysis of $^1$H-NMR spectra (CDCl$_3$)
The following signals are shown (δ, ppm). 8.00 and 6.93 (each 2H, d, J=8.9, anisoyl group), 4.98 (1H, d, J=5.0 Hz, C14-β-H), 3.87 (3H, s, OCH$_3$ of anisoyl group), 3.70, 3.30, 3.28 and 3.25 (each 3H, s, OCH$_3$ at C1, C6, C16 and C18), 0.98 (3H, t, J=7.0 Hz, CH$_3$ of amyl group at the nitrogen atom).

5) Analysis of $^{13}$C-NMR spectra (CDCl$_3$)

The following signals are shown (δ, ppm). 166.0 (carbonyl group), 163.9, 131.7, 113.4 and 122.1 (anisoyl group), 91.1, 83.5, 82.5, 81.9, 79.6, 78.6, 77.3, 74.8 and 71.9 (C16, C6, C1, C15, C14, C8, C18, C13 and C3), 61.9, 59.0, 57.8 and 56.0 (OCH$_3$ at C16, C18, C6 and C1), 55.4 (OCH$_3$ of anisoyl group), 13.1 (CH$_3$ of amyl group at the nitrogen atom).

6) Analysis of Mass spectra m/z: 675 (M$^+$).

7) Elemental analysis

Calculated for C$_{36}$H$_{53}$NO$_{11}$: C, 63.98; H, 7.90; N, 2.07. Found: C, 64.10; H, 8.08; N, 2.03.

(130) Physicochemical parameters and analytical data of de-N-ethyl-N-propyl-14-O-anisoylaconine 1) Property and solubility Colorless and amorphous powder. Soluble in ether, chloroform, benzene, ethanol, methanol, ethylacetate, pyridine and dimethyl sulfoxide. Insoluble in hexane and water.

2) Analysis of IR spectra (KBr)

IR $v_{max}^{KBr}$: 1715 cm$^{-1}$.

3) Analysis of UV spectra (ethanol)

UV $\lambda_{max}^{EtOH}$ (log ε) nm: 258 (4.02).

4) Analysis of $^1$H-NMR spectra (CDCl$_3$)

The following signals are shown (δ, ppm). 7.99 and 6.95 (each 2H, d, J=8.9, anisoyl group), 4.96 (1H, d, J=5.0 Hz, C14-β-H), 3.87 (3H, s, OCH$_3$ of anisoyl group), 3.69, 3.30, 3.29 and 3.24 (each 3H, s, OCH$_3$ at C1, C6, C16 and C18), 1.10 (3H, t, J=7.0 Hz, CH$_3$ of propyl group at the nitrogen atom).

5) Analysis of $^{13}$C-NMR spectra (CDCl$_3$)

The following signals are shown (δ, ppm). 166.0 (carbonyl group), 163.6, 131.8, 122.2 and 113.7 (anisoyl group), 90.8, 83.6, 82.3, 81.8, 79.5, 78.6, 77.3, 74.8 and 71.9 (C16, C6, C1, C15, C14, C8, C18, C13 and C3), 61.8, 59.1, 58.0 and 56.1 (OCH$_3$ at C16, C18, C6 and C1), 55.4 (OCH$_3$ of anisoyl group), 13.0 (CH$_3$ of propyl group at the nitrogen atom).

6) Analysis of Mass spectra m/z: 647 (M$^+$).

7) Elemental analysis

Calculated for C$_{34}$H$_{49}$NO$_{11}$: C, 63.04; H, 7.62; N, 2.16. Found: C, 62.98; H, 7.66; N, 2.15.

(131) Physicochemical parameters and analytical data of de-N-ethyl-N-(4-methyl)pentyl-14-O-anisoylaconine 1) Property and solubility Colorless and amorphous powder. Soluble in ether, chloroform, benzene, ethanol, methanol, ethylacetate, pyridine and dimethyl sulfoxide. Insoluble in hexane and water.

2) Analysis of IR spectra (KBr)

IR $v_{max}^{KBr}$: 1715 cm$^{-1}$.

3) Analysis of UV spectra (ethanol)

UV $\lambda_{max}^{EtOH}$ (log ε) nm: 258 (4.01).

4) Analysis of $^1$H-NMR spectra (CDCl$_3$)

The following signals are shown (δ, ppm). 8.01 and 6.93 (each 2H, d, J=8.9, anisoyl group), 4.96 (1H, d, J=5.0 Hz, C14-β-H), 3.69, 3.29, 3.28 and 3.25 (each 3H, s, OCH$_3$ at C1, C6, C16 and C18), 3.88 (3H, s, OCH$_3$ of anisoyl group), 1.02 (6H, d, J=7.9 Hz, CH$_3$ of 4-methylpentyl group at the nitrogen atom).

5) Analysis of $^{13}$C-NMR spectra (CDCl$_3$)

The following signals are shown (δ, ppm). 166.0 (carbonyl group), 163.9, 131.7, 113.4 and 122.1 (anisoyl group), 90.8, 83.5, 82.4, 81.8, 79.5, 78.6, 77.3, 74.8 and 71.9 (C16, C6, C1, C15, C14, C8, C18, C13 and C3), 61.8, 59.1, 57.8 and 56.0 (OCH$_3$ at C16, C18, C6 and C1), 55.4 (OCH$_3$ of anisoyl group), 21.5 (CH$_3$ of 4-methylpentyl group at the nitrogen atom).

6) Analysis of Mass spectra m/z: 689 (M$^+$).

7) Elemental analysis

Calculated for C$_{37}$H$_{55}$NO$_{11}$: C, 64.42; H, 8.04; N, 2.03. Found: C, 64.55; H, 8.16; N, 2.11.

(132) Physicochemical parameters and analytical data of de-N-ethyl-N-acetyl-14-O-anisoylaconine 1) Property and solubility Colorless and amorphous powder. Soluble in ether, chloroform, benzene, ethanol, methanol, ethylacetate, pyridine and dimethyl sulfoxide. Insoluble in hexane and water.

2) Analysis of IR spectra (KBr)

IR $v_{max}^{KBr}$: 1715, 1655 cm$^{-1}$.

3) Analysis of UV spectra (ethanol)

UV $\lambda_{max}^{EtOH}$ (log ε) nm: 258 (4.02).

4) Analysis of $^1$H-NMR spectra (CDCl$_3$)

The following signals are shown (δ, ppm). 7.99 and 6.94 (each 2H, d, J=8.9, anisoyl group), 4.96 (1H, d, J=5.0 Hz, C14-β-H), 3.70, 3.30, 3.28 and 3.25 (each 3H, s, OCH$_3$ at C1, C6, C16 and C18), 3.87 (3H, s, OCH$_3$ of anisoyl group), 2.32 (3H, s, CH$_3$ of acetyl group at the nitrogen atom).

5) Analysis of $^{13}$C-NMR spectra (CDCl$_3$)

The following signals are shown (δ, ppm). 170.8 (carbonyl of acetyl group), 166.0 (carbonyl of anisoyl group), 163.6, 131.8, 113.7 and 122.2 (anisoyl group), 90.8, 83.6, 81.9, 79.8, 79.5, 78.6, 77.3, 74.8 and 71.9 (C16, C6, C15, C1, C14, C8, C18, C13 and C3), 60.9, 59.1, 58.0 and 55.6 (OCH$_3$ at C16, C18, C6 and C1), 55.4 (OCH$_3$ of anisoyl group), 21.1 (CH$_3$ of acetyl group at the nitrogen atom).

6) Analysis of Mass spectra m/z: 647 (M$^+$).

7) Elemental analysis

Calculated for C$_{33}$H$_{45}$NO$_{12}$: C, 61.19; H, 7.00; N 2.16. Found: C, 61.26; H, 7.21; N, 2.21.

(133) Physicochemical parameters and analytical data of de-N-ethyl-N-benzoyl-14-O-anisoylaconine 1) Property and solubility Colorless and amorphous powder. Soluble in ether, chloroform, benzene, ethanol, methanol, ethylacetate, pyridine and dimethyl sulfoxide. Insoluble in hexane and water.

2) Analysis of IR spectra (KBr)

IR $v_{max}^{KBr}$: 1711, 1653 cm$^{-1}$.

3) Analysis of UV spectra (ethanol)

UV $\lambda_{max}^{EtOH}$ (log ε) nm: 232 (4.10), 258 (4.03).

4) Analysis of $^1$H-NMR spectra (CDCl$_3$)

The following signals are shown (δ, ppm). 7.82-7.10 (5H, m, benzoyl group), 7.99 and 6.93 (each 2H, d, J=8.9, anisoyl group), 4.97 (1H, d, J=5.0 Hz, C14-β-H), 3.70, 3.31, 3.27 and 3.25 (each 3H, s, OCH$_3$ at C1, C6, C16 and C18), 3.87 (3H, s, OCH$_3$ of anisoyl group).

5) Analysis of $^{13}$C-NMR spectra (CDCl$_3$)

The following signals are shown (δ, ppm). 166.0 and 165.7 (carbonyl group), 163.7, 131.7, 113.5 and 122.1 (anisoyl group), 134.0, 133.6, 128.7, 128.2 and 127.6 (benzoyl group), 91.0, 83.5, 81.9, 79.9, 79.6, 78.6, 77.3, 74.8 and 71.9 (C16, C6, C15, C1, C14, C8, C18, C13 and C3), 61.8, 59.1, 57.8 and 56.0 (OCH$_3$ at C16, C18, C6 and C1), 55.4 (OCH$_3$ of anisoyl group).

6) Analysis of Mass spectra m/z: 709 (M$^+$).

7) Elemental analysis

Calculated for C$_{38}$N$_{47}$NO$_{12}$: C, 64.30; H, 6.67; N, 1.97. Found: C, 63.19; H, 6.62; N, 2.08.

(134) Physicochemical parameters and analytical data of de-N-ethyl-3-deoxy-14-O-anisoylaconine 1) Property and solubility Colorless and amorphous powder. Soluble in ether, chloroform, benzene, ethanol, methanol, ethylacetate, pyridine and dimethyl sulfoxide. Insoluble in hexane and water.

2) Analysis of IR spectra (KBr)
  IR $v_{max}^{KBr}$: 1715 cm$^{-1}$.
3) Analysis of UV spectra (ethanol)
  UV $\lambda_{max}^{EtOH}$ (log ε) nm: 258 (4.01).
4) Analysis of $^1$H-NMR spectra (CDCl$_3$)
  The following signals are shown (δ, ppm). 7.99 and 6.95 (each 2H, d, J=8.9 Hz, anisoyl group), 4.97 (1H, d, J=5.0 Hz, C14-β-H), 3.69, 3.31, 3.28 and 3.25 (each 3H, s, OCH$_3$ at C1, C6, C16 and C18), 3.87 (3H, s, OCH$_3$ of anisoyl group).
4) Analysis of $^{13}$C-NMR spectra (CDCl$_3$)
  The following signals are shown (δ, ppm). 166.0 (carbonyl of anisoyl group), 163.7, 131.6, 113.5 and 122.1 (anisoyl group), 90.7, 85.3, 83.6, 81.2, 80.0, 79.5, 78.6 and 75.0 (C16, C1, C6, C18, C15, C14, C8 and C13), 61.9, 59.1, 58.0 and 56.0 (OCH$_3$ at C16, C18 C6 and C1) 55.4 (OCH$_3$ of anisoyl group).
6) Analysis of Mass spectra
  m/z: 589 (M$^+$).
7) Elemental analysis
  Calculated for C$_{31}$H$_{43}$NO$_{10}$: C, 63.14; H, 7.35; N, 2.38. Found: C, 63.31; H, 7.26; N 2.31.

(135) Physicochemical parameters and analytical data of de-N-ethyl-N-amyl-3-deoxy-14-O-anisoylaconine
1) Property and solubility
  Colorless and amorphous powder. Soluble in ether, chloroform, benzene, ethanol, methanol, ethylacetate, pyridine and dimethyl sulfoxide. Insoluble in hexane and water.
2) Analysis of IR spectra (KBr)
  IR $v_{max}^{KBr}$: 1715 cm$^{-1}$.
3) Analysis of UV spectra (ethanol)
  UV $\lambda_{max}^{EtOH}$ (log ε) nm: 257 (4.02).
4) Analysis of $^1$H-NMR spectra (CDCl$_3$)
  The following signals are shown (δ, ppm). 8.00 and 6.93 (each 2H, d, J=8.9 Hz, anisoyl group), 4.98 (1H, d, J=5.0 Hz, C14-β-H), 3.69, 3.31, 3.27 and 3.24 (each 3H, s, OCH$_3$ at C1, C6, C16 and C18), 3.87 (3H, s, OCH$_3$ of anisoyl group), 0.99 (3H, t, J=7.0 Hz, CH$_3$ of amyl group at the nitrogen atom).
5) Analysis of $^{13}$C-NMR spectra (CDCl$_3$)
  The following signals are shown (δ, ppm). 166.0 (carbonyl of anisoyl group), 163.8, 131.8, 113.6 and 122.1 (anisoyl group), 90.8, 85.4, 83.5, 81.0, 80.0, 79.4, 78.6 and 75.0 (C16, C1, C6, C18, C15, C14, C8 and C13), 61.8, 59.1, 57.8 and 56.0 (OCH$_3$ at C16, C18, C6 and C1), 55.4 (OCH$_3$ of anisoyl group), 13.1 (CH$_3$ of amyl group at the nitrogen atom).
6) Analysis of Mass spectra
  m/z: 659 (M$^+$).
7) Elemental analysis
  Calculated for C$_{35}$H$_{53}$NO$_{10}$: C, 65.53; H, 8.10; N, 2.12. Found: C, 65.44; H, 8.15; N, 2.10.

(136) Physicochemical parameters and analytical data of de-N-ethyl-N-propyl-3-deoxy-14-O-anisoylaconine
1) Property and solubility
  Colorless and amorphous powder. Soluble in ether, chloroform, benzene, ethanol, methanol, ethylacetate, pyridine and dimethyl sulfoxide. Insoluble in hexane and water.
2) Analysis of IR spectra (KBr)
  IR $v_{max}^{KBr}$: 1715 cm$^{-1}$.
3) Analysis of UV spectra (ethanol)
  UV $\lambda_{max}^{EtOH}$ (log ε) nm: 258 (4.02).
4) Analysis of $^1$H-NMR spectra (CDCl$_3$)
  The following signals are shown (δ, ppm). 7.99 and 6.94 (each 2H, d, J=8.9, anisoyl group), 4.98 (1H, d, J=5.0 Hz, C14-β-H), 3.87 (3H, s, OCH$_3$ of anisoyl group), 3.70, 3.30, 3.27 and 3.25 (each 3H, s, OCH$_3$ at C1, C6, C16 and C18), 1.10 (3H, t, J=7.0 Hz, CH$_3$ of propyl group at the nitrogen atom).
5) Analysis of $^{13}$C-NMR spectra (CDCl$_3$)
  The following signals are shown (δ, ppm). 165.9 (carbonyl of anisoyl group), 163.6, 131.8, 122.2 and 113.7 (anisoyl group), 90.8, 85.4, 83.3, 81.0, 79.9, 79.5, 78.6 and 75.0 (C16, C1, C6, C18, C15, C14, C8 and C13), 61.7, 59.0, 58.0 and 56.1 (OCH$_3$ at C16, C18, C6 and C1), 55.4 (OCH$_3$ of anisoyl group), 13.0 (CH$_3$ of propyl group at the nitrogen atom).
6) Analysis of Mass spectra
  m/z: 631 (M$^+$).
7) Elemental analysis
  Calculated for C$_{33}$H$_{49}$NO$_{10}$: C, 64.64; H, 7.82; N, 2.22. Found: C, 64.73; H, 7.66; N, 2.18.

(137) Physicochemical parameters and analytical data of de-N-ethyl-N-(4-methyl)pentyl-3-deoxy-14-O-anisoylaconine
1) Property and solubility
  Colorless and amorphous powder. Soluble in ether, chloroform, benzene, ethanol, methanol, ethylacetate, pyridine and dimethyl sulfoxide. Insoluble in hexane and water.
2) Analysis of IR spectra (KBr)
  IR $v_{max}^{KBr}$: 1715 cm$^{-1}$.
3) Analysis of UV spectra (ethanol)
  UV $\lambda_{max}^{EtOH}$ (log ε) nm: 258 (4.01).
4) Analysis of $^1$H-NMR spectra (CDCl$_3$)
  The following signals are shown (δ, ppm). 7.99 and 6.94 (each 2H, d, J=8.9, anisoyl group), 4.97 (1H, d, J=5.0 Hz, C14-β-H), 3.88 (3H, s, OCH$_3$ of anisoyl group), 3.70, 3.30, 3.27 and 3.25 (each 3H, s, OCH$_3$ at C1, C6, C16 and C18), 1.01 (6H, d, J=7.0 Hz, CH$_3$ of 4-methylpentyl group at the nitrogen atom).
5) Analysis of $^{13}$C-NMR spectra (CDCl$_3$)
  The following signals are shown (δ, ppm). 166.0 (carbonyl of anisoyl group), 163.9, 131.7, 113.4 and 122.1 (anisoyl group), 90.7, 85.5, 83.5, 81.0, 79.9, 79.5, 78.6 and 75.0 (C16, C1, C6, C18, C15, C14, C8 and C13), 61.8, 59.0, 58.0 and 56.1 (OCH$_3$ at C16, C18, C6 and C1), 55.4 (OCH$_3$ of anisoyl group), 21.5 (CH$_3$ of 4-methylpentyl group at the nitrogen atom).
6) Analysis of Mass spectra
  m/z: 673 (M$^+$).
7) Elemental analysis
  Calculated for C$_{37}$H$_{55}$NO$_{10}$: C, 65.95; H, 8.23; N 2.08. Found: C, 66.10; H, 8.18; N, 1.96.

(138) Physicochemical parameters and analytical data of de-N-ethyl-N-acetyl-3-deoxy-14-O-anisoylaconine
1) Property and solubility
  Colorless and amorphous powder. Soluble in ether, chloroform, benzene, ethanol, methanol, ethylacetate, pyridine and dimethyl sulfoxide. Insoluble in hexane and water.
2) Analysis of IR spectra (KBr)
  IR $v_{max}^{KBr}$: 1715, 1655 cm$^{-1}$.
3) Analysis of UV spectra (ethanol)
  UV $\lambda_{max}^{EtOH}$ (log ε) nm: 258 (4.02).
4) Analysis of $^1$H-NMR spectra (CDCl$_3$)
  The following signals are shown (δ, ppm). 7.99 and 6.95 (each 2H, d, J=8.9, anisoyl group), 4.97 (1H, d, J=5.0 Hz, C14-β-H), 3.87 (3H, s, OCH$_3$ of anisoyl group), 3.69, 3.31, 3.28 and 3.25 (each 3H, s, OCH$_3$ at C1, C6, C16 and C18), 2.31 (3H, s, CH$_3$ of acetyl group at the nitrogen atom).
5) Analysis of $^{13}$C-NMR spectra (CDCl$_3$)
  The following signals are shown (δ, ppm). 170.8 (carbonyl of acetyl group), 166.0 (carbonyl of anisoyl group), 163.7, 131.6, 113.5 and 122.1 (anisoyl group), 90.7, 83.6, 82.0, 81.2, 80.0, 79.5, 78.6 and 75.0 (C16, C6, C1, C18, C15, C14, C8 and C13), 61.9, 59.1, 58.0 and 56.0 (OCH$_3$ at C16, C18, C6 and C1), 55.4 (OCH$_3$ of anisoyl group), 21.0 (3H, s, CH$_3$ of acetyl group).

6) Analysis of Mass spectra
m/z: 631 (M⁺).

7) Elemental analysis
Calculated for $C_{33}H_{45}NO_{11}$: C, 62.74; H, 7.18; N 2.22.
Found: C, 62.91; H, 7.22; N, 2.36.

(139) Physicochemical parameters and analytical data of de-N-ethyl-N-benzoyl-3-deoxy-14-O-anisoylaconine 1) Property and solubility
Colorless and amorphous powder. Soluble in ether, chloroform, benzene, ethanol, methanol, ethylacetate, pyridine and dimethyl sulfoxide. Insoluble in hexane and water.

2) Analysis of IR spectra (KBr)
IR $v_{max}^{KBr}$: 1711, 1653 cm$^{-1}$.

3) Analysis of UV spectra (ethanol)
UV $\lambda_{max}^{EtOH}$ (log ε) nm: 232 (4.10), 258 (4.03).

4) Analysis of ¹H-NMR spectra (CDCl₃)
The following signals are shown (δ, ppm). 7.81-7.09 (5H, m, benzoyl group), 7.99 and 6.95 (each 2H, d, J=8.9, anisoyl group), 4.96 (1H, d, J=5.0 Hz, C14-β-H), 3.87 (3H, s, OCH₃ of anisoyl group), 3.70, 3.31, 3.27 and 3.25 (each 3H, s, OCH₃ at C1, C6, C16 and C18).

5) Analysis of ¹³C-NMR spectra (CDCl₃)
The following signals are shown (δ, ppm). 166.0 and 165.8 (carbonyl group), 163.8, 131.7, 113.6 and 122.0 (anisoyl group), 133.9, 133.4, 128.6, 128.2 and 127.6 (benzoyl group), 90.7, 83.6, 82.0, 81.0, 79.9, 79.5, 78.6 and 75.0 (C16, C6, C1, C18, C15, C14, C8 and C13), 61.8, 59.1, 57.8 and 56.0 (OCH₃ at C16, C18, C6 and C1), 55.4 (OCH₃ of anisoyl group).

6) Analysis of Mass spectra
m/z: 693 (M⁺).

7) Elemental analysis
Calculated for $C_{38}H_{47}NO_{11}$: C, 65.79; H, 6.83; N, 2.02.
Found: C, 65.81; H, 8.91; N, 2.15.

(140) Physicochemical parameters and analytical data of de-N-ethyl-3,13-dideoxy-14-O-anisoylaconine 1) Property and solubility
Colorless and amorphous powder. Soluble in ether, chloroform, benzene, ethanol, methanol, ethylacetate, pyridine and dimethyl sulfoxide. Insoluble in hexane and water.

2) Analysis of IR spectra (KBr)
IR $v_{max}^{KBr}$: 1715 cm$^{-1}$.

3) Analysis of UV spectra (ethanol)
UV $\lambda_{max}^{EtOH}$ (log ε) nm: 258 (4.01).

4) Analysis of ¹H-NMR spectra (CDCl₃)
The following signals are shown (δ, ppm). 7.99 and 6.95 (each 2H, d, J=8.9, anisoyl group), 5.05 (1H, t, J=4.8 Hz, C14-β-H), 3.87 (3H, s, OCH₃ of anisoyl group), 3.70, 3.31, 3.28 and 3.25 (each 3H, s, OCH₃ at C1, C6, C16 and C18).

5) Analysis of ¹³C-NMR spectra (CDCl₃)
The following signals are shown (δ, ppm). 166.0 (carbonyl of anisoyl group), 163.7, 131.6, 122.1 and 113.3 (anisoyl group), 89.7, 83.6, 82.3, 81.7, 79.9, 78.6 and 77.4 (C16, C6, C1, C18, C15, C8 and C14), 59.1, 57.9, 57.6 and 55.9 (OCH₃ at C18, C16, C6 and C1), 55.4 (OCH₃ of anisoyl group).

6) Analysis of Mass spectra
m/z: 557 (M⁺).

7) Elemental analysis
Calculated for $C_{31}H_{43}NO_9$: C, 64.98; H, 7.55; N, 2.44.
Found: C, 65.02; H, 7.68; N, 2.35.

(141) Physicochemical parameters and analytical data of de-N-ethyl-N-amyl-3,13-dideoxy-14-O-anisoylaconine 1) Property and solubility
Colorless and amorphous powder. Soluble in ether, chloroform, benzene, ethanol, methanol, ethylacetate, pyridine and dimethyl sulfoxide. Insoluble in hexane and water.

2) Analysis of IR spectra (KBr)
IR $v_{max}^{KBr}$: 1715 cm$^{-1}$.

3) Analysis of UV spectra (ethanol)
UV $\lambda_{max}^{EtOH}$ (log ε) nm: 257 (4.02).

4) Analysis of ¹H-NMR spectra (CDCl₃)
The following signals are shown (δ, ppm). 8.01 and 6.93 (each 2H, d, J=8.9, anisoyl group), 5.08 (1H, t, J=4.8 Hz, C14-β-H), 3.67, 3.31, 3.27 and 3.24 (each 3H, s, OCH₃ at C1, C6, C16 and C18), 3.87 (3H, s, OCH₃ of anisoyl group), 0.98 (3H, t, J=7.0 Hz, CH₃ of amyl group at the nitrogen atom).

5) Analysis of ¹³C-NMR spectra (CDCl₃)
The following signals are shown (δ, ppm). 166.0 (carbonyl of anisoyl group), 163.7, 131.8, 113.6 and 122.1 (anisoyl group), 89.8, 85.3, 83.5, 81.6, 79.9, 78.6 and 77.4 (C16, C1, C6, C18, C15, C8 and C14), 59.1, 57.9, 57.5 and 55.9 (OCH₃ at C18, C16, C6 and C1), 55.4 (OCH₃ of anisoyl group), 13.2 (CH₃ of amyl group at the nitrogen atom).

6) Analysis of Mass spectra
m/z: 643 (M⁺).

7) Elemental analysis
Calculated for $C_{36}H_{53}NO_9$: C, 67.16; H, 8.30; N, 2.18.
Found: C, 67.33; H, 8.18; N 2.07.

(142) Physicochemical parameters and analytical data of de-N-ethyl-N-propyl-3,13-dideoxy-14-O-anisoylaconine 1) Property and solubility
Colorless and amorphous powder. Soluble in ether, chloroform, benzene, ethanol, methanol, ethylacetate, pyridine and dimethyl sulfoxide. Insoluble in hexane and water.

2) Analysis of IR spectra (KBr)
IR $v_{max}^{KBr}$: 1715 cm$^{-1}$.

3) Analysis of UV spectra (ethanol)
UV $\lambda_{max}^{EtOH}$ (log ε) nm: 258 (4.02).

4) Analysis of ¹H-NMR spectra (CDCl₃)
The following signals are shown (δ, ppm). 7.99 and 6.95 (each 2H, d, J=8.9, anisoyl group), 5.09 (1H, t, J=4.8 Hz, C14-β-H), 3.67, 3.30, 3.29 and 3.24 (each 3H, s, OCH₃ at C1, C6, C16 and C18), 1.10 (3H, t, J=7.0 Hz, CH₃ of propyl group at the nitrogen atom).

5) Analysis of ¹³C-NMR spectra (CDCl₃)
The following signals are shown (δ, ppm). 166.0 (carbonyl of anisoyl group), 163.6, 131.8, 113.7 and 122.2 (anisoyl group), 89.8, 85.3, 83.4, 81.4, 79.8, 78.6 and 77.4 (C16, C1, C6, C18, C15, C8 and C14), 59.1, 57.9, 57.5 and 55.6 (OCH₃ at C18, C16, C6 and C1), 55.4 (OCH₃ of anisoyl group), 13.0 (CH₃ of propyl group at the nitrogen atom).

6) Analysis of Mass spectra
m/z: 615 (M⁺).

7) Elemental analysis
Calculated for $C_{33}H_{49}NO_9$: C, 66.32; H, 8.02; N, 2.27.
Found: C, 66.46; H, 8.14; N, 2.33.

(143) Physicochemical parameters and analytical data of de-N-ethyl-N-(4-methyl)pentyl-3,13-dideoxy-14-O-anisoylaconine 1) Property and solubility
Colorless and amorphous powder. Soluble in ether, chloroform, benzene, ethanol, methanol, ethylacetate, pyridine and dimethyl sulfoxide. Insoluble in hexane and water.

2) Analysis of IR spectra (KBr)
IR $v_{max}^{KBr}$: 1715 cm$^{-1}$.

3) Analysis of UV spectra (ethanol)
UV $\lambda_{max}^{EtOH}$ (log ε) nm: 258 (4.01).

4) Analysis of ¹H-NMR spectra (CDCl₃)
The following signals are shown (δ, ppm). 8.01 and 6.95 (each 2H, d, J=8.9, anisoyl group), 5.10 (1H, t, J=4.8 Hz, C14-β-H), 3.68, 3.30, 3.27 and 3.24 (each 3H, s, OCH₃ at C1, C6, C16 and C18), 3.88 (3H, s, OCH₃ of anisoyl group), 1.02 (6H, d, J=7.0 Hz, CH₃ of 4-methylpentyl group at the nitrogen atom).

5) Analysis of $^{13}$C-NMR spectra (CDCl$_3$)

The following signals are shown (δ, ppm). 166.0 (carbonyl of anisoyl group), 163.9, 131.8, 113.4 and 122.0 (anisoyl group), 89.8, 85.2, 83.4, 81.5, 79.9, 78.6 and 77.4 (C16, C1, C6, C18, C15, C8 and C14), 59.1, 57.9, 57.5 and 55.9 (OCH$_3$ at C18, C16, C6 and C1), 55.4 (OCH$_3$ of anisoyl group), 21.5 (CH$_3$ of 4-methylpentyl group at the nitrogen atom).

6) Analysis of Mass spectra m/z: 657 (M$^+$).

7) Elemental analysis

Calculated for C$_{37}$H$_{55}$NO$_9$: C, 67.55; H, 8.43; N, 2.13. Found: C, 67.58; H, 8.49; N, 2.02.

(144) Physicochemical parameters and analytical data of de-N-ethyl-N-acetyl-3,13-dideoxy-14-O-anisoylaconine 1) Property and solubility Colorless and amorphous powder. Soluble in ether, chloroform, benzene, ethanol, methanol, ethylacetate, pyridine and dimethyl sulfoxide. Insoluble in hexane and water.

2) Analysis of IR spectra (KBr)

IR $\nu_{max}^{KBr}$: 1715, 1655 cm$^{-1}$.

3) Analysis of UV spectra (ethanol)

UV $\lambda_{max}^{EtOH}$ (log ε) nm: 258 (4.02).

4) Analysis of $^1$H-NMR spectra (CDCl$_3$)

The following signals are shown (δ, ppm). 7.99 and 6.95 (each 2H, d, J=8.9 Hz, anisoyl group), 5.05 (1H, t, J=4.8 Hz, C14-β-H), 3.70, 3.31, 3.28 and 3.25 (each 3H, s, OCH$_3$ at C1, C6, C16 and C18), 3.87 (3H, s, OCH$_3$ of anisoyl group), 2.30 (3H, s, CH$_3$ of acetyl group at the nitrogen atom).

5) Analysis of $^{13}$C-NMR spectra (CDCl$_3$)

The following signals are shown (δ, ppm). 170.8 (carbonyl of acetyl group), 166.0 (carbonyl of anisoyl group), 163.7, 131.6, 122.1 and 113.3 (anisoyl group), 89.7, 83.6, 82.0, 81.7, 79.9, 78.6 and 77.4 (C16, C6, C1, C18, C15, C8 and C14), 59.1, 57.9, 57.6 and 55.9 (OCH$_3$ at C18, C16, C6 and C1), 55.4 (OCH$_3$ of anisoyl group), 21.0 (CH$_3$ of acetyl group at the nitrogen atom).

6) Analysis of Mass spectra m/z: 615 (M$^+$).

7) Elemental analysis

Calculated for C$_{33}$H$_{45}$NO$_{10}$: C, 64.37; H, 7.37; N, 2.27. Found: C, 64.09; H, 7.56; N, 2.16.

(145) Physicochemical parameters and analytical data of de-N-ethyl-N-benzoyl-3,13-dideoxy-14-O-anisoylaconine 1) Property and solubility Colorless and amorphous powder. Soluble in ether, chloroform, benzene, ethanol, methanol, ethylacetate, pyridine and dimethyl sulfoxide. Insoluble in hexane and water.

2) Analysis of IR spectra (KBr)

IR $\nu_{max}^{KBr}$: 1710, 1653 cm$^{-1}$.

3) Analysis of UV spectra (ethanol)

UV $\lambda_{max}^{EtOH}$ (log ε) nm: 232 (4.10), 258 (4.02).

4) Analysis of $^1$H-NMR spectra (CDCl$_3$)

The following signals are shown (δ, ppm). 7.82-7.09 (5H, m, benzoyl group), 7.98 and 6.96 (each 2H, d, J=8.9 Hz, anisoyl group), 5.06 (1H, t, J=4.8 Hz, C14-β-H), 3.87 (3H, s, OCH$_3$ of anisoyl group), 3.68, 3.31, 3.28 and 3.25 (each 3H, s, OCH$_3$ at C1, C6, C16 and C18).

5) Analysis of $^{13}$C-NMR spectra (CDCl$_3$)

The following signals are shown (δ, ppm). 166.0 and 165.8 (carbonyl group), 163.8, 131.7, 122.0 and 113.6 (anisoyl group), 133.9, 133.5, 128.6 and 128.2 (benzoyl group), 89.8, 83.5, 82.0, 81.6, 79.9, 78.6 and 77.4 (C16, C6, C1, C18, C15, C8 and C14), 59.1, 57.9, 57.6 and 55.9 (OCH$_3$ at C18, C16, C6 and C1), 55.4 (OCH$_3$ of anisoyl group).

6) Analysis of Mass spectra m/z: 677 (M$^+$).

7) Elemental analysis

Calculated for C$_{38}$H$_{47}$NO$_{10}$: C, 67.34; H, 6.99; N, 2.07. Found: C, 67.52; H, 7.20; N, 2.13.

(146) Physicochemical parameters and analytical data of de-N-ethyl-16-epi-3,8-dideoxy-14-O-anisoylaconine 1) Property and solubility Colorless and amorphous powder. Soluble in ether, chloroform, benzene, ethanol, methanol, ethylacetate, pyridine and dimethyl sulfoxide. Insoluble in hexane and water.

2) Analysis of IR spectra (KBr)

IR $\nu_{max}^{KBr}$: 1715 cm$^{-1}$.

3) Analysis of UV spectra (ethanol)

UV $\lambda_{max}^{EtOH}$ (log ε) nm: 258 (4.02).

4) Analysis of $^1$H-NMR spectra (CDCl$_3$)

The following signals are shown (δ, ppm). 7.98 and 6.95 (each 2H, d, J=8.9, anisoyl group), 5.14 (1H, d, J=5.0 Hz, C14-β-H), 3.87 (3H, s, OCH$_3$ of anisoyl group), 3.84, 3.30, 3.28 and 3.25 (each 3H, s, OCH$_3$ at C1, C6, C16 and C18).

5) Analysis of $^{13}$C-NMR spectra (CDCl$_3$)

The following signals are shown (δ, ppm). 166.0 (carbonyl of anisoyl group), 163.8, 131.4, 113.5 and 122.2 (anisoyl group), 91.2, 86.2, 85.0, 82.5, 80.1, 76.0 and 72.3 (C16, C1, C6, C18, C14, C13 and C15), 62.2, 59.1, 58.0 and 56.0 (OCH$_3$ at C16, C18, C6 and C1), 55.4 (OCH$_3$ of anisoyl group).

6) Analysis of Mass spectra m/z: 557 (M$^+$).

(147) Physicochemical parameters and analytical data of de-N-ethyl-N-amyl-16-epi-3,8-dideoxy-14-O-anisoylaconine 1) Property and solubility Colorless and amorphous powder. Soluble in ether, chloroform, benzene, ethanol, methanol, ethylacetate, pyridine and dimethyl sulfoxide. Insoluble in hexane and water.

2) Analysis of IR spectra (KBr)

IR $\nu_{max}^{KBr}$: 1715 cm$^{-1}$.

3) Analysis of UV spectra (ethanol)

UV $\lambda_{max}^{EtOH}$ (log ε) nm: 257 (4.02).

4) Analysis of $^1$H-NMR spectra (CDCl$_3$)

The following signals are shown (δ, ppm). 8.00 and 6.93 (each 2H, d, J=8.9, anisoyl group), 5.14 (1H, d, J=5.0 Hz, C14-β-H), 3.87 (3H, s, OCH$_3$ of anisoyl group), 3.83, 3.31, 3.27 and 3.24 (each 3H, s, OCH$_3$ at C1, C6, C16 and C18), 0.99 (3H, t, J=7.0 Hz, CH$_3$ of amyl group at the nitrogen atom).

5) Analysis of $^{13}$C-NMR spectra (CDCl$_3$)

The following signals are shown (δ, ppm). 166.0 (carbonyl of anisoyl group), 163.8, 131.8, 113.6 and 122.1 (anisoyl group), 91.2, 86.0, 85.1, 82.3, 80.2, 76.0 and 72.4 (C16, C1, C6, C18, C14, C13 and C15), 62.2, 59.1, 57.8 and 56.0 (OCH$_3$ at C16, C18, C6 and C1), 55.4 (OCH$_3$ of anisoyl group), 13.1 (CH$_3$ of amyl group at the nitrogen atom).

6) Analysis of Mass spectra m/z: 655 (M$^+$).

(148) Physicochemical parameters and analytical data of de-N-ethyl-N-propyl-16-epi-3,8-dideoxy-14-O-anisoylaconine 1) Property and solubility Colorless and amorphous powder. Soluble in ether, chloroform, benzene, ethanol, methanol, ethylacetate, pyridine and dimethyl sulfoxide. Insoluble in hexane and water.

2) Analysis of IR spectra (KBr)

IR $\nu_{max}^{KBr}$: 1715 cm$^{-1}$.

3) Analysis of UV spectra (ethanol)

UV $\lambda_{max}^{EtOH}$ (log ε) nm: 258 (4.02).

4) Analysis of $^1$H-NMR spectra (CDCl$_3$)

The following signals are shown (δ, ppm). 7.99 and 6.94 (each 2H, d, J=8.9, anisoyl group), 5.13 (1H, d, J=5.0 Hz, C14-β-H), 3.87 (3H, s, OCH$_3$ of anisoyl group), 3.83, 3.30, 3.29 and 3.24 (each 3H, s, OCH$_3$ at C1, C6, C16 and C18), 1.10 (3H, t, J=7.0 Hz, CH$_3$ of propyl group at the nitrogen atom).

5) Analysis of $^{13}$C-NMR spectra (CDCl$_3$)

The following signals are shown (δ, ppm). 165.9 (carbonyl of anisoyl group), 163.6, 131.8, 122.2 and 113.7 (anisoyl group), 91.3, 86.2, 85.0, 82.1, 80.1, 76.1 and 72.2 (C16, C1, C6, C18, C14, C13 and C15), 62.1, 59.0, 58.0 and 56.0 (OCH$_3$ at C16, C18, C6 and C1), 55.4 (OCH$_3$ of anisoyl group), 13.0 (CH$_3$ of propyl group at the nitrogen atom).

6) Analysis of Mass spectra m/z: 627 (M$^+$).

(149) Physicochemical parameters and analytical data of de-N-ethyl-N-(4-methyl)pentyl-16-epi-3,8-dideoxy-14-O-anisoylaconine 1) Property and solubility Colorless and amorphous-powder. Soluble in ether, chloroform, benzene, ethanol, methanol, ethylacetate, pyridine and dimethyl sulfoxide. Insoluble in hexane and water.

2) Analysis of IR spectra (KBr)

IR $v_{max}^{KBr}$: 1715 cm$^{-1}$.

3) Analysis of UV spectra (ethanol)

UV $\lambda_{max}^{EtOH}$ (log ε) nm: 258 (4.01).

4) Analysis of $^1$H-NMR spectra (CDCl$_3$)

The following signals are shown (δ, ppm). 8.00 and 6.94 (each 2H, d, J=8.9, anisoyl group), 5.12 (1H, d, J=5.0 Hz, C14-β-H), 3.84, 3.30, 3.27 and 3.25 (each 3H, s, OCH$_3$ at C1, C6, C16 and C18), 3.88 (3H, s, OCH$_3$ of anisoyl group), 1.02 (6H, d, J=7.0 Hz, CH$_3$ of 4-methylpentyl group at the nitrogen atom).

5) Analysis of $^{13}$C-NMR spectra (CDCl$_3$)

The following signals are shown (δ, ppm). 166.0 (carbonyl of anisoyl group), 163.9, 131.7, 113.4 and 122.1 (anisoyl group), 91.3, 86.1, 86.0, 82.2, 80.1, 76.1 and 72.3 (C16, C1, C6, C18, C14, C13 and C15), 62.2, 59.0, 57.9 and 56.0 (OCH$_3$ at C16, C18, C6 and C1), 55.4 (OCH$_3$ of anisoyl group), 21.5 (CH$_3$ of 4-methylpentyl group at the nitrogen atom).

6) Analysis of Mass spectra m/z: 669 (M$^+$).

(150) Physicochemical parameters and analytical data of de-N-ethyl-N-acetyl-16-epi-3,8-dideoxy-14-O-anisoylaconine 1) Property and solubility Colorless and amorphous powder. Soluble in ether, chloroform, benzene, ethanol, methanol, ethylacetate, pyridine and dimethyl sulfoxide. Insoluble in hexane and water.

2) Analysis of IR spectra (KBr)

IR $v_{max}^{KBr}$: 1715, 1655 cm$^{-1}$.

3) Analysis of UV spectra (ethanol)

UV $\lambda_{max}^{EtOH}$ (log ε) nm: 258 (4.02).

4) Analysis of $^1$H-NMR spectra (CDCl$_3$)

The following signals are shown (δ, ppm). 7.98 and 6.95 (each 2H, d, J=8.9, anisoyl group ), 5.14 (1H, d, J=5.0 Hz, C14-β-H), 3.87 (3H, s, OCH$_3$ of anisoyl group), 3.84, 3.31, 3.28 and 3.25 (each 3H, s, OCH$_3$ at C1, C6, C16 and C18), 2.30 (3H, s, CH$_3$ of acetyl group at the nitrogen atom).

5) Analysis of $^{13}$C-NMR spectra (CDCl$_3$)

The following signals are shown (δ, ppm). 170.8 (carbonyl of acetyl group), 166.0 (carbonyl of anisoyl group), 163.7, 131.6, 113.5 and 122.1 (anisoyl group), 91.2, 85.0, 82.5, 82.0, 80.2, 76.1 and 72.3 (C16, C6, C18, C1, C14, C13 and C15), 62.2, 59.1, 58.0 and 56.0 (OCH$_3$ at C16, C18, C6 and C1), 55.4 (OCH$_3$ of anisoyl group), 21.0 (CH$_3$ of acetyl group at the nitrogen atom).

6) Analysis of Mass spectra m/z: 615 (M$^+$).

(151) Physicochemical parameters and analytical data of de-N-ethyl-N-benzoyl-16-epi-3,8-dideoxy-14-O-anisoylaconine 1) Property and solubility Colorless and amorphous powder. Soluble in ether, chloroform, benzene, ethanol, methanol, ethylacetate, pyridine and dimethyl sulfoxide. Insoluble in hexane and water.

2) Analysis of IR spectra (KBr)

IR $v_{max}^{KBr}$: 1710, 1653 cm$^{-1}$.

3) Analysis of UV spectra (ethanol)

UV $\lambda_{max}^{EtOH}$ (log ε) nm: 232 (4.10), 258 (4.03).

4) Analysis of $^1$H-NMR spectra (CDCl$_3$)

The following signals are shown (δ, ppm). 7.81-7.09 (5H, m, benzoyl group), 7.98 and 6.95 (each 2H, d, J=8.9, anisoyl group), 5.14 (1H, d, J=5.0 Hz, C14-β-H), 3.83, 3.31, 3.27 and 3.25 (each 3H, s, OCH$_3$ at C1, C6, C16 and C18), 3.87 (3H, s, OCH$_3$ of anisoyl group).

5) Analysis of $^{13}$C-NMR spectra (CDCl$_3$)

The following signals are shown (δ, ppm). 166.0 and 165.8 (carbonyl group), 163.8, 131.7, 113.6 and 122.0 (anisoyl group), 133.9, 133.4, 128.6, 128.2 and 127.6 (benzoyl group), 91.3, 85.0, 83.4, 82.0, 80.3, 76.0 and 72.5 (C16, C6, C18, C1, C14, C13 and C15), 62.2, 59.1, 57.8 and 56.0 (OCH$_3$ at C16, C18, C6 and C1), 55.4 (OCH$_3$ of anisoyl group).

6) Analysis of Mass spectra m/z: 678 (M$^+$).

(152) Physicochemical parameters and analytical data of de-N-ethyl-16-epi-3,8,13-trideoxy-14-O-anisoylaconine 1) Property and solubility Colorless and amorphous powder. Soluble in ether, chloroform, benzene, ethanol, methanol, ethylacetate, pyridine and dimethyl sulfoxide. Insoluble in hexane and water.

2) Analysis of IR spectra (KBr)

IR $v_{max}^{KBr}$: 1715 cm$^{-1}$.

3) Analysis of UV spectra (ethanol)

UV $\lambda_{max}^{EtOH}$ (log ε) nm: 258 (4.01).

4) Analysis of $^1$H-NMR spectra (CDCl$_3$)

The following signals are shown (δ, ppm). 7.99 and 6.96 (each 2H, d, J=8.9 Hz, anisoyl group), 5.20 (1H, t, J=4.8 Hz, C14-β-H ), 3.82, 3.31, 3.28 and 3.25 (each 3H, s, OCH$_3$ at C1, C6, C16 and C18), 3.87 (3H, s, OCH$_3$ of anisoyl group).

5) Analysis of $^{13}$C-NMR spectra (CDCl$_3$)

The following signals are shown (δ, ppm). 165.9 (carbonyl of anisoyl group), 163.7, 131.6, 113.4 and 122.2 (anisoyl group), 91.2, 86.3, 84.9, 82.5, 80.2 and 72.5 (C16, C1, C6, C18, C14 and C15), 60.1, 58.7, 57.9 and 56.0 (OCH$_3$ at C18, C16, C6 and C1), 55.4 (OCH$_3$ of anisoyl group).

6) Analysis of Mass spectra m/z: 541 (M$^+$).

(153) Physicochemical parameters and analytical data of de-N-ethyl-N-amyl-16-epi-3,8,13-trideoxy-14-O-anisoylaconine 1) Property and solubility Colorless and amorphous powder. Soluble in ether, chloroform, benzene, ethanol, methanol, ethylacetate, pyridine and dimethyl sulfoxide. Insoluble in hexane and water.

2) Analysis of IR spectra (KBr)

IR $v_{max}^{KBr}$: 1715 cm$^{-1}$.

3) Analysis of UV spectra (ethanol)

UV $\lambda_{max}^{EtOH}$ (log ε) nm: 257 (4.02).

4) Analysis of $^1$H-NMR spectra (CDCl$_3$)

The following signals are shown (δ, ppm). 8.01 and 6.93 (each 2H, d, J=8.9, anisoyl group), 5.20 (1H, t, J=5.0 Hz, C14-β-H), 3.87 (3H, s, OCH$_3$ of anisoyl group), 3.84, 3.31, 3.27 and 3.24 (each 3H, s, OCH$_3$ at C1, C6, C16 and C18), 0.98 (3H, t, J=7.0 Hz, CH$_3$ of amyl group at the nitrogen atom).

5) Analysis of $^{13}$C-NMR spectra (CDCl$_3$)

The following signals are shown (δ, ppm). 166.0 (carbonyl of anisoyl group), 163.7, 131.8, 122.1 and 113.6 (anisoyl group), 91.4, 85.9, 85.1, 82.3, 80.2 and 72.3 (C16, C1, C6, C18, C14 and C15), 60.2, 58.8, 57.9 and 56.0 (OCH$_3$ at C18, C16, C6 and C1), 55.4 (OCH$_3$ of anisoyl group), 13.2 (CH$_3$ of amyl group at the nitrogen atom).

6) Analysis of Mass spectra m/z: 639 (M$^+$).

(154) Physicochemical parameters and analytical data of de-N-ethyl-N-propyl-16-epi-3,8,13-trideoxy-14-O-anisoylaconine 1) Property and solubility Colorless and amorphous powder. Soluble in ether, chloroform, benzene, ethanol, methanol, ethylacetate, pyridine and dimethyl sulfoxide. Insoluble in hexane and water.

2) Analysis of IR spectra (KBr)

IR $\nu_{max}^{KBr}$: 1715 cm$^{-1}$.

3) Analysis of UV spectra (ethanol)

UV $\lambda_{max}^{EtOH}$ (log ε) nm: 258 (4.02).

4) Analysis of $^1$H-NMR spectra (CDCl$_3$)

The following signals are shown (δ, ppm). 7.99 and 6.95 (each 2H, d, J=8.9, anisoyl group), 5.19 (1H, t, J=4.8 Hz, C14-β-H), 3.83, 3.30, 3.29 and 3.24 (each 3H, s, OCH$_3$ at C1, C6, C16 and C18), 1.10 (3H, t, J=7.0 Hz, CH$_3$ of propyl group at the nitrogen atom).

5) Analysis of $^{13}$C-NMR spectra (CDCl$_3$)

The following signals are shown (δ, ppm). 166.0 (carbonyl of anisoyl group), 163.6, 131.8, 122.2 and 113.7 (anisoyl group), 91.4, 86.2, 85.1, 82.0, 80.1 and 72.1 (C16, C1, C6, C18, C14 and C15), 60.1, 58.8, 57.9 and 56.0 (OCH$_3$ at C18, C16, C6 and C1), 55.4 (OCH$_3$ of anisoyl group), 13.0 (CH$_3$ of propyl group at the nitrogen atom).

6) Analysis of Mass spectra m/z: 611 (M$^+$).

(155) Physicochemical parameters and analytical data of de-N-ethyl-N-(4-methyl)pentyl-16-epi-3,8,13-trideoxy-14-O-anisoylaconine 1) Property and solubility Colorless and amorphous powder. Soluble in ether, chloroform, benzene, ethanol, methanol, ethylacetate, pyridine and dimethyl sulfoxide. Insoluble in hexane and water.

2) Analysis of IR spectra (KBr)

IR $\nu_{max}^{KBr}$: 1715 cm$^{-1}$.

3) Analysis of UV spectra (ethanol)

UV $\lambda_{max}^{EtOH}$ (log ε) nm: 258 (4.01).

4) Analysis of $^1$H-NMR spectra (CDCl$_3$)

The following signals are shown (δ, ppm). 8.01 and 6.95 (each 2H, d, J=8.9, anisoyl group), 5.25 (1H, t, J=4.8 Hz, C14-β-H), 3.88 (3H, s, OCH$_3$ of anisoyl group), 3.84, 3.30, 3.27 and 3.25 (each 3H, s, OCH$_3$ at C1, C6, C16 and C18), 1.02 (6H, d, J=7.0 Hz, CH$_3$ of 4-methylpentyl group at the nitrogen atom).

5) Analysis of $^{13}$C-NMR spectra (CDCl$_3$)

The following signals are shown (δ, ppm). 166.0 (carbonyl of anisoyl group), 163.8, 131.7, 113.4 and 122.0 (anisoyl group), 91.3, 86.1, 85.0, 82.2, 80.1 and 72.5 (C16, C1, C6, C18, C14 and C15), 60.0, 58.8, 57.9 and 56.0 (OCH$_3$ at C18, C16, C6 and C1), 55.4 (OCH$_3$ of anisoyl group), 21.5 (CH$_3$ of 4-methylpentyl group at the nitrogen atom).

6) Analysis of Mass spectra m/z: 653 (M$^+$).

(156) Physicochemical parameters and analytical data of de-N-ethyl-N-acetyl-16-epi-3,8,13-trideoxy-14-O-anisoylaconine 1) Property and solubility Colorless and amorphous powder. Soluble in ether, chloroform, benzene, ethanol, methanol, ethylacetate, pyridine and dimethyl sulfoxide. Insoluble in hexane and water.

2) Analysis of IR spectra (KBr)

IR $\nu_{max}^{KBr}$: 1715, 1655 cm$^{-1}$.

3) Analysis of UV spectra (ethanol)

UV $\lambda_{max}^{EtOH}$ (log ε) nm: 258 (4.02).

4) Analysis of $^1$H-NMR spectra (CDCl$_3$)

The following signals are shown (δ, ppm). 7.99 and 6.95 (each 2H, d, J=8.9, anisoyl group), 5.19 (1H, t, J=4.8 Hz, C14-β-H), 3.82, 3.31, 3.28 and 3.25 (each 3H, s, OCH$_3$ at C1, C6, C16 and C18), 3.87 (3H, s, OCH$_3$ of anisoyl group), 2.28 (3H, s, CH$_3$ of acetyl group at the nitrogen atom).

5) Analysis of $^{13}$C-NMR spectra (CDCl$_3$)

The following signals are shown (δ, ppm). 171.8 (carbonyl of acetyl group), 166.0 (carbonyl of anisoyl group), 163.7, 131.6, 113.4 and 122.2 (anisoyl group), 91.2, 84.9, 82.5, 82.0, 80.2 and 72.4 (C16, C6, C18, C1, C14 and C15), 60.1, 58.7, 57.9 and 56.0 (OCH$_3$ at C18, C16, C6 and C1), 55.4 (OCH$_3$ of anisoyl group), 21.0 (CH$_3$ of acetyl group at the nitrogen atom).

6) Analysis of Mass spectra m/z: 611 (M$^+$).

(157) Physicochemical parameters and analytical data of de-N-ethyl-N-benzoyl-16-epi-3,8,13-trideoxy-14-O-anisoylaconine 1) Property and solubility Colorless and amorphous powder. Soluble in ether, chloroform, benzene, ethanol, methanol, ethylacetate, pyridine and dimethyl sulfoxide. Insoluble in hexane and water.

2) Analysis of IR spectra (KBr)

IR $\nu_{max}^{KBr}$: 1710, 1653 cm$^{-1}$.

3) Analysis of UV spectra (ethanol)

UV $\lambda_{max}^{EtOH}$ (log ε) nm: 232 (4.10), 258 (4.03).

4) Analysis of $^1$H-NMR spectra (CDCl$_3$)

The following signals are shown (δ, ppm). 7.82-7.09 (5H, m, benzoyl group), 7.98 and 6.96 (each 2H, d, J=8.9, anisoyl group), 5.21 (1H, t, J=4.8, C14-β-H), 3.88 (3H, s, OCH$_3$ of anisoyl group), 3.83, 3.30, 3.27 and 3.24 (each 3H, s, OCH$_3$ at C1, C6, C16 and C18).

5) Analysis of $^{13}$C-NMR spectra (CDCl$_3$)

The following signals are shown (δ, ppm). 166.0 and 165.8 (carbonyl group), 163.8, 131.7, 113.6 and 122.0 (anisoyl group), 133.9, 133.4, 128.6, 128.2 and 127.6 (benzoyl group), 91.3, 85.0, 82.4, 82.0, 80.3 and 72.6 (C16, C6, C18, C1, C14 and C15), 60.2, 58.8, 57.9 and 56.0 (OCH$_3$ at C18, C16, C6 and C1), 55.4 (OCH$_3$ of anisoyl group).

6) Analysis of Mass spectra m/z: 662 (M$^+$).

(158) Physicochemical parameters and analytical data of 16-epi-14-O-m-chlorobenzoylpyroaconine 1) Property and solubility Colorless and amorphous powder. Soluble in ether, chloroform, benzene, ethanol, methanol, ethylacetate, pyridine and dimethyl sulfoxide. Insoluble in hexane and water.

2) Analysis of IR spectra (KBr)

IR $\nu_{max}^{KBr}$: 1715 cm$^{-1}$.

3) Analysis of UV spectra (ethanol)

UV $\lambda_{max}^{EtOH}$ (log ε) nm: 231 (4.09), 280 (3.28), 289 (3.25).

4) Analysis of $^1$H-NMR spectra (CDCl$_3$)

The following signals are shown (δ, ppm). 7.98-7.30 (5H, m, m-chlorobenzoyl group), 5.40 (1H, d, J=5.0 Hz, C14-β-H), 3.80, 3.30, 3.28 and 3.26 (each 3H, s, OCH$_3$ at C1, C6, C16 and C18), 1.05 (3H, t, J=7.0 Hz, CH$_3$ of C$_2$H$_5$ at the nitrogen atom).

5) Analysis of $^{13}$C-NMR spectra (CDCl$_3$)

The following signals are shown (δ, ppm). 211.6 (carbonyl group at C15), 165.0 (carbonyl of m-chlorobenzoyl group), 131.6, 129.8, 129.5, 138.0 and 128.4 (m-chlorobenzoyl group), 86.1, 84.1, 83.6, 78.3, 77.4, 76.8 and 71.9 (C16, C6, C1, C14, C13, C18 and C3), 62.3, 59.2, 57.8 and 56.1 (OCH$_3$ at C16, C18, C6 and C1), 49.1 (CH$_2$ of C$_2$H$_5$ at the nitrogen atom), 13.4 (CH$_3$ of C$_2$H$_5$ at the nitrogen atom).

6) Analysis of Mass spectra
 m/z: 619, 621 (M$^+$).

7) Elemental analysis
 Calculated for C$_{32}$H$_{42}$NO$_9$Cl: C, 61.98; H, 6.83; N, 2.26. Found: C, 62.05; H, 6.91; N, 2.05.

(159) Physicochemical parameters and analytical data of 16-epi-14-O-acetylpyroaconine 1) Property and solubility
 Colorless and amorphous powder. Soluble in ether, chloroform, benzene, ethanol, methanol, ethylacetate, pyridine and dimethyl sulfoxide. Insoluble in hexane and water.

2) Analysis of IR spectra (KBr)
 IR $v_{max}^{KBr}$: 1713 cm$^{-1}$.

3) Analysis of $^1$H-NMR spectra (CDCl$_3$)
 The following signals are shown (δ, ppm). 5.24 (1H, d, J=5.0 Hz, C14-β-H), 3.81, 3.29, 3.25 and 3.25 (each 3H, s, OCH$_3$ at C1, C6, C16 and C18), 1.03 (3H, t, J=7.0 Hz, CH$_3$ of C$_2$H$_5$ at the nitrogen atom), 2.04 (3H, s, CH$_3$ of acetyl group).

4) Analysis of $^{13}$C-NMR spectra (CDCl$_3$)
 The following signals are shown (δ, ppm). 211.5 (carbonyl group at C15), 171.3 (carbonyl of acetyl group), 86.1, 84.0, 83.5, 78.3, 77.5, 76.8 and 71.9 (C16, C6, C1, C14, C13, C18 and C3), 62.4, 59.1, 57.8 and 56.1 (OCH$_3$ at C16, C18, C6 and C1), 49.1 (CH$_2$ of C$_2$H$_5$ at the nitrogen atom), 13.4 (CH$_3$ of C$_2$H$_5$ at the nitrogen atom), 21.4 (CH$_3$ of acetyl group).

5) Analysis of Mass spectra
 m/z: 523 (M$^+$).

6) Elemental analysis
 Calculated for C$_{27}$H$_{41}$NO$_9$: C, 61.93; H, 7.89; N, 2.67. Found: C, 61.88; H, 7.77; N, 2.45.

(160) Physicochemical parameters and analytical data of 16-epi-14-O-methylpyroaconine 1) Property and solubility
 Colorless and amorphous powder. Soluble in ether, chloroform, benzene, ethanol, methanol, ethylacetate, pyridine and dimethyl sulfoxide. Insoluble in hexane and water.

2) Analysis of IR spectra (KBr)
 IR $v_{max}^{KBr}$: 1711 cm$^{-1}$.

3) Analysis of $^1$H-NMR spectra (CDCl$_3$)
 The following signals are shown (δ, ppm). 3.82, 3.30, 3.27, 3.26 and 3.38 (each 3H, s, OCH$_3$ at C1, C6, C16, C18 and C14), 1.05 (3H, t, J=7.0 Hz, CH$_3$ of C$_2$H$_5$ at the nitrogen atom).

4) Analysis of $^{13}$C-NMR spectra (CDCl$_3$)
 The following signals are shown (δ, ppm). 211.6 (carbonyl group at C15), 86.2, 84.1, 83.6, 81.3, 77.5, 76.8 and 71.9 (C16, C6, C1, C14, C13, C18 and C3), 62.4, 59.1, 58.1, 57.8 and 56.1 (OCH$_3$ at C16, C18, C14, C6 and C1), 49.1 (CH$_2$ of C$_2$H$_5$ at the nitrogen atom), 13.4 (CH$_3$ of C$_2$H$_5$ at the nitrogen atom).

5) Analysis of Mass spectra
 m/z: 495 (M$^+$).

6) Elemental analysis
 Calculated for C$_{26}$H$_{41}$NO$_8$: C, 63.01; H, 8.34; N, 2.83. Found: C, 63.20; H, 8.33; N, 2.61.

(161) Physicochemical parameters and analytical data of de-N-ethyl-N-benzoyl-16-epi-pyrojesaconitine 1) Property and solubility
 Colorless and amorphous powder. Soluble in ether, chloroform, benzene, ethanol, methanol, ethylacetate, pyridine and dimethyl sulfoxide. Insoluble in hexane and water.

2) Analysis of IR spectra (KBr)
 IR $v_{max}^{KBr}$: 1711, 1653 cm$^{-1}$.

3) Analysis of UV spectra (ethanol)
 UV $\lambda_{max}^{EtOH}$ (log ε) nm: 231 (4.10), 258 (4.03).

4) Analysis of $^1$H-NMR spectra (CDCl$_3$)
 The following signals are shown (δ, ppm). 7.93 and 6.94 (each 2H, d, J=8.9, anisoyl group), 7.82-7.10 (5H, m, benzoyl group), 5.39 (1H, d, J=5.0 Hz, C14-β-H), 3.80, 3.30, 3.26 and 3.26 (each 3H, s, OCH$_3$ at C1, C6, C16 and C18), 3.87 (3H, s, OCH$_3$ of anisoyl group).

5) Analysis of $^{13}$C-NMR spectra (CDCl$_3$)
 The following signals are shown (δ, ppm). 211.6 (carbonyl group at C15), 166.0 and 165.7 (carbonyl group), 86.1, 84.1, 80.0, 78.2, 77.5, 76.7 and 72.0 (C16, C6, C1, C14, C13, C18 and C3), 62.3, 59.2, 57.8 and 56.1 (OCH$_3$ at C16, C18, C6 and C1), 55.4 (OCH$_3$ of anisoyl group), 164.0, 131.8, 121.6 and 113.8 (anisoyl group), 133.2, 129.8, 129.5 and 128.3 (benzoyl group).

6) Analysis of Mass spectra
 m/z: 691 (M$^+$).

7) Elemental analysis
 Calculated for C$_{38}$H$_{45}$NO$_{11}$: C, 65.98; H, 6.56; N, 2.02. Found: C, 66.17; H, 6.34; N, 1.98.

(162) Physicochemical parameters and analytical data of de-N-ethyl-N-propyl-16-epi-pyrojesaconitine 1) Property and solubility
 Colorless and amorphous powder. Soluble in ether, chloroform, benzene, ethanol, methanol, ethylacetate, pyridine and dimethyl sulfoxide. Insoluble in hexane and water.

2) Analysis of IR spectra (KBr)
 IR $v_{max}^{KBr}$: 1715 cm$^{-1}$.

3) Analysis of UV spectra (ethanol)
 UV $\lambda_{max}^{EtOH}$ (log ε) nm: 258 (4.01).

4) Analysis of $^1$H-NMR spectra (CDCl$_3$)
 The following signals are shown (δ, ppm). 7.94 and 6.94 (each 2H, d, J=8.9, anisoyl group), 5.40 (1H, d, J=5.0 Hz, C14-β-H), 3.80, 3.30, 3.26 and 3.26 (each 3H, s, OCH$_3$ at C1, C6, C16 and C18), 1.10 (3H, t, J=7.0 Hz, CH$_3$ of propyl group at the nitrogen atom), 3.87 (3H, s, OCH$_3$ of anisoyl group).

5) Analysis of $^{13}$C-NMR spectra (CDCl$_3$)
 The following signals are shown (δ, ppm). 211.6 (carbonyl group at C15), 166.0 (carbonyl of anisoyl group), 164.0, 131.9, 121.5 and 113.7 (anisoyl group), 86.1, 84.0, 83.6, 78.1, 77.4, 76.6 and 71.9 (C16, C6, C1, C14, C13, C18 and C3), 62.3, 59.3, 57.8 and 56.1 (OCH$_3$ at C16, C18, C6 and C1), 55.4 (OCH$_3$ of anisoyl group), 13.0 (CH$_3$ of propyl group at the nitrogen atom).

6) Analysis of Mass spectra
 m/z: 629 (M$^+$).

7) Elemental analysis
 Calculated for C$_{34}$H$_{47}$NO$_{10}$: C, 64.85; H, 7.52; N, 2.22. Found: C, 65.03; H, 7.49; N, 2.11.

(163) Physicochemical parameters and analytical data of de-N-ethyl-N-acetyl-16-epi-pyrojesaconitine 1) Property and solubility
 Colorless and amorphous powder. Soluble in ether, chloroform, benzene, ethanol, methanol, ethylacetate, pyridine and dimethyl sulfoxide. Insoluble in hexane and water.

2) Analysis of IR spectra (KBr)
 IR $v_{max}^{KBr}$: 1715, 1655 cm$^{-1}$.

3) Analysis of UV spectra (ethanol)
 UV $\lambda_{max}^{EtOH}$ (log ε) nm: 258 (4.02).

4) Analysis of $^1$H-NMR spectra (CDCl$_3$)

The following signals are shown (δ, ppm). 7.95 and 6.94 (each 2H, d, J=8.9, anisoyl group), 5.40 (1H, d, J=5.0 Hz, C14-β-H), 3.81, 3.30, 3.26 and 3.26 (each 3H, s, OCH$_3$ at C1, C6, C16 and C18), 2.30 (3H, s, CH$_3$ of acetyl group), 3.87 (3H, s, OCH$_3$ of anisoyl group).

5) Analysis of $^{13}$C-NMR spectra (CDCl$_3$)

The following signals are shown (δ, ppm). 211.6 (carbonyl group at C15), 170.8 (carbonyl of acetyl group), 166.0 (carbonyl of anisoyl group), 164.0, 131.8, 121.6 and 113.8 (anisoyl group), 86.1, 84.0, 80.0, 78.0, 77.5, 76.6 and 71.9 (C16, C6, C1, C14, C13, C18 and C3), 62.3, 59.3, 57.9 and 56.0 (OCH$_3$ at C16, C18, C6 and C1), 55.4 (OCH$_3$ of anisoyl group), 21.1 (CH$_3$ of acetyl group at the nitrogen atom).

6) Analysis of Mass spectra m/z: 629 (M$^+$).

7) Elemental analysis

Calculated for C$_{33}$H$_{43}$NO$_{11}$: C, 62.94; H, 6.88; N, 2.22. Found: C, 63.18; H, 7.01; N, 2.05.

(164) Physicochemical parameters and analytical data of 3-deoxy-16-epi-14-O-m-chlorobenzoyl-pyroaconine 1) Property and solubility Colorless and amorphous powder. Soluble in ether, chloroform, benzene, ethanol, methanol, ethylacetate, pyridine and dimethyl sulfoxide. Insoluble in hexane and water.

2) Analysis of IR spectra (KBr)

IR $v_{max}^{KBr}$: 1715 cm$^{-1}$.

3) Analysis of UV spectra (ethanol)

UV λ$_{max}^{EtOH}$ (log ε) nm: 231 (4.09), 280 (3.29), 289 (3.22).

4) Analysis of $^1$H-NMR spectra (CDCl$_3$)

The following signals are shown (δ, ppm). 7.97-7.30 (5H, m, m-chlorobenzoyl group), 5.39 (1H, d, J=5.0 Hz, C14-β-H), 3.81, 3.30, 3.27 and 3.25 (each 3H, s, OCH$_3$ at C1, C6, C16 and C18), 1.04 (3H, t, J=7.0 Hz, CH$_3$ of C$_2$H$_5$ at the nitrogen atom).

5) Analysis of $^{13}$C-NMR spectra (CDCl$_3$)

The following signals are shown (δ, ppm). 211.6 (carbonyl group at C15), 165.1 (carbonyl of m-chlorobenzoyl group), 131.8, 129.7, 129.5, 135.0 and 128.4 (m-chlorobenzoyl group), 86.2, 85.0, 83.7, 80.2, 78.4 and 77.4 (C16, C1, C6, C18, C14 and C13), 62.3, 59.2, 57.8 and 56.0 (OCH$_3$ at C16, C18, C6 and C$_1$), 49.0 (CH$_2$ of C$_2$H$_5$ at the nitrogen atom), 13.5 (CH$_3$ of C$_2$H$_5$ at the nitrogen atom).

6) Analysis of Mass spectra m/z: 603, 605 (M$^+$).

7) Elemental analysis

Calculated for C$_{32}$H$_{42}$NO$_8$Cl: C, 63.62; H,7.01; N, 2.32. Found: C, 63.41; H, 6.94; N, 2.22.

(165) Physicochemical parameters and analytical data of 3-deoxy-16-epi-14-O-acetyl-pyroaconine 1) Property and solubility Colorless and amorphous powder. Soluble in ether, chloroform, benzene, ethanol, methanol, ethylacetate, pyridine and dimethyl sulfoxide. Insoluble in hexane and water.

2) Analysis of IR spectra (KBr)

IR $v_{max}^{KBr}$: 1713 cm$^{-1}$.

3) Analysis of $^1$H-NMR spectra (CDCl$_3$)

The following signals are shown (δ, ppm). 5.20 (1H, d, J=5.0 Hz, C14-β-H), 3.80, 3.30, 3.24 and 3.24 (each 3H, s, OCH$_3$ at C1, C6, C16 and C18), 1.05 (3H, t, J=7.0 Hz, CH$_3$ of C$_2$H$_5$ at the nitrogen atom), 2.05 (3H, s, CH$_3$ of acetyl group).

4) Analysis of $^{13}$C-NMR spectra (CDCl$_3$)

The following signals are shown (δ, ppm). 211.6 (carbonyl group at C15), 171.2 (carbonyl of acetyl group), 86.3, 85.1, 83.5, 80.3, 78.4 and 77.2 (C16, C1, C6, C18, C14 and C13), 62.4, 59.1, 57.9 and 56.0 (OCH$_3$ at C16, C18, C6 and C1), 49.1 (CH$_2$ of C$_2$H$_5$ at the nitrogen atom), 13.2 (CH$_3$ of C$_2$H$_5$ at the nitrogen atom), 21.4 (CH$_3$ of acetyl group).

5) Analysis of Mass spectra m/z: 507 (M$^+$).

6) Elemental analysis

Calculated for C$_{27}$H$_{41}$NO$_8$: C, 63.89; H, 8.14; N, 2.76. Found: C, 64.11; H, 8.36; N, 2.51.

(166) Physicochemical parameters and analytical data of 3-deoxy-16-epi-14-O-methyl-pyroaconine 1) Property and solubility Colorless and amorphous powder. Soluble in ether, chloroform, benzene, ethanol, methanol, ethylacetate, pyridine and dimethyl sulfoxide. Insoluble in hexane and water.

2) Analysis of IR spectra (KBr)

IR $v_{max}^{KBr}$: 1711 cm$^{-1}$.

3) Analysis of $^1$H-NMR spectra (CDCl$_3$)

The following signals are shown (δ, ppm). 3.81, 3.30, 3.27, 3.26 and 3.38 (each 3H, s, OCH$_3$ at C1, C6, C16, C18 and C14), 1.05 (3H, t, J=7.0 Hz, CH$_3$ of C$_2$H$_5$ at the nitrogen atom).

4) Analysis of $^{13}$C-NMR spectra (CDCl$_3$)

The following signals are shown (δ, ppm). 211.6 (carbonyl group at C15), 86.2, 85.1, 83.6, 80.2, 78.5 and 77.3 (C16, C1, C6, C18, C14 and C13), 62.5, 59.1, 58.1, 57.8 and 56.0 (OCH$_3$ at C16, C18, C14, C6 and C1), 49.1 (CH$_2$ of C$_2$H$_5$ at the nitrogen atom), 13.3 (CH$_3$ of C$_2$H$_5$ at the nitrogen atom).

5) Analysis of Mass spectra m/z: 479 (M$^+$).

6) Elemental analysis

Calculated for C$_{26}$H$_{41}$NO$_7$: C, 65.11; H, 8.62; N 2.92. Found: C, 65.30; H, 8.51; N, 3.01.

(167) Physicochemical parameters and analytical data of de-N-ethyl-N-benzoyl-3-deoxy-16-epi-pyrojesaconitine 1) Property and solubility Colorless and amorphous powder. Soluble in ether, chloroform, benzene, ethanol, methanol, ethylacetate, pyridine and dimethyl sulfoxide. Insoluble in hexane and water.

2) Analysis of IR spectra (KBr)

IR $v_{max}^{KBr}$: 1711, 1653 cm$^{-1}$.

3) Analysis of UV spectra (ethanol)

UV λ$_{max}^{EtOH}$ (log ε) nm: 231 (4.10), 258 (4.03).

4) Analysis of $^1$H-NMR spectra (CDCl$_3$)

The following signals are shown (δ, ppm). 7.93 and 6.94 (each 2H, d, J=8.9, anisoyl group), 7.82-7.09 (5H, m, benzoyl group), 5.40 (1H, d, J=5.0 Hz, C14-β-H), 3.80, 3.30, 3.26 and 3.26 (each 3H, s, OCH$_3$ at C1, C6, C16 and C18), 3.87 (3H, s, OCH$_3$ of anisoyl group).

5) Analysis of $^{13}$C-NMR spectra (CDCl$_3$)

The following signals are shown (δ, ppm). 211.6 (carbonyl group at C15), 166.0 and 165.7 (carbonyl group), 86.1, 83.5, 82.0, 80.3, 78.2 and 77.5 (C16, C6, C1, C18, C14 and C13), 62.3, 59.2, 57.8 and 56.0 (OCH$_3$ at C16, C18, C6 and C1), 55.4 (OCH$_3$ of anisoyl group), 164.0, 131.8, 121.6 and 113.8 (anisoyl group), 133.2, 129.8, 129.5 and 128.3 (benzoyl group).

6) Analysis of Mass spectra m/z: 675 (M$^+$).

7) Elemental analysis

Calculated for C$_{38}$H$_{45}$NO$_{10}$: C, 67.54; H, 6.71; N, 2.07. Found: C, 67.66; H, 6.52; N, 1.95.

(168) Physicochemical parameters and analytical data of de-N-ethyl-N-propyl-3-deoxy-16-epi-pyrojesaconitine 1) Property and solubility Colorless and amorphous powder. Soluble in ether, chloroform, benzene, ethanol, methanol, ethylacetate, pyridine and dimethyl sulfoxide. Insoluble in hexane and water.

2) Analysis of IR spectra (KBr)

IR $v_{max}^{KBr}$: 1715 cm$^{-1}$.

3) Analysis of UV spectra (ethanol)

UV $\lambda_{max}^{EtOH}$ (log ε) nm: 258 (4.01).

4) Analysis of $^1$H-NMR spectra (CDCl$_3$)

The following signals are shown (δ, ppm). 7.94 and 6.94 (each 2H, d, J=8.9, anisoyl group), 5.40 (1H, d, J=5.0 Hz, C14-β-H), 3.80, 3.30, 3.26 and 3.26 (each 3H, s, OCH$_3$ at C1, C6, C16 and C18), 1.10 (3H, t, J=7.0 Hz, CH$_3$ of propyl group at the nitrogen atom), 3.87 (3H, s, OCH$_3$ of anisoyl group).

5) Analysis of $^{13}$C-NMR spectra (CDCl$_3$)

The following signals are shown (δ, ppm). 211.6 (carbonyl group at C15), 166.0 (carbonyl of anisoyl group), 164.0, 131.9, 121.5 and 113.7 (anisoyl group), 86.2, 85.1, 83.5, 80.2, 78.2 and 77.4 (C16, C1, C6, C18, C14 and C13), 62.3, 59.4, 57.9 and 56.0 (OCH$_3$ at C16, C18, C6 and C1), 55.4 (OCH$_3$ of anisoyl group), 13.0 (CH$_3$ of propyl group at the nitrogen atom).

6) Analysis of Mass spectra m/z: 613 (M$^+$).

7) Elemental analysis

Calculated for C$_{34}$H$_{47}$NO$_9$: C, 66.54; H, 7.72; N, 2.28. Found: C, 66.74; H, 7.65; N, 2.20.

(169) Physicochemical parameters and analytical data of de-N-ethyl-N-acetyl-3-deoxy-16-epi-pyrojesaconitine 1) Property and solubility Colorless and amorphous powder. Soluble in ether, chloroform, benzene, ethanol, methanol, ethylacetate, pyridine and dimethyl sulfoxide. Insoluble in hexane and water.

2) Analysis of IR spectra (KBr)

IR $v_{max}^{KBr}$: 1715, 1654 cm$^{-1}$.

3) Analysis of UV spectra (ethanol)

UV $\lambda_{max}^{EtOH}$ (log ε) nm: 258 (4.02)

4) Analysis of $^1$H-NMR spectra (CDCl$_3$)

The following signals are shown (δ, ppm). 7.95 and 6.96 (each 2H, d, J=8.9 Hz, anisoyl group), 5.41 (1H, d, J=5.0 Hz, C14-β-H), 3.81, 3.30, 3.26 and 3.25 (each 3H, s, OCH$_3$ at C1, C6, C16 and C18), 2.32 (3H, s, CH$_3$ of acetyl group), 3.87 (3H, s, OCH$_3$ of anisoyl group).

5) Analysis of $^{13}$C-NMR spectra (CDCl$_3$)

The following signals are shown (δ, ppm). 211.5 (carbonyl group at C15), 171.4 (carbonyl of acetyl group), 166.0 (carbonyl of anisoyl group), 164.1, 131.8, 121.6 and 113.8 (anisoyl group), 86.2, 83.4, 82.0, 80.3, 78.2 and 77.3 (C16, C6, C1, C18, C14 and C13), 62.3, 59.4, 57.9 and 56.0 (OCH$_3$ at C16, C18, C6 and C1), 55.4 (OCH$_3$ of anisoyl group), 21.1 (CH$_3$ of acetyl group at the nitrogen atom).

6) Analysis of Mass spectra m/z: 613 (M$^+$).

7) Elemental analysis

Calculated for C$_{33}$H$_{43}$NO$_{10}$: C, 64.59; H, 7.06; N, 2.28. Found: C, 64.41; H, 7.00; N, 2.35.

(170) Physicochemical parameters and analytical data of 3,13-dideoxy-16-epi-14-O-m-chlorobenzoyl-pyroaconine 1) Property and solubility Colorless and amorphous powder. Soluble in ether, chloroform, benzene, ethanol, methanol, ethylacetate, pyridine and dimethyl sulfoxide. Insoluble in hexane and water.

2) Analysis of IR spectra (KBr)

IR $v_{max}^{KBr}$: 1715 cm$^{-1}$.

3) Analysis of UV spectra (ethanol)

UV $\lambda_{max}^{EtOH}$ (log ε) nm: 231 (4.09), 280 (3.29), 289 (3.22).

4) Analysis of $^1$H-NMR spectra (CDCl$_3$)

The following signals are shown (δ, ppm). 7.96-7.35 (5H, m, m-chlorobenzoyl group), 5.50 (1H, t, J=5.0 Hz, C14-β-H), 3.63, 3.30, 3.27 and 3.25 (each 3H, s, OCH$_3$ at C1, C6, C16 and C18), 1.04 (3H, t, J=7.0 Hz, CH$_3$ of C$_2$H$_5$ at the nitrogen atom).

5) Analysis of $^{13}$C-NMR spectra (CDCl$_3$)

The following signals are shown (δ, ppm). 211.6 (carbonyl group at C15), 165.0 (carbonyl of m-chlorobenzoyl group), 131.8, 129.7, 129.5, 135.0 and 128.4 (m-chlorobenzoyl group), 85.2, 85.0, 83.7, 80.2 and 78.4 (C16, C1, C6, C18 and C14), 61.1, 59.2, 57.8 and 56.0 (OCH$_3$ at C16, C18, C6 and C1), 49.0 (CH$_2$ of C$_2$H$_5$ at the nitrogen atom), 13.4 (CH$_3$ of C$_2$H$_5$ at the nitrogen atom).

6) Analysis of Mass spectra m/z: 587, 589 (M$^+$).

7) Elemental analysis

Calculated for C$_{32}$H$_{42}$NO$_7$Cl: C, 65.35; H, 7.20; N, 2.38. Found: C, 65.51; H, 7.25; N, 2.09.

(171) Physicochemical parameters and analytical data of 3,13-dideoxy-16-epi-14-O-acetyl-pyroaconine 1) Property and solubility Colorless and amorphous powder. Soluble in ether, chloroform, benzene, ethanol, methanol, ethylacetate, pyridine and dimethyl sulfoxide. Insoluble in hexane and water.

2) Analysis of IR spectra (KBr) IR $v_{max}^{KBr}$: 1713 cm$^{-1}$.

3) Analysis of $^1$H-NMR spectra (CDCl$_3$)

The following signals are shown (δ, ppm). 5.38 (1H, t, J=5.0 Hz, C14-β-H), 3.65, 3.30, 3.25 and 3.25 (each 3H, s, OCH$_3$ at C1, C6, C16 and C18), 1.05 (3H, t, J=7.0 Hz, CH$_3$ of C$_2$H$_5$ at the nitrogen atom), 2.05 (3H, s, CH$_3$ of acetyl group).

4) Analysis of $^{13}$C-NMR spectra (CDCl$_3$)

The following signals are shown (δ, ppm). 211.6 (carbonyl group at C15), 171.2 (carbonyl of acetyl group), 85.3, 85.1, 83.5, 80.3 and 78.4 (C16, C1, C6, C18 and C14), 61.4, 59.1, 57.9 and 56.0 (OCH$_3$ at C16, C18, C6 and C1), 49.1 (CH$_2$ of C$_2$H$_5$ at the nitrogen atom), 13.1 (CH$_3$ of C$_2$H$_5$ at the nitrogen atom), 21.4 (CH$_3$ of acetyl group).

5) Analysis of Mass spectra m/z: 491 (M$^+$).

6) Elemental analysis

Calculated for C$_{27}$H$_{41}$NO$_7$: C, 65.96; H, 8.41; N, 2.85. Found: C, 66.26; H, 8.55; N, 2.97.

(172) Physicochemical parameters and analytical data of 3,13-dideoxy-16-epi-14-O-methyl-pyroaconine 1) Property and solubility Colorless and amorphous powder. Soluble in ether, chloroform, benzene, ethanol, methanol, ethylacetate, pyridine and dimethyl sulfoxide. Insoluble in hexane and water.

2) Analysis of IR spectra (KBr)

IR $v_{max}^{KBr}$: 1711 cm$^{-1}$.

3) Analysis of $^1$H-NMR spectra (CDCl$_3$)

The following signals are shown (δ, ppm). 3.66, 3.30, 3.27, 3.26 and 3.38 (each 3H, s, OCH$_3$ at C1, C6, C16, C18 and C14), 1.05 (3H, t, J=7.0 Hz, CH$_3$ of C$_2$H$_5$ at the nitrogen atom).

4) Analysis of $^{13}$C-NMR spectra (CDCl$_3$)

The following signals are shown (δ, ppm). 211.6 (carbonyl group at C15), 85.2, 85.0, 83.6, 80.2 and 78.6 (C16, C1, C6, C18 and C14), 61.3, 59.1, 58.1, 57.8 and 56.0 (OCH$_3$ at C16, C18, C14, C6 and C1), 49.0 (CH$_2$ of C$_2$H$_5$ at the nitrogen atom), 13.2 (CH$_3$ of C$_2$H$_5$ at the nitrogen atom).

5) Analysis of Mass spectra m/z: 463 (M$^+$).

6) Elemental analysis

Calculated for C$_{26}$H$_{41}$NO$_6$: C, 67.36; H, 8.91; N, 3.02. Found: C, 67.41; H, 9.02; N 2.89.

(173) Physicochemical parameters and analytical data of de-N-ethyl-N-benzoyl-3,13-dideoxy-16-epi-pyrojesaconitine 1) Property and solubility Colorless and amorphous powder. Soluble in ether, chloroform, benzene, ethanol, methanol, ethylacetate, pyridine and dimethyl sulfoxide. Insoluble in hexane and water.

2) Analysis of IR spectra (KBr)
IR $v_{max}^{KBr}$: 1711, 1653 cm$^{-1}$.
3) Analysis of UV spectra (ethanol)
UV $\lambda_{max}^{EtOH}$ (log ε) nm: 231 (4.10), 258 (4.03).
4) Analysis of $^1$H-NMR spectra (CDCl$_3$)
The following signals are shown (δ, ppm). 7.94 and 6.94 (each 2H, d, J=8.9, anisoyl group), 7.82-7.10 (5H, m, benzoyl group), 5.45 (1H, t, J=5.0 Hz, C14-β-H), 3.65, 3.30, 3.25 and 3.25 (each 3H, s, OCH$_3$ at C1, C6, C16 and C18), 3.87 (3H, s, OCH$_3$ of anisoyl group).
5) Analysis of $^{13}$C-NMR spectra (CDCl$_3$)
The following signals are shown (δ, ppm). 211.6 (carbonyl group at C15), 166.0 and 165.7 (carbonyl group), 85.4, 83.5, 82.0, 80.2 and 78.2 (C16, C6, C1, C18 and C14), 61.2, 59.0, 57.8 and 56.0 (OCH$_3$ at C16, C18, C6 and C1), 55.4 (OCH$_3$ of anisoyl group), 164.0, 131.8, 121.6 and 113.8 (anisoyl group), 133.2, 129.8, 129.5 and 128.3 (benzoyl group).
6) Analysis of Mass spectra
m/z: 659 (M$^+$).
7) Elemental analysis
Calculated for C$_{38}$H$_{45}$NO$_9$: C, 69.18; H, 6.87; N 2.12. Found: C, 69.20; H, 6.69; N, 2.01.
(174) Physicochemical parameters and analytical data of de-N-ethyl-N-propyl-3,13-dideoxy-16-epi-pyrojesaconitine
1) Property and solubility
Colorless and amorphous powder. Soluble in ether, chloroform, benzene, ethanol, methanol, ethylacetate, pyridine and dimethyl sulfoxide. Insoluble in hexane and water.
2) Analysis of IR spectra (KBr)
IR $v_{max}^{KBr}$: 1715 cm$^{-1}$.
3) Analysis of UV spectra (ethanol)
UV $\lambda_{max}^{EtOH}$ (log ε) nm: 258 (4.01).
4) Analysis of $^1$H-NMR spectra (CDCl$_3$)
The following signals are shown (δ, ppm). 7.94 and 6.95 (each 2H, d, J=8.9, anisoyl group), 5.46 (1H, t, J=5.0 Hz, C14-β-H), 3.64, 3.30, 3.26 and 3.26 (each 3H, s, OCH$_3$ at C1, C6, C16 and C18), 1.10 (3H, t, J=7.0 Hz, CH$_3$ of propyl group at the nitrogen atom), 3.87 (3H, s, OCH$_3$ of anisoyl group).
5) Analysis of $^{13}$C-NMR spectra (CDCl$_3$)
The following signals are shown (δ, ppm). 211.6 (carbonyl group at C15), 166.0 (carbonyl of anisoyl group), 164.0, 131.9, 121.5 and 113.8 (anisoyl group), 85.4, 85.1, 83.5, 80.0 and 78.4 (C16, C1, C6, C18 and C14), 61.3, 59.5, 57.9 and 56.0 (OCH$_3$ at C16, C18, C6 and C1), 55.4 (OCH$_3$ of anisoyl group), 13.0 (CH$_3$ of propyl group at the nitrogen atom).
6) Analysis of Mass spectra
m/z: 597 (M$^+$).
7) Elemental analysis
Calculated for C$_{34}$H$_{47}$NO$_8$: C, 68.32; H, 7.93; N, 2.34. Found: C, 68.01; H, 8.16; N, 2.16.
(175) Physicochemical parameters and analytical data of de-N-ethyl-N-acetyl-3,13-dideoxy-16-epi-pyrojesaconitine
1) Property and solubility
Colorless and amorphous powder. Soluble in ether, chloroform, benzene, ethanol, methanol, ethylacetate, pyridine and dimethyl sulfoxide. Insoluble in hexane and water.
2) Analysis of IR spectra (KBr)
IR $v_{max}^{KBr}$: 1715, 1654 cm$^{-1}$.
3) Analysis of UV spectra (ethanol)
UV $\lambda_{max}^{EtOH}$ (log ε) nm: 258 (4.02).
4) Analysis of $^1$H-NMR spectra (CDCl$_3$)
The following signals are shown (δ, ppm). 7.96 and 6.96 (each 2H, d, J=8.9, anisoyl group), 5.46 (1H, t, J=5.0 Hz, C14-β-H), 3.64, 3.30, 3.26 and 3.25 (each 3H, s, OCH$_3$ at C1, C6, C16 and C18), 2.30 (3H, s, CH$_3$ of acetyl group), 3.87 (3H, s, OCH$_3$ of anisoyl group).
5) Analysis of $^{13}$C-NMR spectra (CDCl$_3$)
The following signals are shown (δ, ppm). 211.5 (carbonyl group at C15), 171.4 (carbonyl of acetyl group), 166.0 (carbonyl of anisoyl group), 164.1, 131.8, 121.6 and 113.8 (anisoyl group), 85.4, 83.4, 82.0, 80.2 and 78.0 (C16, C6, C1, C18 and C14), 61.3, 59.4, 57.9 and 56.0 (OCH$_3$ at C16, C18, C6 and C1), 55.4 (OCH$_3$ of anisoyl group), 21.1 (CH$_3$ of acetyl group at the nitrogen atom).
6) Analysis of Mass spectra
m/z: 597 (M$^+$).
7) Elemental analysis
Calculated for C$_{33}$H$_{43}$NO$_9$: C, 66.31; H, 7.25; N, 2.34. Found: C, 66.51; H, 7.20; N, 2.28.
(176) Physicochemical parameters and analytical data of de-N-ethyl-N-(2-methyltetrahydrofurfuryl)-8-deoxy-14-O-anisoylaconine
1) Property and solubility
Colorless and amorphous powder. Soluble in ether, chloroform, benzene, ethanol, methanol, ethylacetate, pyridine and dimethyl sulfoxide. Insoluble in hexane and water.
2) Analysis of IR spectra (KBr)
IR $v_{max}^{KBr}$: 1715 cm$^{-1}$.
3) Analysis of UV spectra (ethanol)
UV $\lambda_{max}^{EtOH}$ (log ε) nm: 258 (4.01).
4) Analysis of $^1$H-NMR spectra (CDCl$_3$)
The following signals are shown (δ, ppm). 7.98 and 6.94 (each 2H, d, J=8.9, anisoyl group), 4.93 (1H, d, J=5.0 Hz, C14-β-H), 3.69, 3.30, 3.29 and 3.25 (each 3H, s, OCH$_3$ at C1, C6, C16 and C18), 3.87 (3H, s, OCH$_3$ of anisoyl group), 1.52 (3H, s, CH$_3$ of tetrahydrofurfuryl group).
5) Analysis of $^{13}$C-NMR spectra (CDCl$_3$)
The following signals are shown (δ, ppm). 165.8 (carbonyl of anisoyl group), 163.7, 131.8, 121.1 and 113.8 (anisoyl group), 94.2, 85.0, 83.7, 80.2, 77.5, 75.1, 72.3 and 72.0 (C16, C6, C1, C14, C18, C13, C15 and C3), 61.9, 59.0, 57.9 and 56.0 (OCH$_3$ at C16, C18, C6 and C1), 55.4 (OCH$_3$ of anisoyl group), 21.5 (CH$_3$ of 2-methyltetrahydrofurfuryl group).
6) Analysis of Mass spectra
m/z: 687 (M$^+$).
7) Elemental analysis
Calculated for C$_{37}$H$_{53}$NO$_{11}$: C, 64.61; H, 7.77; N, 2.04. Found: C, 64.48; H, 7.69; N, 2.11.
(177) Physicochemical parameters and analytical data of de-N-ethyl-N-(2-methyltetrahydrofurfuryl)-3,8-dideoxy-14-O-anisoylaconine
1) Property and solubility
Colorless and amorphous powder. Soluble in ether, chloroform, benzene, ethanol, methanol, ethylacetate, pyridine and dimethyl sulfoxide. Insoluble in hexane and water.
2) Analysis of IR spectra (KBr)
IR $v_{max}^{KBr}$: 1715 cm$^{-1}$.
3) Analysis of UV spectra (ethanol)
UV $\lambda_{max}^{EtOH}$ (log ε) nm: 258 (4.01).
4) Analysis of $^1$H-NMR spectra (CDCl$_3$)
The following signals are shown (δ, ppm). 7.99 and 6.94 (each 2H, d, J=8.9, anisoyl group), 4.95 (1H, d, J=5.0 Hz, C14-β-H), 3.70, 3.30, 3.29 and 3.23 (each 3H, s, OCH$_3$ at C1, C6, C16 and C18), 3.87 (3H, s, OCH$_3$ of anisoyl group), 1.52 (3H, s, CH$_3$ of tetrahydrofurfuryl group).
5) Analysis of $^{13}$C-NMR spectra (CDCl$_3$)
The following signals are shown (δ, ppm). 165.9 (carbonyl of anisoyl group), 163.7, 131.8, 122.2 and 113.7 (anisoyl group), 94.3, 86.0, 85.1, 82.1, 80.0, 75.3, 72.1 and 72.0 (C16, C6, C1, C18, C14, C13 and C15), 61.7, 59.0, 58.0 and 56.0 (OCH$_3$ at C16, C18, C6 and C1), 55.4 (OCH$_3$ of anisoyl group), 21.5 (CH$_3$ of 2-methyltetrahydrofurfuryl group).

6) Analysis of Mass spectra
m/z: 671 (M+).
7) Elemental analysis
Calculated for $C_{37}H_{53}NO_{10}$: C, 66.15; H, 7.95; N, 2.08. Found: C, 65.89; H, 7.72; N, 1.98.

(178) Physicochemical parameters and analytical data of de-N-ethyl-N-(2-methyltetrahydrofurfuryl)-3,8,13-trideoxy-14-O-anisoylaconine 1) Property and solubility
Colorless and amorphous powder. Soluble in ether, chloroform, benzene, ethanol, methanol, ethylacetate, pyridine and dimethyl sulfoxide. Insoluble in hexane and water.
2) Analysis of IR spectra (KBr)
IR $\nu_{max}^{KBr}$: 1715 cm$^{-1}$.
3) Analysis of UV spectra (ethanol)
UV $\lambda_{max}^{EtOH}$ (log ε) nm: 257 (4.01).
4) Analysis of $^1$H-NMR spectra (CDCl$_3$)
The following signals are shown (δ, ppm). 7.99 and 6.97 (each 2H, d, J=8.9, anisoyl group), 5.06 (1H, t, J=4.8 Hz, C14-β-H), 3.69, 3.31, 3.29 and 3.24 (each 3H, s, OCH$_3$ at C1, C6, C16 and C18), 3.87 (3H, s, OCH$_3$ of anisoyl group), 1.51 (3H, s, CH$_3$ of tetrahydrofurfuryl group).
5) Analysis of $^{13}$C-NMR spectra (CDCl$_3$)
The following signals are shown (δ, ppm). 166.0 (carbonyl of anisoyl group), 163.6, 131.8, 122.2 and 113.7 (anisoyl group), 94.3, 86.2, 85.1, 82.0, 80.0 and 72.1 (C16, C1, C6, C18, C14 and C15), 59.3, 58.8, 57.9 and 56.0 (OCH$_3$ at C18, C16, C6 and C1), 55.4 (OCH$_3$ of anisoyl group), 21.5 (CH$_3$ of 2-methyltetrahydrofurfuryl group).
6) Analysis of Mass spectra
m/z: 655 (M+).
7) Elemental analysis
Calculated for $C_{37}H_{53}NO_9$: C, 67.76; H, 8.15; N, 2.14. Found: C, 67.91; H, 8.13; N, 2.05.

(179) Physicochemical parameters and analytical data of de-N-ethyl-N-(2-methyltetrahydrofurfuryl)-14-O-anisoylaconine 1) Property and solubility
Colorless and amorphous powder. Soluble in ether, chloroform, benzene, ethanol, methanol, ethylacetate, pyridine and dimethyl sulfoxide. Insoluble in hexane and water.
2) Analysis of IR spectra (KBr)
IR $\nu_{max}^{KBr}$: 1715 cm$^{-1}$.
3) Analysis of UV spectra (ethanol)
UV $\lambda_{max}^{EtOH}$ (log ε) nm: 258 (4.02).
4) Analysis of $^1$H-NMR spectra (CDCl$_3$)
The following signals are shown (δ, ppm). 7.99 and 6.95 (each 2H, d, J=8.9, anisoyl group), 4.96 (1H, d, J=5.0 Hz, C14-β-H), 3.69, 3.30, 3.29 and 3.24 (each 3H, s, OCH$_3$ at C1, C6, C16 and C18), 3.87 (3H, s, OCH$_3$ of anisoyl group), 1.51 (3H, s, CH$_3$ of tetrahydrofurfuryl group).
5) Analysis of $^{13}$C-NMR spectra (CDCl$_3$)
The following signals are shown (δ, ppm). 166.0 (carbonyl of anisoyl group), 163.6, 131.7, 122.1 and 113.8 (anisoyl group), 90.8, 83.6, 82.3, 81.8, 79.5, 78.5, 77.2, 74.8 and 72.0 (C16, C6, C1, C15, C14, C8, C18, C13 and C3), 61.8, 59.1, 58.0 and 56.1 (OCH$_3$ at C16, C18, C6 and C1), 55.4 (OCH$_3$ of anisoyl group), 21.6 (CH$_3$ of 2-methyltetrahydrofurfuryl group).
6) Analysis of Mass spectra
m/z: 703 (M+).
7) Elemental analysis
Calculated for $C_{37}H_{53}NO_{12}$: C, 63.14; H, 7.59; N, 1.99. Found: C, 63.02; H, 7.65; N, 2.08.

(180) Physicochemical parameters and analytical data of de-N-ethyl-N-(2-methyltetrahydrofurfuryl)-3-deoxy-14-O-anisoylaconine 1) Property and solubility
Colorless and amorphous powder. Soluble in ether, chloroform, benzene, ethanol, methanol, ethylacetate, pyridine and dimethyl sulfoxide. Insoluble in hexane and water.
2) Analysis of IR spectra (KBr)
IR $\nu_{max}^{KBr}$: 1715 cm$^{-1}$.
3) Analysis of UV spectra (ethanol)
UV $\lambda_{max}^{EtOH}$ (log ε) nm: 258 (4.02).
4) Analysis of $^1$H-NMR spectra (CDCl$_3$)
The following signals are shown (δ, ppm). 8.00 and 6.94 (each 2H, d, J=8.9, anisoyl group), 4.98 (1H, d, J=5.0 Hz, C14-β-H), 3.70, 3.30, 3.27 and 3.25 (each 3H, s, OCH$_3$ at C1, C6, C16 and C18), 3.87 (3H, s, OCH$_3$ of anisoyl group), 1.52 (3H, s, CH$_3$ of tetrahydrofurfuryl group).
5) Analysis of $^{13}$C-NMR spectra (CDCl$_3$)
The following signals are shown (δ, ppm). 165.9 (carbonyl of anisoyl group), 163.6, 131.8, 122.1 and 113.8 (anisoyl group), 90.8, 85.4, 83.3, 81.0, 79.9, 79.5, 78.6 and 75.0 (C16, C1, C6, C18, C13, C15, C14, C8 and C13), 61.7, 59.0, 58.0 and 56.1 (OCH$_3$ at C16, C18, C6 and C1), 55.4 (OCH$_3$ of anisoyl group), 21.4 (CH$_3$ of 2-methyltetrahydrofurfuryl group).
6) Analysis of Mass spectra
m/z: 687 (M+).
7) Elemental analysis
Calculated for $C_{37}H_{53}NO_{11}$: C, 64.61; H, 7.77; N, 2.04. Found: C, 64.43; H, 7.92; N, 1.87.

(181) Physicochemical parameters and analytical data of de-N-ethyl-N-(2-methyltetrahydrofurfuryl)-3,13-dideoxy-14-O-anisoylaconine 1) Property and solubility
Colorless and amorphous powder. Soluble in ether, chloroform, benzene, ethanol, methanol, ethylacetate, pyridine and dimethyl sulfoxide. Insoluble in hexane and water.
2) Analysis of IR spectra (KBr)
IR $\nu_{max}^{KBr}$: 1715 cm$^{-1}$.
3) Analysis of UV spectra (ethanol)
UV $\lambda_{max}^{EtOH}$ (log ε) nm: 258 (4.01).
4) Analysis of $^1$H-NMR spectra (CDCl$_3$)
The following signals are shown (δ, ppm). 7.99 and 6.95 (each 2H, d, J=8.9, anisoyl group), 5.08 (1H, t, J=4.8 Hz, C14-β-H), 3.67, 3.30, 3.29 and 3.24 (each 3H, s, OCH$_3$ at C1, C6, C16 and C18), 3.87 (3H, s, OCH$_3$ of anisoyl group), 1.52 (3H, s, CH$_3$ of tetrahydrofurfuryl group).
5) Analysis of $^{13}$C-NMR spectra (CDCl$_3$)
The following signals are shown (δ, ppm). 165.8 (carbonyl of anisoyl group), 163.6, 131.8, 122.2 and 113.7 (anisoyl group), 89.8, 85.3, 83.4, 81.4, 79.8, 78.6 and 77.4 (C16, C1, C6, C18, C15, C8 and C14), 59.1, 57.9, 57.5 and 55.9 (OCH$_3$ at C18, C16, C6 and C1), 55.4 (OCH$_3$ of anisoyl group), 21.5 (CH$_3$ of 2-methyltetrahydrofurfuryl group).
6) Analysis of Mass spectra
m/z: 671 (M+).
7) Elemental analysis
Calculated for $C_{37}H_{53}NO_{10}$: C, 66.15; H, 7.95; N, 2.08. Found: C, 66.01; H, 8.16; N, 1.99.

(182) Physicochemical parameters and analytical data of de-N-ethyl-N-(2-methyltetrahydrofurfuryl)-16-epi-8-deoxy-14-O-anisoylaconine 1) Property and solubility
Colorless and amorphous powder. Soluble in ether, chloroform, benzene, ethanol, methanol, ethylacetate, pyridine and dimethyl sulfoxide. Insoluble in hexane and water.
2) Analysis of IR spectra (KBr)
IR $\nu_{max}^{KBr}$: 1715 cm$^{-1}$.
3) Analysis of UV spectra (ethanol)
UV $\lambda_{max}^{EtOH}$ (log ε) nm: 258 (4.02).

4) Analysis of $^1$H-NMR spectra (CDCl$_3$)

The following signals are shown (δ, ppm). 7.99 and 6.94 (each 2H, d, J=8.9, anisoyl group), 5.12 (1H, d, J=5.0 Hz, C14-β-H), 3.84, 3.30, 3.29 and 3.24 (each 3H, s, OCH$_3$ at C1, C6, C16 and C18), 3.87 (3H, s, OCH$_3$ of anisoyl group), 1.52 (3H, s, CH$_3$ of tetrahydrofurfuryl group).

5) Analysis of $^{13}$C-NMR spectra (CDCl$_3$)

The following signals are shown (δ, ppm). 166.0 (carbonyl of anisoyl group), 163.6, 131.8, 122.2 and 113.8 (anisoyl group), 91.2, 85.1, 83.6, 80.2, 77.5, 76.0, 72.3 and 71.9 (C16, C6, C1, C14, C18, C13, C15 and C3), 62.2, 59.1, 57.9 and 56.1 (OCH$_3$ at C16, C18, C6 and C1), 55.4 (OCH$_3$ of anisoyl group), 21.5 (CH$_3$ of 2-methyltetrahydrofurfuryl group).

6) Analysis of Mass spectra m/z: 687 (M$^+$).

(183) Physicochemical parameters and analytical data of de-N-ethyl-N-(2-methyltetrahydrofurfuryl)-16-epi-3,8-dideoxy-14 -O-anisoylaconine 1) Property and solubility Colorless and amorphous powder. Soluble in ether, chloroform, benzene, ethanol, methanol, ethylacetate, pyridine and dimethyl sulfoxide. Insoluble in hexane and water.

2) Analysis of IR spectra (KBr)

IR $\nu_{max}^{KBr}$: 1715 cm$^{-1}$.

3) Analysis of UV spectra (ethanol)

UV $\lambda_{max}^{EtOH}$ (log ε) nm: 258 (4.01).

4) Analysis of $^1$H-NMR spectra (CDCl$_3$)

The following signals are shown (δ, ppm). 7.99 and 6.94 (each 2H, d, J=8.9, anisoyl group), 5.14 (1H, d, J=5.0 Hz, C14-β-H), 3.84, 3.30, 3.29 and 3.24 (each 3H, s, OCH$_3$ at C1, C6, C16 and C18), 3.87 (3H, s, OCH$_3$ of anisoyl group), 1.51 (3H, s, CH$_3$ of tetrahydrofurfuryl group).

5) Analysis of $^{13}$C-NMR spectra (CDCl$_3$)

The following signals are shown (δ, ppm). 166.0 (carbonyl of anisoyl group), 163.6, 131.8, 122.1 and 113.8 (anisoyl group), 91.3, 86.2, 85.0, 82.1, 80.1, 76.1 and 77.2 (C16, C1, C6, C15, C18, C14, C13 and C15), 62.1, 59.0, 58.0 and 56.0 (OCH$_3$ at C16, C18, C6 and C1), 55.4 (OCH$_3$ of anisoyl group), 21.5 (CH$_3$ of 2-methyltetrahydrofurfuryl group).

6) Analysis of Mass spectra m/z: 671 (M$^+$).

(184) Physicochemical parameters and analytical data of de-N-ethyl-N-(2-methyltetrahydrofurfuryl)-3,8,13-trideoxy-14 -O-anisoylaconine 1) Property and solubility Colorless and amorphous powder. Soluble in ether, chloroform, benzene, ethanol, methanol, ethylacetate, pyridine and dimethyl sulfoxide. Insoluble in hexane and water.

2) Analysis of IR spectra (KBr)

IR $\nu_{max}^{KBr}$: 1715 cm$^{-1}$.

3) Analysis of UV spectra (ethanol)

UV $\lambda_{max}^{EtOH}$ (log ε) nm: 258 (4.02).

4) Analysis of $^1$H-NMR spectra (CDCl$_3$)

The following signals are shown (δ, ppm). 7.99 and 6.95 (each 2H, d, J=8.9, anisoyl group), 5.19 (1H, t, J=4.8 Hz, C14-β-H), 3.83, 3.30, 3.29 and 3.24 (each 3H, s, OCH$_3$ at C1, C6, C16 and C18), 3.87 (3H, s, OCH$_3$ of anisoyl group), 1.52 (3H, s, CH$_3$ of tetrahydrofurfuryl group).

5) Analysis of $^{13}$C-NMR spectra (CDCl$_3$)

The following signals are shown (δ, ppm). 166.0 (carbonyl of anisoyl group), 163.6, 131.8, 122.2 and 113.7 (anisoyl group), 91.4, 86.2, 85.1, 82.0, 80.1 and 72.1 (C16, C1, C6, C18, C14 and C15), 60.1, 58.8, 57.9 and 56.0 (OCH$_3$ at C18, C16, C6 and C1), 55.4 (OCH$_3$ of anisoyl group), 21.5 (CH$_3$ of 2-methyltetrahydrofurfuryl group).

6) Analysis of Mass spectra m/z: 655 (M$^+$).

(185) Physicochemical parameters and analytical data of 3,13,15-trideoxyjesaconitine 1) Property and solubility Colorless needles. m.p. 153°–154° C. Soluble in ether, chloroform, benzene, ethanol, methanol, ethylacetate, pyridine and dimethyl sulfoxide. Insoluble in hexane and water.

2) Analysis of IR spectra (KBr)

IR $\nu_{max}^{KBr}$: 1713, 1715 cm$^{-1}$.

3) Analysis of UV spectra (ethanol)

UV $\lambda_{max}^{EtOH}$ (log ε) nm: 258 (4.02).

4) Analysis of $^1$H-NMR spectra (CDCl$_3$)

The following signals are shown (δ, ppm). 8.00 and 6.90 (each 2H, d, J=8.9 Hz, anisoyl group), 5.04 (1H, t, J=4.5 Hz, C14-β-H), 3.85 (3H, s, OCH$_3$ of anisoyl group), 3.37, 3.28, 3.26 and 3.17 (each 3H, s, OCH$_3$ at C1, C6, C16 and C18), 1.08 (3H, t, J=7.1 Hz, CH$_3$ of C$_2$H$_5$ at the nitrogen atom).

5) Analysis of $^{13}$C-NMR spectra (CDCl$_3$)

The following signals are shown (δ, ppm). 169.8 (carbonyl of acetyl group), 166.2 (carbonyl of anisoyl group), 163.5, 131.8, 123.0 and 113.7 (anisoyl group), 85.9, 85.1, 83.5, 82.9, 80.4 and 75.4 (C8, C1, C16, C6, C18 and C14), 59.1, 57.8, 56.6 and 56.0 (OCH$_3$ at C18, C16, C6 and C1), 55.4 (OCH$_3$ of anisoyl group), 49.0 (CH$_2$ of C$_2$H$_5$ at the nitrogen atom), 13.4 (CH$_3$ of C$_2$H$_5$ at the nitrogen atom), 21.8 (CH$_3$ of acetyl group).

6) Analysis of Mass spectra m/z: 627 (M$^+$).

7) Analysis of high resolution Mass spectra

Calculated for 627.3407 (C$_{35}$H$_{49}$NO$_3$). found: 627.3394.

(186) Physicochemical parameters and analytical data of 14-O-p-chlorobenzoylmesaconine 1) Solubility Colorless and amorphous powder. Soluble in ether, chloroform, benzene, ethanol, methanol, acetone, ethylacetate, pyridine and dimethyl sulfoxide. Insoluble in hexane and water.

2) Analysis of IR spectra (KBr)

IR $\nu_{max}^{KBr}$: 1715 cm$^{-1}$.

3) Analysis of UV spectra (ethanol)

UV $\lambda_{max}^{EtOH}$ (log ε) nm: 230 (3.98).

4) Analysis of $^1$H-NMR spectra (CDCl$_3$)

The following signals are shown (δ, ppm). 8.00 and 7.43 (each 2H, d, J=8.8 Hz, p-chlorobenzoyl group), 4.95 (1H, d, J=5.4 Hz, C14-β-H), 3.70, 3.32, 3.29 and 3.24 (each 3H, s, OCH$_3$ at C1, C6, C16 and C18), 2.38 (3H, s, CH$_3$ at the nitrogen atom).

5) Analysis of $^{13}$C-NMR spectra (CDCl$_3$)

The following signals are shown (δ, ppm). 165.4 (carbonyl of p-chlorobenzoyl group), 140.0, 131.8, 129.1 and 128.4 (p-chlorobenzoyl group), 90.2, 82.9, 81.9, 81.7, 79.4, 78.3, 77.0, 74.4 and 71.8 (C16, C1, C15, C14, C8, C18 and C13), 60.5, 59.3, 58.2 and 55.9 (OCH$_3$ at C16, C18, C6 and C1), 42.7 (CH$_3$ at the nitrogen atom).

6) Analysis of EI-Mass spectra m/z: 623, 625 (M$^+$).

(187) Physicochemical parameters and analytical data of 14-p-fluorobenzoylaconine 1) Property and solubility Colorless and odorless powder. Soluble in ether, chloroform, benzene, ethanol, methanol, acetone, ethylacetate, pyridine and dimethyl sulfoxide. Insoluble in hexane and water.

2) Analysis of IR spectra (KBr)

IR $\nu_{max}^{KBr}$: 1725 cm$^{-1}$.

3) Analysis of UV spectra (ethanol)

UV $\lambda_{max}^{EtOH}$ (log ε) nm: 240 (4.00).

4) Analysis of $^1$H-NMR spectra (CDCl$_3$)

The following signals are shown (δ, ppm). 8.00 and 7.42 (each 2H, d, J=8.91 Hz, p-fluorobenzoyl group), 5.02 (1H, d, J=5.2 Hz, C14-β-H), 3.76, 3.33, 3.31 and 3.23 (each 3H, s, OCH$_3$ at C1, C6, C16 and C18), 1.15 (3H, t, J=7.2 Hz, CH$_3$ of C$_2$H$_5$ at the nitrogen atom).

5) Analysis of $^{13}$C-NMR spectra (CDCl$_3$)

The following signals are shown (δ, ppm). 164.8 (carbonyl of p-fluorobenzoyl group), 160.1, 131.0, 126.5 and 124.8 (p-fluorobenzoyl group), 90.5, 82.8, 82.4, 81.6, 79.5, 78.6, 76.9, 74.4 and 71.4 (C16, C6, C1, C15, C14, C8, C18, C13 and C3), 49.0 (CH$_2$ of C$_2$H$_5$ at the nitrogen atom), 13.1 (CH$_3$ of C$_2$H$_5$ at the nitrogen atom).

6) Analysis of EI-Mass spectra m/z: 621 (M$^+$).

(188) Physicochemical parameters and analytical data of 14-O-p-bromobenzoylaconine 1) Property and solubility Colorless and amorphous powder. Soluble in ether, chloroform, benzene, ethanol, methanol, acetone, ethylacetate, pyridine and dimethyl sulfoxide. Insoluble in hexane and water.

2) Analysis of IR spectra (KBr)

IR $v_{max}^{KBr}$: 1723 cm$^{-1}$.

3) Analysis of UV spectra (ethanol)

UV $\lambda_{max}^{EtOH}$ (log ε) nm: 240 (4.02).

4) Analysis of $^1$H-NMR spectra (CDCl$_3$)

The following signals are shown (δ, ppm). 8.04 and 7.42 (each 2H, d, J=8.9, p-bromobenzoyl group), 5.04 (1H, d, J=5.4 Hz, C14-β-H), 3.72, 3.30, 3.29 and 3.27 (each 3H, s, OCH$_3$ at C1, C6, C16 and C18), 1.13 (3H, t, J=7.2 Hz, CH$_3$ of C$_2$H$_5$ at the nitrogen atom).

5) Analysis of $^{13}$C-NMR spectra (CDCl$_3$)

The following signals are shown (δ, ppm). 165.0 (carbonyl of p-bromobenzoyl group), 140.1, 131.4, 129.2 and 128.6 (p-bromobenzoyl group), 90.5, 83.2, 82.5, 81.7, 80.1, 78.4, 77.0, 74.7 and 71.6 (C16, C6, C1, C15, C14, C8, C18, C13 and C3), 59.6, 59.0, 57.8 and 55.6 (OCH$_3$ at C16, C18, C6 and C1), 49.1 (CH$_2$ of C$_2$H$_5$ at the nitrogen atom), 13.3 (CH$_3$ of C$_2$H$_5$ at the nitrogen atom).

6) Analysis of EI-Mass spectra m/z: 681, 683 (M$^+$).

(189) Physicochemical parameters and analytical data of de-N-ethyl-14-O-p-chlorobenzoylaconine 1) Solubility Colorless and odorless powder. Soluble in ether, chloroform, benzene, ethanol, methanol, acetone, ethylacetate, pyridine and dimethyl sulfoxide. Insoluble in hexane and water.

2) Analysis of IR spectra (KBr)

IR $v_{max}^{KBr}$: 1720 cm$^{-1}$.

3) Analysis of UV spectra (ethanol)

UV $\lambda_{max}^{EtOH}$ (log ε) nm: 240 (3.98).

4) Analysis of $^1$H-NMR spectra (CDCl$_3$)

The following signals are shown (δ, ppm). 8.02 and 7.47 (each 2H, d, J=8.9 Hz, p-chlorobenzoyl group), 5.01 (1H, d, J=5.2 Hz, C14-β-H), 3.71, 3.31, 3.30 and 3.25 (each 3H, s, OCH$_3$ at C1, C6, C16 and C18).

5) Analysis of $^{13}$C-NMR spectra (CDCl$_3$)

The following signals are shown (δ, ppm). 165.2 (carbonyl of p-chlorobenzoyl group), 139.8, 131.6, 129.0 and 128.2 (p-chlorobenzoyl group), 90.9, 83.1, 82.5, 81.6, 79.8, 78.6, 77.0, 74.4 and 71.5 (C16, C6, C1, C15, C14, C8, C18, C13 and C3), 60.9, 59.0, 57.8 and 55.6 (OCH$_3$ at C16, C18, C6 and C1).

6) Analysis of EI-Mass spectra m/z: 609, 611 (M$^+$).

(190) Physicochemical parameters and analytical data of 1,14-di-O-acetylneoline

1) Solubility

Colorless powder. Soluble in ether, chloroform, benzene, ethanol, methanol, acetone, ethyl acetate, pyridine and dimethyl sulfoxide. Very poorly soluble in hexane. Insoluble in water.

2) Analysis of IR spectra (CHCl$_3$)

IR $v_{max}^{KBr}$: 3580, 1720 cm$^{-1}$.

3) Analysis of $^1$H-NMR spectra (CDCl$_3$)

The following signals are shown (δ, ppm). 4.86 (1H, t, J=4.6 Hz, C14βH), 4.30 (1H, t, J=3.1 Hz, C1-H), 4.11 (1H, d, J=6.4 Hz), 3.63 (1H, d, J=8.1 Hz), 3.34, 3.33 and 3.27 (each 3H, s, methoxy group), 3.26 (1H, d, J=8.1 Hz), 2.06 and 2.02 (each 3H, s, CH$_3$ of acetyl group), 1.14 (3H, t, J=7.2 Hz, CH$_3$ of C$_2$H$_5$ at the nitrogen atom).

4) Analysis of $^{13}$C-NMR spectra (CDCl$_3$)

The following signals are shown (δ, ppm). 170.4 and 170.1 (each carbonyl of acetyl group), 83.2, 82.0, 80.2, 77.3, 74.7, 74.0 and 63.5 (C6, C16, C18, C14, C8, C1 and C17), 59.1, 58.2 and 56.1 (methoxy group), 57.0 (C19), 48.3 (CH$_2$ of C$_2$H$_5$ at the nitrogen atom), 21.3 and 21.5 (CH$_3$ of acetyl group), 13.0 (CH$_3$ of C$_2$H$_5$ at the nitrogen atom).

5) Analysis of EI-Mass spectra m/z: 521 (M$^+$).

(191) Physicochemical parameters and analytical data of 14-O-(3-chloropropionyl)aconine 1) Solubility Colorless powder. Soluble in ether, chloroform, benzene, ethanol, methanol, acetone, ethylacetate, pyridine and dimethyl sulfoxide. Insoluble in hexane and water.

2) Analysis of IR spectra (CHCl$_3$)

IR $v_{max}^{KBr}$: 1715 cm$^{-1}$.

3) Analysis of $^1$H-NMR spectra (CDCl$_3$)

The following signals are shown (δ, ppm). 4.83 (1H, d, J=5.0 Hz, C14-H), 3.70, 3.31, 3.30 and 3.25 (each 3H, s, OCH$_3$ at C1, C6, C16 and C18), 4.10 and 3.47 (each 2H, t, J=7.2 Hz, CH$_2$ of 3-chloropropionyl group), 1.10 (3H, t, J=7.0 Hz, CH$_3$ of C$_2$H$_5$ at the nitrogen atom).

4) Analysis of $^{13}$C-NMR spectra (CDCl$_3$)

The following signals are shown (δ, ppm). 170.2 (carbonyl of 3-chloropropionyl group), 90.8, 83.4, 82.3, 79.8, 79.5, 78.6, 77.3, 74.8 and 72.0 (C16, C6, C1, C15, C14, C8, C18, C13 and C3), 60.9, 59.1, 58.0 and 55.6 (OCH$_3$ at C16, C18, C6 and C1), 49.0 (CH$_2$ of C$_2$H$_5$ at the nitrogen atom), 13.3 (CH$_3$ of C$_2$H$_5$ at the nitrogen atom).

5) Analysis of EI-Mass spectra m/z: 589, 591 (M$^+$).

(192) Physicochemical parameters and analytical data of 14-O-(4-hydroxybutyl)aconine 1) Solubility Colorless powder. Soluble in ether, chloroform, benzene, ethanol, methanol, acetone, ethylacetate, pyridine and dimethyl sulfoxide. Insoluble in hexane and water.

2) Analysis of IR spectra (CHCl$_3$)

IR $v_{max}^{KBr}$: 3260 cm$^{-1}$.

3) Analysis of $^1$H-NMR spectra (CDCl$_3$)

The following signals are shown (δ, ppm). 3.64, 3.33, 3.31 and 3.28 (each 3H, s, OCH$_3$ at C1, C6, C16 and C18), 1.10 (3H, t, J=7.0 Hz, CH$_3$ of C$_2$H$_5$ at the nitrogen atom).

4) Analysis of $^{13}$C-NMR spectra (CDCl$_3$)

The following signals are shown (δ, ppm). 90.7, 83.5, 82.1, 82.0, 79.5, 78.8, 77.3, 74.5 and 72.0 (C16, C6, C1, C15, C14, C8, C18, C13 and C3), 62.7 and 61.3 (CH$_2$ of 4-hydroxybutyl group), 60.9, 59.1, 57.9 and 55.5 (OCH$_3$ at C16, C18, C6 and C1), 49.1 (CH$_2$ of C$_2$H$_5$ at the nitrogen atom), 13.2 (CH$_3$ of C$_2$H$_5$ at the nitrogen atom).

5) Analysis of EI-Mass spectra
m/z: 571 (M$^+$).

(193) Physicochemical parameters and analytical data of 14-O-(4-methylcyclohexyl)aconine 1) Solubility Colorless powder. Soluble in ether, chloroform, benzene, ethanol, methanol, acetone, ethylacetate, pyridine and dimethyl sulfoxide. Insoluble in hexane and water.

2) Analysis of IR spectra (CHCl$_3$)
IR $\nu_{max}^{KBr}$: 3300 cm$^{-1}$.

3) Analysis of $^1$H-NMR spectra (CDCl$_3$)

The following signals are shown ($\delta$, ppm). 3.70, 3.32, 3.30 and 3.26 (each 3H, s, OCH$_3$ at C1, C6, C16 and C18), 1.11 (3H, t, J=7.0 Hz, CH$_3$ of C$_2$H$_5$ at the nitrogen atom).

4) Analysis of $^{13}$C-NMR spectra (CDCl$_3$)

The following signals are shown ($\delta$, ppm). 90.6, 83.2, 82.1, 81.9, 79.5, 78.9, 77.4, 74.5 and 71.9 (C16, C6, C1, C15, C14, C8, C18, C13 and C3), 70.4 and 66.4 (C1 of 4-methylcyclohexyl group), 60.9, 59.1, 57.9 and 55.6 (OCH$_3$ at C16, C18, C6 and C1), 49.0 (CH$_2$ of C$_2$H$_5$ at the nitrogen atom), 13.0 (CH$_3$ of C$_2$H$_5$ at the nitrogen atom), 23.1 and 18.8 (each CH$_3$ of 4-methylcyclohexyl group).

5) Analysis of EI-Mass spectra
m/z: 595 (M$^+$).

(194) Physicochemical parameters and analytical data of de-N-ethyl-N-(p-anisoyl)-14-O-benzoylaconine 1) Solubility Colorless and odorless powder. Soluble in ether, chloroform, benzene, ethanol, methanol, acetone, ethylacetate, pyridine and dimethyl sulfoxide. Insoluble in hexane and water.

2) Analysis of IR spectra (KBr)
IR $\nu_{max}^{KBr}$: 1715, 1655 cm$^{-1}$.

3) Analysis of UV spectra (ethanol)
UV $\lambda_{max}^{EtOH}$ (log $\epsilon$) nm: 259 (4.01), 231 (3.98).

4) Analysis of $^1$H-NMR spectra (CDCl$_3$)

The following signals are shown ($\delta$, ppm). 7.90 and 6.88 (each 2H, d, J=8.9 Hz, p-anisoyl group), 7.82-7.10 (5H, m, benzoyl group), 3.89, 3.72, 3.30, 3.29 and 3.26 (each 3H, s, OCH$_3$ of anisoyl group, C1, C6, C16 and C18).

5) Analysis of $^{13}$C-NMR spectra (CDCl$_3$)

The following signals are shown ($\delta$, ppm). 166.3 (carbonyl of p-anisoyl group), 166.0 (carbonyl of benzoyl group), 164.0, 131.8, 126.1 and 113.8 (p-anisoyl group), 133.1, 129.7, 129.6 and 128.4 (benzoyl group), 90.9, 83.0, 81.9, 81.8, 79.6, 78.5, 77.2, 74.6 and 72.0 (C16, C6, C1, C15, C14, C8, C18, C13 and C3), 60.9, 59.1, 57.9, 55.4 and 55.1 (OCH$_3$ of anisoyl group, C16, C18, C6 and C1).

6) Analysis of EI-Mass spectra
m/z: 733 (M$^+$).

(195) Physicochemical parameters and analytical data of de-N-ethyl-N-(3-chloropropionyl)-14-O-benzoylaconine 1) Solubility Colorless and odorless powder. Soluble in ether, chloroform, benzene, ethanol, methanol, acetone, ethylacetate, pyridine and dimethyl sulfoxide. Insoluble in hexane and water.

2) Analysis of IR spectra (KBr)
IR $\nu_{max}^{KBr}$: 1715, 1655 cm$^{-1}$.

3) Analysis of $^1$H-NMR spectra (CDCl$_3$)

The following signals are shown ($\delta$, ppm). 8.04-7.37 (5H, m, benzoyl group), 5.00 (1H, d, J=5.0 Hz, C14-H), 3.72, 3.31, 3.28 and 3.25 (each 3H, s, OCH$_3$ at C1, C6, C16 and C18), 4.10 (2H, t, J=7.0 Hz, CH$_2$ of 3-chloropropionyl group).

4) Analysis of $^{13}$C-NMR spectra (CDCl$_3$)

The following signals are shown ($\delta$, ppm). 172.0 (carbonyl of 3-chloropropionyl group), 166.0 (carbonyl of benzoyl group), 133.1, 129.8, 129.7 and 128.3 (benzoyl group), 90.7, 83.1, 82.0, 81.8, 79.5, 78.6, 77.3, 74.7 and 72.0 (C16, C6, C1, C15, C14, C8, C18, C13 and C3), 60.9, 59.1, 58.0 and 55.4 (OCH$_3$ at C16, C18, C6 and C1).

5) Analysis of EI-Mass spectra
m/z: 665, 667 (M$^+$).

(196) Physicochemical parameters and analytical data of de-N-ethyl-N-crotyl-14-O-benzoylaconine 1) Solubility Colorless and odorless powder. Soluble in ether, chloroform, benzene, ethanol, methanol, acetone, ethylacetate, pyridine and dimethyl sulfoxide. Insoluble in hexane and water.

2) Analysis of IR spectra (KBr)
IR $\nu_{max}^{KBr}$: 1720 cm$^{-1}$.

3) Analysis of $^1$H-NMR spectra (CDCl$_3$)

The following signals are shown ($\delta$, ppm). 8.00-7.20 (5H, m, benzoyl group), 5.01 (1H, d, J=5.0 Hz, C14-H), 3.72, 3.31, 3.28 and 3.25 (each 3H, s, OCH$_3$ at C1, C6, C16 and C18), 5.70 (2J, m, CH=CH of crotyl group), 1.68 (3H, d, J=6.2 Hz, CH$_3$ of crotyl group).

4) Analysis of $^{13}$C-NMR spectra (CDCl$_3$)

The following signals are shown ($\delta$, ppm). 165.9 (carbonyl of benzoyl group), 133.2, 129.8, 129.6 and 128.4 (benzoyl group), 131.2 and 122.6 (crotyl group), 90.7, 83.3, 82.1, 81.9, 79.5, 78.6, 77.3, 74.7 and 72.0 (C16, C6, C1, C15, C14, C8, C18, C13 and C3), 60.9, 59.1, 58.0 and 55.4 (OCH$_3$ at C16, C18, C6 and C1), 13.0 (CH$_3$ of crotyl group).

5) Analysis of EI-Mass spectra
m/z: 629 (M$^+$).

(197) Physicochemical parameters and analytical data of de-N-ethyl-N-(4-methylcyclohexyl)-14-O-benzoylaconine 1) Solubility Colorless and odorless powder. Soluble in ether, chloroform, benzene, ethanol, methanol, acetone, ethylacetate, pyridine and dimethyl sulfoxide. Insoluble in hexane and water.

2) Analysis of IR spectra (KBr)
IR $\nu_{max}^{KBr}$: 1715 cm$^{-1}$.

3) Analysis of $^1$H-NMR spectra (CDCl$_3$)

The following signals are shown ($\delta$, ppm). 8.04-7.35 (5H, m, benzoyl group), 5.01 (1H, d, J=5.0 Hz, C14-H), 3.70, 3.31, 3.28 and 3.28 (each 3H, s, OCH$_3$ at C1, C6, C16 and C18).

4) Analysis of $^{13}$C-NMR spectra (CDCl$_3$)

The following signals are shown ($\delta$, ppm). 166.0 (carbonyl of benzoyl group), 133.1, 129.7, 129.6 and 128.3 (benzoyl group), 90.6, 83.4, 82.3, 82.0, 79.4, 78.6, 77.3, 74.7 and 72.0 (C16, C6, C1, C15, C14, C8, C18, C13 and C3), 60.9, 59.0, 58.0 and 55.5 (OCH$_3$ at C16, C18, C6 and C1), 58.6 and 53.2 (each C1 of 4-methylcyclohexyl group), 23.0 and 19.3 (each CH$_3$ of 4-methylcyclohexyl group).

5) Analysis of EI-Mass spectra
m/z: 671 (M$^+$).

(198) Physicochemical parameters and analytical data of de-N-ethyl-N-(4-hydroxybutyl)-14-O-benzoylaconine 1) Solubility Colorless and odorless powder. Soluble in ether, chloroform, benzene, ethanol, methanol, acetone, ethylacetate, pyridine and dimethyl sulfoxide. Insoluble in hexane and water.

2) Analysis of IR spectra (KBr)
IR $\nu_{max}^{KBr}$: 1710 cm$^{-1}$.

3) Analysis of $^1$H-NMR spectra (CDCl$_3$)

The following signals are shown ($\delta$, ppm). 8.02-7.10 (5H, m, benzoyl group), 5.02 (1H, d, J=4.9 Hz, C14-H), 3.71, 3.31, 3.29 and 3.26 (each 3H, s, OCH$_3$ at C1, C6, C16 and C18).

4) Analysis of $^{13}$C-NMR spectra (CDCl$_3$)

The following signals are shown (δ, ppm). 166.0 (carbonyl of benzoyl group), 133.2, 129.8, 129.5 and 128.3 (benzoyl group), 90.8, 83.4, 82.3, 82.0, 79.4, 78.6, 77.3, 74.7 and 72.0 (C16, C6, C1, C15, C14, C8, C18, C13 and C3), 60.9, 59.1, 57.9 and 55.6 (OCH$_3$ at C16, C18, C6 and C1), 63.0 (C4 of 4-hydroxybutyl group).

5) Analysis of EI-Mass spectra m/z: 647 (M$^+$).

(199) Physicochemical parameters and analytical data of 14-O-(2-pyridylmethyl)-aconine 1) Solubility Colorless powder. Soluble in ether, chloroform, benzene, ethanol, methanol, acetone, ethylacetate, pyridine and dimethyl sulfoxide. Insoluble in hexane and water.

2) Analysis of IR spectra (KBr)

IR $v_{max}^{KBr}$: 3300 cm$^{-1}$.

3) Analysis of UV spectra (ethanol)

UV $\lambda_{max}^{EtOH}$ (log ε) nm: 265 (3.24).

4) Analysis of $^1$H-NMR spectra (CDCl$_3$)

The following signals are shown (δ, ppm). 8.21-6.94 (4H, m, pyridine ring), 5.01 (1H, d, J=5.0 Hz, C14-H), 4.68 (2H, s, CH$_2$ at pyridine ring), 3.69, 3.30, 3.29 and 3.24 (each 3H, s, OCH$_3$ at C1, C6, C16 and C18), 1.11 (3H, t, J=7.0 Hz, CH$_3$ of C$_2$H$_5$ at the nitrogen atom).

5) Analysis of $^{13}$C-NMR spectra (CDCl$_3$)

The following signals are shown (δ, ppm). 163.4, 149.3, 136.4 and 120.9 (pyridine ring), 90.8, 83.4, 82.0, 81.8, 79.5, 78.8, 77.3, 74.6 and 71.9 (C16, C6, C1, C15, C14, C8, C18, C13 and C3), 61.7, 59.1, 57.8 and 55.9 (OCH$_3$ at C16, C18, C6 and C1), 49.0 (CH$_2$ of C$_2$H$_5$ at the nitrogen atom), 13.3 (CH$_3$ of C$_2$H$_5$ at the nitrogen atom).

6) Analysis of EI-Mass spectra m/z: 590 (M$^+$).

7) Elemental analysis

Calculated for C$_{31}$H$_{46}$N$_2$O$_9$: C, 63.03; H, 7.85; N, 4.74. Found: C, 63.11; H, 7.88; N, 4.69.

(200) Physicochemical parameters and analytical data of 14-O-(2-methyltetrahydrofurfuryl)-aconine 1) Solubility Colorless powder. Soluble in ether, chloroform, benzene, ethanol, methanol, acetone, ethylacetate, pyridine and dimethyl sulfoxide. Insoluble in hexane and water.

2) Analysis of IR spectra (CHCl$_3$)

IR $v_{max}^{KBr}$: 3300 cm$^{-1}$.

3) Analysis of $^1$H-NMR spectra (CDCl$_3$)

The following signals are shown (δ, ppm). 5.01 (1H, d, C14-H), 3.71, 3.36, 3.30 and 3.28 (each 3H, s, OCH$_3$ at C1, C6, C16 and C18), 1.50 (3H, s, CH$_3$ of 2-methyltetrahydrofurfuryl group), 1.10 (3H, t, J=7.0 Hz, CH$_3$ of C$_2$H$_5$ at the nitrogen atom).

4) Analysis of $^{13}$C-NMR spectra (CDCl$_3$)

The following signals are shown (δ, ppm). 90.8, 83.5, 82.1, 81.0, 79.4, 78.8, 77.5, 74.4 and 72.0 (C16, C6, C1, C15, C14, C8, C18, C13 and C3), 60.9, 59.1, 57.9 and 55.6 (OCH$_3$ at C16, C18, C6 and C1), 49.1 (CH$_2$ of C$_2$H$_5$ at the nitrogen atom), 13.2 (CH$_3$ of C$_2$H$_5$ at the nitrogen atom), 21.5 (CH$_3$ of 2-methyltetrahydrofurfuryl group).

5) Analysis of EI-Mass spectra m/z: 587 (M$^+$).

6) Elemental analysis

Calculated for C$_{31}$H$_{51}$NO$_{10}$: C, 63.36; H, 7.03; N, 2.38. Found: C, 63.42; H, 7.16; N, 2.11.

(201) Physicochemical parameters and analytical data of 14-O-cyclohexanecarbonylaconine 1) Solubility Colorless powder. Soluble in ether, chloroform, benzene, ethanol, methanol, acetone, ethylacetate, pyridine and dimethyl sulfoxide. Insoluble in hexane and water.

2) Analysis of IR spectra (CHCl$_3$)

IR $v_{max}^{KBr}$: 1720 cm$^{-1}$.

3) Analysis of $^1$H-NMR spectra (CDCl$_3$)

The following signals are shown (δ, ppm). 4.95 (1H, d, C14-H), 3.71, 3.31, 3.29 and 3.25 (each 3H, s, OCH$_3$ at C1, C6, C16 and C18), 1.10 (3H, t, J=7.0 Hz, CH$_3$ of C$_2$H$_5$ at the nitrogen atom).

4) Analysis of $^{13}$C-NMR spectra (CDCl$_3$)

The following signals are shown (δ, ppm). 171.2 (carbonyl of cyclohexanecarbonyl), 90.7, 83.5, 82.3, 79.8, 79.5, 78.7, 77.4, 74.5 and 71.9 (C16, C6, C1, C15, C14, C8, C18, C13 and C3), 60.9, 59.2, 58.0 and 55.6 (OCH$_3$ at C16, C18, C6 and C1), 49.0 (CH$_2$ of C$_2$H$_5$ at the nitrogen atom), 13.3 (CH$_3$ of C$_2$H$_5$ at the nitrogen atom).

5) Analysis of EI-Mass spectra m/z: 609 (M$^+$).

6) Elemental analysis

Calculated for C$_{32}$H$_{51}$NO$_{10}$: C, 63.03; H, 8.43; N, 2.30. Found: C, 63.16; H, 8.25; N, 2.18.

(202) Physicochemical parameters and analytical data of de-N-ethyl-N-(cyclohexanecarbonyl)14-O-benzoylaconine 1) Solubility Colorless and odorless powder. Soluble in ether, chloroform, benzene, ethanol, methanol, acetone, ethylacetate, pyridine and dimethyl sulfoxide. Insoluble in hexane and water.

2) Analysis of IR spectra (KBr)

IR $v_{max}^{KBr}$: 1715 cm$^{-1}$.

3) Analysis of UV spectra (ethanol)

UV $\lambda_{max}^{EtOH}$ (log ε) nm: 231 (3.98).

4) Analysis of $^1$H-NMR spectra (CDCl$_3$)

The following signals are shown (δ, ppm). 8.02-7.30 (5H, m, benzoyl group), 4.91 (1H, d, J=5.0 Hz, C14-β-H), 3.69, 3.30, 3.29 and 3.26 (each 3H, s, OCH$_3$ at C1, C6, C16 and C18).

5) Analysis of $^{13}$C-NMR spectra (CDCl$_3$)

The following signals are shown (δ, ppm). 171.4 (carbonyl of cyclohexanecarbonyl group), 165.9 (carbonyl of benzoyl group), 132.6, 129.9 and 128.5 (benzoyl group), 90.8, 83.5, 82.0, 81.3, 79.2, 78.3, 77.1, 74.5 and 71.7 (C16, C6, C1, C15, C14, C8, C18, C13 and C3), 61.9, 59.0, 57.8 and 56.0 (OCH$_3$ at C16, C18, C6 and C1).

6) Analysis of EI-Mass spectra m/z: 685 (M$^+$).

7) Elemental analysis

Calculated for C$_{37}$H$_{51}$NO$_{11}$: C, 64.80; H, 7.50; N, 2.04. Found: C, 64.85; H, 7.76; N, 2.18.

(203) Physicochemical parameters and analytical data of de-N-ethyl-N-(α-methyl(4-α-methylacetic acid)phenylacetyl)- 14-O-benzoylaconine 1) Solubility Colorless and odorless powder. Soluble in ether, chloroform, benzene, ethanol, methanol, acetone, ethylacetate, pyridine and dimethyl sulfoxide. Insoluble in hexane and water.

2) Analysis of IR spectra (KBr)

IR $v_{max}^{KBr}$: 1715 cm$^{-1}$.

3) Analysis of UV spectra (ethanol)

UV $\lambda_{max}^{EtOH}$ (log ε) nm: 220 (4.03), 256 (3.89).

4) Analysis of $^1$H-NMR spectra (CDCl$_3$)

The following signals are shown (δ, ppm). 8.01-7.28 (9H, m, benzene), 4.90 (1H, d, J=4.8 Hz, C14-β-H), 3.70, 3.30, 3.30 and 3.26 (each 3H, s, OCH$_3$ at C1, C6, C16 and C18), 3.65 (2H, q, CH of α-methylacetyl and α-methylacetic acid), 1.41 (6H, d, J=7.0 Hz, CH$_3$ of α-methylacetyl and α-methylacetic acid).

5) Analysis of $^{13}$C-NMR spectra (CDCl$_3$)

The following signals are shown (δ, ppm). 179.8 (carbonyl group), 166.0 (carbonyl of benzoyl group), 140.5, 139.8, 128.2 and 127.0 (benzene), 132.7, 129.9 and 128.5 (benzoyl group), 90.8, 83.5, 81.9, 81.2, 79.3, 78.4, 77.0, 74.6 and 71.8 (C16, C6, C1, C15, C14, C8, C18, C13 and C3), 61.9, 59.1, 57.8 and 56.0 (OCH$_3$ at C16, C18, C6 and C1), 60.4 and 60.2 (CH of α-methylacetyl and α-methylacetic acid), 18.2 and 18.1 (CH$_3$ of α-methylacetyl and α-methylacetic acid).

6) Analysis of EI-Mass spectra
m/z: 779 (M$^+$).

7) Elemental analysis
Calculated for C$_{42}$H$_{53}$NO$_{13}$: C, 64.68; H, 6.85; N, 1.80.
Found: C, 64.46; H, 6.90; N, 1.68.

(204) Physicochemical parameters and analytical data of de-N-ethyl-N-(2-pyridylmethyl)-14-O-benzoylaconine 1) Solubility
Colorless powder. Soluble in ether, chloroform, benzene, ethanol, methanol, acetone, ethylacetate, pyridine and dimethyl sulfoxide. Insoluble in hexane and water.

2) Analysis of IR spectra (CHCl$_3$)
IR $\nu_{max}^{KBr}$: 1715 cm$^{-1}$.

3) Analysis of UV spectra (ethanol)
UV $\lambda_{max}^{EtOH}$ (log ε) nm: 230 (4.01), 264 (3.25).

4) Analysis of $^1$H-NMR spectra (CDCl$_3$)
The following signals are shown (δ, ppm). 8.20-6.96 (9H, m, pyridyl ring and benzoyl group), 4.93 (1H, d, J=5.0 Hz, C14-H), 4.50 (2H, s, CH$_2$ of pyridyl ring), 3.69, 3.30, 3.29 and 3.24 (each 3H, s, OCH$_3$ at C1, C6, C16 and C18).

5) Analysis of $^{13}$C-NMR spectra (CDCl$_3$)
The following signals are shown (δ, ppm). 165.9 (carbonyl of benzoyl group), 132.5, 129.9 and 128.5 (benzoyl group), 163.6, 150.1, 136.1 and 120.6 (pyridyl ring), 90.8, 83.6, 82.1, 81.6, 79.2, 78.3, 77.1, 74.6 and 71.7 (C16, C6, C1, C15, C14, C8, C18, C13 and C3), 61.9, 59.0, 57.8 and 56.0 (OCH$_3$ at C16, C18, C6 and C1).

6) Analysis of Mass spectra
m/z: 666 (M$^+$).

7) Elemental analysis
Calculated for C$_{36}$H$_{46}$N$_2$O$_{10}$: C, 64.85; H, 6.95; N, 4.20.
Found: C, 64.66; H, 7.03; N, 4.01.

(205) Physicochemical parameters and analytical data of 1,14-di-O-acetylneoline

1) Solubility
Colorless powder. Soluble in ether, chloroform, benzene, ethanol, methanol, acetone, ethylacetate, pyridine and dimethyl sulfoxide. Very poorly soluble in hexane. Insoluble in water.

2) Analysis of IR spectra (CHCl$_3$)
IR $\nu_{max}^{KBr}$: 3580, 1720 cm$^{-1}$.

3) Analysis of $^1$H-NMR spectra (CDCl$_3$)
The following signals are shown (δ, ppm). 4.86 (1H, t, J=4.6 Hz, C14-H), 4.30 (1H, t, J=3.1 Hz, C1-H), 3.34, 3.33 and 3.27 (each 3H, s, methoxy group), 2.06 and 2.02 (each 3H, s, CH$_3$ of acetyl group), 1.14 (3H, t, J=7.2 Hz, CH$_3$ of C$_2$H$_5$ at the nitrogen atom).

4) Analysis of $^{13}$C-NMR spectra (CDCl$_3$)
The following signals are shown (δ, ppm). 170.4 and 170.1 (each carbonyl of acetyl group), 83.2, 82.0, 80.2, 77.3, 74.4 and 74.0 (C6, C16, C18, C14, C8 and C1), 59.1, 58.2 and 56.1 (methoxy group), 48.3 (CH$_2$ of C$_2$H$_5$ at the nitrogen atom), 21.3 and 21.5 (CH$_3$ of acetyl group), 13.0 (CH$_3$ of C$_2$H$_5$ at the nitrogen atom).

5) Analysis of EI-Mass spectra
m/z: 521 (M$^+$).

(206) Physicochemical parameters and analytical data of 14-O-anisoylneoline

1) Solubility
Colorless powder. Soluble in ether, chloroform, benzene, ethanol, methanol, acetone, ethylacetate, pyridine and dimethyl sulfoxide. Very poorly soluble in hexane. Insoluble in water.

2) Analysis of IR spectra (CHCl$_3$)
IR $\nu_{max}^{KBr}$: 3580, 1720 cm$^{-1}$.

3) Analysis of UV spectra (ethanol)
UV $\lambda_{max}^{EtOH}$ (log ε) nm: 258 (3.88).

4) Analysis of $^1$H-NMR spectra (CDCl$_3$)
The following signals are shown (δ, ppm). 8.00 and 6.89 (each 2H, d, J=8.9 Hz, anisoyl group), 5.18 (1H, t, J=4.6 Hz, C14-H), 3.93 (3H, s, OCH$_3$ of anisoyl group), 3.36, 3.36 and 3.25 (each 3H, s, methoxy group), 1.13 (3H, t, J=7.2 Hz, CH$_3$ of C$_2$H$_5$ at the nitrogen atom).

5) Analysis of $^{13}$C-NMR spectra (CDCl$_3$)
The following signals are shown (δ, ppm). 166.0 (carbonyl of anisoyl group), 163.5, 131.9, 123.0 and 113.6 (anisoyl group), 83.3, 83.1, 80.1, 75.4, 74.4 and 72.4 (C6, C16, C18, C14, C8 and C1), 59.0, 57.6 and 56.5 (methoxy group), 55.4 (OCH$_3$ of anisoyl group), 48.3 (CH$_2$ of C$_2$H$_5$ at the nitrogen atom), 13.0 (CH$_3$ of C$_2$H$_5$ at the nitrogen atom).

6) Analysis of EI-Mass spectra
m/z 571 (M$^+$).

7) Elemental analysis
Calculated for C$_{32}$H$_{45}$NO$_8$: C, 67.23; H, 7.93; N, 2.45.
Found: C, 67.36; H, 8.10; N, 2.19.

(207) Physicochemical parameters and analytical data of 1,14-di-O-butanoylneoline 1) Solubility
Colorless powder. Soluble in ether, chloroform, benzene, ethanol, methanol, acetone, ethyl acetate, pyridine and dimethyl sulfoxide. Very poorly soluble in hexane. Insoluble in water.

2) Analysis of IR spectra (CHCl$_3$)
IR $\nu_{max}^{KBr}$: 3580, 1720 cm$^{-1}$.

3) Analysis of $^1$H-NMR spectra (CDCl$_3$)
The following signals are shown (δ, ppm). 4.86 (1H, t, J=4.6 Hz, C14-H), 4.30 (1H, t, J=3.1 Hz, C1-H), 3.31, 3.30 and 3.26 (each 3H, s, methoxy group), 1.05 and 1.07 (each 3H, t, J=7.0 Hz, CH$_3$ of butanoyl group), 1.10 (3H, t, J=7.2 Hz, CH$_3$ of C$_2$H$_5$ at the nitrogen atom).

4) Analysis of $^{13}$C-NMR spectra (CDCl$_3$)
The following signals are shown (δ, ppm). 170.4 and 170.1 (each carbonyl of butanoyl group), 83.4, 83.3, 80.2, 77.4, 75.0 and 74.3 (C6, C16, C18, C1, C14 and C8), 59.1, 58.0 and 56.1 (methoxy group), 48.9 (CH$_2$ of C$_2$H$_5$ at the nitrogen atom), 13.8 and 13.6 (CH$_3$ of butanoyl group), 13.5 (CH$_3$ of C$_2$H$_5$ at the nitrogen atom).

5) Analysis of EI-Mass spectra
m/z: 577 (M$^+$).

6) Elemental analysis
Calculated for C$_{32}$H$_{51}$NO$_8$: C, 66.52; H, 8.90; N, 2.42.
Found: C, 66.73; H, 8.87; N, 2.33.

(208) Physicochemical parameters and analytical data of 1,14-di-O-p-chlorobenzoylneoline 1) Solubility
Colorless powder. Soluble in ether, chloroform, benzene, ethanol, methanol, acetone, ethyl acetate, pyridine and dimethyl sulfoxide. Very poorly soluble in hexane. Insoluble in water.

2) Analysis of IR spectra (CHCl$_3$)
IR $\nu_{max}^{KBr}$: 3580, 1720 cm$^{-1}$.

3) Analysis of UV spectra (ethanol)
UV $\lambda_{max}^{EtOH}$ (log ε) nm: 246 (4.10).

4) Analysis of $^1$H-NMR spectra (CDCl$_3$)
The following signals are shown (δ, ppm). 7.90 and 7.35 (each 4H, d, J=8.5 Hz, p-chlorobenzoyl group), 5.25-4.96 (2H, m, 1,14-H), 3.37, 3.33 and 3.10 (each 3H, s, methoxy group), 1.18 (3H, t, J=7.2 Hz, CH$_3$ of C$_2$H$_5$ at the nitrogen atom).

5) Analysis of $^{13}$C-NMR spectra (CDCl$_3$)

The following signals are shown (δ, ppm). 166.0 and 165.8 (carbonyl of p-chlorobenzoyl group), 140.1, 139.7, 131.7, 131.3, 129.3, 128.9, 128.7 and 128.4 (p-chlorobenzoyl group), 83.5, 83.0, 79.9, 77.8, 75.4 and 74.2 (C6, C16, C18, C14, C1 and C8), 59.0, 57.8 and 56.6 (methoxy group), 48.2 (CH$_2$ of C$_2$H$_5$ at the nitrogen atom), 13.2 (CH$_3$ of C$_2$H$_5$ at the nitrogen atom).

6) Analysis of EI-Mass spectra m/z: 714, 716, 718 (M$^+$).

7) Elemental analysis

Calculated for C$_{38}$H$_{45}$NO$_8$Cl$_2$: C, 63.86; H, 6.35; N, 1.96. Found: C, 63.62; H, 6.38; N, 2.01.

(209) Physicochemical parameters and analytical data of 1,14-di-O-p-anisoylneoline 1) Solubility Colorless powder. Soluble in ether, chloroform, benzene, ethanol, methanol, acetone, ethyl acetate, pyridine and dimethyl sulfoxide. Very poorly soluble in hexane. Insoluble in water.

2) Analysis of IR spectra (CHCl$_3$)

IR $v_{max}^{KBr}$: 3580, 1720 cm$^{-1}$.

3) Analysis of UV spectra (ethanol)

UV $\lambda_{max}^{EtOH}$ (log ε) nm: 258 (4.01).

4) Analysis of $^1$H-NMR spectra (CDCl$_3$)

The following signals are shown (δ, ppm). 7.98 and 6.89 (each 4H, d, J=8.9 Hz, anisoyl group), 4.98–5.23 (2H, m, 1,14-H), 3.83 (6H, s, OCH$_3$ of anisoyl group), 3.36, 3.33 and 3.10 (each 3H, s, methoxy group), 1.13 (3H, t, J=7.2 Hz, CH$_3$ of C$_2$H$_5$ at the nitrogen atom).

5) Analysis of $^{13}$C-NMR spectra (CDCl$_3$)

The following signals are shown (δ, ppm). 166.0 and 165.8 (carbonyl of anisoyl group), 163.7, 163.5, 132.2, 131.9, 123.4, 123.0, 114.1 and 113.6 (anisoyl group), 83.5, 83.2, 80.0, 77.9, 75.5 and 74.3 (C6, C16, C18, C1, C14 and C8), 59.1, 57.8 and 56.5 (methoxy group), 55.4 (OCH$_3$ of anisoyl group), 48.3 (CH$_2$ of C$_2$H$_5$ at the nitrogen atom), 13.0 (CH$_3$ of C$_2$H$_5$ at the nitrogen atom).

6) Analysis of EI-Mass spectra m/z: 705 (M$^+$).

7) Elemental analysis

Calculated for C$_{40}$H$_{51}$NO$_{10}$: C, 68.07; H, 7.28; N, 1.98. Found: C, 68.11; H, 7.43; N, 1.84.

Examples of experiment with respect to the pharmacological property and acute toxicity of the compound shown in formula (I) mentioned above are described below.

Experiment example 1 (Analgesic action)

Measurement of analgesic activity by the acetic acid-induced writhing method.

Male mice of the Std:ddY Strain (20–25 g) were used. All mice were maintained at room temperature of 24°–25° C. on a 12 hours light and dork cycle and were given food and water ad libitum. Test compound was used in 3% suspension in gum arabic 0.7% acetic acid in 0.9% physiological saline solution was injected i.p. (10 ml/kg) at 30 minutes after test compound was administered s.c. After 10 minutes, the number of writhing movements was counted for a period of 10 minutes. 3% gum arabic solution in 0.9% physiological saline solution was used as a negative control. The ED$_{50}$ values were calculated in accordance with the Litchfield-Wilcoxon's method based on judging to be possitive in case of half and under the writhing number of negative control group. The results are shown in Table 1. It was demonstrated in Table 1 that the compounds of this invention had a dose-dependent potent analgesic activity.

Experiment example 2 (Antiinflammatory action)

Measurement of the antiinflammatory activity on the carrageenin-induced hind paw edema in mice.

Male mice of Std:ddY strain (20–25 g) were used. Thirty minutes after the oral administration of test compound, 25 μl of carrageenin (0.5 mg/25 μl) was injected s.c. under the plantar surface of the right hind paw. To the control group, 25 μl of 0.9% physiological saline solution was injected S.C. under the plantar surface of the left hind paw. The volume of the paw was measured at one hour intervals for 6 hours with a dial gauge calliper. The results were described as a difference in foot pad thickness between the right and left feet. The results are shown in Table 2. As shown in Table 2, it was demonstrated that the compound of this invention had the inhibitory action against the carrageenin-induced hind paw edema.

Experiment example 3 (Acute toxicity)

Male mice of the Std:ddY Strain (20–25 g) were used. The LD$_{50}$ values were calculated using the method of Litchfield-Wilcoxon from the mortality during 72 hours after test compound was administered s.c. The results are shown in Table 3. As shown in Table 3, it was demonstrated that the compound of this invention was found to be lower in toxicity than mesaconitine, aconitine, hypaconitine and jesaconitine.

As mentioned above, it was indicated that the compound shown in formula (I) had lower toxicity than mesaconitine, aconitine, hypaconitine and jesaconitine and had potent analgesic and antiinflammatory activity.

The dose of the compound of the formula (I) for clinical use as analgesic/anti-inflammatory agent according to the invention is preferably 1–1,000 mg/day for adults. The agent according to the present invention is presented for actual application after formed into any desired dosage form by conventional methods using customarily used carriers or excipients.

Oral preparations such as tablets, powders, granules and capsules may contain conventional excipients such as calcium carbonate, magnesium carbonate, calcium phosphate, corn starch, potato starch, sugar, lactose, talc, magnesium stearate and gum arabic. Tablets may be coated by conventional methods. Oral liquid preparations may be aqueous or oily suspensions, solutions, syrups, elixirs etc.

For injectable preparations, the compounds of the formula (I) may be used in the form of a salt thereof, and preferably reconstituted upon use. Such preparations may contain different adjuvants such as suspending, stabilizing or dispersing agents. They may contain sterilized distilled water, refined oils such as peanut oil and corn oil, non-aqueous solvents, polyethylene glycol, polypropylene glycol, etc.

Preparations for rectal administration are presented in the form of compositions for suppository and may contain pharmaceutical carriers well known in the art such as polyethylene glycol, lanolin and coconut oil.

Preparations for topical application are presented in the form of compositions for ointment, plaster or poultice and may contain pharmaceutical carriers well known in the art such as vaseline, paraffin, hydrous lanolin, plastibase, kaolin, bentonite, talc, aluminum silicate, propylene glycol, sorbitol, hydrophilic petrolatum, macrogols, wax, resin, purified lanolin, gum, glycerin, gelatin, polyacrylic acid, polyacrylic acid salt, polyvinyl alcohol, polyvinyl pyrrolidone and polyethylene oxide.

TABLE 1

| Test compound | $ED_{50}$ value, mg/kg (95% confidence Limits) |
|---|---|
| aconitine | 0.060 (0.020–0.180) |
| mesaconitine | 0.037 (0.017–0.081) |
| hypaconitine | 0.120 (0.057–0.252) |
| jesaconitine | 0.031 (0.013–0.071) |
| 8-deoxy-14-O-benzoylmesaconine | 1.57 (0.65–3.77) |
| 3,8-dideoxy- 14-O-benzoylmesaconine | 3.03 (0.99–4.16) |
| 3,13-dideoxy-14-O-benzoylmesaconine | 3.67 (1.85–7.27) |
| 3,8,13-trideoxy-14-O-benzoylmesaconine | 4.25 (2.18–8.29) |
| 3,13-dideoxymesaconitine | 0.090 (0.045–0.200) |
| 8-deoxy-14-O-benzoylaconine | 2.44 (1.11–5.37) |
| 3-deoxy-14-O-benzoylaconine | 3.56 (1.62–7.83) |
| 3,8-dideoxy-14-O-benzoylaconine | 4.13 (1.99–8.59) |
| 3,13-dideoxy-14-O-benzoylaconine | 4.14 (2.24–7.66) |
| 3,8,13-trideoxy-14-O-benzoylaconine | 6.28 (3.08–12.81) |
| 4-O-anisoylmesaconine | 1.01 (0.51–2.02) |
| 8-deoxy-14-O-anisoylmesaconine | 2.02 (1.04–3.92) |
| 3-deoxy-14-O-anisoylmesaconine | 3.95 (1.88–7.43) |
| 3,8-dideoxy-14-O-anisoylmesaconine | 4.19 (2.00–8.80) |
| 3,13-dideox5,-14-O-anisoylmeaconine | 3.12 (1.68–5.80) |
| 3,8,13-trideoxy-14-O-anisoylmesaconine | 4.33 (2.26–8.31) |
| 8-deoxy-14-O-anisoylaconine | 1.18 (0.47–2.97) |
| 3-deoxy-14-O-anisoylaconine | 4.30 (2.44–7.57) |
| 3,8-dideoxy-14-O-anisoylaconine | 4.50 (2.20–9.23) |
| 3,13-dideoxy-14-O-anisoylaconine | 2.87 (1.59–5.17) |
| 3,8,13-trideoxy-14-O-anisoylaconine | 4.38 (2.34–8.59) |
| 3,13-dideoxyjesaconitine | 0.10 (0.05–0.20) |
| 8-deoxy-14-O-veratroylaconine | 9.78 (3.24–29.49) |
| 8-deoxy-14-O-trimethylgalloylaconine | 9.23 (3.21–26.55) |
| 8-deoxy-14-O-m-anisoylaconine | 5.62 (1.75–18.07) |
| 8-deoxy-14-O-p-chlorobenzoylaconine | 21.6 (6.55–71.28) |
| 8-deoxy-14-O-m-chlorobenzoylaconine | 10.5 (3.60–30.20) |
| 8-deoxy-14-O-o-chlorobenzoylaconine | 28.4 (9.48–85.06) |
| 8-deoxy-14-O-acetylaconine | 33.4 (10.76–103.64) |
| 8-deoxy-14-O-methylaconine | 40.7 (12.71–130.28) |
| 8-deoxy-14-O-amylaconine | 27.3 (8.78–84.93) |
| 8-deoxy-14-O-benzylaconine | 31.2 (10.63–91.60) |
| 8-deoxy-14-O-crotylaconine | 27.2 (9.74–75.97) |
| 8-deoxy-14-O-α-methyl(4-(α-methyl-acetic acid)phenyl)acetylaconine | 31.3 (11.70–83.73) |
| 8-deoxy-14-O-(4-methylpentyl)aconine | 28.5 (9.34–86.93) |
| 8-deoxy-14-O-m-fluorobenzoylaconine | 17.8 (6.72–47.17) |
| 8-deoxy-14-O-m-bromobenzoylaconine | 20.2 (6.30–64.74) |
| 8-deoxy-14-O-p-methoxybenzylaconine | 10.4 (3.59–30.14) |
| de-N-ethyl-N-propyl-8-deoxy-14-O-anisoylaconine | 31.8 (11.34–89.17) |
| de-N-ethyl-N-amyl-8-deoxy-14-O-anisoylaconine | 27.5 (10.28–73.54) |
| de-N-ethyl-N-(4-methylpentyl)-8-deoxy-14-O-anisoylaconine | 29.8 (11.72–75.78) |
| de-N-ethyl-N-acethyl-8-deoxy-14-O-anisoylaconine | 23.4 (7.66–71.51) |
| de-N-ethyl-N-benzoyl-8-deoxy-14-O-anisoylaconine | 30.5 (9.65–96.44) |
| de-N-ethyl-N-(2-methyltetrahydrofurfuryl)-8-deoxy-14-O-anisoylaconine | 31.4 (10.12–97.40) |
| de-N-ethyl-jesaconitine | 1.86 (0.68–5.06) |
| 3,13-dideoxy-14-O-veratroylaconine | 11.3 (4.51–28.28) |
| 3,13-dideoxy-14-O-acethylaconine | 31.7 (10.78–93.20) |
| 3,13-dideoxy-14-O-benzylaconine | 29.6 (10.71–81.81) |
| 3,13-dideoxy-14-O-crotylaconine | 30.1 (9.63–94.06) |
| 3,13-dideoxy-14-O-(4-methylpentyl)aconine | 30.2 (9.07–100.60) |
| 3-deoxy-14-O-veratroylaconine | 12.3 (3.61–41.89) |
| 3-deoxy-14-O-acetylaconine | 28.8 (9.58–86.60) |
| 3-deoxy-14-O-benzylaconine | 27.3 (9.75–76.41) |
| 3-deoxy-14-O-crotylaconine | 31.2 (8.91–109.26) |
| 3-deoxy-14-O-(4-methylpentyl)aconine | 27.8 (8.54–90.46) |
| 3,8,13-trideoxy-14-O-veratroylaconine | 10.6 (3.69–30.48) |
| 3,8,13-trideoxy-14-O-acetylaconine | 32.5 (10.39–101.69) |
| 3,8,13-trideoxy-14-O-benzylaconine | 25.8 (7.83–85.01) |
| 3,8,13-trideoxy-14-O-crotylaconine | 33.3 (10.85–102.16) |
| 3,8,13-trideoxy-14-O-(4-methylpentyl)aconine | 26.2 (8.45–81.25) |
| de-N-ethyl-N-propyl-3,13-dideoxy-14-O-anisoylaconine | 31.3 (10.17–96.31) |
| de-N-ethyl-N-(4-methylpentyl)-3,13-dideoxy-14-O-anisoylaconine | 25.8 (8.16–81.58) |
| de-N-ethyl-N-acetyl-3,13-dideoxy-14-O-anisoylaconine | 24.1 (8.36–69.46) |
| de-N-ethyl-N-benzoyl-3,13-dideoxy-14-O-anisoylaconine | 30.8 (8.89–106.72) |
| de-N-ethyl-N-(2-methyltetrahydrofurfuryl)-3,13-dideoxy-14-O-anisoylaconine | 32.6 (9.94–106.90) |
| de-N-ethyl-N-propyl-3-deoxy-14-O-anisoylaconine | 32.4 (11.46–91.59) |
| de-N-ethyl-N-(4-methylpentyl)-3-deoxy-14-O-anisoylaconine | 28.7 (9.59–85.90) |
| de-N-ethyl-N-acetyl-3-deoxy-14-O-anisoylaconine | 29.4 (9.14–94.52) |
| de--N-ethyl-N-benzoyl-3-deoxy-14-O-anisoylaconine | 30.4 (8.67–106.55) |
| de-N-ethyl-N-(2-methyltetrahydrofurfuryl)-3-deoxy-14-O-anisoylaconine | 31.2 (9.73–100.03) |
| de-N-ethyl-N-propyl-3,8,13-trideoxy-14-O-anisoylaconine | 29.7 (9.24–95.49) |
| de-N-ethyl-N-(4-methylpentyl)-3,8,13-trideoxy-14-O-anisoylaconine | 30.8 (9.33–101.64) |
| de-N-ethyl-N-acetyl-3,8,13-trideoxy-14-O-anisoylaconine | 28.8 (9.05–91.70) |
| de-N-ethyl-N-benzoyl-3,8,13-trideoxy-14-O-anisoylaconine | 32.2 (11.32–91.61) |
| de-N-ethyl-N-(2-methyltetrahydrofurfuryl)-3,8,13-trideoxy-14-O-anisoylaconine | 31.6 (10.13–98.56) |
| 3-deoxy-14-O-m-chlorobenzoyl-16-epi-pyroaconine | 10.1 (3.51–29.10) |
| 3-deoxy-14-O-acetyl-16-epi-pyroaconine | 30.4 (9.79–94.36) |
| 3-deoxy-14-O-methyl-16-epi-pyroaconine | 34.8 (10.38–116.68) |
| 3,13-dideoxy-14-O-m-chlorobenzoyl-16-epi-pyroaconine | 11.0 (3.41–35.46) |
| 3,13-dideoxy-14-O-acetyl-16-epi-pyroaconine | 29.7 (10.21–86.40) |
| 3,13-dideoxy-14-O-methyl-16-epi-pyroaconine | 36.6 (11.40–117.52) |
| 14-O-m-chlorobenzoyl-16-epi-pyroaconine | 11.9 (3.76–37.68) |
| 14-O-acetyl-16-epi-pyroaconine | 24.8 (8.53–72.14) |
| 14-O-methyl-16-epi-pyroaconine | 30.4 (11.31–81.75) |
| de-N-ethyl-N-benzoyl-3-deoxy-16-epi-pyrojesaconitine | 18.8 (5.60–63.07) |
| de-N-ethyl-N-propyl-3-deoxy-16-epi-pyrojesaconitine | 31.2 (10.96–88.80) |
| de-N-ethyl-N-acetyl-3-deoxy-16-epi-pyrojesaconitine | 27.4 (8.55–887.2) |
| de-N-ethyl-N-benzoyl-3,13-dideoxy-16-epi-pyrojesaconitine | 21.3 (6.74–67.35) |
| de-N-ethyl-N-propyl-3,13-dideoxy-16-epi-pyrojesaconitine | 27.6 (9.93–76.70) |
| de-N-ethyl-N-acetyl-3,13-dideoxy-16-epi-pyrojesaconitine | 32.8 (9.51–113.16) |
| de-N-ethyl-N-benzoyl-16-epi-pyrojesaconitine | 13.2 (4.45–39.14) |
| de-N-ethyl-N-propyl-16-epi-pyrojesaconitine | 29.4 (9.02–95.87) |
| de-N-ethyl-N-acetyl-16-epi-pyrojesaconitine | 24.8 (7.50–82.01) |
| 14-O-p-chlorobenzoylmesaconine | 5.85 (2.28–15.02) |
| 14-O-p-fluorobenzoylaconine | 8.26 (2.86–23.88) |
| 14-O-p-bromobenzoylaconine | 6.42 (2.13–19.39) |
| de-N-ethyl-14-O-p-chlorobenzoylaconine | 7.25 (2.44–21.55) |
| 14-O-p-chlorobenzoylpyraconine | 9.61 (3.86–23.95) |
| 14-O-p-bromobenzoylpyraconine | 10.4 (3.76–28.80) |
| 14-O-p-fluorobenzoylpyraconine | 11.5 (3.58–36.94) |
| de-N-ethyl-N-amyl-14-O-benzoylpyraconine | 20.4 (7.02–59.30) |
| 14-O-(3-chloropropionyl)-aconine | 15.8 (5.57–44.79) |
| 14-O-(4-hydroxybutyl)-aconine | 18.3 (8.89–37.68) |
| 14-O-(4-methylcyclohexyl)-aconine | 10.7 (4.20–27.25) |
| de-N-ethyl-N-(p-anisoyl)-14-O-benzoylaconine | 17.4 (5.75–52.43) |
| de-N-ethyl-N-(3-chloropropionyl)-14-O- | 10.4 (4.43–24.43) |

TABLE 1-continued

| Test compound | ED$_{50}$ value, mg/kg (95% confidence Limits) |
|---|---|
| benzoylaconine de-N-ethyl-N-crotyl-14-O-benzoylaconine | 11.3 (4.76–26.83) |
| de-N-ethyl-N-(4-methylcyclohexyl)-14-O-benzoylaconine | 9.24 (3.86–22.12) |
| de-N-ethyl-N-(4-hydroxybutyl)-14-O-benzoylaconine | 9.56 (3.20–28.59) |
| 14-O-(2-pyridylmethyl)aconine | 15.3 (5.74–40.79) |
| 14-O-(2-methyltetrahydrofurfuryl)aconine | 13.3 (4.61–38.33) |
| 14-O-cyclohexanecarbonylaconine | 11.8 (4.31–32.27) |
| de-N-ethyl-N-cyclohexanecarbonyl-14-O-benzoylaconine | 10.2 (3.41–30.55) |
| de-N-ethyl-N-α-methyl(4-(α-methylacetic acid)phenyl)acetyl-14-O-benzoylaconine | 12.7 (4.47–36.11) |
| de-N-ethyl-N-(2-pyridylmethyl)-14-O-benzoylaconine | 9.86 (3.52–27.60) |
| 14-O-anisoylneoline | 25.8 (8.30–80.24) |
| 1,14-di-O-butanoylneoline | 29.5 (10.3–83.90) |
| 1,14-di-p-chlorobenzoylneoline | 27.6 (9.32–81.70) | n = 6.

TABLE 2

| Test compound | Dose (mg/kg) | Difference in foot pad thickness between right and left feet ( × 10$^{-2}$ mm) | | | | | | |
|---|---|---|---|---|---|---|---|---|
| | | 0 | 1 | 2 | 3 | 4 | 5 | 6 (h) |
| control | 0 | 2 ± 3 | 68 ± 6 | 85 ± 5 | 106 ± 5 | 110 ± 5 | 100 ± 8 | 95 ± 7 |
| 8-deoxy-14-O-benzoylmesaconine | 10 | 2 ± 1 | 71 ± 4 | 75 ± 9 | 80 ± 7 | 84 ± 10 | 72 ± 11 | 80 ± 5 |
| | 30 | −1 ± 5 | 55 ± 7 | 54 ± 11* | 65 ± 5* | 78 ± 10* | 69 ± 9* | 65 ± 10 |
| 3,8-dideoxy-14-O-benzoylmesaconine | 10 | 3 ± 3 | 62 ± 9 | 68 ± 5 | 73 ± 7 | 69 ± 7* | 66 ± 4** | 68 ± 7 |
| | 30 | 1 ± 1 | 52 ± 6 | 61 ± 12 | 70 ± 10 | 68 ± 9* | 65 ± 8* | 68 ± 11 |
| 3,13-dideoxy-14-O-benzoylmesaconine | 10 | 2 ± 1 | 58 ± 4 | 60 ± 10 | 57 ± 7** | 60 ± 9** | 62 ± 12* | 68 ± 8 |
| | 30 | 4 ± 2 | 43 ± 10 | 48 ± 8* | 52 ± 11** | 49 ± 12** | 57 ± 7** | 55 ± 5** |
| 3,8,13-trideoxy-14-O-benzoylmesaconine | 10 | −5 ± 2 | 70 ± 6 | 72 ± 5 | 80 ± 7 | 82 ± 6* | 86 ± 9 | 83 ± 9 |
| | 30 | 2 ± 1 | 60 ± 4 | 50 ± 7* | 56 ± 12* | 51 ± 7** | 61 ± 10* | 63 ± 8* |
| 3,13-dideoxymesaconitine | 1 | 1 ± 2 | 69 ± 5 | 66 ± 8 | 68 ± 8* | 72 ± 9* | 68 ± 12* | 68 ± 10 |
| | 3 | 2 ± 1 | 65 ± 9 | 59 ± 5* | 40 ± 10** | 39 ± 11** | 48 ± 7** | 51 ± 9** |
| 8-deoxy-14-O-benzoylaconine | 10 | 3 ± 2 | 58 ± 12 | 55 ± 10* | 60 ± 11** | 57 ± 7** | 55 ± 9** | 58 ± 7* |
| | 30 | 3 ± 4 | 45 ± 11* | 48 ± 10* | 56 ± 4** | 55 ± 9** | 59 ± 5** | 57 ± 6* |
| 3-deoxy-14-O-benzoylaconine | 10 | 0 ± 3 | 69 ± 8 | 73 ± 4 | 80 ± 5 | 77 ± 9* | 79 ± 10 | 77 ± 11 |
| | 30 | 2 ± 2 | 62 ± 13 | 65 ± 12 | 72 ± 10* | 68 ± 11* | 75 ± 9 | 70 ± 12 |
| 3,8-dideoxy-14-O-benzoylaconine | 10 | 0 ± 3 | 60 ± 4 | 62 ± 7 | 59 ± 9** | 63 ± 9** | 70 ± 10 | 66 ± 7* |
| | 30 | 0 ± 1 | 55 ± 9 | 48 ± 5* | 56 ± 10** | 54 ± 13** | 57 ± 11** | 59 ± 10* |
| 3,13-dideoxy-14-O-benzoylaconine | 10 | 3 ± 4 | 72 ± 6 | 68 ± 6 | 69 ± 9* | 73 ± 4* | 70 ± 8 | 72 ± 7 |
| | 30 | 1 ± 5 | 64 ± 13 | 70 ± 8 | 65 ± 12* | 68 ± 7* | 64 ± 12* | 69 ± 10 |
| 3,8,13-trideoxy-14-O-benzoylaconine | 10 | 2 ± 3 | 68 ± 5 | 69 ± 7 | 74 ± 9* | 77 ± 4* | 80 ± 10 | 78 ± 12 |
| | 30 | 5 ± 4 | 69 ± 6 | 67 ± 9 | 71 ± 5* | 70 ± 9* | 67 ± 11* | 69 ± 8 |
| 4-O-anisoylmesaconine | 10 | 2 ± 2 | 70 ± 12 | 78 ± 8 | 80 ± 13 | 85 ± 5* | 90 ± 7 | 95 ± 7 |
| | 30 | −1 ± 3 | 53 ± 8 | 64 ± 10 | 60 ± 11** | 57 ± 7** | 64 ± 10* | 62 ± 6* |
| 8-deoxy-14-O-anisoylmesaconine | 10 | 0 ± 4 | 66 ± 6 | 70 ± 9 | 92 ± 7 | 90 ± 4 | 86 ± 10 | 91 ± 11 |
| | 30 | 3 ± 2 | 60 ± 5 | 68 ± 6 | 68 ± 9* | 70 ± 8* | 66 ± 8* | 68 ± 9 |
| 3-deoxy-14-O-anisoylmesaconine | 10 | 3 ± 2 | 70 ± 4 | 68 ± 7 | 72 ± 6* | 69 ± 9* | 69 ± 11* | 72 ± 8 |
| | 30 | 2 ± 1 | 56 ± 10 | 58 ± 11 | 62 ± 7** | 65 ± 10** | 60 ± 9* | 62 ± 11* |
| 3,8-dideoxy-14-O-anisoylmesaconine | 10 | −1 ± 2 | 66 ± 5 | 75 ± 8 | 80 ± 10 | 89 ± 7 | 93 ± 9 | 92 ± 9 |
| | 30 | 1 ± 1 | 65 ± 7 | 69 ± 7 | 72 ± 4** | 67 ± 8** | 74 ± 6 | 70 ± 10 |
| 3,13-dideoxy-14-O-anisoylmesaconine | 10 | 1 ± 3 | 61 ± 12 | 66 ± 13 | 70 ± 9* | 75 ± 10* | 72 ± 10 | 78 ± 11 |
| | 30 | 0 ± 2 | 58 ± 4 | 57 ± 9* | 62 ± 7** | 60 ± 12** | 64 ± 8* | 59 ± 8* |
| 3,8,13-trideoxy-14-O-anisoylmesaconine | 10 | 4 ± 4 | 67 ± 15 | 69 ± 12 | 72 ± 8* | 69 ± 14* | 71 ± 7 | 70 ± 9 |
| | 30 | 0 ± 1 | 66 ± 7 | 61 ± 10 | 64 ± 9* | 63 ± 8** | 60 ± 11* | 62 ± 6* |
| 8-deoxy-14-O-anisoylaconine | 10 | 2 ± 4 | 62 ± 4 | 64 ± 9 | 67 ± 6* | 70 ± 8* | 68 ± 7* | 69 ± 9 |
| | 30 | −2 ± 2 | 61 ± 5 | 59 ± 7* | 65 ± 4* | 62 ± 8** | 59 ± 10** | 60 ± 9* |
| 3-deoxy-14-O-anisoylaconine | 10 | 0 ± 2 | 70 ± 8 | 77 ± 6 | 76 ± 9* | 74 ± 10* | 75 ± 7 | 76 ± 11 |
| | 30 | 3 ± 1 | 55 ± 8 | 61 ± 8 | 63 ± 11* | 60 ± 6** | 65 ± 7* | 63 ± 9* |
| 3,8-dideoxy-14-O-anisoylaconine | 10 | 1 ± 2 | 62 ± 6 | 65 ± 10 | 67 ± 4** | 69 ± 7* | 69 ± 5* | 68 ± 7 |
| | 30 | 1 ± 1 | 52 ± 11 | 59 ± 13 | 65 ± 7* | 64 ± 15* | 66 ± 10* | 64 ± 10* |
| 3,13-dideoxy-14-O-anisoylaconine | 10 | 3 ± 3 | 74 ± 10 | 78 ± 7 | 80 ± 10 | 79 ± 6* | 81 ± 7 | 82 ± 4 |
| | 30 | 2 ± 2 | 69 ± 6 | 67 ± 9 | 66 ± 8* | 70 ± 5* | 72 ± 10 | 72 ± 11 |
| 3,8,13-trideoxy-14-O-anisoylaconine | 10 | −1 ± 4 | 65 ± 5 | 69 ± 7 | 70 ± 10 | 70 ± 9* | 68 ± 8* | 71 ± 8 |
| | 30 | 4 ± 1 | 57 ± 13 | 60 ± 7 | 59 ± 12** | 58 ± 14** | 63 ± 8* | 66 ± 10 |
| 3,13-dideoxyjesaconitine | 1 | 0 ± 2 | 68 ± 4 | 77 ± 5 | 81 ± 3* | 85 ± 7 | 90 ± 5 | 87 ± 6 |
| | 3 | 2 ± 3 | 71 ± 10 | 73 ± 7 | 70 ± 11* | 72 ± 6* | 69 ± 9* | 67 ± 12 |
| 8-deoxy-14-O-veratroylaconine | 10 | −3 ± 3 | 62 ± 8 | 67 ± 10 | 72 ± 6* | 80 ± 4 | 78 ± 8 | 76 ± 11 |
| | 20 | 0 ± 2 | 56 ± 5 | 59 ± 6* | 62 ± 9** | 65 ± 9** | 66 ± 10* | 69 ± 10 |
| 8-deoxy-14-O-trimethylgalloylaconine | 10 | 1 ± 2 | 60 ± 9 | 68 ± 8 | 66 ± 5* | 69 ± 7* | 71 ± 9 | 68 ± 13 |
| | 20 | 1 ± 3 | 49 ± 4* | 48 ± 9* | 53 ± 6** | 57 ± 5** | 59 ± 6** | 57 ± 8* |
| 8-deoxy-14-O-m-anisoylaconine | 10 | 2 ± 1 | 67 ± 6 | 72 ± 9 | 79 ± 8 | 86 ± 10 | 85 ± 12 | 81 ± 7 |
| | 30 | 1 ± 2 | 59 ± 11 | 62 ± 12 | 61 ± 11** | 65 ± 8** | 61 ± 11* | 58 ± 13* |
| 8-deoxy-14-O-p-chlorobenzoyl- | 10 | 0 ± 2 | 43 ± 4** | 44 ± 6** | 49 ± 7** | 48 ± 4** | 45 ± 5** | 51 ± 3** |
| | 30 | 1 ± 2 | 39 ± 4** | 38 ± 4** | 38 ± 4** | 39 ± 4** | 41 ± 4** | 45 ± 4** |

TABLE 2-continued

| Test compound | Dose (mg/kg) | Difference in foot pad thickness between right and left feet ($\times 10^{-2}$ mm) | | | | | | |
|---|---|---|---|---|---|---|---|---|
| | | 0 | 1 | 2 | 3 | 4 | 5 | 6 (h) |
| aconine | | | | | | | | |
| 8-deoxy-14-O-m-chlorobenzoyl-aconine | 10 | −1 ± 3 | 59 ± 5 | 62 ± 12 | 68 ± 11* | 73 ± 7* | 70 ± 8 | 72 ± 9 |
| | 30 | 2 ± 1 | 53 ± 8 | 57 ± 9* | 60 ± 9** | 62 ± 10** | 60 ± 5** | 63 ± 9* |
| 8-deoxy-14-O-o-chlorobenzoyl-aconine | 10 | 3 ± 2 | 53 ± 7 | 55 ± 8* | 59 ± 9** | 58 ± 13** | 59 ± 11** | 62 ± 9* |
| | 30 | 4 ± 3 | 46 ± 12* | 49 ± 10* | 48 ± 7** | 46 ± 6** | 48 ± 12** | 51 ± 10** |
| 8-deoxy-14-O-acetylaconine | 10 | 2 ± 2 | 61 ± 9 | 68 ± 7 | 73 ± 13 | 82 ± 5 | 79 ± 7 | 79 ± 12 |
| | 30 | 3 ± 2 | 58 ± 7 | 62 ± 9 | 63 ± 10* | 66 ± 8** | 63 ± 5** | 61 ± 9* |
| 8-deoxy-14-O-methylaconine | 10 | 1 ± 3 | 71 ± 5 | 76 ± 10 | 81 ± 8 | 89 ± 7 | 83 ± 12 | 84 ± 9 |
| | 30 | −3 ± 4 | 66 ± 9 | 65 ± 13 | 66 ± 4** | 65 ± 6** | 68 ± 8* | 70 ± 14 |
| 8-deoxy-14-O-amylaconine | 10 | 0 ± 1 | 68 ± 11 | 69 ± 8 | 75 ± 6* | 79 ± 12 | 77 ± 11 | 79 ± 5 |
| | 30 | 4 ± 3 | 62 ± 7 | 64 ± 6 | 66 ± 9* | 67 ± 8* | 69 ± 7* | 71 ± 10 |
| 8-deoxy-14-O-benzylaconine | 10 | 2 ± 2 | 56 ± 13 | 59 ± 11 | 63 ± 5** | 69 ± 6* | 65 ± 11* | 63 ± 5* |
| | 30 | 3 ± 3 | 52 ± 6 | 51 ± 7* | 54 ± 10** | 60 ± 8** | 62 ± 8* | 61 ± 9* |
| 8-deoxy-14-O-crotylaconine | 10 | 2 ± 1 | 69 ± 9 | 76 ± 8 | 87 ± 12 | 86 ± 9 | 81 ± 6 | 82 ± 7 |
| | 30 | −2 ± 1 | 64 ± 6 | 70 ± 11 | 71 ± 7* | 73 ± 4* | 75 ± 4* | 71 ± 5 |
| 8-deoxy-14-O-β-methyl(4-(β-methylacetic acid)phenyl)acetyl-aconine | 10 | 0 ± 2 | 63 ± 8 | 65 ± 10 | 69 ± 9* | 68 ± 9* | 70 ± 13 | 72 ± 6 |
| | 30 | 2 ± 2 | 57 ± 10 | 59 ± 12 | 62 ± 10* | 63 ± 9** | 68 ± 10* | 69 ± 12 |
| 8-deoxy-14-O-(4-methylpentyl)aconine | 10 | 2 ± 2 | 58 ± 8 | 65 ± 6 | 74 ± 9 | 81 ± 5* | 84 ± 7 | 85 ± 10 |
| | 30 | 0 ± 2 | 56 ± 6 | 55 ± 9* | 58 ± 4** | 62 ± 10** | 68 ± 9* | 66 ± 7* |
| 8-deoxy-14-O-m-fluorobenzoyl-aconine | 10 | 0 ± 1 | 70 ± 12 | 70 ± 6 | 80 ± 6 | 86 ± 11 | 84 ± 11 | 87 ± 13 |
| | 30 | 1 ± 3 | 59 ± 8 | 60 ± 10 | 59 ± 8** | 64 ± 5** | 61 ± 13* | 63 ± 12 |
| 8-deoxy-14-O-m-bromobenzoylaconine | 10 | 3 ± 2 | 64 ± 4 | 61 ± 5 | 69 ± 10 | 73 ± 5* | 87 ± 13 | 90 ± 6 |
| | 30 | 3 ± 1 | 57 ± 10 | 56 ± 10* | 60 ± 9** | 59 ± 14** | 63 ± 8* | 61 ± 9* |
| 8-deoxy-14-O-p-methoxybenzyl-aconine | 10 | 2 ± 1 | 62 ± 9 | 69 ± 7 | 73 ± 9 | 72 ± 8* | 75 ± 12 | 71 ± 11 |
| | 20 | 1 ± 1 | 59 ± 5 | 62 ± 8 | 61 ± 11* | 63 ± 6** | 66 ± 9* | 63 ± 10* |
| de-N-ethyl-N-propyl-8-deoxy-14-O-anisoylaconine | 10 | −4 ± 2 | 66 ± 9 | 59 ± 11 | 64 ± 7** | 68 ± 12* | 68 ± 5* | 72 ± 10 |
| | 30 | 0 ± 3 | 49 ± 10 | 52 ± 7* | 57 ± 6** | 56 ± 4** | 51 ± 8** | 53 ± 12* |
| de-N-ethyl-N-amyl-8-deoxy-14-O-anisoylaconine | 10 | 2 ± 2 | 71 ± 11 | 60 ± 13 | 69 ± 10* | 72 ± 8* | 79 ± 9 | 77 ± 9 |
| | 30 | 2 ± 2 | 52 ± 7 | 54 ± 7* | 55 ± 8** | 58 ± 6** | 62 ± 11* | 60 ± 6* |
| de-N-ethyl-N-(4-methylpentyl)-8-deoxy-14-O-anisoylaconine | 10 | 1 ± 3 | 68 ± 5 | 65 ± 5 | 68 ± 10* | 76 ± 9* | 80 ± 5 | 75 ± 8 |
| | 30 | 3 ± 1 | 60 ± 8 | 62 ± 9 | 65 ± 8* | 62 ± 9** | 63 ± 7* | 61 ± 6* |
| de-N-ethyl-N-acetyl-8-deoxy-14-O-anisoylaconine | 10 | −2 ± 2 | 67 ± 11 | 56 ± 8* | 59 ± 6** | 65 ± 12* | 61 ± 9* | 66 ± 13 |
| | 30 | 3 ± 2 | 65 ± 13 | 60 ± 9 | 57 ± 9** | 59 ± 13** | 56 ± 10** | 59 ± 11* |
| de-N-ethyl-N-benzoyl-8-deoxy-14-O-anisoylaconine | 10 | 0 ± 4 | 73 ± 6 | 72 ± 9 | 70 ± 11* | 79 ± 7* | 82 ± 6 | 80 ± 9 |
| | 30 | 0 ± 2 | 64 ± 4 | 62 ± 11 | 64 ± 5** | 65 ± 10** | 68 ± 10* | 67 ± 7* |
| de-N-ethyl-N-(2-methyltetrahydrofurfuryl)-8-deoxy-14-O-anisoylaconine | 10 | 1 ± 1 | 70 ± 10 | 68 ± 7 | 76 ± 13 | 83 ± 9 | 89 ± 5 | 88 ± 13 |
| | 30 | 2 ± 3 | 68 ± 8 | 61 ± 9 | 59 ± 10** | 65 ± 7** | 63 ± 11* | 62 ± 10* |
| de-N-ethyl-jesaconitine | 1 | 2 ± 2 | 65 ± 4 | 64 ± 10 | 77 ± 9 | 86 ± 13 | 83 ± 6 | 85 ± 7 |
| | 3 | 2 ± 4 | 65 ± 11 | 60 ± 6 | 68 ± 7* | 65 ± 5** | 69 ± 11* | 71 ± 5 |
| 3,13-dideoxy-14-O-veratroylaconine | 10 | 3 ± 3 | 60 ± 9 | 59 ± 11 | 64 ± 10* | 77 ± 5* | 80 ± 12 | 79 ± 10 |
| | 20 | −1 ± 3 | 56 ± 8 | 55 ± 7* | 61 ± 7** | 59 ± 11** | 62 ± 6* | 65 ± 8* |
| 3,13-dideoxy-14-O acetylaconine | 10 | 0 ± 2 | 65 ± 13 | 62 ± 9 | 68 ± 8* | 74 ± 10* | 71 ± 8 | 72 ± 9 |
| | 30 | 1 ± 2 | 58 ± 8 | 59 ± 12 | 62 ± 8** | 65 ± 4** | 59 ± 6** | 64 ± 8* |
| 3,13-dideoxy-14-O-benzylaconine | 10 | −3 ± 3 | 73 ± 5 | 61 ± 9 | 66 ± 6** | 70 ± 8* | 64 ± 6* | 73 ± 12 |
| | 30 | 1 ± 1 | 61 ± 10 | 53 ± 13* | 57 ± 10** | 45 ± 9** | 59 ± 11** | 64 ± 8* |
| 3,13-dideoxy-14-O-crotylaconine | 16 | 1 ± 4 | 67 ± 9 | 72 ± 12 | 74 ± 11 | 83 ± 10 | 78 ± 8 | 80 ± 6 |
| | 30 | 0 ± 2 | 62 ± 8 | 59 ± 5* | 66 ± 9* | 61 ± 8* | 63 ± 9* | 62 ± 10* |
| 3,13-dideoxy-14-O-(4-methylpentyl)aconine | 10 | 5 ± 3 | 69 ± 11 | 59 ± 9 | 78 ± 6 | 75 ± 9* | 76 ± 6 | 82 ± 11 |
| | 30 | 3 ± 2 | 59 ± 8 | 52 ± 10* | 61 ± 9** | 59 ± 7** | 63 ± 5** | 66 ± 13 |
| 3-deoxy-14-O-veratroylaconine | 10 | 4 ± 1 | 64 ± 5 | 64 ± 7 | 69 ± 11* | 68 ± 6** | 70 ± 8 | 75 ± 6 |
| | 20 | 4 ± 2 | 59 ± 12 | 61 ± 6 | 57 ± 7** | 49 ± 9** | 57 ± 7** | 62 ± 10* |
| 3-deoxy-14-O-acetylaconine | 10 | 0 ± 2 | 63 ± 10 | 70 ± 10 | 73 ± 13 | 78 ± 11 | 73 ± 10 | 69 ± 5* |
| | 30 | −3 ± 2 | 63 ± 6 | 66 ± 12 | 68 ± 7* | 69 ± 11* | 66 ± 13* | 64 ± 9* |
| 3-deoxy-14-O-benzylaconine | 10 | 2 ± 1 | 71 ± 8 | 61 ± 8 | 76 ± 8* | 75 ± 13 | 70 ± 11 | 81 ± 7 |
| | 30 | 4 ± 2 | 65 ± 5 | 57 ± 4** | 62 ± 10* | 61 ± 8** | 57 ± 6** | 63 ± 13 |
| 3-deoxy-14-O-crotylaconine | 10 | 3 ± 1 | 67 ± 11 | 68 ± 6 | 74 ± 9 | 76 ± 8* | 72 ± 7 | 79 ± 6 |
| | 30 | 4 ± 2 | 63 ± 10 | 60 ± 5 | 63 ± 6* | 70 ± 8* | 65 ± 10* | 69 ± 7 |

TABLE 2-continued

| Test compound | Dose (mg/kg) | Difference in foot pad thickness between right and left feet ($\times 10^{-2}$ mm) | | | | | | |
|---|---|---|---|---|---|---|---|---|
| | | 0 | 1 | 2 | 3 | 4 | 5 | 6 (h) |
| 3-deoxy-14-O-(4-methylpentyl)aconine | 10 | 2 ± 3 | 60 ± 7 | 72 ± 10 | 68 ± 12* | 81 ± 9 | 78 ± 5 | 83 ± 8 |
| | 30 | −1 ± 3 | 58 ± 9 | 62 ± 7 | 61 ± 11** | 77 ± 5* | 62 ± 8* | 67 ± 11 |
| 3,8,13-trideoxy-14-O-veratroylaconine | 10 | 3 ± 2 | 62 ± 13 | 59 ± 9 | 64 ± 8* | 82 ± 11 | 81 ± 8 | 85 ± 12 |
| | 20 | 0 ± 1 | 60 ± 8 | 57 ± 6* | 59 ± 7** | 68 ± 10* | 60 ± 8* | 70 ± 6 |
| 3,8,13-trideoxy-14-O-acetylaconine | 10 | 2 ± 3 | 64 ± 10 | 63 ± 6 | 68 ± 11* | 73 ± 7* | 75 ± 7 | 79 ± 5 |
| | 30 | 1 ± 1 | 61 ± 6 | 59 ± 7* | 62 ± 6** | 69 ± 8* | 58 ± 13** | 60 ± 7* |
| 3,8,13-trideoxy-14-O-benzylaconine | 10 | −2 ± 2 | 71 ± 9 | 68 ± 12 | 69 ± 8* | 71 ± 5* | 72 ± 11 | 79 ± 9 |
| | 30 | 2 ± 3 | 66 ± 6 | 61 ± 10 | 59 ± 5** | 65 ± 10** | 66 ± 12* | 70 ± 9 |
| 3,8,13-trideoxy-14-O-crotylaconine | 10 | 1 ± 1 | 68 ± 8 | 73 ± 8 | 76 ± 9 | 75 ± 7* | 70 ± 8 | 81 ± 10 |
| | 30 | 4 ± 2 | 60 ± 11 | 67 ± 6 | 68 ± 10* | 70 ± 12* | 65 ± 7* | 69 ± 8 |
| 3,8,13-trideoxy-14-O-(4-methylpentyl)aconine | 10 | −3 ± 2 | 65 ± 12 | 69 ± 7 | 74 ± 7* | 73 ± 12 | 69 ± 10* | 66 ± 12 |
| | 30 | 2 ± 1 | 62 ± 10 | 61 ± 11 | 69 ± 9* | 70 ± 11* | 59 ± 9** | 63 ± 9* |
| de-N-ethyl-N-propyl-3,13-dideoxy-14-O-anisoylaconine | 10 | 2 ± 2 | 65 ± 9 | 69 ± 7 | 89 ± 10 | 87 ± 8 | 89 ± 4 | 85 ± 6 |
| | 30 | 1 ± 1 | 59 ± 5 | 62 ± 5 | 71 ± 12 | 72 ± 4* | 69 ± 11* | 73 ± 7 |
| de-N-ethyl-N-(4-methylpentyl)-3,13-dideoxy-14-O-anisoylaconine | 10 | −1 ± 1 | 70 ± 11 | 77 ± 9 | 77 ± 7 | 80 ± 4* | 82 ± 13 | 79 ± 3 |
| | 30 | 0 ± 1 | 62 ± 9 | 58 ± 3** | 63 ± 5** | 71 ± 9* | 66 ± 12* | 73 ± 12 |
| de-N-ethyl-N-acetyl-3,13-dideoxy-14-O-anisoylaconine | 10 | 3 ± 3 | 60 ± 13 | 69 ± 7 | 72 ± 8* | 74 ± 12 | 77 ± 9 | 79 ± 10 |
| | 30 | 0 ± 4 | 58 ± 8 | 56 ± 6* | 68 ± 6* | 66 ± 11* | 70 ± 7 | 68 ± 7 |
| de-N-ethyl-N-benzoyl-3,13-dideoxy-14-O-anisoylaconine | 10 | 3 ± 4 | 69 ± 6 | 62 ± 10 | 67 ± 11* | 72 ± 9* | 71 ± 3* | 74 ± 13 |
| | 30 | 4 ± 1 | 66 ± 10 | 60 ± 8 | 58 ± 6** | 62 ± 5** | 59 ± 8** | 63 ± 7* |
| de-N-ethyl-N-(2-methyl-tetrahydrofurfuryl)-3,13-dideoxy-14-O-anisoylaconine | 10 | 2 ± 2 | 62 ± 3 | 69 ± 9 | 80 ± 5* | 79 ± 7* | 86 ± 9 | 84 ± 12 |
| | 30 | 1 ± 2 | 57 ± 8 | 55 ± 6** | 62 ± 3** | 62 ± 6** | 66 ± 12* | 69 ± 8 |
| de-N-ethyl-N-propyl-3-deoxy-14-O-anisoylaconine | 10 | −1 ± 1 | 66 ± 8 | 72 ± 5 | 71 ± 7* | 74 ± 8* | 80 ± 6 | 82 ± 8 |
| | 30 | 2 ± 2 | 55 ± 4 | 59 ± 8 | 69 ± 13* | 63 ± 13* | 61 ± 9* | 65 ± 11 |
| de-N-ethyl-N-(4-methylpentyl)-3-deoxy-14-O-anisoylaconine | 10 | 3 ± 4 | 69 ± 4 | 77 ± 10 | 79 ± 4* | 81 ± 5* | 77 ± 9 | 79 ± 9 |
| | 30 | 2 ± 2 | 49 ± 9* | 67 ± 11 | 68 ± 6* | 72 ± 4* | 67 ± 4* | 70 ± 10 |
| de-N-ethyl-N-acetyl-3-deoxy-14-O-anisoylaconine | 10 | 3 ± 1 | 72 ± 6 | 73 ± 10 | 69 ± 12 | 75 ± 7* | 79 ± 8 | 76 ± 7 |
| | 30 | 1 ± 3 | 61 ± 11 | 58 ± 8* | 57 ± 6** | 62 ± 5** | 59 ± 10* | 63 ± 10* |
| de-N-ethyl-N-benzoyl-3-deoxy-14-O-anisoylaconine | 10 | 1 ± 2 | 61 ± 12 | 60 ± 7 | 75 ± 3** | 79 ± 8* | 83 ± 7 | 80 ± 9 |
| | 30 | 4 ± 1 | 61 ± 10 | 52 ± 9* | 62 ± 7** | 61 ± 5** | 67 ± 5* | 66 ± 4* |
| de-N-ethyl-N-(2-methyl-tetrahydrofurfuryl)-3-deoxy-14-O-anisoylaconine | 10 | −4 ± 3 | 67 ± 9 | 69 ± 10 | 78 ± 13 | 83 ± 12 | 91 ± 9 | 82 ± 6 |
| | 30 | 2 ± 2 | 57 ± 10 | 59 ± 6* | 66 ± 6** | 69 ± 8* | 71 ± 5* | 67 ± 3* |
| de-N-ethyl-N-propyl-3,8,13-trideoxy-14-O-anisoylaconine | 10 | −2 ± 4 | 68 ± 6 | 71 ± 10 | 75 ± 5* | 79 ± 12 | 78 ± 8 | 81 ± 13 |
| | 30 | 0 ± 3 | 60 ± 9 | 63 ± 4 | 67 ± 7** | 71 ± 11* | 68 ± 7* | 71 ± 9 |
| de-N-ethyl-N-(4-methylpentyl)-3,8,13-trideoxy-14-O-anisoylaconine | 10 | 0 ± 2 | 62 ± 8 | 77 ± 10 | 82 ± 12 | 89 ± 8 | 91 ± 13 | 89 ± 8 |
| | 30 | −3 ± 2 | 48 ± 12 | 53 ± 8* | 59 ± 9** | 62 ± 11** | 64 ± 5** | 67 ± 9 |
| de-N-ethyl-N-acetyl-3,8,13-trideoxy-14-O-anisoylaconine | 10 | 4 ± 2 | 70 ± 7 | 82 ± 4 | 90 ± 5 | 92 ± 12 | 89 ± 9 | gl ± 5 |
| | 30 | 2 ± 1 | 65 ± 9 | 61 ± 3 | 63 ± 6** | 60 ± 8** | 58 ± 6** | 59 ± 4** |
| de-N-ethyl-N-benzoyl-3,8,13-trideoxy-14-O-anisoylaconine | 10 | 1 ± 1 | 59 ± 6 | 86 ± 12 | 95 ± 11 | 94 ± 10 | 95 ± 5 | 90 ± 12 |
| | 30 | 3 ± 2 | 60 ± 8 | 59 ± 7* | 58 ± 6** | 64 ± 4** | 66 ± 11* | 68 ± 6* |
| de-N-ethyl-N-(2-methyl-tetrahydrofurfuryl)-3,8,13-trideoxy-14-O-anisoylaconine | 10 | 0 ± 3 | 69 ± 13 | 68 ± 14 | 70 ± 7* | 77 ± 13 | 74 ± 7 | 72 ± 7 |
| | 30 | −2 ± 2 | 59 ± 7* | 64 ± 5 | 66 ± 6** | 69 ± 7* | 72 ± 10 | 69 ± 13 |

TABLE 2-continued

| Test compound | Dose (mg/kg) | Difference in foot pad thickness between right and left feet ($\times 10^{-2}$ mm) | | | | | | |
|---|---|---|---|---|---|---|---|---|
| | | 0 | 1 | 2 | 3 | 4 | 5 | 6 (h) |
| 3-deoxy-14-O-m-chlorobenzoyl-16-epi-pyroaconine | 10 | 2 ± 1 | 65 ± 9 | 76 ± 9 | 75 ± 10* | 74 ± 7* | 78 ± 12 | 77 ± 8 |
| | 20 | 1 ± 2 | 53 ± 8* | 59 ± 4* | 63 ± 8* | 68 ± 11* | 62 ± 4** | 67 ± 6* |
| 3-deoxy-14-O-acetyl-16-epi-pyroaconine | 10 | −2 ± 2 | 63 ± 5 | 66 ± 14 | 69 ± 9* | 72 ± 13 | 80 ± 12 | 76 ± 4 |
| | 30 | 0 ± 3 | 49 ± 9* | 52 ± 11* | 54 ± 6** | 56 ± 7** | 59 ± 10** | 59 ± 7* |
| 3-deoxy-14-O-methyl-16-epi-pyroaconine | 10 | 4 ± 1 | 68 ± 13 | 72 ± 6 | 74 ± 5* | 73 ± 10* | 72 ± 9 | 81 ± 6 |
| | 30 | 2 ± 3 | 52 ± 7* | 60 ± 4 | 58 ± 13** | 62 ± 8** | 59 ± 5** | 62 ± 11* |
| 3,13-dideoxy-14-O-m-chlorobenzoyl-16-epi-pyroaconine | 10 | 1 ± 1 | 70 ± 6 | 82 ± 10 | 91 ± 7 | 94 ± 8 | 90 ± 11 | 84 ± 6 |
| | 20 | 0 ± 1 | 60 ± 8 | 64 ± 8 | 61 ± 10* | 64 ± 12* | 70 ± 4* | 69 ± 13 |
| 3,13-dideoxy-14-O-acetyl-16-epi-pyroaconine | 10 | 2 ± 2 | 62 ± 12 | 68 ± 7 | 73 ± 11 | 70 ± 10* | 73 ± 11 | 76 ± 5 |
| | 30 | 3 ± 1 | 56 ± 7* | 55 ± 9* | 60 ± 9** | 62 ± 6** | 67 ± 7* | 71 ± 10 |
| 3,13-dideoxy-14-O-methyl-16-epi-pyroaconine | 10 | 1 ± 2 | 67 ± 9 | 75 ± 7 | 75 ± 11 | 78 ± 12 | 79 ± 10 | 84 ± 5 |
| | 30 | 3 ± 3 | 61 ± 10 | 63 ± 13 | 59 ± 12** | 57 ± 8** | 61 ± 9* | 63 ± 4* |
| 14-O-m-chlorobenzoyl-16-epi-pyroaconine | 10 | −1 ± 1 | 63 ± 14 | 64 ± 11 | 67 ± 12* | 65 ± 7** | 69 ± 5 | 66 ± 14 |
| | 20 | 4 ± 2 | 57 ± 8* | 60 ± 13 | 63 ± 8** | 62 ± 9** | 59 ± 6** | 56 ± 9* |
| 14-O-acetyl-16-epi-pyroaconine | 10 | 3 ± 3 | 61 ± 8 | 67 ± 12 | 66 ± 9* | 69 ± 5** | 65 ± 8* | 69 ± 7 |
| | 30 | 3 ± 2 | 58 ± 6* | 62 ± 10 | 64 ± 10* | 60 ± 9** | 63 ± 11* | 59 ± 9* |
| 14-O-methyl-16-epi-pyroaconine | 10 | 2 ± 2 | 62 ± 8 | 65 ± 11 | 72 ± 10* | 79 ± 7 | 82 ± 5 | 81 ± 9 |
| | 30 | 0 ± 3 | 55 ± 10 | 59 ± 8 | 60 ± 9** | 64 ± 11** | 66 ± 8* | 63 ± 11* |
| de-N-ethyl-N-benzoyl-3-deoxy-16-epi-pyrojesaconitine | 10 | 1 ± 2 | 68 ± 13 | 76 ± 9 | 79 ± 4* | 90 ± 10 | 88 ± 10 | 82 ± 13 |
| | 30 | 1 ± 1 | 52 ± 9 | 68 ± 7 | 68 ± 5** | 67 ± 6** | 67 ± 6* | 69 ± 6 |
| de-N-ethyl-N-propyl-3-deoxy-16-epi-pyrojesaconitine | 10 | −3 ± 2 | 70 ± 5 | 79 ± 14 | 83 ± 8 | 82 ± 9 | 83 ± 7 | 85 ± 8 |
| | 30 | 2 ± 2 | 56 ± 6 | 62 ± 11 | 73 ± 4** | 75 ± 6* | 78 ± 9 | 77 ± 5 |
| de-N-ethyl-N-acetyl-3-deoxy-16-epi-pyrojesaconitine | 10 | 4 ± 3 | 60 ± 10 | 82 ± 6 | 89 ± 11 | 87 ± 4 | 89 ± 5 | 85 ± 11 |
| | 30 | 1 ± 3 | 59 ± 12 | 61 ± 8 | 68 ± 6* | 73 ± 9* | 72 ± 15 | 70 ± 6 |
| de-N-ethyl-N-benzoyl-3,13-dideoxy-16-epi-pyrojesaconitine | 10 | 2 ± 1 | 59 ± 7 | 65 ± 9 | 70 ± 7* | 75 ± 8* | 71 ± 13 | 74 ± 14 |
| | 30 | 2 ± 4 | 46 ± 12* | 53 ± 6* | 66 ± 10* | 62 ± 12* | 65 ± 9* | 69 ± 5* |
| de-N-ethyl-N-propyl-3,13-dideoxy-16-epi-pyrojesaconitine | 10 | 3 ± 1 | 64 ± 7 | 66 ± 12 | 77 ± 9 | 80 ± 13 | 75 ± 4* | 70 ± 13 |
| | 30 | −1 ± 1 | 60 ± 9 | 55 ± 8* | 59 ± 5** | 55 ± 5** | 58 ± 10** | 61 ± 11* |
| de-N-ethyl-N-acetyl-3,13-dideoxy-16-epi-pyrojesaconitine | 10 | 0 ± 2 | 67 ± 8 | 72 ± 11 | 78 ± 13 | 76 ± 10* | 84 ± 14 | 77 ± 12 |
| | 30 | 2 ± 3 | 60 ± 6 | 68 ± 7 | 67 ± 8* | 74 ± 9* | 70 ± 10 | 67 ± 5* |
| de-N-ethyl-N-benzoyl-16-epi-pyrojesaconitine | 10 | 4 ± 3 | 58 ± 6 | 64 ± 5 | 69 ± 7* | 74 ± 6* | 78 ± 9 | 69 ± 11 |
| | 30 | −2 ± 1 | 53 ± 9 | 58 ± 8* | 60 ± 10** | 63 ± 11* | 59 ± 8** | 56 ± 7* |
| de-N-ethyl-N-propyl-16-epi-pyrojesaconitine | 10 | 2 ± 3 | 63 ± 8 | 73 ± 4 | 76 ± 10 | 83 ± 8 | 85 ± 13 | 78 ± 9 |
| | 30 | 0 ± 1 | 49 ± 4* | 53 ± 11* | 58 ± 9** | 61 ± 10** | 62 ± 8* | 59 ± 10* |
| de-N-ethyl-N-acetyl-16-epi-pyrojesaconitine | 10 | 3 ± 4 | 66 ± 5 | 81 ± 13 | 90 ± 5 | 93 ± 12 | 91 ± 6 | 89 ± 4 |
| | 30 | 1 ± 3 | 64 ± 9 | 68 ± 8 | 67 ± 7* | 75 ± 10* | 77 ± 9 | 74 ± 12 |
| 14-O-p-chlorobenzoylmesaconine | 10 | 5 ± 2 | 65 ± 9 | 74 ± 5 | 73 ± 7* | 78 ± 8* | 81 ± 11 | 85 ± 9 |
| | 30 | 4 ± 3 | 51 ± 11 | 59 ± 6* | 56 ± 10** | 64 ± 6** | 76 ± 10 | 74 ± 10* |
| 14-O-p-fluorobenzoylaconine | 10 | 1 ± 4 | 67 ± 8 | 80 ± 10 | 85 ± 7 | 94 ± 8 | 89 ± 12 | 88 ± 9 |
| | 30 | 4 ± 4 | 57 ± 10 | 63 ± 8 | 61 ± 6** | 69 ± 10* | 72 ± 6* | 73 ± 13 |
| 14-O-p-bromobenzoylaconine | 10 | 2 ± 3 | 60 ± 8 | 66 ± 10 | 71 ± 13 | 74 ± 7* | 73 ± 14 | 76 ± 9 |
| | 30 | 5 ± 2 | 58 ± 9 | 53 ± 8* | 59 ± 9** | 62 ± 6** | 68 ± 7** | 71 ± 18 |
| de-N-ethyl-14-O-p-chlorobenzoylaconine | 10 | −3 ± 4 | 69 ± 6 | 78 ± 9 | 77 ± 8 | 79 ± 12 | 80 ± 8 | 83 ± 9 |
| | 30 | 2 ± 1 | 65 ± 10 | 69 ± 11 | 70 ± 8* | 66 ± 7** | 71 ± 10 | 69 ± 7* |
| 14-O-p-chlorobenzoylpyraconine | 10 | 3 ± 1 | 59 ± 11 | 64 ± 5* | 67 ± 7* | 69 ± 7** | 68 ± 15 | 72 ± 14 |
| | 30 | 1 ± 2 | 58 ± 8 | 58 ± 10* | 63 ± 7** | 61 ± 9** | 59 ± 6** | 59 ± 9* |
| 14-O-p-bromobenzoylpyraconine | 10 | 2 ± 4 | 72 ± 7 | 77 ± 11 | 76 ± 8* | 79 ± 6* | 77 ± 10 | 79 ± 13 |
| | 30 | −1 ± 3 | 68 ± 8 | 68 ± 10 | 69 ± 9* | 67 ± 6** | 68 ± 12* | 70 ± 7* |
| 14-O-p-fluorobenzoylpyraconine mesaconine | 10 | 5 ± 3 | 74 ± 14 | 75 ± 8 | 80 ± 13 | 84 ± 10 | 82 ± 11 | 80 ± 5 |
| | 30 | 3 ± 1 | 59 ± 8 | 62 ± 11 | 65 ± 6** | 75 ± 8* | 69 ± 9* | 75 ± 10 |
| 14-O-(3-chloropropionyl)aconine | 10 | 2 ± 1 | 59 ± 12 | 63 ± 5 | 62 ± 8* | 69 ± 6** | 66 ± 4** | 73 ± 7 |
| | 30 | 3 ± 2 | 52 ± 8 | 57 ± 4* | 60 ± 10** | 68 ± 5** | 65 ± 8* | 68 ± 10 |
| 14-O-(4-hydroxy- | 10 | 2 ± 4 | 67 ± 9 | 65 ± 12 | 68 ± 6* | 60 ± 10** | 62 ± 12* | 68 ± 11 |

TABLE 2-continued

| Test compound | Dose (mg/kg) | Difference in foot pad thickness between right and left feet ($\times 10^{-2}$ mm) | | | | | | |
|---|---|---|---|---|---|---|---|---|
| | | 0 | 1 | 2 | 3 | 4 | 5 | 6 (h) |
| butyl)-aconine | 30 | −1 ± 2 | 54 ± 10 | 58 ± 6* | 61 ± 10** | 49 ± 12** | 67 ± 7* | 65 ± 5** |
| 14-O-(4-methyl- | 10 | −2 ± 2 | 75 ± 11 | 72 ± 9 | 70 ± 7* | 82 ± 9 | 86 ± 9 | 83 ± 9 |
| cyclohexyl)-aconine | 30 | 4 ± 1 | 59 ± 15 | 62 ± 8 | 65 ± 12* | 54 ± 7** | 61 ± 10* | 63 ± 7* |
| de-N-ethyl-N- | 10 | 3 ± 3 | 63 ± 7 | 66 ± 6 | 69 ± 8* | 72 ± 9* | 78 ± 12 | 78 ± 10 |
| (p-anisoyl)-14-O-benzoylaconine | 30 | 1 ± 3 | 61 ± 9 | 59 ± 7* | 62 ± 9** | 59 ± 11** | 68 ± 7* | 61 ± 9* |
| de-N-ethyl-N- | 10 | 3 ± 2 | 68 ± 9 | 70 ± 8 | 73 ± 7* | 74 ± 10* | 72 ± 5* | 75 ± 8 |
| ar-etyl-14-O-benzoylpyraconine | 30 | 3 ± 3 | 62 ± 10 | 64 ± 9 | 63 ± 8** | 61 ± 12** | 63 ± 10* | 65 ± 10* |
| de-N-ethyl-N- | 10 | −1 ± 4 | 72 ± 9 | 75 ± 12 | 72 ± 15 | 77 ± 7* | 68 ± 9* | 78 ± 7* |
| (3-chloro-propionyl)-14-O-benzoylaconine | 30 | 4 ± 2 | 68 ± 11 | 68 ± 8 | 69 ± 7** | 65 ± 6** | 69 ± 5* | 67 ± 6* |
| de-N-ethyl-N- | 10 | 3 ± 2 | 66 ± 7 | 68 ± 4 | 70 ± 5* | 77 ± 6* | 79 ± 10 | 77 ± 11 |
| crotyl-14-O-benzoylaconine | 30 | 0 ± 3 | 58 ± 11 | 63 ± 12 | 65 ± 10* | 68 ± 11* | 65 ± 9* | 70 ± 12 |
| de-N-ethyl-N-(4- | 10 | 4 ± 3 | 67 ± 10 | 62 ± 7 | 66 ± 5* | 63 ± 9** | 70 ± 12 | 66 ± 8* |
| methylcyclohexyl)-14-O-benzoyl-aconine | 30 | 3 ± 1 | 65 ± 8 | 68 ± 5* | 63 ± 7** | 64 ± 13** | 67 ± 10* | 69 ± 9 |
| de-N-ethyl-N- | 10 | 3 ± 2 | 70 ± 9 | 72 ± 12 | 75 ± 11 | 74 ± 9* | 77 ± 8 | 74 ± 8 |
| (4-hydroxybutyl)-14-O-benzoylaconine | 30 | 2 ± 2 | 65 ± 11 | 66 ± 8 | 65 ± 7* | 68 ± 7** | 70 ± 10 | 70 ± 9 |
| 14-O-(2-pyridyl- | 10 | 4 ± 3 | 71 ± 6 | 73 ± 7 | 74 ± 12 | 76 ± 8* | 80 ± 7 | 73 ± 7 |
| methyl-)aconine | 30 | 1 ± 1 | 62 ± 9 | 61 ± 8* | 65 ± 6** | 63 ± 9** | 66 ± 9* | 64 ± 6* |
| 14-O-(2-methyl-tetrahydrofurfuryl)aconine | 10 | 2 ± 2 | 68 ± 8 | 69 ± 8 | 69 ± 8* | 67 ± 10* | 68 ± 8* | 70 ± 13 |
| | 30 | −2 ± 2 | 61 ± 10 | 62 ± 6* | 62 ± 9** | 59 ± 12** | 62 ± 5** | 68 ± 10 |
| 14-O-cyclohexane-carbonylaconine | 10 | 1 ± 4 | 65 ± 7 | 68 ± 9 | 70 ± 13* | 72 ± 15 | 75 ± 9 | 77 ± 8 |
| | 30 | 0 ± 2 | 60 ± 9 | 61 ± 14 | 64 ± 7** | 66 ± 10** | 63 ± 7* | 62 ± 6* |
| de-N-ethyl-N-cyclohexane-carbonyl-14-O-benzoylaconine | 10 | 3 ± 1 | 72 ± 8 | 74 ± 8 | 73 ± 13 | 78 ± 6* | 80 ± 9 | 82 ± 12 |
| | 30 | 1 ± 3 | 67 ± 7 | 64 ± 9 | 66 ± 10* | 68 ± 9* | 64 ± 10* | 69 ± 10 |
| de-N-ethyl-N-β-methyl-(4-(β-methylacetic acid)phenyl)acetyl-14-O-benzoylaconine | 10 | −1 ± 2 | 69 ± 5 | 64 ± 10 | 68 ± 9* | 70 ± 10* | 71 ± 7 | 73 ± 15 |
| | 30 | 2 ± 4 | 63 ± 11 | 60 ± 6 | 61 ± 9** | 63 ± 8** | 64 ± 11* | 64 ± 8* |
| de-N-ethyl-N-(2-pyridylmethyl)-14-O-benzoylaconine | 10 | 3 ± 2 | 72 ± 9 | 74 ± 9 | 72 ± 13 | 73 ± 14 | 75 ± 8 | 78 ± 8 |
| | 30 | 4 ± 4 | 61 ± 10 | 62 ± 10 | 61 ± 10** | 64 ± 9** | 67 ± 9* | 69 ± 13 |
| 14-O-anisoylneoline | 10 | 3 ± 4 | 68 ± 8 | 71 ± 11 | 73 ± 8 | 72 ± 13 | 74 ± 9 | 76 ± 10 |
| | 30 | −2 ± 2 | 63 ± 7 | 59 ± 6* | 62 ± 9** | 58 ± 10** | 64 ± 12* | 62 ± 11 |
| 1,14-O-di-butanoyl-neoline | 10 | 2 ± 2 | 65 ± 10 | 70 ± 9 | 72 ± 8* | 70 ± 7* | 75 ± 7 | 78 ± 7 |
| | 30 | 4 ± 1 | 60 ± 10 | 64 ± 9 | 65 ± 10* | 67 ± 9** | 68 ± 11* | 69 ± 9 |
| 1,14-O-di-p-chloro-benzoylneoline | 10 | 2 ± 1 | 71 ± 7 | 70 ± 9 | 69 ± 9* | 72 ± 8* | 71 ± 6* | 75 ± 13 |
| | 30 | 4 ± 4 | 62 ± 9 | 62 ± 8 | 63 ± 10* | 66 ± 8** | 64 ± 8* | 65 ± 5* | n = 5.
*P < 0.05,
**P < 0.01.

TABLE 3

| Test compound | $LD_{50}$ value, mg/kg (95% confidence limits) |
|---|---|
| aconitine | 0.55 (0.30–1.01) |
| mesaconitine | 0.25 (0.20–0.31) |
| hypaconitine | 1.90 (1.52–2.37) |
| jesaconitine | 0.23 (0.18–0.29) |
| 8-deoxy-14-O-benzoylmesaconine | 30< |
| 3,8-dideoxy-14-O-benzoylmesaconine | 40< |
| 3,13-dideoxy-14-O-benzoylmesaconine | 40< |
| 3,8,13-trideoxy-14-O-benzoylmesaconine | 40< |
| 3,13-dideoxymesaconitine | 2< |
| 8-deoxy-14-O-benzoylaconine | 30< |
| 3-deoxy-14-O-benzoylaconine | 30< |
| 3,8-dideoxy-14-O-benzoylaconine | 30< |
| 3,13-dideoxy-14-O-benzoylaconine | 30< |
| 3,8,13-trideoxy-14-O-benzoylaconine | 30< |
| 14-O-anisoylmesaconine | 100< |
| 8-deoxy-14-O-anisoylmesaconine | 10< |
| 3-deoxy-14-O-anisoylmesaconine | 30< |
| 3,8-dideoxy-14-O-anisoylmesaconine | 20< |
| 3,13-dideoxy-14-O-anisoylmesaconine | 20< |
| 3,8,13-trideoxy-14-O-anisoylmesaconine | 30< |
| 8-deoxy-14-O-anisoylaconine | 40< |
| 3-deoxy-14-O-anisoylaconine | 30< |
| 3,8-dideoxy-14-O-anisoylaconine | 20< |
| 3,13-dideoxy-14-O-anisoylaconine | 20< |
| 3,8,13-trideoxy-14-O-anisoylaconine | 20< |
| 3,13-dideoxyjesaconitine | 3< |
| 8-deoxy-14-O-veratroylaconine | 20< |
| 8-deoxy-14-O-trimethylgalloylaconine | 20< |

TABLE 3-continued

| Test compound | LD$_{50}$ value, mg/kg (95% confidence limits) |
|---|---|
| 8-deoxy-14-O-m-anisoylaconine | 30< |
| 8-deoxy-14-O-p-chlorobenzoylaconine | 30< |
| 8-deoxy-14-O-m-chlorobenzoylaconine | 20< |
| 8-deoxy-14-O-o-chlorobenzoylaconine | 30< |
| 8-deoxy-14-O-acetylaconine | 30< |
| 8-deoxy-14-O-methylaconine | 30< |
| 8-deoxy-14-O-amylaconine | 30< |
| 8-deoxy-14-O-benzylaconine | 30< |
| 8-deoxy-14-O-crotylaconine | 30< |
| 8-deoxy-14-O-α-methyl(4-(α-methyl-acetic acid)phenyl)acetyl-aconine | 30< |
| 8-deoxy-14-O-(4-methylpentyl)aconine | 30< |
| 8-deoxy-14-O-m-fluorobenzoylaconine | 30< |
| 8-deoxy-14-O-m-bromobenzoylaconine | 30< |
| 8-deoxy-14-O-p-methoxybenzylaconine | 20< |
| de-N-ethyl-N-propyl-8-deoxy-14-O-anisoylaconine | 30< |
| de-N-ethyl-N-amyl-8-deoxy-14-O-anisoylaconine | 30< |
| de-N-ethyl-N-(4-methylpentyl)-8-deoxy-14-O-anisoylaconine | 30< |
| de-N-ethyl-N-acetyl-8-deoxy-14-O-anisoylaconine | 30< |
| de-N-ethyl-N-benzoyl-8-deoxy-14-O-anisoylaconine | 30< |
| de-N-ethyl-N-(2-methyltetrahydrofurfuryl)-8-deoxy-14-O-anisoylaconine | 30< |
| de-N-ethyl-jesaconitine | 10< |
| 3,13-dideoxy-14-O-veratroylaconine | 20< |
| 3,13-dideoxy-14-O-acetylaconine | 30< |
| 3,13-dideoxy-14-O-benzylaconine | 30< |
| 3,13-dideoxy-14-O-crotylaconine | 30< |
| 3,13-dideoxy-14-O-(4-methylpentyl)-aconine | 30< |
| 3-deoxy-14-O-veratroylaconine | 20< |
| 3-deoxy-14-O-acetylaconine | 30< |
| 3-deoxy-14-O-benzylaconine | 30< |
| 3-deoxy-14-O-crotylaconine | 30< |
| 3-deoxy-14-O-(4-methylpentyl)-aconine | 30< |
| 3,8,13-trideoxy-14-O-veratroylaconine | 20< |
| 3,8,13-trideoxy-14-O-acetylaconine | 30< |
| 3,8,13-trideoxy-14-O-benzylaconine | 30< |
| 3,8,13-trideoxy-14-O-crotylaconine | 30< |
| 3,8,13-trideoxy-14-O-(4-methylpentyl)-aconine | 30< |
| de-N-ethyl-N-propyl-3,13-dideoxy-14-O-anisoylaconine | 30< |
| de-N-ethyl-N-(4-methylpentyl)-3,13-dideoxy-14-O-anisoylaconine | 30< |
| de-N-ethyl-N-acetyl-3,13-dideoxy-14-O-anisoylaconine | 30< |
| de-N-ethyl-N-benzoyl-3,13-dideoxy-14-O-anisoylaconine | 30< |
| de-N-ethyl-N-(2-methyltetrahydrofurfuryl)-3,13-dideoxy-14-O-anisoylaconine | 30< |
| de-N-ethyl-N-propyl-3-deoxy-14-O-anisoylaconine | 30< |
| de-N-ethyl-N-(4-methylpentyl)-3-deoxy-14-O-anisoylaconine | 30< |
| de-N-ethyl-N-acetyl-3-deoxy-14-O-anisoylaconine | 30< |
| de-N-ethyl-N-benzoyl-3-deoxy-14-O-anisoylaconine | 30< |
| de-N-ethyl-N-(2-methyltetrahydrofurfuryl)-3-deoxy-14-O-anisoylaconine | 30< |
| de-N-ethyl-N-propyl-3,8,13-trideoxy-14-O-anisoylaconine | 30< |
| de-N-ethyl-N-(4-methylpentyl)-3,8,13-trideoxy-14-O-anisoylaconine | 30< |
| de-N-ethyl-N-acetyl-3,8,13-trideoxy-14-O-anisoylaconine | 30< |
| de-N-ethyl-N-benzoyl-3,8,13-trideoxy-14-O-anisoylaconine | 30< |
| de-N-ethyl-N-(2-methyltetrahydrofurfuryl)-3,8,13-trideoxy-14-O-anisoylaconine | 30< |
| 3-deoxy-14-O-m-chlorobenzoyl-16-epi-pyroaconine | 20< |
| 3-deoxy-14-O-acetyl-16-epi-pyroaconine | 30< |
| 3-deoxy-14-O-methyl-16-epi-pyroaconine | 30< |
| 3,13-dideoxy-14-O-m-chlorobenzoyl-16-epi-pyroaconine | 20< |
| 3,13-dideoxy-14-O-acetyl-16-epi-pyroaconine | 30< |
| 3,13-dideoxy-14-O-methyl-16-epi-pyroaconine | 30< |
| 14-O-m-chlorobenzoyl-16-epi-pyroaconine | 20< |
| 14-O-acetyl-16-epi-pyroaconine | 30< |
| 14-O-methyl-16-epi-pyroaconine | 30< |
| de-N-ethyl-N-benzoyl-3-deoxy-16-epi-pyrojesaconitine | 30< |
| de-N-ethyl-N-propyl-3-deoxy-16-epi-pyrojesaconitine | 30< |
| de-N-ethyl-N-acetyl-3-deoxy-16-epi-pyrojesaconitine | 30< |
| de-N-ethyl-N-benzoyl-3,13-dideoxy-16-epi-pyrojesaconitine | 30< |
| de-N-ethyl-N-propyl-3,13-dideoxy-16-epi-pyrojesaconitine | 30< |
| de-N-ethyl-N-acetyl-3,13-dideoxy-16-epi-pyrojesaconitine | 30< |
| de-N-ethyl-N-benzoyl-16-epi-pyrojesaconitine | 30< |
| de-N-ethyl-N-propyl-16-epi-pyrojesaconitine | 30< |
| de-N-ethyl-N-acetyl-16-epi-pyrojesaconitine | 30< |
| 14-O-p-chlorobenzoylmesaconine | 30< |
| 14-O-p-fluorobenzoylaconine | 30< |
| 14-O-p-bromobenzoylaconine | 30< |
| de-N-ethyl-14-O-p-chlorobenzoylaconine | 30< |
| 14-O-p-chlorobenzoylpyraconine | 30< |
| 14-O-p-bromobenzoylpyraconine | 30< |
| 14-O-p-fluorobenzoylpyraconine | 30< |
| de-N-ethyl-N-amyl-14-benzoylpyraconine | 30< |
| 14-O-(3-chloropropionyl)-aconine | 30< |
| 14-O-(4-hydroxybutyl)-aconine | 30< |
| 14-O-(4-methylcyclohexyl)-aconine | 30< |
| de-N-ethyl-N-(p-anisoyl)-14-O-benzoylaconine | 30< |
| de-N-ethyl-N-(3-chloropropionyl)-14-O-benzoylaconine | 30< |
| de-N-ethyl-N-crotyl-14-O-benzoylaconine | 30< |
| de-N-ethyl-N-(4-methylcyclohexyl)-14-O-benzoylaconine | 30< |
| de-N-ethyl-N-(4-hydroxybutyl)-14-O-benzoylaconine | 30< |
| 14-O-(2-pyridylmethyl)aconine | 30< |
| 14-O-(2-methyltetrahydrofurfuryl)aconine | 30< |
| 14-O-cyclohexanecarbonylaconine | 30< |
| de-N-ethyl-N-cyclohexanecarbonyl-14-O-benzoylaconine | 30< |
| de-N-ethyl-N-α-methyl(4-(α-methylacetic acid)phenyl)acetyl-14-O-benzoylaconine | 30< |
| de-N-ethyl-N-(2-pyridylmethyl)-14-O-benzoylaconine | 30< |
| 14-O-anisoylneoline | 30< |
| 1,14-di-butanoylneoline | 30< |
| 1,14-di-p-chlorobenzoylneoline | 30< |

We claim:

1. An aconitine compound of the formula (1) or a salt thereof:

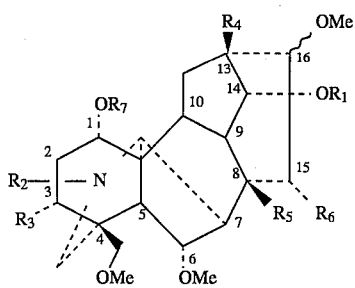

wherein $R_1$ and $R_2$ are independently (i) hydrogen, (ii) an acyclic or or cyclic, saturated or unsaturated alkyl having 1–8 carbon atoms, (iii) an oxygen- or nitrogen-containing 5- or 6-membered heterocyclic group, (iv) acyl derived from an acyclo- or cyclo- aliphatic, aromatic or aromatic-aliphatic carboxylic acid, or (v) aralkyl;

$R_3$ and $R_4$ are hydrogen or hydroxyl;

$R_5$ is hudrogen;

$R_6$ is a group forming carbonyl together with the carbon atom at the position 15; and $R_7$ is methyl;

provided that if $R_1$ is benzoyl or anisoyl then $R_2$ is acyl derived from an aliphatic or aromatic carboxylic acid.

2. An analgesic/anti-inflammatory composition containing as an active ingredient an aconitine compound as claimed in claim 1 together with an excipient.

* * * * *